(12) United States Patent
Akhremichev et al.

(10) Patent No.: US 12,269,036 B2
(45) Date of Patent: Apr. 8, 2025

(54) DEVICES, SYSTEMS, AND METHODS FOR INCREASING DROPLET FORMATION EFFICIENCY

(71) Applicant: 10x Genomics, Inc., Pleasanton, CA (US)

(72) Inventors: Ivan Akhremichev, San Leandro, CA (US); Rajiv Bharadwaj, Pleasanton, CA (US); Lynna Chen, Oakland, CA (US); Mohammad Rahimi Lenji, Livermore, CA (US); Alireza Salmanzadeh, San Francisco, CA (US); Martin Sauzade, Pleasanton, CA (US); Tobias Daniel Wheeler, Pleasanton, CA (US); Yiran Zhang, Castro Valley, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 752 days.

(21) Appl. No.: 17/458,757

(22) Filed: Aug. 27, 2021

(65) Prior Publication Data

US 2021/0387195 A1 Dec. 16, 2021

Related U.S. Application Data

(63) Continuation of application No. PCT/US2020/020486, filed on Feb. 28, 2020.
(Continued)

(51) Int. Cl.
*B01L 3/00* (2006.01)
*B01F 23/00* (2022.01)
(Continued)

(52) U.S. Cl.
CPC ........ *B01L 3/502784* (2013.01); *B01F 23/41* (2022.01); *B01F 25/31423* (2022.01);
(Continued)

(58) Field of Classification Search
CPC ....... B01L 3/502784; B01L 2200/0673; B01L 2300/0816; B01L 2300/0858;
(Continued)

(56) References Cited

U.S. PATENT DOCUMENTS 5,700,692 A 12/1997 Sweet
5,842,787 A 12/1998 Kopf-Sill et al.
(Continued)

FOREIGN PATENT DOCUMENTS

EP 1684078 A2 7/2006
WO WO-2007/138178 A2 12/2007
(Continued)

OTHER PUBLICATIONS

Abate et al., "High-throughput injection with microfluidics using picoinjectors," Proc Natl Acad Sci U S A. 107(45): 19163-6 (2010)(Oct. 20, 2010).
(Continued)

*Primary Examiner* — Jennifer Wecker
*Assistant Examiner* — Oyeleye Alexander Alabi
(74) *Attorney, Agent, or Firm* — Clark & Elbing LLP

(57) ABSTRACT

Devices, systems, and their methods of use, for generating and collecting droplets are provided. The device includes a collection region comprising a side wall canted at an angle. The invention further provides multiplex devices that increase droplet formation.

20 Claims, 68 Drawing Sheets

Related U.S. Application Data

(60) Provisional application No. 62/960,955, filed on Jan. 14, 2020, provisional application No. 62/872,196, filed on Jul. 9, 2019, provisional application No. 62/811,823, filed on Feb. 28, 2019, provisional application No. 62/811,992, filed on Feb. 28, 2019.

(51) Int. Cl.

| | | |
|---|---|---|
| *B01F 23/41* | (2022.01) | |
| *B01F 25/314* | (2022.01) | |
| *B01F 33/3011* | (2022.01) | |
| *B01F 101/23* | (2022.01) | |
| *B23Q 17/24* | (2006.01) | |
| *C07K 14/705* | (2006.01) | |
| *C12M 1/34* | (2006.01) | |
| *C12Q 1/04* | (2006.01) | |
| *C12Q 1/18* | (2006.01) | |
| *C12Q 1/686* | (2018.01) | |
| *G01N 15/1492* | (2024.01) | |
| *G01N 21/3577* | (2014.01) | |
| *G01N 21/359* | (2014.01) | |
| *G01N 21/39* | (2006.01) | |
| *G01N 21/45* | (2006.01) | |
| *G01N 21/64* | (2006.01) | |
| *G01N 27/414* | (2006.01) | |
| *G01N 30/12* | (2006.01) | |
| *G01N 30/68* | (2006.01) | |
| *G01N 30/70* | (2006.01) | |
| *G01N 30/72* | (2006.01) | |
| *G01N 30/88* | (2006.01) | |
| *G01N 33/00* | (2006.01) | |
| *G01N 33/18* | (2006.01) | |
| *G01N 33/50* | (2006.01) | |
| *G01N 33/53* | (2006.01) | |
| *G01N 33/543* | (2006.01) | |
| *G01N 33/68* | (2006.01) | |
| *G01N 33/74* | (2006.01) | |
| *H10K 10/46* | (2023.01) | |
| *H10K 85/00* | (2023.01) | |
| *H10K 85/20* | (2023.01) | |
| *G01N 15/10* | (2006.01) | |
| *G01N 15/14* | (2006.01) | |
| *G01N 15/149* | (2024.01) | |

(52) U.S. Cl.
CPC ...... *B01F 33/3011* (2022.01); *G01N 15/1492* (2024.01); *B01F 23/4144* (2022.01); *B01F 2215/0422* (2013.01); *B01L 2200/0673* (2013.01); *B01L 2300/0816* (2013.01); *B01L 2300/0858* (2013.01); *B01L 2400/0487* (2013.01); *G01N 2015/1006* (2013.01); *G01N 15/1459* (2013.01); *G01N 2015/1481* (2013.01); *G01N 15/149* (2024.01)

(58) Field of Classification Search
CPC ...... B01L 2400/0487; B01L 2300/0851; B01F 23/41; B01F 25/31423; B01F 33/3011; B01F 23/4144; B01F 2215/0422; B01F 25/31422; G01N 15/1459; G01N 15/149; G01N 2015/1006; G01N 2015/1481; G01N 15/1023; G01N 2015/1028; G01N 15/1492; G01N 15/1031; G01N 15/147; C12M 23/16; C12M 25/01
See application file for complete search history.

(56) References Cited

U.S. PATENT DOCUMENTS

| | | |
|---|---|---|
| 5,872,010 A | 2/1999 | Karger et al. |
| 6,296,020 B1 | 10/2001 | McNeely et al. |
| 6,328,421 B1 | 12/2001 | Kojima et al. |
| 6,432,290 B1 | 8/2002 | Harrison et al. |
| 6,778,724 B2 | 8/2004 | Wang et al. |
| 6,808,075 B2 | 10/2004 | Bohm et al. |
| 6,877,528 B2 | 4/2005 | Gilbert et al. |
| 6,880,576 B2 | 4/2005 | Karp et al. |
| 6,994,218 B2 | 2/2006 | Kawano et al. |
| 7,264,972 B2 | 9/2007 | Foster |
| 7,452,725 B2 | 11/2008 | Leary et al. |
| 7,699,767 B2 | 4/2010 | Mueth et al. |
| 7,901,947 B2 | 3/2011 | Pollack et al. |
| 7,943,671 B2 | 5/2011 | Herminghaus et al. |
| 8,096,421 B2 | 1/2012 | Shinoda |
| 8,186,913 B2 | 5/2012 | Toner et al. |
| 8,387,803 B2 | 3/2013 | Thorslund et al. |
| 8,467,040 B2 | 6/2013 | Luscher |
| 8,524,173 B2 | 9/2013 | Yamanaka et al. |
| 8,529,026 B2 | 9/2013 | Clarke et al. |
| 8,592,221 B2 | 11/2013 | Fraden et al. |
| 8,741,192 B2 | 6/2014 | Torii et al. |
| 8,820,538 B1 | 9/2014 | Lin |
| 8,821,006 B2 | 9/2014 | Norikane et al. |
| 8,871,500 B2 | 10/2014 | Foster et al. |
| 8,944,083 B2 | 2/2015 | Collier et al. |
| 9,017,623 B2 | 4/2015 | Fraden et al. |
| 9,133,009 B2 | 9/2015 | Baroud et al. |
| 9,399,215 B2 | 7/2016 | Cauley, III et al. |
| 9,403,294 B2 | 8/2016 | Cauley, III |
| 9,638,620 B2 | 5/2017 | Di Carlo et al. |
| 9,700,891 B2 | 7/2017 | Smith et al. |
| 10,011,872 B1 | 7/2018 | Belgrader et al. |
| 10,323,278 B2 | 6/2019 | Belgrader et al. |
| 10,357,771 B2 | 7/2019 | Bharadwaj et al. |
| 10,549,269 B2 | 2/2020 | Schaadt et al. |
| 10,583,440 B2 | 3/2020 | Bharadwaj et al. |
| 10,610,865 B2 | 4/2020 | Bharadwaj et al. |
| 10,766,032 B2 | 9/2020 | Bharadwaj et al. |
| 10,815,525 B2 | 10/2020 | Lucero et al. |
| 10,821,442 B2 | 11/2020 | Bharadwaj et al. |
| 10,898,900 B2 | 1/2021 | Bharadwaj et al. |
| 11,919,002 B2 * | 3/2024 | Rahimi Lenji ......... B01L 3/021 |
| 2001/0036669 A1 | 11/2001 | Jedrzejewski et al. |
| 2003/0005967 A1 | 1/2003 | Karp |
| 2004/0109793 A1 | 6/2004 | McNeely et al. |
| 2005/0172476 A1 | 8/2005 | Stone et al. |
| 2006/0163385 A1 | 7/2006 | Link et al. |
| 2007/0003442 A1 | 1/2007 | Link et al. |
| 2007/0065808 A1 | 3/2007 | Bohm et al. |
| 2007/0166200 A1 | 7/2007 | Zhou et al. |
| 2008/0038810 A1 | 2/2008 | Pollack et al. |
| 2008/0050283 A1 | 2/2008 | Chou et al. |
| 2009/0269824 A1 | 10/2009 | Kim et al. |
| 2010/0006441 A1 | 1/2010 | Renaud et al. |
| 2010/0018584 A1 | 1/2010 | Bransky et al. |
| 2010/0021984 A1 | 1/2010 | Edd et al. |
| 2011/0000560 A1 | 1/2011 | Miller et al. |
| 2011/0053798 A1 | 3/2011 | Hindson et al. |
| 2011/0086377 A1 | 4/2011 | Thwar et al. |
| 2011/0223314 A1 | 9/2011 | Zhang et al. |
| 2012/0091059 A1 | 4/2012 | Beer et al. |
| 2012/0121480 A1 | 5/2012 | Frenz et al. |
| 2012/0142018 A1 | 6/2012 | Jiang |
| 2012/0236299 A1 | 9/2012 | Chiou et al. |
| 2012/0315690 A1 | 12/2012 | Di Carlo et al. |
| 2013/0146461 A1 | 6/2013 | Pamula et al. |
| 2013/0236901 A1 | 9/2013 | Potier et al. |
| 2013/0260447 A1 | 10/2013 | Link |
| 2014/0024023 A1 | 1/2014 | Cauley, III et al. |
| 2014/0179544 A1 | 6/2014 | Steenblock et al. |
| 2014/0312543 A1 | 10/2014 | Nakagawa et al. |
| 2014/0326339 A1 | 11/2014 | Toner et al. |
| 2015/0034163 A1 | 2/2015 | Abate et al. |
| 2015/0224466 A1 | 8/2015 | Hindson et al. |

(56) References Cited

U.S. PATENT DOCUMENTS

| | | | |
|---|---|---|---|
| 2015/0258543 | A1 | 9/2015 | Baroud et al. |
| 2015/0267246 | A1 | 9/2015 | Baroud et al. |
| 2015/0292988 | A1 | 10/2015 | Bharadwaj et al. |
| 2015/0298091 | A1 | 10/2015 | Weitz et al. |
| 2015/0298157 | A1 | 10/2015 | Weitz et al. |
| 2015/0336096 | A1 | 11/2015 | Smith et al. |
| 2015/0360236 | A1 | 12/2015 | Garcia et al. |
| 2016/0003729 | A1 | 1/2016 | Lo et al. |
| 2016/0097087 | A1 | 4/2016 | Wiyatno et al. |
| 2016/0250637 | A1 | 9/2016 | Neild et al. |
| 2016/0271576 | A1 | 9/2016 | Arab et al. |
| 2016/0332163 | A1 | 11/2016 | Wang et al. |
| 2017/0114385 | A1 | 4/2017 | Di Carlo et al. |
| 2017/0151536 | A1 | 6/2017 | Weitz et al. |
| 2017/0165663 | A1 | 6/2017 | Hong et al. |
| 2017/0165669 | A1 | 6/2017 | Hung et al. |
| 2017/0189908 | A1 | 7/2017 | Dzenitis et al. |
| 2018/0056294 | A1 | 3/2018 | Di Carlo et al. |
| 2018/0169656 | A1 | 6/2018 | Trietsch et al. |
| 2018/0193829 | A1 | 7/2018 | Boitard et al. |
| 2018/0334670 | A1 | 11/2018 | Bharadwaj et al. |
| 2020/0032184 | A1 | 1/2020 | Tashiro et al. |
| 2020/0206742 | A1 | 7/2020 | Bharadwaj et al. |
| 2020/0230606 | A1 | 7/2020 | Bharadwaj et al. |
| 2020/0290048 | A1 | 9/2020 | Bharadwaj et al. |
| 2020/0391211 | A1 | 12/2020 | Wheeler et al. |
| 2022/0080424 | A1 | 3/2022 | Akhremichev et al. |

FOREIGN PATENT DOCUMENTS

| | | |
|---|---|---|
| WO | WO-2009/005680 A1 | 1/2009 |
| WO | WO-2010/128858 A1 | 11/2010 |
| WO | WO-2010/151776 A2 | 12/2010 |
| WO | WO-2012/156744 A2 | 11/2012 |
| WO | WO-2013/112121 A1 | 8/2013 |
| WO | WO-2015/132317 A1 | 9/2015 |
| WO | WO-2015/132318 A1 | 9/2015 |
| WO | WO-2015/160919 A1 | 10/2015 |
| WO | WO-2015/191534 A2 | 12/2015 |
| WO | WO-2016/035284 A1 | 3/2016 |
| WO | WO-2016/065056 A1 | 4/2016 |
| WO | WO-2016/075172 A1 | 5/2016 |
| WO | WO-2016/151107 A1 | 9/2016 |
| WO | WO-2016/193758 A1 | 12/2016 |
| WO | WO-2017/005872 A1 | 1/2017 |
| WO | WO-2017/075549 A1 | 5/2017 |
| WO | WO-2017/083375 A1 | 5/2017 |
| WO | WO-2017/117490 A1 | 7/2017 |
| WO | WO-2017/180949 A1 | 10/2017 |
| WO | WO-2018/009766 A1 | 1/2018 |
| WO | WO-2018/163943 A1 | 9/2018 |
| WO | WO-2019/040637 A1 | 2/2019 |
| WO | WO-2019/083852 A1 | 5/2019 |
| WO | WO-2019/157529 A1 | 8/2019 |
| WO | WO-2022/051529 A1 | 3/2022 |

OTHER PUBLICATIONS

Abate et al., "Valve based flow focusing for drop formation," Appl Phys Lett. 94(2):023503-1-3 (2009) (Jan. 14, 2009) (3 pages).

AGC Chemicals, "Amorphous Fluoropolymer CYTOP: Chemistry for a Blue Planet," Jul. 2015 (10 pages).

Akartuna et al., "Chemically induced coalescence in droplet-based microfluidics," Lab Chip. 15(4):1140-4 (2014) (Dec. 16, 2014) (5 pages).

Attia et al., "Micro-injection moulding of polymer microfluidic devices," Microfluid Nanofluidics. 7(1): 1-28 (2009) (Feb. 28, 2009) (30 pages).

Barea et al., "Recent Advances in Droplet-based Microfluidic Technologies for Biochemistry and Molecular Biology," Micromachines (Basel). 10(6):412 (2019) (25 pages).

Baret et al., "Fluorescence-activated droplet sorting (FADS): efficient microfluidic cell sorting based on enzymatic activity," Lab Chip. 9(13): 1850-1859 (2009) (Apr. 23, 2009).

Becker et al., "Polymer microfabrication technologies for microfluidic systems," Anal Bioanal Chem. 390(1): 89-111 (2008) (Nov. 8, 2007).

Bransky et al., "A microfluidic droplet generator based on a piezoelectric actuator," Lab Chip. 9(4): 516-520 (2009) (Nov. 20, 2008).

Brouzes et al., "Droplet microfluidic technology for single-cell high-throughput screening," Proc Natl Acad Sci U S A. 106(34): 14195-14200 (2009) (Jul. 15, 2009).

Brower et al., "Optimized double emulsion flow cytometry with high-throughput single droplet isolation," bioRxiv preprint posted online Nov. 8, 2019; doi: http://dx.doi.org/10.1101/803460 (35 pages).

Chakraborty et al., "Microfluidic step-emulsification in axisymmetric geometry," Lab Chip. 17(21): 3609-3620 (2017) (Oct. 25, 2017).

Cheung et al., "Characterization of acoustic droplet formation in a microfluidic flow-focusing device," Phys Rev E Stat Nonlin Soft Matter Phys. 84(6 Pt 2):066310 (2011) (10 pages).

Chokkalingam et al., "Self-synchronizing pairwise production of monodisperse droplets by microfluidic step emulsification," Appl Phys Lett. 93(25): 254101-1-254101-3 (2008) (Dec. 22, 2008).

Chokkalingam et al., "Template-free Preparation of Mesoporous Silica Spheres through Optimized Microfluidics," ChemPhysChem. 11(10):2091-5 (2010).

Chou et al., "Disposable microdevices for DNA analysis and cell sorting," Proc Solid-State Sensor and Actuator Workshop, Jun. 8-11, Hilton Head, SC, pp. 11-14 (1998).

Dangla et al., "Droplet microfluidics driven by gradients of confinement," Proc Natl Acad Sci U S A. 110(3): 853-858 (2013) (Jan. 2, 2013).

Dangla et al., "The physical mechanisms of step emulsification," J Phys D Appl Phys. 46(11):114003 (2013) (8 pages) (Feb. 22, 2013).

de Mello et al., Chip technology for micro-separation. *Microsystem Technology: Biomethods*, vol. 10. Köhler J.M., Mejevaia T., Saluz H.P., 129-177 (1999).

Demirci et al., "Single cell epitaxy by acoustic picolitre droplets," Lab Chip. 7(9): 1139-1145 (2007) (Jan. 10, 2007).

Doerr, "The smallest bioreactor," Nat Methods. 2(5): 326 (2005) (May 2005).

Draper et al., "Compartmentalization of electrophoretically separated analytes in a multiphase microfluidic platform," Anal Chem. 84(13): 5801-5808 (2012) (Jun. 13, 2012).

Eggersdorfer et al., "Supplementary Information: Tandem emulsification for high-throughput production of double emulsions," Lab Chip. 17(5):936-942 (2017) (Feb. 28, 2017) (2 pages).

Eggersdorfer et al., "Tandem emulsification for high-throughput production of double emulsions," Lab Chip. 17(5): 936-942 (2017) (Feb. 28, 2017).

Eggersdorfer et al., "Wetting controls of droplet formation in step emulsification," Proc Natl Acad Sci USA. 115(38):9479-84 (2018).

Fredrickson et al., "Macro-to-micro interfaces for microfluidic devices," Lab Chip. 4(6): 526-533 (2004) (Nov. 10, 2004).

Galambos et al., "Precision alignment packaging for microsystems with multiple fluid connections," Proceedings of 2001 ASME: International Mechanical Engineering Conference and Exposition, November 11-16, New York, NY. pp. 1-8 (2001).

Garstecki et al., "Formation of monodisperse bubbles in a microfluidic flow-focusing device," Appl Phys Lett. 85(13): 2649-2651 (2004) (Sep. 28, 2004).

Guldiken et al., "Sheathless size-based acoustic particle separation," Sensors (Basel). 12(1):905-22 (2012) (Jan. 16, 2012).

Hati et al., "Production of monodisperse drops from viscous fluids," Lab Chip. DOI: 10.1039/c7lc01322a (2018) (7 pages) (Feb. 13, 2018).

He et al., "Selective encapsulation of single cells and subcellular organelles into picoliter- and femtoliter-volume droplets," Anal Chem. 77(6): 1539-1544 (2005) (Mar. 15, 2005).

Huang et al., "Coating of poly(dimethylsiloxane) with n-dodecyl-Beta-D-maltoside to minimize nonspecific protein adsorption," Lab Chip. 5(10):1005-1007 (2005) (Sep. 5, 2005).

(56) References Cited

OTHER PUBLICATIONS

Huang et al., "Collective generation of milliemulsions by step-emulsification," RSC Adv. 7(24):14932-14938 (2017) (Mar. 7, 2017).

Hwang et al., "Surface modification of cyclic olefin copolymer substrate by oxygen plasma treatment," Surf Coat Tech. 202(15): 3669-3674 (2008) (Apr. 25, 2008).

International Search Report and Written Opinion for International Patent Application No. PCT/US2020/020486, mailed Jun. 17, 2020 (13 pages).

Kahkeshani et al., "Drop formation using ferrofluids driven magnetically in a step emulsification device," Lab Chip. 16(13): 2474-2480 (2016) (Jun. 2, 2016).

Kawai et al., "Mass-production system of nearly monodisperse diameter gel particles using droplets formation in a microchannel." *Micro Total Analysis Systems 2002*, vol. 1. Baba Y., Shoji S., van den Berg A., 368-370 (2002) (Dec. 2002).

Kobayashi et al., "Effect of slot aspect ratio on droplet formation from silicon straight-through microchannels," J Colloid Interface Sci. 279(1): 277-80 (2004) (Nov. 1, 2004).

Kobayashi et al., "Preparation characteristics of oil-in-water emulsions using differently charged surfactants in straight-through microchannel emulsification," Colloids Surf A Physicochem Eng Asp. 229(1-3): 33-41 (2003) (Aug. 7, 2003).

Lee et al., "Microfluidic mixing: a review," Int J Mol Sci. 12(5):3263-87 (2011).

Lee et al., "Passive mixers in microfluidic systems: a review," Chem Eng J. 288:146-160 (2016).

Li et al., "Step-emulsification in a microfluidic device," Lab Chip. 15(4): 1023-31 (2015) (Feb. 21, 2015) (10 pages).

Luo et al., "Microfluidic Single-Cell Manipulation and Analysis: Methods and Applications," Micromachines (Basel). 10(2):104 (2019) (31 pages).

Maan et al., "Microfluidic emulsification in food processing," J Food Eng. 147:1-7 (2015) (Feb. 2015).

Mazutis et al., "Single-cell analysis and sorting using droplet-based microfluidics," available in PMC Aug. 11, 2014, published in final edited form as: Nat Protoc. 8(5):870-91 (2013) (48 pages).

Mittal et al., "Dynamics of step-emulsification: From a single to a collection of emulsion droplet generators," Phys Fluids. 26: 082109-1-082109-14 (2014) (Aug. 19, 2014).

Sahin et al., "Microfluidic EDGE emulsification: the importance of interface interactions on droplet formation and pressure stability," Sci Rep. 6:26407 (2016) (May 27, 2016) (7 pages).

Schuler et al., "Digital droplet PCR on disk," Lab Chip. 16 (1): 208-216 (2016) (Jan. 7, 2016).

Shaikh et al., "A modular microfluidic architecture for integrated biochemical analysis," Proc Natl Acad Sci U S A. 102(28):9745-50 (2005).

Shim et al., "Supporting Information: Control and measurement of the phase behavior of aqueous solutions using microfluidics," S1-S13 (2007) (Jun. 20, 2007) (13 pages).

Song et al., "Reactions in Droplets in Microfluidic Channels," available in PMC Jan. 10, 2007, published in final edited form as: Angew Chem Int Ed Engl. 45(44):7336-56 (2006) (Nov. 13, 2006) (58 pages).

Stolovicki et al., "Throughput enhancement of parallel step emulsifier devices by shear-free and efficient nozzle clearance," Lab Chip. DOI: 10.1039/c7lc01037k (2017) (Dec. 19, 2017) (7 pages).

Su et al., "Microfluidics-Based Biochips: Technology Issues, Implementation Platforms, and Design-Automation Challenges," IEEE Transactions on Computer-Aided Design of Integrated Circuits and Systems. 25(2):211-23 (2006) (Feb. 21, 2006).

Suh et al., "A Review on Mixing Microfluidics," Micromachines. 1(3):82-111 (2010).

Tan et al., "Droplet coalescence by geometrically mediated flow in microfluidic channels," Microfluid Nanofluid. 3:495-499 (2007).

van Dijke et al., "EDGE emulsification for food-grade dispersions," Journal of Food Engineering. 97(3):348-354 (2010) (Apr. 2010).

van Dijke et al., "Effect of viscosities of dispersed and continuous phases in microchannel oil-in-water emulsification," Microfluid Nanofluid. 9(1):77-85 (2010) (Nov. 11, 2009).

van Dijke et al., "Microchannel Emulsification: From Computational Fluid Dynamics to Predictive Analytical Model," Langmuir. 24(18): 10107-10115 (2008) (Aug. 15, 2008).

van Dijke et al., "Parallelized edge-based droplet generation (EDGE) devices," Lab Chip. 9(19): 2824-2830 (2009) (Jul. 6, 2009).

van Dijke et al., "Simultaneous Formation of Many Droplets in a Single Microfluidic Droplet Formation Unit," AIChE J. 56(3): 833-836 (2010) (Sep. 25, 2009).

van Dijke et al., "The mechanism of droplet formation in microfluidic EDGE systems," Soft Matter. 6(2): 321-330 (2010) (Nov. 5, 2009).

Wang et al., "Inertial particle focusing and spacing control in microfluidic devices," Microfluid Nanofluid. 22:25 (Feb. 15, 2018) (12 pages).

Xia et al., "Soft Lithography," Angew Chem Int Ed Engl. 37(5):550-575 (1998) (26 pages).

Zeng et al., "High-performance single cell genetic analysis using microfluidic emulsion generator arrays," Anal Chem. 82(8):3183-90 (2010) (Apr. 15, 2010).

Edd et al., "Controlled encapsulation of single-cells into monodisperse picolitre drops," Lab Chip. 8(8):: 1262-1264 (Aug. 2008).

Tan et al., "Microfluidic mixing in a Y-junction open channel," AIP Advances 2. (12 pages) (Aug. 2012).

* cited by examiner

Fig. 10A
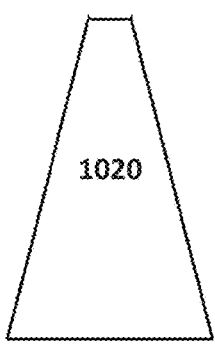
Fig. 10B
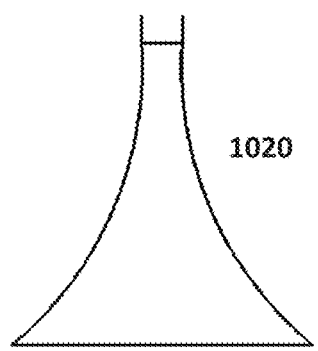
Fig. 10C
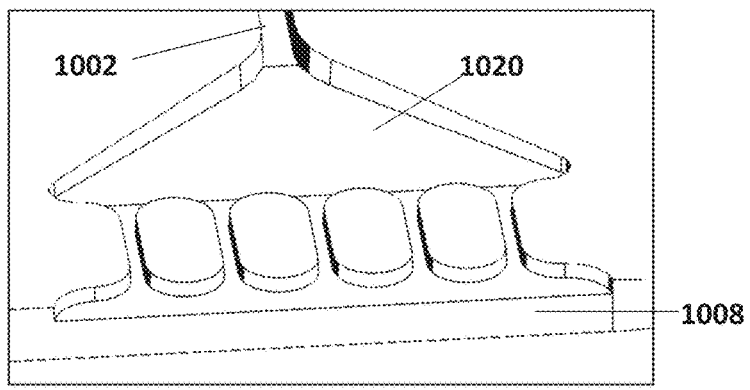
Fig. 10D
Fig. 10E
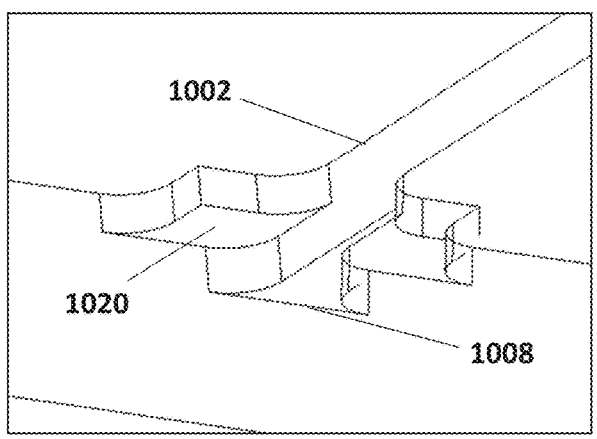
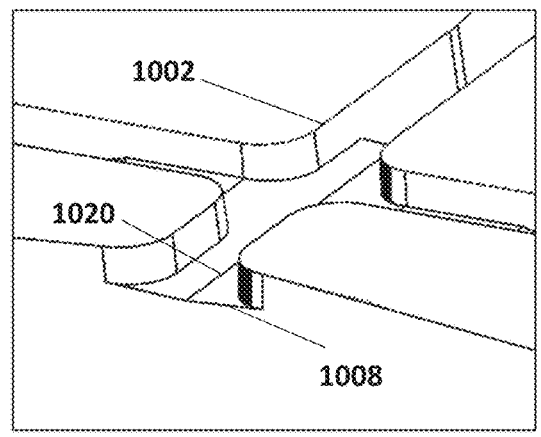

Fig. 13A
Fig. 13B
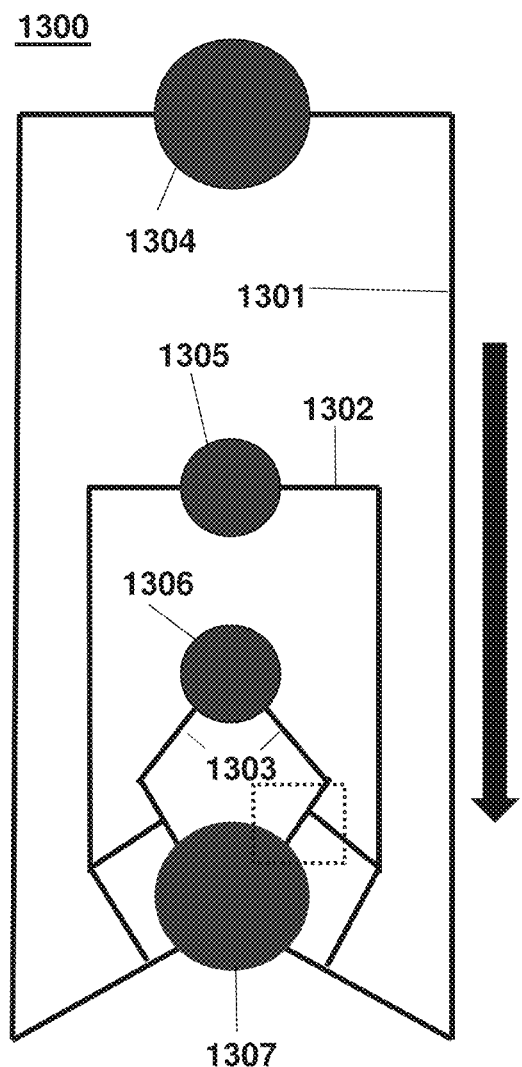
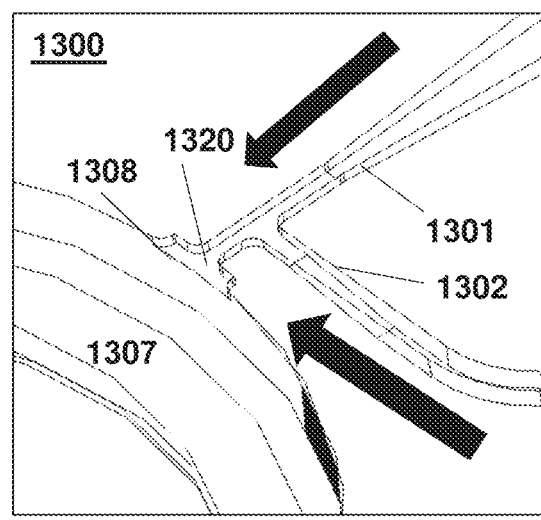

1400

1400

FIG. 27A
FIG. 27B
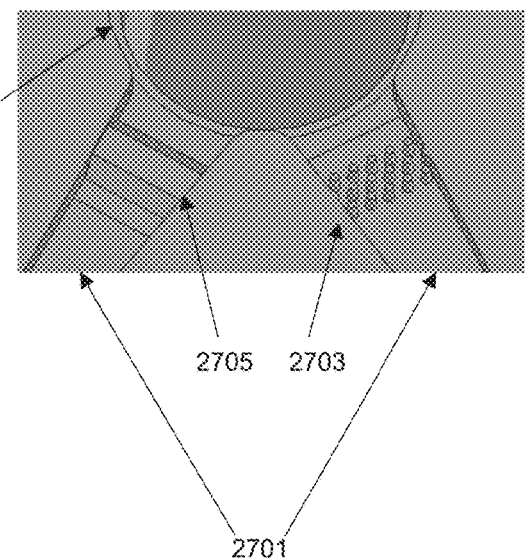
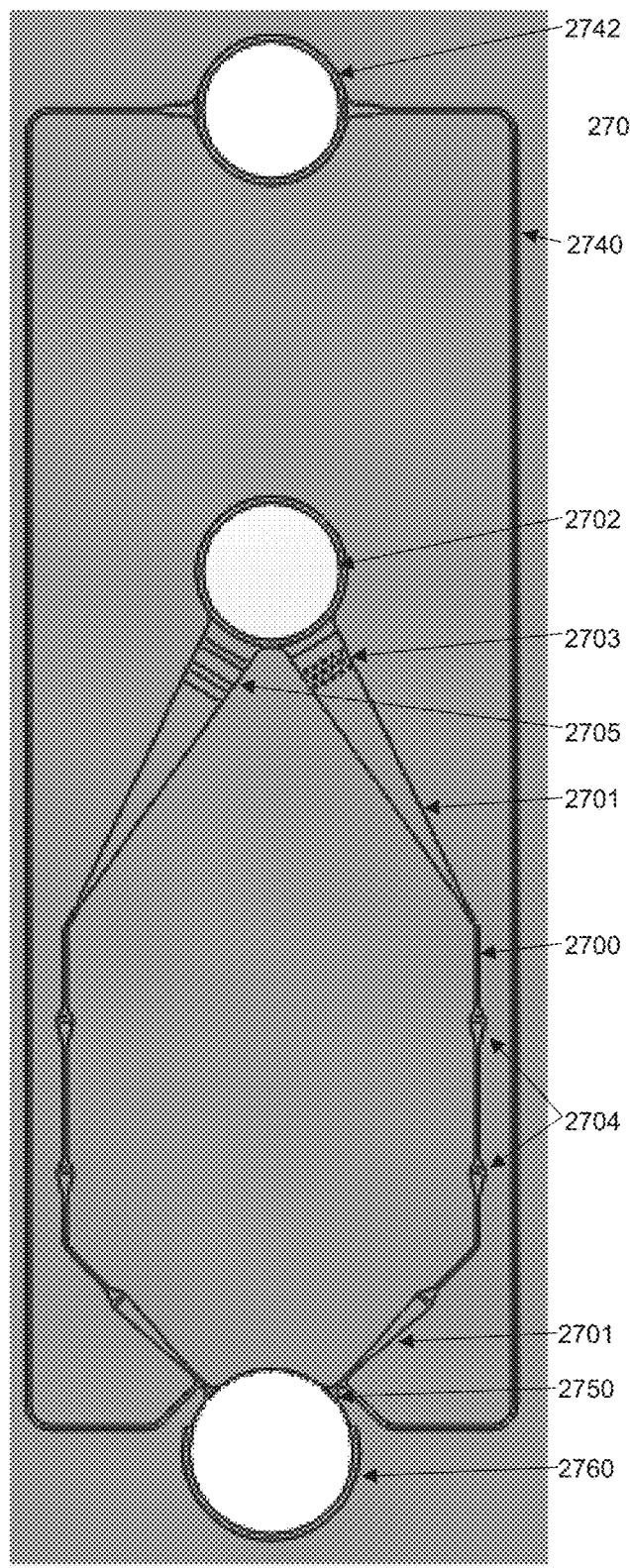

FIG. 29A
FIG. 29B
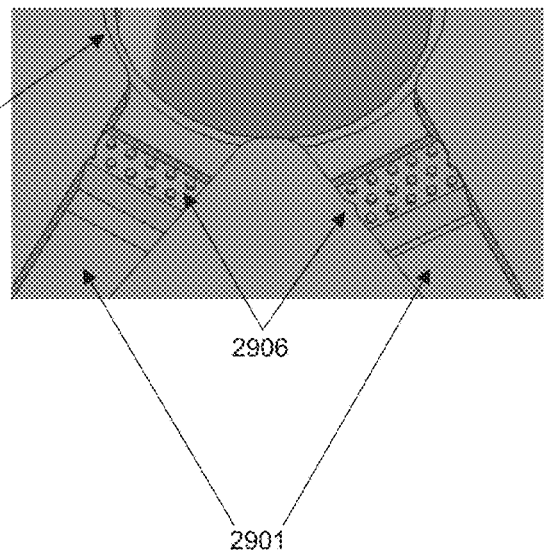
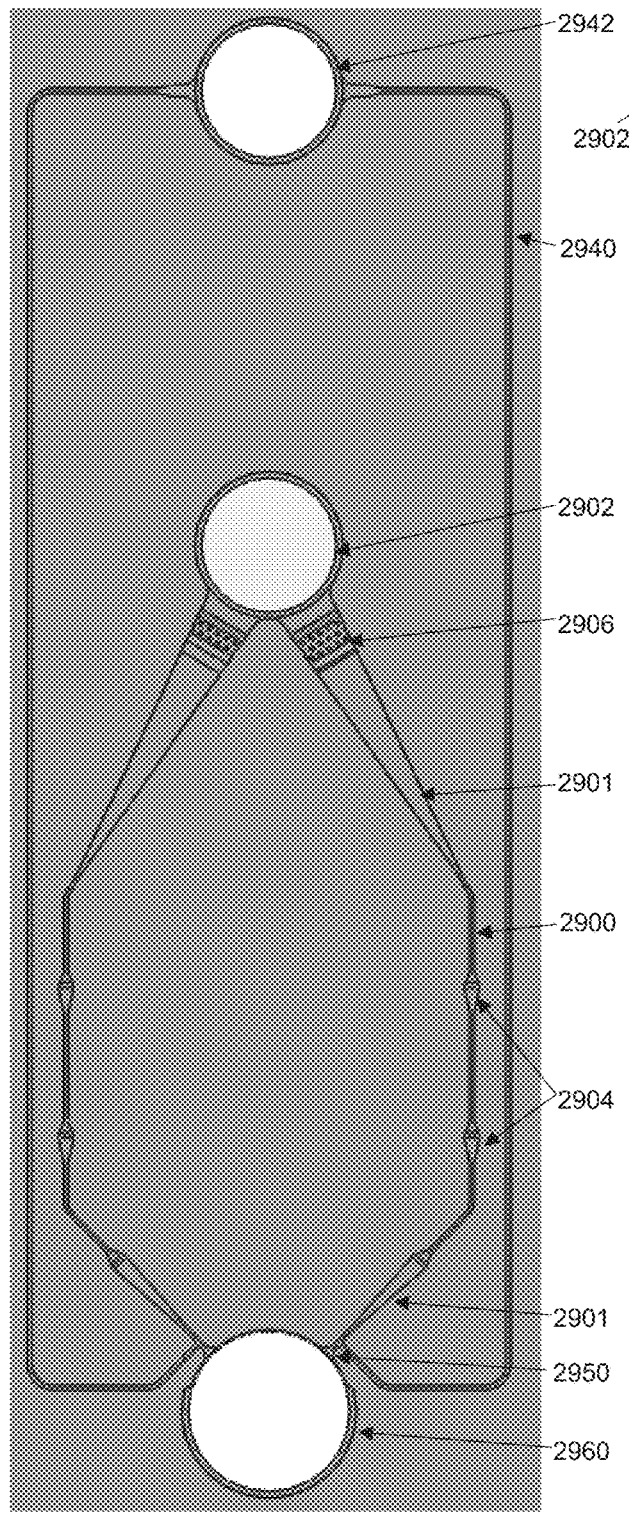

FIG. 30A
FIG. 30B
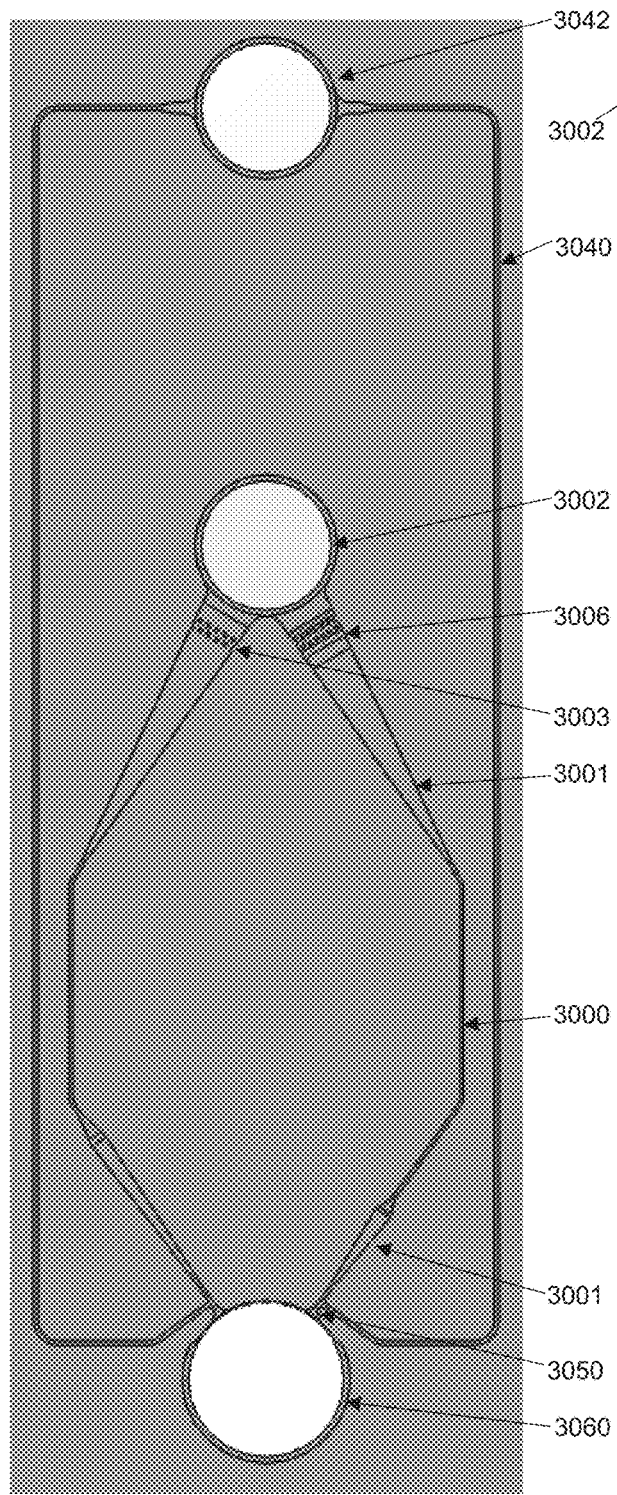
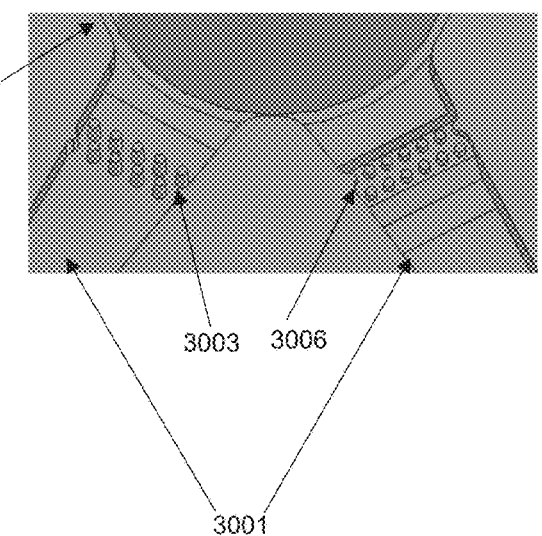

FIG. 31A
FIG. 31B
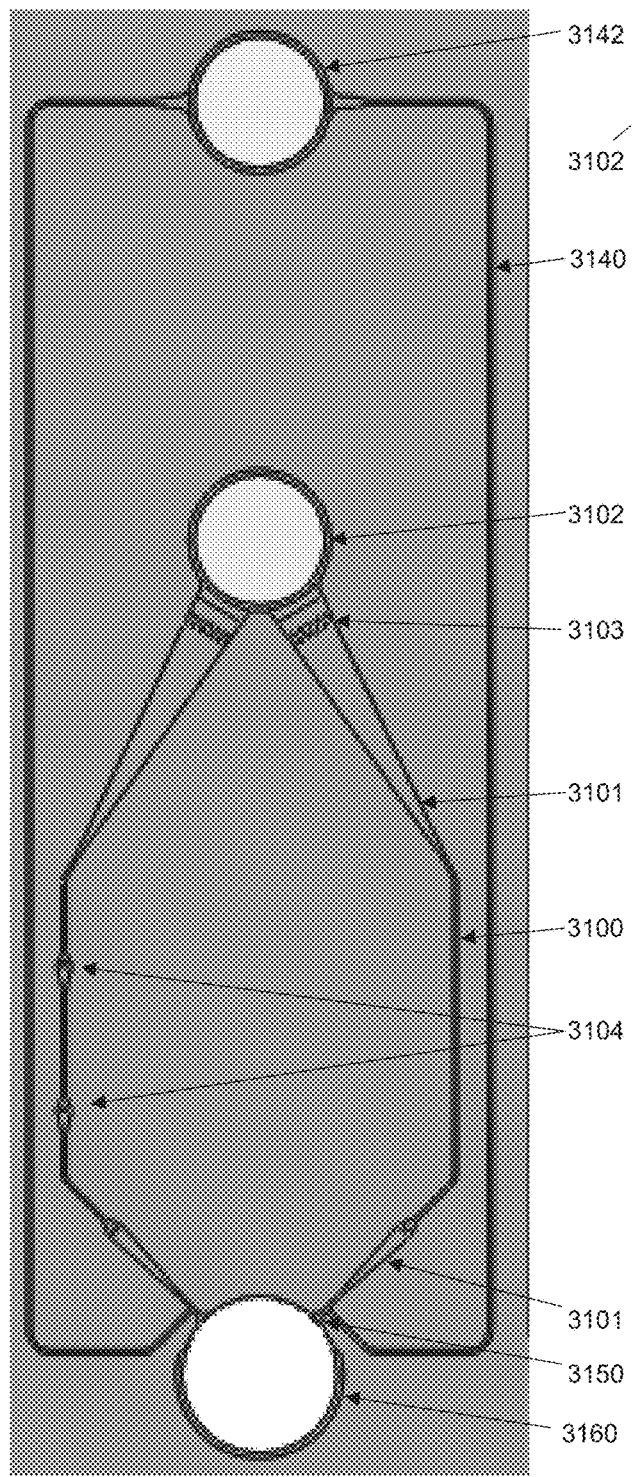
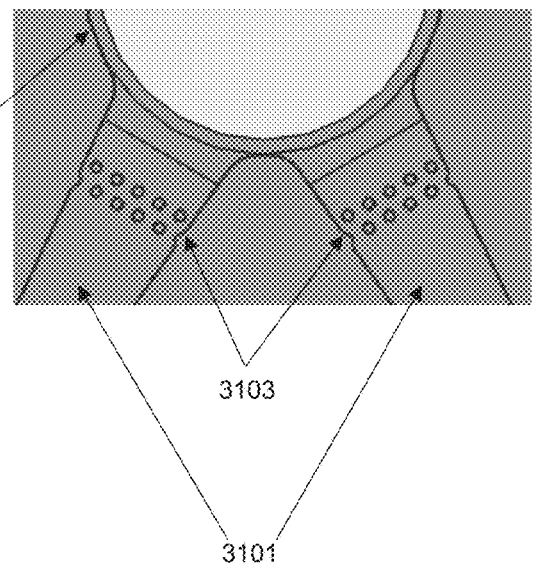

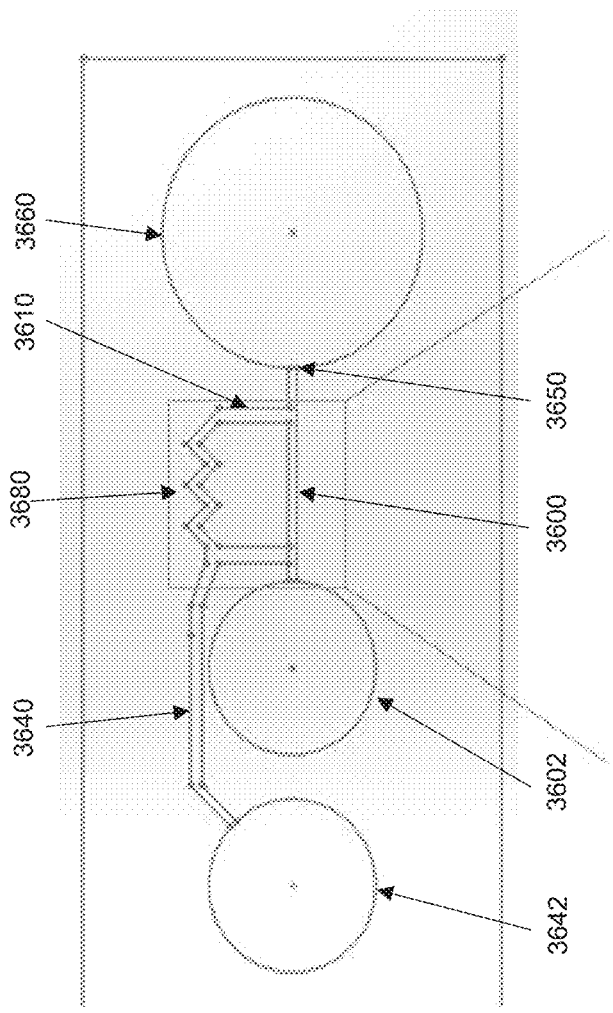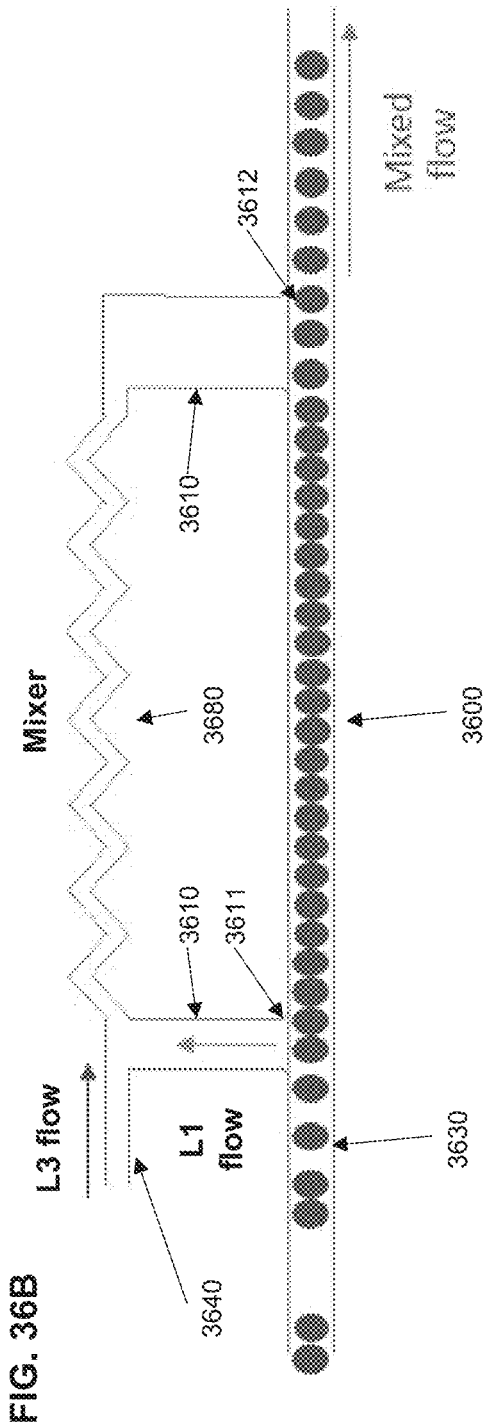
FIG. 36A
FIG. 36B

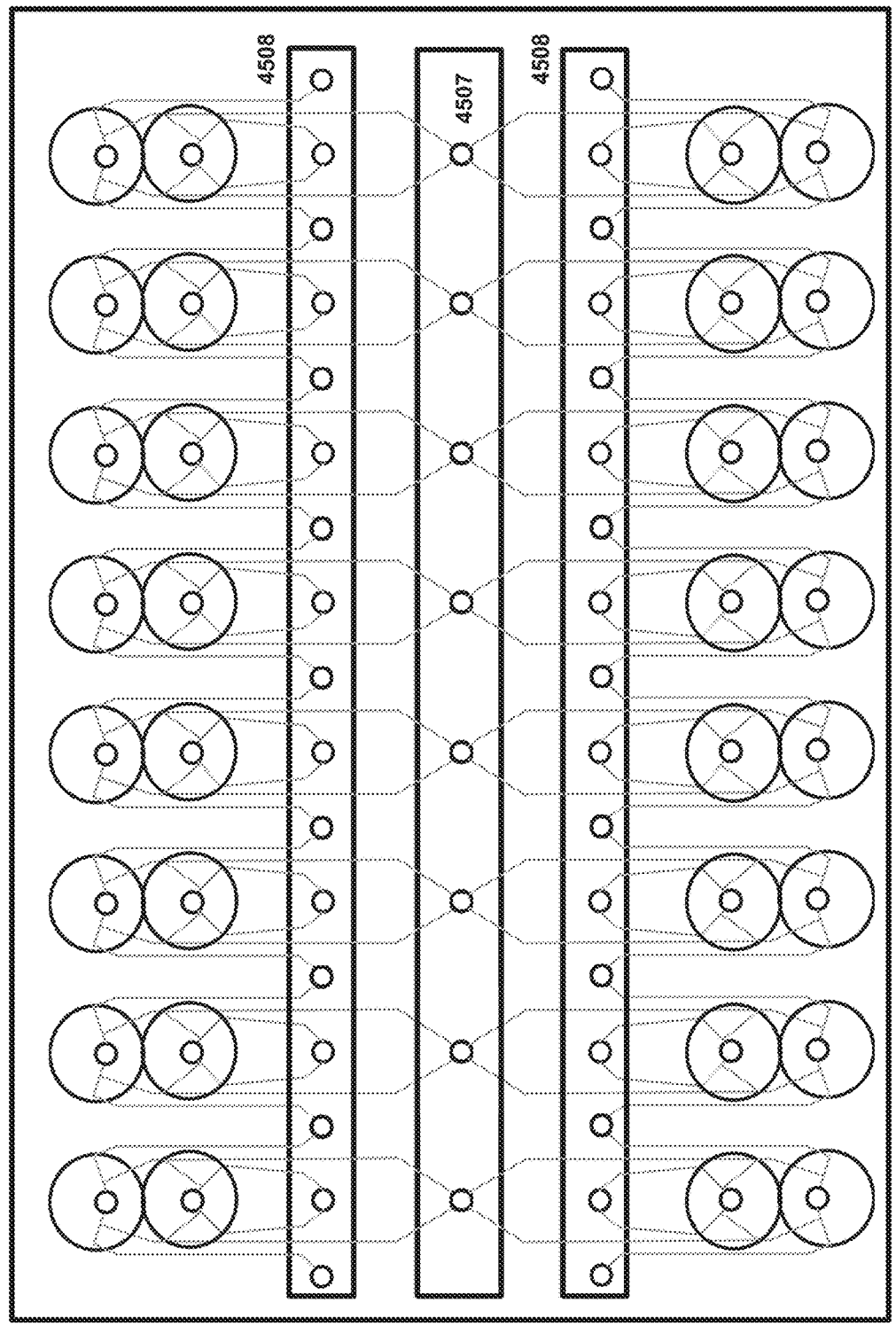
FIG. 48
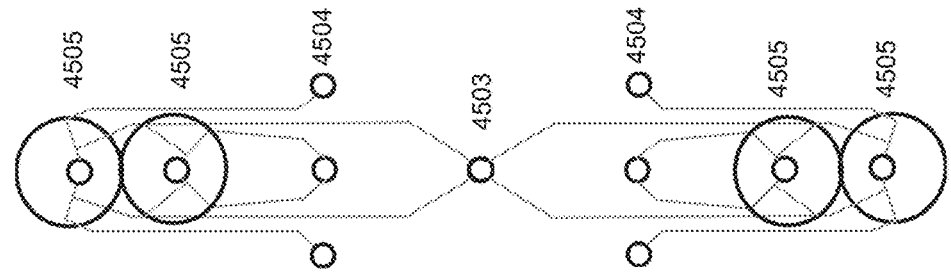

i)                      ii)                    iii)

GB well    Sample well    Production well

DEVICES, SYSTEMS, AND METHODS FOR INCREASING DROPLET FORMATION EFFICIENCY

FIELD OF THE INVENTION

The invention provides devices, systems, and methods for droplet formation. For example, devices, systems, and methods of the invention may be used for forming droplets (e.g., emulsions) containing particles (e.g., droplets containing single particles) or for mixing liquids, e.g., prior to droplet formation.

BACKGROUND OF THE INVENTION

Many biomedical applications rely on high-throughput assays of samples combined with one or more reagents in droplets. For example, in both research and clinical applications, high-throughput genetic tests using target-specific reagents are able to provide information about samples in drug discovery, biomarker discovery, and clinical diagnostics, among others.

Improved devices, systems, and methods for producing and collecting droplets would be beneficial.

SUMMARY OF THE INVENTION

In one aspect, the invention provides a device for producing droplets including a) a first channel having a first depth, a first width, a first proximal end, and a first distal end; b) a droplet formation region in fluid communication with the first channel; and c) a collection reservoir in fluid communication with the droplet formation region and configured to collect droplets formed in the droplet formation region, wherein the collection reservoir includes a side wall canted at an angle less than 90°, e.g., between 89.5° and 4°, e.g., between 85° and 5°, wherein the first channel and droplet formation region are configured to produce droplets of the first liquid in the second liquid. In certain embodiments, the side wall is canted at about a 45° angle. In certain embodiments, the side wall is canted at an angle between 89.5° and 4°, e.g., 85° and 5° for a vertical expanse for between 1 and 20 mm. The device may further include a second channel having a second depth, a second width, a second proximal end, and a second distal end, wherein the second channel intersects the first channel between the first proximal and first distal ends. In certain embodiments, the droplet formation region includes a shelf region having a third depth, a third width, at least one inlet, and at least one outlet, wherein the third width is greater than the first width to allow the first liquid to expand in at least one dimension. In certain embodiments, the droplet formation region further includes a step region having a fourth depth greater than the first depth. In certain embodiments, the device is configured to produce droplets that are substantially stationary in the collection reservoir. In certain embodiments, the device further includes a first reservoir in fluid communication with the first proximal end. In certain embodiments, the device further includes a second reservoir in fluid communication with the second proximal end. In certain embodiments, the collection reservoir includes a first sidewall section canted at an angle between 89.5° and 4°, e.g., between 85° and 5° and a second sidewall section canted at a different angle between 89.5° and 4°, e.g., between 85° and 5°.

In one aspect, the invention provides a method of producing droplets by a) providing a device including i) a first channel having a first depth, a first width, a first proximal end, and a first distal end; ii) a droplet formation region in fluid communication with the first channel; and iii) a collection reservoir configured to collect droplets formed in the droplet formation region, wherein the collection reservoir includes a side wall canted at an angle less than 90°, e.g., between 89.5° and 4°, e.g., between 85° and 5°; wherein the collection reservoir includes the second liquid; and wherein the first liquid is immiscible with the second liquid; b) allowing the first liquid to flow from the first channel to the droplet formation region to produce droplets of the first liquid in the second liquid; c) collecting the droplets in the collection reservoir; and d) removing the droplets from the collection reservoir. In certain embodiments, the side wall is canted at about a 45° angle. In certain embodiments, the side wall is canted at an angle between 89.5° and 4°, e.g., between 85° and 5° for a vertical expanse for between 1 and 20 mm. In certain embodiments, the removal of droplets includes use of a pipette. In certain embodiments, the device further includes a second channel having a second depth, a second width, a second proximal end, and a second distal end, wherein the second channel intersects the first channel between the first proximal and first distal ends. In certain embodiments, the droplet formation region includes a shelf region having a third depth, a third width, at least one inlet, and at least one outlet, wherein the third width is greater than the first width. In certain embodiments, the droplet formation region further includes a step region having a fourth depth that is greater than the first depth. In certain embodiments, the droplets are substantially stationary in the collection reservoir. In certain embodiments, the first liquid includes particles. In certain embodiments, the collection reservoir includes a first sidewall section canted at an angle between 89.5° and 4°, e.g., between 85° and 5° and a second sidewall section canted at a different angle between 89.5° and 4°, e.g., between 85° and 5°.

In one aspect, the invention provides system for producing droplets including a) a device including i) first channel having a first depth, a first width, a first proximal end, and a first distal end; ii) a droplet formation region in fluid communication with the first channel; and iii) a collection reservoir configured to collect droplets formed in the droplet formation region, wherein the collection reservoir includes a side wall canted at an angle less than 90°, e.g., between 89.5° and 4°, e.g., between 85° and 5°; wherein the collection reservoir includes the second liquid; and wherein the first liquid is substantially immiscible with the second liquid; and b) particles in the first channel and/or droplets in the collection reservoir. In certain embodiments, the side wall is canted at about a 45° angle. In certain embodiments, the side wall is canted at an angle between 89.5° and 4°, e.g., between 85° and 5° for a vertical distance of between 1 and 20 mm. In certain embodiments, the device further includes a second channel having a second depth, a second width, a second proximal end, and a second distal end, wherein the second channel intersects the first channel between the first proximal and first distal ends. In certain embodiments, the droplet formation region includes a shelf region having a third depth, a third width, at least one inlet, and at least one outlet, wherein the third width is greater than the first width. In certain embodiments, the droplet formation region further includes a step region having a fourth depth that is greater than the first depth. In certain embodiments, the first liquid includes particles. In certain embodiments, the device further includes a first reservoir in fluid communication with the first proximal end. In certain embodiments, the device further includes a second reservoir in fluid communication with the second proximal end. In certain embodiments, the collection reservoir includes a first sidewall section canted at an angle between 89.5° and 4°, e.g., between 85° and 5° and a second sidewall section canted at a different angle between 89.5° and 4°, e.g., between 85° and 5°.

In one aspect, the invention provides a device for producing droplets including a) a first reservoir in fluid communication with a first channel having a first depth, a first width, a first proximal end, and a first distal end, wherein the first reservoir comprises a side wall canted at an angle between 89.5° and 4°; b) a droplet formation region in fluid communication with the first channel; and c) a collection reservoir in fluid communication with the droplet formation region and configured to collect droplets formed in the droplet formation region, wherein the first channel and droplet formation region are configured to produce droplets of a first liquid in a second liquid. In some embodiments, the side wall is canted at about a 45° angle. In certain embodiments, the side wall is canted at an angle between 89.5° and 4° for a vertical expanse for between 1 and 20 mm. The device may further include a second reservoir in fluid communication with a second channel having a second depth, a second width, a second proximal end, and a second distal end, wherein the second channel intersects the first channel between the first proximal and first distal ends, wherein the second reservoir comprises a side wall canted at an angle between 89.5° and 4°. In certain embodiments, the droplet formation region includes a shelf region having a third depth, a third width, at least one inlet, and at least one outlet, wherein the third width is greater than the first width to allow the first liquid to expand in at least one dimension. In certain embodiments, the droplet formation region includes a step region having a fourth depth greater than the first depth. In some embodiments, the device is configured to produce droplets that are substantially stationary in the collection reservoir. In certain embodiments, the device may further include a first reservoir in fluid communication with the first proximal end. In certain embodiments, the device may further include a second reservoir in fluid communication with the second proximal end. In certain embodiments, the first reservoir comprises a first sidewall section canted at an angle between 89.5° and 4° and a second sidewall section canted at a different angle between 89.5° and 4°. In certain embodiments, the second reservoir comprises a first sidewall section canted at an angle between 89.5° and 4° and a second sidewall section canted at a different angle between 89.5° and 4°.

In one aspect, the invention provides a method of for producing droplets by a) providing any device of any one of the preceding aspects; wherein droplet formation region includes a second liquid; and b) allowing a first liquid to flow from the first channel to the droplet formation region to produce droplets of the first liquid in the second liquid.

In one aspect, the invention provides a system for producing droplets including a) any device of any one of the preceding aspects; and b) particles in the first channel or first reservoir and/or droplets in the collection reservoir.

In one aspect, the invention provides a device for producing droplets, including a) a sample inlet; b) first, second, and third sample channels, each of which is in fluid communication with the sample inlet; c) first and second reagent inlets; d) first, second, and third reagent channels; wherein the first and second reagent channels are in fluid communication with the first reagent inlet, the third reagent channel is in fluid communication with the second reagent inlet; the first sample channel and the first reagent channel intersect at a first intersection, the second sample channel and the second reagent channel intersect at a second intersection, and the third sample channel and the third reagent channel intersect at a third intersection; e) first, second, and third droplet formation regions; and f) first and second collection reservoirs. The first droplet formation region is fluidically disposed between the first intersection and the first collection reservoir, the second droplet formation region is fluidically disposed between the second intersection and the first collection reservoir, and the third droplet formation region is fluidically disposed between the third intersection and the second collection reservoir.

In certain embodiments, the device further includes i) a fourth sample channel in fluid communication with the sample inlet; ii) a fourth reagent channel in fluid communication with the second reagent inlet, and iii) a fourth droplet formation region, wherein the fourth sample channel and fourth reagent channel intersect at a fourth intersection, and the fourth droplet formation region is fluidically disposed between the fourth intersection and the second collection reservoir. In certain embodiments, the inlets are arranged substantially linearly. In certain embodiments, the first, second, and third sample channels are co-planar. In certain embodiments, the first, second, and third reagent channels are co-planar. In certain embodiments, the length of the first reagent channel is at least 85% the length of the second reagent channel. In other embodiments, the length of the first sample channel is at least 85% the length of the second sample channel. In some embodiments, the length of the third reagent channel is at least 85% the length of the fourth reagent channel. In certain embodiments, the length of the fourth reagent channel is at least 85% the length of the fourth sample channel. In certain embodiments, the device includes a plurality of reagent inlets, first and second sample inlets, first and second collection reservoirs, first, second, third, and fourth sample channels, first, second, third, and fourth reagent channels, first, second, third, and fourth intersections, and first, second, third, and fourth droplet formation regions. In other embodiments, a) at least two of the plurality of reagent inlets are in fluid communication with each other via a connecting channel; or b) a sample channel in fluid communication with one of the plurality of sample inlets and one of the plurality of collection reservoirs intersects with a sample channel in fluid communication with a separate one of the plurality of sample inlets and a separate one of the plurality of collection reservoirs. In certain embodiments, at least one of the droplet formation regions includes a shelf that allows a liquid to expand in one dimension and a step that allows the liquid to expand in an orthogonal dimension.

In certain embodiments, the device further includes one or more troughs, wherein the one or more troughs connect the plurality of sample inlets, the plurality of first reagent inlets, and/or the plurality of second reagent inlets.

In some embodiments, the device further includes g) fifth, sixth, and seventh sample channels, each of which is in fluid communication with the sample inlet; h) third and fourth reagent inlets; j) fifth, sixth, and seventh reagent channels, wherein the fifth and sixth reagent channels are in fluid communication with the third reagent inlet; the seventh reagent channel is in fluid communication with the fourth reagent inlet; the fifth sample channel and the fifth reagent channel intersect at a fifth intersection, the sixth sample channel and the sixth reagent channel intersect at a sixth intersection, and the seventh sample channel and the seventh reagent channel intersect at a seventh intersection; k) fifth, sixth, and seventh droplet formation regions; and l) third and fourth collection reservoirs. The fifth droplet formation region is fluidically disposed between the fifth intersection and the third collection reservoir, the sixth droplet formation region is fluidically disposed between the sixth intersection and the third collection reservoir, and the seventh droplet formation region is fluidically disposed between the seventh intersection and the fourth collection reservoir.

In certain embodiments, the device further includes iii) an eighth sample channel in fluid communication with the sample inlet, iv) an eighth reagent channel in fluid communication with the third reagent inlet, and v) an eighth droplet formation region, wherein the eighth sample channel and the eighth reagent channel intersect at an eighth intersection, and the eighth droplet formation region is fluidically disposed between the eighth intersection and the fourth collection reservoir. In certain embodiments, the inlets are arranged substantially linearly. In certain embodiments the fifth, sixth, and seventh sample channels are co-planar. In certain embodiments, the fifth, sixth, and seventh reagent channels are co-planar. In certain embodiments, at least one of the droplet formation regions includes a shelf that allows a liquid to expand in one dimension and a step that allows the liquid to expand in an orthogonal dimension. In some embodiments, the first, second, third, and fourth sample channels, the first, second, and third reagent inlets, and the first, second, third, and fourth reagent channels are on one side of the sample inlets while the fifth, sixth, seventh, and eighth sample channels, the fourth, fifth, and sixth reagent inlets, and the fifth, sixth, seventh, and eighth reagent channels are on the opposite side of the first and second sample inlets.

In one aspect, the invention provides a method for producing droplets by a) providing a device that includes i) a sample inlet; ii) first, second, and third sample channels, each of which is in fluid communication with the sample inlet; iii) first and second reagent inlets; iv) first, second, and third reagent channels, wherein the first and second reagent channels are in fluid communication with the first reagent inlet; the third reagent channel is in fluid communication with the second reagent inlet; the first sample channel and the first reagent channel intersect at a first intersection, the second sample channel and the second reagent channel intersect at a second intersection, and the third sample channel and the third reagent channel intersect at a third intersection; v) first, second, and third droplet formation regions each including a second liquid; and vi) first and second collection reservoirs, wherein the first droplet formation region is fluidically disposed between the first intersection and the first collection reservoir, the second droplet formation region is fluidically disposed between the second intersection and the first collection reservoir, and the third droplet formation region is fluidically disposed between the third intersection and the second collection reservoir; and b) allowing a first liquid to flow from the sample inlet via the first, second, and third sample channels to the first, second, and third intersections, and allowing a third liquid to flow from the first reagent inlet via the first and second reagent channels, and allowing the third liquid to flow from the second reagent inlet via the third reagent channel to the first, second, and third intersections, wherein the first liquid and third liquid combine at the first, second, and third intersections and produce droplets in the second liquid at the first, second, and third droplet formation regions.

In some embodiments, the device further includes i) a fourth sample channel in fluid communication with the sample inlet; ii) a fourth reagent channel in fluid communication with the second reagent inlet, and iii) a fourth droplet formation region, wherein the fourth sample channel and fourth reagent channel intersect at a fourth intersection, and the fourth droplet formation region is fluidically disposed between the fourth intersection and the second collection reservoir, the method further including allowing the first liquid to flow from the sample inlet via the fourth sample channel to the fourth intersection, and allowing the third liquid to flow from the second reagent inlet via the fourth reagent channel to the fourth intersection, wherein the first liquid and the third liquid combine at the fourth intersection and produce droplets in the second liquid at the fourth droplet formation region.

In one aspect, the invention provides a system for producing droplets. The system includes a) a device including i) a sample inlet; ii) first, second, and third sample channels, each of which is in fluid communication with the sample inlet; iii) first and second reagent inlets; iv) first, second, and third reagent channels, wherein the first and second reagent channels are in fluid communication with the first reagent inlet; the third reagent channel is in fluid communication with the second reagent inlet; the first sample channel and the first reagent channel intersect at a first intersection, the second sample channel and the second reagent channel intersect at a second intersection, and the third sample channel and the third reagent channel intersect at a third intersection; v) first, second, and third droplet formation regions; and vi) first and second collection reservoirs, wherein the first droplet formation region is fluidically disposed between the first intersection and the first collection reservoir, the second droplet formation region is fluidically disposed between the second intersection and the first collection reservoir, and the third droplet formation region is fluidically disposed between the third intersection and the second collection reservoir; and b) particles in the sample inlet, first and/or second reagent inlet, and/or droplets in the first and/or second collection reservoir.

In another embodiment, the device of the system further includes i) a fourth sample channel in fluid communication with the sample inlet; ii) a fourth reagent channel in fluid communication with the second reagent inlet, and iii) a fourth droplet formation region, wherein the fourth sample channel and fourth reagent channel intersect at a fourth intersection, and the fourth droplet formation region is fluidically disposed between the fourth intersection and the second collection reservoir.

In certain embodiments, the inlets are arranged substantially linearly. In some embodiments the first, second, and third sample channels are co-planar. In some embodiments the first, second, and third reagent channels are co-planar. In some embodiments the length of the first reagent channel is at least 85% of the length of the second reagent channel. In some embodiments, the length of the third reagent channel is at least 85% of the length of the fourth reagent channel.

In another embodiment, the system features a device that includes a plurality of reagent inlets, sample inlets, first and second collection reservoirs, first, second, third, and fourth sample channels, first, second, third, and fourth reagent channels, first, second, third, and fourth intersections, and first, second, third, and fourth droplet formation regions. In certain embodiments, i) at least two of the plurality of reagent inlets are in fluid communication with each other via a connecting channel; or ii) a sample channel in fluid communication with one of the plurality of sample inlets and one of the plurality of collection reservoirs intersects with a sample channel in fluid communication with a separate one of the plurality of sample inlets and a separate one of the plurality of collection reservoirs. In some embodiments of the system, at least one of the droplet formation regions includes a shelf that allows a liquid to expand in one dimension and a step that allows the liquid to expand in an orthogonal dimension. In another embodiment, the system further includes one or more troughs, wherein the one or more troughs connects the plurality of sample inlets, the plurality of first reagent inlets, and/or the plurality of second reagent inlets.

In one aspect, the invention provides a device for producing droplets, the device including a) first and second sample inlets; b) first, second, and third sample channels, wherein the first and second sample channels are in fluid communication with the first sample inlet, and the third sample channel is in fluid communication with the second sample inlet; c) first, second, and third reagent inlets; d) first, second, and third reagent channels, wherein the first reagent channel is in fluid communication with the first reagent inlet; the second reagent channel is in fluid communication with the second reagent inlet; and the third reagent channel is in fluid communication with the third reagent inlet, the first sample channel and the first reagent channel intersect at a first intersection, the second sample channel and the second reagent channel intersect at a second intersection, and the third sample channel and the third reagent channel intersect at a third intersection; e) first, second, and third droplet formation regions; and f) one or more collection reservoirs. The first droplet formation region is fluidically disposed between the first intersection and the one or more collection reservoirs, the second droplet formation region is fluidically disposed between the second intersection and the one or more collection reservoirs, and the third droplet formation region is fluidically disposed between the third intersection and the one or more collection reservoirs.

In certain embodiments, the device further includes i) a fourth sample channel in fluid communication with the second sample inlet; ii) a fourth reagent inlet; iii) a fourth reagent channel in fluid communication with the fourth reagent inlet; and iv) a fourth droplet formation region, wherein the fourth sample channel and the fourth reagent channel intersect at a fourth intersection, and the fourth droplet formation region is fluidically disposed between the fourth intersection and the one or more collection reservoirs. In certain embodiments, the device further includes i) a fifth reagent channel in fluid communication with the first reagent inlet and ii) a fifth droplet formation region, wherein the second sample channel splits into first and second branches, wherein the first branch leads to the second intersection and the second branch intersects with the fifth reagent channel to form a fifth intersection, wherein the fifth droplet formation region is fluidically disposed between the fifth intersection and the one or more collection reservoirs. In certain embodiments, the device further includes i) a fifth reagent channel in fluid communication with the first reagent inlet; ii) a fifth sample channel; and iii) a fifth droplet formation region, wherein the fifth sample channel is in fluid communication with the first sample inlet and intersects with the fifth reagent channel to form a fifth intersection, wherein the fifth droplet formation region is fluidically disposed between the fifth intersection and the one or more collection reservoirs. In certain embodiments, the one or more collection reservoirs includes first and second reservoirs, wherein the first droplet formation region is fluidically disposed between the first intersection and the first reservoir and the second droplet formation region is fluidically disposed between the second intersection and the second reservoir. In certain embodiments, the one or more collection reservoirs includes a first reservoir, wherein the first droplet formation region is fluidically disposed between the first intersection and the first reservoir and the second droplet formation region is fluidi-cally disposed between the second intersection and the second reservoir. In certain embodiments, the device further includes i) a sixth reagent channel in fluid communication with the second reagent inlet and ii) a sixth droplet formation region, wherein the third sample channel splits into first and second branches, wherein the first branch leads to the third intersection and the second branch intersects with the sixth reagent channel to form a sixth intersection, wherein the sixth droplet formation region is fluidically disposed between the sixth intersection and the one or more collection reservoirs. In certain embodiments, the device further includes i) a sixth reagent channel in fluid communication with the second reagent inlet; ii) a sixth sample channel; and ii) a sixth droplet formation region, wherein the sixth sample channel is in fluid communication with the second sample inlet and intersects with the sixth reagent channel to form a sixth intersection, wherein the sixth droplet formation region is fluidically disposed between the sixth intersection and the one or more collection reservoirs.

In certain embodiments, the device further includes i) a seventh reagent channel in fluid communication with the third reagent inlet and ii) a seventh droplet formation region, wherein the fourth sample channel splits into first and second branches, wherein the first branch leads to the fourth intersection and the second branch intersects with the seventh reagent channel to form a seventh intersection, wherein the seventh droplet formation region is fluidically disposed between the seventh intersection and the one or more collection reservoirs.

In certain embodiments, the device further includes i) a seventh reagent channel in fluid communication with the third reagent inlet, ii) a seventh sample channel, and iii) a seventh droplet formation region, wherein the seventh sample channel is in fluid communication with the second sample inlet and intersects with the seventh reagent channel to form a seventh intersection, wherein the seventh droplet formation region is fluidically disposed between the seventh intersection and the one or more collection reservoirs.

In certain embodiments, the device further includes i) a fifth reagent inlet, ii) an eighth reagent channel in fluid communication with the fifth reagent inlet, and iii) an eighth droplet formation region, wherein the first sample channel splits into first and second branches, wherein the first branch leads to the first intersection and the second branch intersects with the eighth reagent channel to form an eighth intersection, wherein the eighth droplet formation region is fluidically disposed between the eighth intersection and the one or more collection reservoirs.

In certain embodiments, the device further includes i) a fifth reagent inlet, ii) and eighth reagent channel in fluid communication with the fifth reagent inlet, iii) an eighth sample channel, and iv) an eighth droplet formation region, wherein the eighth sample channel is in fluid communication with the first sample inlet and intersects with the eighth reagent channel to form an eighth intersection, wherein the eighth droplet formation region is fluidically disposed between the eighth intersection and the one or more collection reservoirs.

In certain embodiments, the one or more collection reservoirs includes a first and a second collection reservoir, and the first and second collection reservoirs are disposed radially about the first sample inlet. The device further includes i) a sixth reagent inlet, ii) a ninth reagent channel in fluid communication with the sixth reagent inlet; iii) a ninth sample channel; and iv) a ninth droplet formation region, wherein the ninth sample channel is in fluid communication with the first sample inlet and intersects with the ninth reagent channel to form a ninth intersection, wherein the first droplet formation region is fluidically disposed between the first intersection and the first collection reservoir, and wherein the ninth droplet formation region is fluidically disposed between the ninth intersection and the second collection reservoir.

In certain embodiments, the device further includes i) a seventh reagent inlet; ii) a tenth reagent channel in fluid communication with the seventh reagent inlet; iii) a tenth sample channel; and iv) a tenth droplet formation region, wherein the tenth sample channel is in fluid communication with the first sample inlet and intersects with the tenth reagent channel to form a tenth intersection, wherein the tenth droplet formation region is fluidically disposed between the tenth intersection and the one or more collection reservoirs.

In certain embodiments, the one or more collection reservoirs includes a third and a fourth collection reservoir, and the third and fourth collection reservoirs are disposed radially about the second sample inlet. The device further includes i) an eighth reagent inlet; ii) an eleventh reagent channel in fluid communication with the eighth reagent inlet; iii) an eleventh sample channel; and iv) an eleventh droplet formation region, wherein the eleventh sample channel is in fluid communication with the second sample inlet and intersects with the eleventh reagent channel to form an eleventh intersection, wherein the third droplet formation region is fluidically disposed between the third intersection and the third collection reservoir, and wherein the eleventh droplet formation region is fluidically disposed between the eleventh intersection and the fourth collection reservoir.

In certain embodiments, the device further includes i) a ninth reagent inlet; ii) a twelfth reagent channel in fluid communication with the ninth reagent inlet; iii) a twelfth sample channel; and iv) a twelfth droplet formation region, wherein the twelfth sample channel is in fluid communication with the second sample inlet and intersects with the twelfth reagent channel to form a twelfth intersection, wherein the third droplet formation region is fluidically disposed between the third intersection and the third collection reservoir, and wherein the twelfth droplet formation region is fluidically disposed between the twelfth intersection and the fourth collection reservoirs.

In certain embodiments, the device further includes i) a thirteenth reagent channel in fluid communication with the sixth reagent inlet, and ii) a thirteenth droplet formation region, wherein the tenth sample channel splits into first and second branches, wherein the first branch leads to the tenth intersection and the second branch intersects with the thirteenth reagent channel to form a thirteenth intersection, wherein the thirteenth droplet formation region is fluidically disposed between the thirteenth intersection and the one or more collection reservoirs.

In certain embodiments, the device further includes i) a thirteenth reagent channel in fluid communication with the sixth reagent inlet; ii) a thirteenth sample channel; and iii) a thirteenth droplet formation region, wherein the thirteenth sample channel is in fluid communication with the first sample inlet and intersects with the thirteenth reagent channel to form a thirteenth intersection, wherein the thirteenth droplet formation region is fluidically disposed between the thirteenth intersection and the one or more collection reservoirs.

In certain embodiments, the device further includes i) a fourteenth reagent channel in fluid communication with the seventh reagent inlet, and ii) a fourteenth droplet formation region, wherein the eleventh sample channel splits into first and second branches, wherein the first branch leads to the eleventh intersection and the second branch intersects with the fourteenth reagent channel to form a fourteenth intersection, wherein the fourteenth droplet formation region is fluidically disposed between the fourteenth intersection and the one or more collection reservoirs.

In certain embodiments, the device further includes i) a fourteenth reagent channel in fluid communication with the seventh reagent inlet; ii) a fourteenth sample channel; and iii) a fourteenth droplet formation region, wherein the fourteenth sample channel is in fluid communication with the second sample inlet and intersects with the fourteenth reagent channel to form a fourteenth intersection, wherein the fourteenth droplet formation region is fluidically disposed between the fourteenth intersection and the one or more collection reservoirs.

In certain embodiments, the device further includes i) a fifteenth reagent channel in fluid communication with the eighth reagent inlet, and ii) a fifteenth droplet formation region, wherein the twelfth sample channel splits into first and second branches, wherein the first branch leads to the twelfth intersection and the second branch intersects with the fifteenth reagent channel to form a fifteenth intersection, wherein the fifteenth droplet formation region is fluidically disposed between the fifteenth intersection and the one or more collection reservoirs.

In certain embodiments, the device further includes i) a fifteenth reagent channel in fluid communication with the eighth reagent inlet; ii) a fifteenth sample channel; and iii) a fifteenth droplet formation region, wherein the fifteenth sample channel is in fluid communication with the second sample inlet and intersects with the fifteenth reagent channel to form a fifteenth intersection, wherein the fifteenth droplet formation region is fluidically disposed between the fifteenth intersection and the one or more collection reservoirs.

In certain embodiments, the device further includes i) a sixteenth reagent channel in fluid communication with the tenth reagent inlet, and ii) a sixteenth droplet formation region, wherein the ninth sample channel splits into first and second branches, wherein the first branch leads to the ninth intersection and the second branch intersects with the sixteenth reagent channel to form a sixteenth intersection, wherein the sixteenth droplet formation region is fluidically disposed between the sixteenth intersection and the one or more collection reservoirs.

In certain embodiments, the device further includes i) a tenth reagent inlet, ii) a sixteenth reagent channel in fluid communication with the tenth reagent inlet; iii) a sixteenth sample channel; and iv) a sixteenth droplet formation region, wherein the sixteenth sample channel is in fluid communication with the first sample inlet and intersects with the sixteenth reagent channel to form a sixteenth intersection, wherein the sixteenth droplet formation region is fluidically disposed between the sixteenth intersection and the one or more collection reservoirs.

In certain embodiments, at least one of the droplet formation regions includes (e.g., all of the droplet formation regions) a shelf that allows a liquid to expand in one dimension and a step that allows the liquid to expand in an orthogonal dimension. In certain embodiments, the device further includes a first trough connecting the first and second sample inlets. In certain embodiments, the device further includes a second trough connecting at least two of the first, second, and third reagent inlets. In certain embodiments, the second trough connects the first, second, and third reagent inlets. In some embodiments, the first and second sample inlets are surrounded by at least one common wall and are separated by a dividing wall, wherein at least a portion of the dividing wall is shorter than the one common wall.

In certain embodiments, the invention provides a method for producing droplets. The method includes the steps of a) providing any device of the preceding aspect, wherein the first, second, and third droplet formation regions include the second liquid; and b) allowing the first liquid to flow from the first sample inlet via the first and second sample channels to the first and second intersections, and allowing a third liquid to flow from the first and second reagent inlets via the first and second reagent channels to the first and second intersections, wherein the first liquid and the third liquid combine at the first and second intersections and produce droplets in the second liquid at the first and second droplet formation regions, and allowing the first liquid to flow from the second sample inlet via the third sample channel to the third intersection, and allowing the third liquid to flow from the third reagent inlet via the third reagent channel to the third intersection, wherein the first liquid and the third liquid combine at the third intersection and produce droplets in the second liquid at the third droplet formation regions.

In another embodiment, the invention provides a method for producing droplets. The method includes the steps of a) providing any device of the preceding aspect, wherein the first through sixteenth droplet formation regions include the second liquid; and b) allowing the first liquid to flow from the first through fourth sample inlets via the first through sixteenth sample channels to the first through sixteenth intersections, and allowing a third liquid to flow from the first through tenth reagent inlets via the first through sixteenth reagent channels wherein the first liquid and the third liquid combine at the first through sixteenth intersections and produce droplets in the second liquid at the first through sixteenth droplet formation regions.

In another embodiment, the invention provides a system for producing droplets of a first liquid in a second liquid, the system includes a) any device of the preceding aspect; and b) particles in the sample inlets and/or the first and second reagent inlets, and/or droplets in the one or more collection reservoirs.

In one aspect, the invention provides a device for producing droplets, the device including a) one or more sample inlets; b) one or more sample channels in fluid communication with the one or more sample inlets; c) one or more reagent inlets; d) one or more reagent channels, wherein the one or more reagent channels intersect with the one or more sample inlets to form one or more intersections; e) one or more droplet formation regions; f) one or more collection reservoirs; and g) one or more troughs. The one or more droplet formation regions are fluidically disposed between the one or more intersections and the one or more collection reservoirs, provided that the one or more sample inlets includes at least two sample inlets or the one or more reagent inlets includes at least two reagent inlets, wherein one of the one or more troughs connects the at least two sample inlets or the at least two reagent inlets.

In certain embodiments, the one or more sample inlets include the at least two inlets. In certain embodiments, the one or more reagent inlets include the at least two inlets. In certain embodiments, the one or more troughs include a single trough that connects the at least two sample inlets or the at least two reagent inlets. In certain embodiments, the one or more troughs include first and second troughs, wherein the first trough connects the at least two sample inlets and the second trough connects the at least two reagent inlets. In certain embodiments, at least one of the droplet formation regions (e.g., all of the droplet formation regions) includes a shelf that allows a liquid to expand in one dimension and a step that allows the liquid to expand in an orthogonal dimension.

In another embodiment, the invention provides a method for producing droplets. The method includes the steps of a) providing any device of the preceding aspect, wherein the one or more droplet formation regions include a second liquid; and b) allowing a first liquid to flow from the one or more sample inlets via the one or more sample channels to the one or more intersections, and allowing a third liquid to flow from the one or more reagent inlets via the one or more reagent channels to the one or more intersections, wherein the first and third liquids combine at the one or more intersections and produce droplets in the second liquid at the one or more droplet formation regions.

In another embodiment, the invention provides a system for producing droplets. The system includes a) a device of the preceding aspect; and b) particles in one of the one or more reagent inlets or one of the one or more sample inlets, and/or droplets in one of the one or more collection reservoirs.

In one aspect, the invention provides a device for producing droplets. The device includes a plurality of flow paths. Each flow path includes a) one or more sample inlets; b) one or more sample channels in fluid communication with the one or more sample inlets; c) one or more reagent inlets; d) one or more reagent channels in fluid communication with the one or more reagent inlets, and wherein the one or more reagent channels intersect with the one or more sample channels to form one or more intersections; e) one or more droplet formation regions; and f) one or more collection reservoirs; wherein the one or more droplet formation regions are fluidically disposed between the one or more intersections and the one or more collection reservoirs, provided that the one or more sample inlets includes at least two sample inlets or the one or more reagent inlets include at least two reagents inlets. The maximum cross sectional dimension of the sample channels is 250 µm, and/or the maximum cross-sectional dimension of the reagent channels is 250 µm, and the number of droplet formation regions is at least 4 per collection reservoir, wherein the pitch between adjacent flow paths is less than 20 mm, wherein the one or more sample channels and reagent channels are co-planar.

In certain embodiments, the number of droplet formation regions is at least 8 per collection reservoir. In some embodiments, the one or more droplet formation regions include a shelf that allows a liquid to expand in one dimension and a step that allows the liquid to expand in an orthogonal dimension. In other embodiments, the device further includes one or more troughs, wherein the one or more sample inlets include at least two sample inlets, or the one or more reagent inlets include at least two reagent inlets, and one of the one or more troughs connects the at least two sample inlets or the at least two reagent inlets.

In another embodiment, the invention provides a method of producing droplets. The method includes the steps of a) providing any device of the preceding aspects, wherein the droplet formation regions include a second liquid; and b) allowing a first liquid to flow from the one or more sample inlets via the one or more sample channels to the one or more intersections, and allowing a third liquid to flow from the one or more reagent inlets via the one or more reagent channels to the one or more intersections, wherein the first liquid and the third liquid combine at the one or more intersections and produce droplets in the second liquid at the one or more droplet formation regions.

In another embodiment, the invention provides a system for producing droplets of, including a) any device of the preceding aspects; and b) particles in the one or more sample or reagent inlets and/or droplets in the one or more collection reservoirs.

In one aspect, the invention provides a device for producing droplets, the device includes a) a common inlet; b) two or more secondary inlets; c) two or more tertiary inlets; d) two or more sets of channels, wherein each set intersects to form an intersection and renders one of the secondary inlets and one of the tertiary inlets in fluid communication with the common inlet; and e) two or more droplet formation regions, wherein each droplet formation region is fluidically disposed between the common inlet and one of the intersections or fluidically between one of the secondary or tertiary inlets and one of the intersections. In certain embodiments, at least one of the droplet formation regions (e.g., all of the droplet formation regions) includes a shelf that allows a liquid to expand in one dimension and a step that allows the liquid to expand in an orthogonal dimension. In certain embodiments, the common inlet is a collection reservoir and each droplet formation region is fluidically disposed between the common inlet and one of the intersections. In certain embodiments, the secondary or tertiary inlets are collection reservoirs and each droplet formation region is fluidically disposed between one of the secondary or tertiary inlets and one of the intersections.

In another embodiment, the common inlet is a sample inlet, the two or more secondary inlets include first and second reagent inlets, and the two or more tertiary inlets are collection reservoirs. A first of the two or more sets of channels includes a first sample channel in fluid communication with the sample inlet and a first reagent channel in fluid communication with a first reagent inlet, where the first sample channel and first reagent channel intersect to form a first intersection, and a first of the two or more droplet formation regions is fluidically disposed between the first intersection and a first of the collection reservoirs. A second of the two or more sets of channels includes a second sample channel in fluid communication with the sample inlet and a second reagent channel in fluid communication with a second reagent inlet, where the second sample channel and second reagent channel intersect at a second intersection, and a second of the two or more droplet formation regions is fluidically disposed between the second intersection and a second of the collection reservoirs.

In certain embodiments, the first sample channel, first reagent inlet, first reagent channel, first intersection, first droplet formation region, and first collection reservoir define a flow path, and the device further includes a plurality of flow paths disposed radially around and in fluid communication with the sample inlet. In some embodiments, the device further includes a third reagent channel in fluid communication with the second reagent inlet and a fourth reagent channel in fluid communication with the first reagent inlet, the first sample channel splits to form two branches, where a first branch leads to the first intersection and a second branch intersects with the third reagent channel to form a third intersection, and a third droplet formation region is fluidically disposed between the third intersection and the second collection reservoir. In some embodiments, the sample inlet, first sample channel, first and second branches, first and second reagent inlets, first, second, third, and fourth reagent channels, first, second, and third intersections, first, second, and third droplet formation regions, and first and second collection reservoirs define a flow path, and the device further includes a plurality of flow paths disposed radially around and in fluid communication with the sample inlet.

In certain embodiments, the second sample channel of each of the plurality of flow paths splits to form first and second branches, wherein for a given flow path, the first branch leads to the second intersection of the given flow path and the second branch intersects with the fourth reagent channel of an adjacent flow path to form a fourth intersection. A fourth droplet formation region is fluidically disposed between the fourth intersection and the first collection reservoir of the adjacent flow path.

In certain embodiments, the common inlet is a collection reservoir, the two or more secondary inlets include first and second reagent inlets, the two or more tertiary inlets are sample inlets. A first of the two or more sets of channels includes a first sample channel in fluid communication with a first sample inlet and a first reagent channel in fluid communication with a first reagent inlet, the first sample channel and first reagent channel intersect to form a first intersection, and a first of the two or more droplet formation regions is fluidically disposed between the first intersection and the collection reservoir. A second of the two or more sets of channels includes a second sample channel in fluid communication with a second sample inlet and a second reagent channel in fluid communication with a second reagent inlet. The second sample channel and second reagent channel intersect at a second intersection, and a second of the two or more droplet formation regions is fluidically disposed between the second intersection and the collection reservoir.

In some embodiments, the first sample channel, first reagent inlet, first reagent channel, first intersection, first droplet formation, and first sample inlet define a flow path, and the device further includes a plurality of flow paths disposed radially around and in fluid communication with the collection reservoir.

In some embodiments, the device further includes a third reagent channel in fluid communication with the second reagent inlet and a fourth reagent channel in fluid communication with the first reagent inlet, wherein the first sample channel splits to form two branches, wherein a first branch leads to the first intersection and a second branch intersects with the third reagent channel to form a third intersection, wherein a third droplet formation region is fluidically disposed between the third intersection and the collection reservoir.

In some embodiments, the first and second sample inlets, first sample channel, first and second branches, first and second reagent inlets, first, second, third, and fourth reagent channels, first, second, and third intersections, first, second, and third droplet formation regions, and collection reservoir define a flow path, and the device further includes a plurality of flow paths disposed radially around and in fluid communication with the collection reservoir. In some embodiments the second sample channel of each of the plurality of flow paths splits to form first and second branches, wherein for a given flow path, the first branch leads to the second intersection of the given flow path and the second branch intersects with the fourth reagent channel of an adjacent flow path to form a fourth intersection, wherein a fourth droplet formation region is fluidically disposed between the fourth intersection and the first collection reservoir of the adjacent flow path.

In certain embodiments, at least one of the droplet formation regions (e.g., all the droplet formation regions)

includes a shelf that allows a liquid to expand in one dimension and a step that allows the liquid to expand in an orthogonal dimension In another embodiment, the invention provides a method of producing droplets. The method includes the steps of a) providing any device of the preceding aspects, wherein the droplet formation regions include a second liquid, wherein each set includes a sample channel and a reagent channel; and b) allowing a first liquid to flow from the common inlet via the sample channels to the intersections, and allowing a third liquid to flow from the one or more secondary inlets via the one or more reagent channels to the one or more intersections, wherein the first and third liquids combine at the one or more intersections and produce droplets in the second liquid at the one or more droplet formation regions.

In another embodiment, the invention provides a system for producing droplets. The system includes a) any device of the preceding aspects; and b) particles in the common inlet, the secondary inlets, or the tertiary inlets and/or droplets in the common inlet, secondary inlets, or tertiary inlets.

In another embodiment, the invention provides a method for producing droplets. The method includes the steps of a) providing a device of certain embodiments of the aspect, wherein the droplet formation regions include a second liquid, and wherein each set includes a sample and reagent channel; and b) allowing a first liquid to flow from the tertiary inlets via the sample channels to the one or more intersections, and allowing a third liquid to flow from the one or more secondary inlets via the one or more reagent channels to the intersections, wherein the first and third liquids combine at the one or more intersections and produce droplets in the second liquid at the one or more droplet formation regions In another embodiment, the invention provides a system for producing droplets. The system includes a) a device of certain embodiments of the aspect; and b) particles in the common inlet, the secondary inlets, or the tertiary inlets and/or droplets in the common inlet, secondary inlets, or tertiary inlets.

In one aspect, the invention provides a device for producing droplets, the device includes a) a first sample inlet; b) a reagent inlet; c) first and second collection reservoirs; d) first, second, third, and fourth sample channels in fluid communication with the first sample inlet, where the first and second sample channels are in fluid communication with the first collection reservoir; and the third and fourth sample channels are in fluid communication with the second collection reservoir; e) first, second, third, and fourth reagent channels in fluid communication with the reagent inlet, where the first and second reagent channels are in fluid communication with the first collection reservoir; the third and fourth reagent channels are in fluid communication with the second collection reservoir; and the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and f) first, second, third, and fourth droplet formation regions, where the first droplet formation region is fluidically disposed between the first intersection and the first collection reservoir, the second droplet formation region is fluidically disposed between the second intersection and the first collection reservoir, the third droplet formation region is fluidically disposed between the third intersection and the second collection reservoir, and the fourth droplet formation region is fluidically disposed between the fourth intersection and the second collection reservoir.

In certain embodiments, the first sample inlet, the reagent inlet, and the first and second collection reservoirs are arranged substantially linearly. In other embodiments, the first, second, third, and fourth sample channels are co-planar. In another embodiment, the first, second, third, and fourth reagent channels are co-planar.

In some embodiments, at least one of the droplet formation regions (e.g., all the droplet formation regions) includes a shelf that allows a liquid to expand in one dimension and a step that allows the liquid to expand in an orthogonal dimension.

In certain embodiments, the device further includes g) a second sample inlet; h) third and fourth collection reservoirs; i) fifth, sixth, seventh, and eighth sample channels in fluid communication with the second sample inlet, wherein the fifth and sixth sample channels are in fluid communication with the third collection reservoir; and the seventh and eighth sample channels are in fluid communication with the fourth collection reservoir; j) fifth, sixth, seventh, and eighth reagent channels in fluid communication with the reagent inlet, wherein the fifth and sixth reagent channels are in fluid communication with the third collection reservoir; the seventh and eighth reagent channels are in fluid communication with the fourth collection reservoir; and the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and k) fifth, sixth, seventh, and eighth droplet formation regions, wherein the fifth droplet formation region is fluidically disposed between the fifth intersection and the third collection reservoir, the sixth droplet formation region is fluidically disposed between the sixth intersection and the third collection reservoir, the seventh droplet formation region is fluidically disposed between the seventh intersection and the fourth collection reservoir, and the eighth droplet formation region is disposed between the eighth intersection and the fourth collection reservoir.

In some embodiments, the second sample inlet, the reagent inlet, and the third and fourth collection reservoirs are arranged substantially linearly. In other embodiments, the fifth, sixth, seventh, and eighth sample channels are co-planar. In some embodiments, the fifth, sixth, seventh, and eighth reagent channels are co-planar. In another embodiment, at least one of the droplet formation regions (e.g., all the droplet formation regions) includes a shelf that allows a liquid to expand in one dimension and a step that allows the liquid to expand in an orthogonal dimension.

In another embodiment, the device further includes one or more troughs that connect the plurality of reagent inlets, the plurality of first sample inlets, and/or the plurality of second sample inlets.

In one aspect, the invention provides a method for producing droplets. The method includes the steps of a) providing a device including i) a first sample inlet; ii) a reagent inlet; iii) first and second collection reservoirs; iv) first, second, third, and fourth sample channels in fluid communication with the first sample inlet, wherein the first and second sample channels are in fluid communication with the first collection reservoir; and the third and fourth sample channels are in fluid communication with the second collection reservoir; v) first, second, third, and fourth reagent channels in fluid communication with the reagent inlet, wherein the first and second reagent channels are in fluid communication with the first collection reservoir; the third and fourth reagent channels are in fluid communication with the second collection reservoir; and the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and vi) first, second, third, and fourth droplet formation regions each including a second liquid, wherein the first droplet formation region is fluidically disposed between the first intersection and the first collection reservoir, the second droplet formation region is fluidically disposed between the second intersection and the first collection reservoir, the third droplet formation region is fluidically disposed between the third intersection and the second collection reservoir, and the fourth droplet formation region is fluidically disposed between the fourth intersection and the second collection reservoir; and b) allowing a first liquid to flow from the first sample inlet via the first, second, third, and fourth sample channels to the first, second, third, and fourth intersections, and allowing a third liquid to flow from the reagent inlet via the first, second, third, and fourth reagent channels to the first, second, third, and fourth intersections, wherein the first liquid and the third liquid combine at the first, second, third, and fourth intersections and produce droplets in the second liquid at the first, second, third, and fourth droplet formation regions.

In some embodiments, at least one of the droplet formation regions (e.g., all the droplet formation regions) includes a shelf that allows a liquid to expand in one dimension and a step that allows the liquid to expand in an orthogonal dimension.

In certain embodiments, the method further includes a) a device of the aspect which further includes vii) a second sample inlet; viii) third and fourth collection reservoirs; ix) fifth, sixth, seventh, and eighth sample channels in fluid communication with the second sample inlet, wherein the fifth and sixth sample channels are in fluid communication with the third collection reservoir; and the seventh and eighth sample channels are in fluid communication with the fourth collection reservoir; x) fifth, sixth, seventh, and eighth reagent channels in fluid communication with the reagent inlet, wherein the fifth and sixth reagent channels are in fluid communication with the third collection reservoir; the seventh and eighth reagent channels are in fluid communication with the fourth collection reservoir; and the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and xi) fifth, sixth, seventh, and eighth droplet formation regions each including the second liquid, wherein the fifth droplet formation region is fluidically disposed between the fifth intersection and the third collection reservoir, the sixth droplet formation region is fluidically disposed between the sixth intersection and the third collection reservoir, the seventh droplet formation region is fluidically disposed between the seventh intersection and the fourth collection reservoir, and the eighth droplet formation region is disposed between the eighth intersection and the fourth collection reservoir; and b) allowing a first liquid to flow from the second sample inlet via the fifth, sixth, seventh, and eighth sample channels to the fifth, sixth, seventh, and eighth intersections, and allowing a third liquid to flow from the fifth, sixth, seventh, and eighth reagent channels to the fifth, sixth, seventh, and eighth intersections, wherein the first liquid and the third liquid combine at the fifth, sixth, seventh, and eighth intersections and produce droplets in the second liquid at the fifth, sixth, seventh, and eighth droplet formation regions.

In one aspect, the invention provides a system for producing droplets. The system including a) a device including i) a first sample inlet; ii) a reagent inlet; iii) first and second collection reservoirs; iv) first, second, third, and fourth sample channels in fluid communication with the first sample inlet, wherein the first and second sample channels are in fluid communication with the first collection reservoir; and the third and fourth sample channels are in fluid communication with the second collection reservoir; v) first, second, third, and fourth reagent channels in fluid communication with the reagent inlet, wherein the first and second reagent channels are in fluid communication with the first collection reservoir; the third and fourth reagent channels are in fluid communication with the second collection reservoir; and the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and vi) first, second, third, and fourth droplet formation regions, wherein the first droplet formation region is fluidically disposed between the first intersection and the first collection reservoir, the second droplet formation region is fluidically disposed between the second intersection and the first collection reservoir, the third droplet formation region is fluidically disposed between the third intersection and the second collection reservoir, and the fourth droplet formation region is fluidically disposed between the fourth intersection and the second collection reservoir; and b) particles in the sample inlet and/or reagent inlet, and/or droplets in the first and/or second collection reservoir.

In some embodiments of the system, the first sample inlet, the reagent inlet, and the first and second collection reservoirs are arranged substantially linearly. In some embodiments, the first, second, third, and fourth sample channels are co-planar. In some embodiments, the first, second, third, and fourth reagent channels are co-planar. In some embodiments of the system, at least one of the droplet formation regions includes a shelf that allows a liquid to expand in one dimension and a step that allows the liquid to expand in an orthogonal dimension.

In certain embodiments, the system further includes vii) a second sample inlet; viii) third and fourth collection reservoirs; ix) fifth, sixth, seventh, and eighth sample channels in fluid communication with the second sample inlet, wherein the fifth and sixth sample channels are in fluid communication with the third collection reservoir; and the seventh and eighth sample channels are in fluid communication with the fourth collection reservoir; x) fifth, sixth, seventh, and eighth reagent channels in fluid communication with the reagent inlet, wherein the fifth and sixth reagent channels are in fluid communication with the third collection reservoir; the seventh and eighth reagent channels are in fluid communication with the fourth collection reservoir; and the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and xi) fifth, sixth, seventh, and eighth droplet formation regions, wherein the fifth droplet formation region is fluidically disposed between the fifth intersection and the third collection reservoir, the sixth droplet formation region is fluidically disposed between the sixth intersection and the third collection reservoir, the seventh droplet formation region is fluidically disposed between the seventh intersection and the fourth collection reservoir, and the eighth droplet formation region is disposed between the eighth intersection and the fourth collection reservoir.

In another embodiment, the first and second sample inlets, the reagent inlet, first through fourth collection reservoirs, first through eighth sample channels, first through eighth reagent channels, first through eighth intersections, and first through eighth droplet formation regions of the device define a flow path, and the device further includes a plurality of flow paths. In some embodiments, the second sample inlet, the reagent inlet, and the third and fourth collection reservoirs are arranged substantially linearly. In some embodiments, the fifth, sixth, seventh, and eighth sample channels are co-planar. In some embodiments, the fifth, sixth, seventh, and eighth reagent channels are co-planar. In certain embodiments, least one of the droplet formation regions includes a shelf that allows a liquid to expand in one dimension and a step that allows the liquid to expand in an orthogonal dimension. In other embodiments, the system further includes one or more troughs, wherein the one or more troughs connect the plurality of reagent inlets, the plurality of first sample inlets, and/or the plurality of second sample inlets.

In one aspect, the invention provides a device for producing droplets. The device includes: a) a reagent inlet; b) first and second sample inlets; c) a collection reservoir; d) first, second, third, and fourth reagent channels in fluid communication with the reagent inlet; e) first, second, third, and fourth sample channels, where the first and second sample channels are in fluid communication with the first sample inlet and the third and fourth sample channels are in fluid communication with the second sample inlet; where the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and f) first, second, third, and fourth droplet formation regions, where the first droplet formation region is fluidically disposed between the first intersection and the collection reservoir, the second droplet formation region is fluidically disposed between the second intersection and the collection reservoir, the third droplet formation region is fluidically disposed between the third intersection and the third collection reservoir, and the fourth droplet formation region is fluidically disposed between the fourth intersection and the collection reservoir.

In some embodiments, the reagent inlet, the first and second sample inlets, and the collection reservoir are arranged substantially linearly. In some embodiments, the first, second, third, and fourth reagent channels are co-planar. In certain embodiments, the first, second, third, and fourth sample channels are co-planar. In other embodiments, at least one of the droplet formation regions includes a shelf that allows a liquid to expand in one dimension and a step that allows the liquid to expand in an orthogonal dimension.

In some embodiments, the device further includes g) third and fourth sample inlets; h) a second collection reservoir; i) fifth, sixth, seventh, and eighth reagent channels in fluid communication with the reagent inlet; j) fifth, sixth, seventh, and eighth sample channels, where the fifth and sixth sample channels are in fluid communication with the third sample inlet and the seventh and eighth sample channels are in fluid communication with the fourth sample inlet; where the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and k) fifth, sixth, seventh, and eighth droplet formation regions, where the fifth droplet formation region is fluidically disposed between the fifth intersection and the collection reservoir, the sixth droplet formation region is fluidically disposed between the sixth intersection and the collection reservoir, the seventh droplet formation region is fluidically disposed between the seventh intersection and the seventh collection reservoir, and the eighth droplet formation region is fluidically disposed between the eighth intersection and the collection reservoir.

In certain embodiments, the first through fourth sample inlets, the reagent channel, the first through eighth reagent channels, the first through eighth sample channels, the first through eighth droplet formation regions, and the first and second reagent inlets define a flow path, and the device further includes a plurality of flow paths.

In certain embodiments, the device further includes one or more troughs, wherein the one or more troughs connect the plurality of reagent inlets, and/or the plurality of sample inlets.

In certain embodiments, the reagent inlet, the third and fourth sample inlets, and the collection reservoir are arranged substantially linearly. In other embodiments, the fifth, sixth, seventh, and eighth reagent channels are co-planar. In another embodiment, the fifth, sixth, seventh, and eighth sample channels are co-planar.

In certain embodiments, at least one of the droplet formation regions (e.g., all the droplet formation regions) includes a shelf that allows a liquid to expand in one dimension and a step that allows the liquid to expand in an orthogonal dimension.

In one aspect, the invention provides a method for producing droplets. The method including the steps of a) providing a device including i) a reagent inlet; ii) first and second sample inlets; iii) a collection reservoir; iv) first, second, third, and fourth reagent channels in fluid communication with the reagent inlet; v) first, second, third, and fourth sample channels, wherein the first and second sample channels are in fluid communication with the first sample inlet and the third and fourth sample channels are in fluid communication with the second sample inlet; wherein the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and vi) first, second, third, and fourth droplet formation regions each including a second liquid, wherein the first droplet formation region is fluidically disposed between the first intersection and the collection reservoir, the second droplet formation region is fluidically disposed between the second intersection and the collection reservoir, the third droplet formation region is fluidically disposed between the third intersection and the third collection reservoir, and the fourth droplet formation region is fluidically disposed between the fourth intersection and the collection reservoir; and b) allowing a first liquid to flow from the first and second sample inlets via the first, second, third, and fourth sample channels to the first, second, third, or fourth intersections, and allowing a third liquid to flow from the reagent inlet via the first, second, third, and fourth reagent channels to the first, second, third, and fourth intersections, wherein the first liquid and the third liquid combine at the first, second, third, and fourth intersections and produce droplets in the second liquid at the first, second, third, and fourth droplet formation regions.

In some embodiments, the method further includes a) providing a device further including vii) third and fourth sample inlets; viii) a second collection reservoir; ix) fifth, sixth, seventh, and eighth reagent channels in fluid communication with the reagent inlet; x) fifth, sixth, seventh, and eighth sample channels, wherein the fifth and sixth sample channels are in fluid communication with the third sample inlet and the seventh and eighth sample channels are in fluid communication with the fourth sample inlet; wherein the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and xi) fifth, sixth, seventh, and eighth droplet formation regions each including the second liquid, wherein the fifth droplet formation region is fluidically disposed between the fifth intersection and the second collection reservoir, the sixth droplet formation region is fluidically disposed between the sixth intersection and the second collection reservoir, the seventh droplet formation region is fluidically disposed between the seventh intersection and the second collection reservoir, and the eighth droplet formation region is fluidically disposed between the eighth intersection and the second collection reservoir; and b) allowing a first liquid to flow from the third sample inlet via the fifth and sixth sample channels to the fifth and sixth intersections, allowing the first liquid to flow from the fourth sample inlet via the seventh and eighth sample channels to the seventh and eighth intersections, allowing a third liquid to flow from the reagent inlet via the fifth, sixth, seventh, and eighth reagent channels to the fifth, sixth, seventh, and eighth intersections, wherein the first and third liquids combine at the fifth, sixth, seventh, and eighth intersections and produce droplets in the second liquid at the fifth, sixth, seventh, and eighth droplet formation regions.

In one aspect, the invention provides a system for producing droplets. The system includes: a) a device including i) a reagent inlet; ii) first and second sample inlets; iii) a collection reservoir; iv) first, second, third, and fourth reagent channels in fluid communication with the reagent inlet; v) first, second, third, and fourth sample channels, wherein the first and second sample channels are in fluid communication with the first sample inlet and the third and fourth sample channels are in fluid communication with the second sample inlet; wherein the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and vi) first, second, third, and fourth droplet formation regions, wherein the first droplet formation region is fluidically disposed between the first intersection and the collection reservoir, the second droplet formation region is fluidically disposed between the second intersection and the collection reservoir, the third droplet formation region is fluidically disposed between the third intersection and the third collection reservoir, and the fourth droplet formation region is fluidically disposed between the fourth intersection and the collection reservoir; and b) particles in the reagent inlet and/or sample inlet, and/or droplets in the collection reservoir.

In some embodiments, the system further includes vii) third and fourth sample inlets; viii) a second collection reservoir; ix) fifth, sixth, seventh, and eighth reagent channels in fluid communication with the reagent inlet; x) fifth, sixth, seventh, and eighth sample channels, wherein the fifth and sixth sample channels are in fluid communication with the third sample inlet and the seventh and eighth sample channels are in fluid communication with the fourth sample inlet; wherein the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and xi) fifth, sixth, seventh, and eighth droplet formation regions, wherein the fifth droplet formation region is fluidically disposed between the fifth intersection and the second collection reservoir, the sixth droplet formation region is fluidically disposed between the sixth intersection and the second collection reservoir, the seventh droplet formation region is fluidically disposed between the seventh intersection and the second collection reservoir, and the eighth droplet formation region is fluidically disposed between the eighth intersection and the second collection reservoir.

In certain embodiments, the first through fourth sample inlets, the reagent inlet, the first through eighth reagent channels, first through eighth sample channels, first through eighth droplet formation regions, and first and second collection reservoirs of the device define a flow path and the device further includes a plurality of flow paths. In some embodiments, the reagent inlet, the third and fourth sample inlets, and the second collection reservoir are arranged substantially linearly. In some embodiments, the fifth, sixth, seventh, and eighth reagent channels are co-planar. In some embodiments, the fifth, sixth, seventh, and eighth sample channels are co-planar. In certain embodiments, at least one of the droplet formation regions (e.g., all the droplet formation regions) includes a shelf that allows a liquid to expand in one dimension and a step that allows the liquid to expand in an orthogonal dimension. In certain embodiments, the system further includes one or more troughs, wherein the one or more troughs include a first trough connecting the plurality of reagent inlets.

In one aspect, the invention provides a device for producing droplets. The device includes i) one or more first channels, each first channel having independently a first depth, a first width, a first proximal end, and a first distal end, the first distal end including a first channel outlet; ii) one or more second channels, each second channel having independently a second depth, a second width, a second proximal end, and a second distal end, wherein each second channel intersects one of the first channels between the first proximal and first distal ends; iii) a droplet collection region;

and iv) one or more droplet formation regions in fluid communication with the first channel outlets and the droplet collection region; wherein at least one of the one or more first channels bifurcates into two downstream first channels after the intersection between the first channel and the second channel, and the downstream first channels are fluidically connected to the one or more droplet formation regions; and wherein the first channels, the downstream first channels, the second channels, the droplet formation region, and the droplet collection region are configured to produce droplets.

In certain embodiments, the two downstream first channels are curved. In some embodiments, at least one of the second channels includes a funnel. In some embodiments, the funnel is disposed between the second proximal end and the intersection between the first channel and the second channel. In certain embodiments, the first channel includes a mixer. In some embodiments, the mixer is disposed between the first distal end and the intersection between the first channel and the second channel. In other embodiments, the mixer is a herringbone mixer.

In one aspect, the invention provides a system for producing droplets. The system including a) a device including i) one or more first channels, each first channel having independently a first depth, a first width, a first proximal end, and a first distal end, the first distal end including a first channel outlet; ii) one or more second channels, each second channel having independently a second depth, a second width, a second proximal end, and a second distal end, wherein each second channel intersects one of the first channels between the first proximal and first distal ends; iii) a droplet collection region; and iv) a droplet formation region including a shelf region, wherein the droplet formation region is in fluid communication with the first channel outlets and the droplet collection region, and wherein the width of the droplet formation region is at least five times greater than the combined widths of the first channel outlets, or wherein the droplet formation region includes a protrusion from the first channel outlet towards the droplet collection region; b) a first liquid disposed in the first channel; c) a second liquid disposed in the droplet collection region; and d) a third liquid disposed in the second channel; wherein the first liquid and the second liquid are immiscible; wherein the first liquid and the third liquid are miscible; and wherein the system is configured to produce droplets of the first and third liquids in the second liquid.

In certain embodiments of the system, the device is any device of the preceding aspect.

In another aspect, the invention provides a system for producing droplets. The system including a) a device including i) one or more first channels, each first channel having independently a first depth, a first width, a first proximal end, and a first distal end, the first distal end including a first channel outlet; ii) one or more second channels, each second channel having independently a second depth, a second width, a second proximal end, and a second distal end, wherein each second channel intersects one of the first channels between the first proximal and first distal ends; iii) a droplet collection region; and iv) one or more droplet formation regions in fluid communication with the first channel outlets and the droplet collection region; wherein at least one of the one or more first channels bifurcates into two downstream first channels after the intersection between the first channel and the second channel, and the downstream first channels are fluidically connected to the one or more droplet formation regions; b) a first liquid disposed in the first channel; c) a second liquid disposed in the droplet collection region; and d) a third liquid disposed in the second channel; wherein the first liquid and the second liquid are immiscible; wherein the first liquid and the third liquid are miscible; and wherein the system is configured to produce droplets of the first and third liquids in the second liquid.

In certain embodiments of the system, the two downstream first channels of the device are curved.

In some embodiments of the system, at least one of the second channels includes a funnel. In some embodiments, the funnel is disposed between the second proximal end and the intersection between the first channel and the second channel. In certain embodiments, the first channel includes a mixer. In some embodiments, the mixer is disposed between the first distal end and the intersection between the first channel and the second channel. In other embodiments, the mixer is a herringbone mixer.

In certain embodiments, the system further includes a plurality of particles disposed in the first channel.

In certain embodiments, the invention provides a method of producing droplets in a second liquid. The droplets including a first liquid and a third liquid. The method including a) providing the system of any one of the two preceding aspects; and b) allowing the first liquid to flow from the first channel to the droplet formation region and produce droplets in the second liquid, the droplets including the first liquid and the third liquid.

In one aspect, the invention provides a device for producing droplets. The device including a) one or more sample inlets; b) one or more sample channels in fluid communication with the one or more sample inlets; c) one or more reagent inlets; d) one or more reagent channels in fluid communication with the one or more reagent inlets and wherein the one or more reagent channels intersect with the one or more sample channels to form one or more intersections; e) one or more droplet formation regions; and f) one or more collection reservoirs, wherein the one or more droplet formation regions are fluidically disposed between the one or more intersections and the one or more collection reservoirs; wherein the one or more sample inlets, one or more reagent inlets, one or more collection reservoirs, one or more sample channels, one or more reagent channels, one or more intersections, and one or more droplet formation regions define a flow path; and wherein the one or more sample inlets, one or more reagent inlets, and one or more collection reservoirs are sized and spaced to be in a linear sequence according to a row or column of a multi-well plate.

In certain embodiments, the one or more sample inlets include a first sample inlet, the one or more reagent inlets include a first reagent inlet, the one or more collection reservoirs include a first collection reservoir, the one or more sample channels include a first sample channel in fluid communication with the first sample inlet, the one or more reagent channels include a first reagent channel in fluid communication with the first reagent inlet, the one or more intersections include a first intersection, the one or more droplet formation regions include a first droplet formation region, the first reagent channel intersects the first sample channel at the first intersection, and the first droplet formation region is fluidically disposed between the first intersection and the first collection reservoir.

In some embodiments, the device further includes a second sample channel in fluid communication with the first sample inlet, a second reagent channel in fluid communication with the first reagent inlet, a second intersection, and a second droplet formation region; where the second reagent channel intersects the second sample channel at the second intersection, and the second droplet formation region is fluidically disposed between the second intersection and the first collection reservoir.

In some embodiments, the device further includes a second reagent inlet, a second collection reservoir, a third sample channel in fluid communication with the first sample inlet, a third reagent channel in fluid communication with the second reagent inlet, a third intersection, and a third droplet formation region, where the third sample channel intersects the third reagent channel at the third intersection, where the third droplet formation region is fluidically disposed between the third intersection and the second collection reservoir; and where the first and second collection reservoirs and the first and second reagent inlets are disposed ±90 or 180° radially about the sample inlet.

In some embodiments the device further includes a fourth sample channel in fluid communication with the first sample inlet, and a fourth reagent channel in fluid communication with the second reagent inlet, a fourth intersection, and a fourth droplet formation region, where the fourth sample channel intersects the fourth reagent channel at the fourth intersection, and where the fourth droplet formation region is fluidically disposed between the fourth intersection and the second collection reservoir.

In some embodiments, at least one of the one or more droplet formation regions (e.g., all the droplet formation regions) includes a shelf that allows a liquid to expand in one dimension and a step that allows the liquid to expand in an orthogonal dimension.

In some embodiments the device further includes a plurality of flow paths, where each flow path is disposed in alignment with a row or column of the multi well plate. In other embodiments, the multi well plate is a 96 well plate, a 384 well plate, or a 1536 well plate.

In certain embodiments, the invention provides a method for producing droplets by a) providing any of the devices of the aspect or its embodiments, where the one or more droplet formation regions include a second liquid; and b) allowing the first liquid to flow from the one or more sample inlets via the one or more sample channels to the one or more intersections, and allowing a third liquid to flow from the one or more reagent inlets via the one or more reagent channels to the one or more intersections, such that the first liquid and the third liquid combine at the one or more intersections and produce droplets in the second liquid at the one or more droplet formation regions.

In certain embodiments, the invention provides a system for producing. The system includes a) any one of the devices of the aspect or its embodiments; and b) particles in the one or more sample inlets and/or the one or more reagent inlets, and/or droplets in the one or more collection reservoirs.

In one aspect, the invention provides a device for producing droplets. The device includes: a) a sample inlet; b) first, second, third, and fourth sample channels, each of which is in fluid communication with the sample inlet; c) first and second reagent inlets; d) first, second, third, and fourth reagent channels, wherein the first and second reagent channels are in fluid communication with the first reagent inlet; wherein the third and fourth reagent channels are in fluid communication with the second reagent inlet; wherein the first sample channel and the first reagent channel intersect at a first intersection, the second sample channel and the second reagent channel intersect at a second intersection, the third sample channel and the third reagent channel intersect at a third intersection, and the fourth sample channel and the fourth reagent channel intersect at a fourth intersection; e) first, second, third, and fourth droplet formation regions; and f) a collection reservoir, wherein the first droplet formation region is fluidically disposed between the first intersection and the collection reservoir, the second droplet formation region is fluidically disposed between the second intersection and the collection reservoir, the third droplet formation region is fluidically disposed between the third intersection and the collection reservoir, and the fourth droplet formation region is fluidically disposed between the fourth intersection and the collection reservoir. In certain embodiments, the device further includes g) a third reagent inlet; h) fifth and sixth sample channels, each of which is in fluid communication with the sample inlet; i) fifth and sixth reagent channels, each of which is in fluid communication with the third reagent inlet, wherein the fifth sample channel and the fifth reagent channel intersect at a fifth intersection, and the sixth sample channel and sixth reagent channel intersect at a sixth intersection; and j) fifth and sixth droplet formation regions, wherein the fifth droplet formation region is fluidically disposed between the fifth intersection and the collection reservoir, and the sixth droplet formation region is fluidically disposed between the sixth intersection and the collection reservoir. In another embodiment, the device further includes k) a fourth reagent inlet; j) seventh, and eighth sample channels, each of which is in fluid communication with the sample inlet; k) seventh, and eighth reagent channels, each of which is in fluid communication with the reagent inlet, wherein the fifth sample channel and the fifth reagent channel intersect at a fifth intersection, the sixth sample channel and sixth reagent channel intersect at a sixth intersection, the seventh sample channel and the seventh reagent channel intersect at a seventh intersection, and the eighth sample channel and the eighth reagent channel intersect at an eighth intersection; and l) fifth, sixth, seventh, and eighth droplet formation regions; wherein the seventh droplet formation region is fluidically disposed between the seventh intersection and the collection reservoir, and the eighth droplet formation region is fluidically disposed between the eighth intersection and the collection reservoir. In certain embodiments, the device further includes at least one trough connecting at least two of the reagent inlets.

In certain embodiments, the sample inlet, first through fourth sample channels, first and second reagent inlets, first through fourth reagent channels, first through fourth intersections, and first through fourth droplet formation regions define a flow path and the device includes a plurality of flow paths disposed radially about the sample inlet. In other embodiments, the sample inlet, first through eighth sample channels, first through fourth reagent inlets, first through eighth reagent channels, first through eighth intersection, and first through eighth droplet formation regions define a flow path and the device includes a plurality of flow paths disposed radially about the sample inlet. In some embodiments, the first, second, third, and fourth sample channels are co-planar. In some embodiment, the first, second, third, and fourth reagent channels are co-planar. In certain embodiments, the length of each of the first through fourth reagent channels is at least 85% of the length of each other reagent channel.

In certain embodiments, the invention provides a method for producing droplets. The method includes the steps of a) providing any device of the preceding aspect, wherein first through fourth droplet formation regions include a second liquid; and b) allowing a first liquid to flow from the sample inlet via the first through fourth sample channels to the first through fourth intersections, and allowing a third liquid to flow from the first and second reagent inlets via the first through fourth reagent channels to the first through fourth intersections, wherein the first liquid and the third liquid combine at the first through fourth intersections and produce droplets in the second liquid at the first through fourth droplet formation regions.

In another embodiment, the invention provides a system for producing droplets. The system includes a) a device of any of the preceding aspects; and b) particles in the sample inlet and/or the first and/or second reagent inlets, and/or droplets in the collection reservoir.

In certain embodiments of any aspect described herein, sample channels and reagent channels do not intersect any other channel except as specifically described.

Devices may be multiplexed by including multiples of flow paths and/or various inlets and channels, e.g., arranged side by side, and as exemplified in the disclosure.

In any aspect described herein, adjacent inlets and channels may be in fluid communication with each other in certain embodiments. In particular, adjacent inlets or collection reservoirs may be connected by a trough or by a connecting channel. Adjacent inlets that are otherwise not in fluidic communication may also be controllable by the same pressure outlet, as described herein.

The invention also provides methods of producing droplets using any of the devices or systems described herein.

It will be understood, that although channels, reservoirs, and inlets are labeled as "sample" and "reagent" herein, each channel, reservoir, and inlet may be for either a sample or a reagent during use. In certain embodiments, sample channels, sample reservoirs, and sample inlets may be used as reagent channels, reagent reservoirs, and reagent inlets. In certain embodiments, reagent channels, reagent reservoirs, and reagent inlets may be used as sample channels, sample reservoirs, and sample inlets.

In embodiments of any aspect described herein, two or more sample channels or reagent channels in fluid communication with the same sample or reagent inlet may have substantially equal lengths, e.g., to maintain substantially equal fluidic resistance. For example, one sample or reagent channel may be at least 85% of the length of another sample or reagent channel in fluid communication with the same sample or reagent inlet, e.g., at least 90, 95, or 99% or 100% of the length of the other channel, and no greater than 150% of the length of the other channel, e.g., at most 115, 110, 105, or 101%. Alternatively, two or more sample channels or reagent channels in fluid communication with the same sample or reagent inlet may have, substantially equal fluidic resistance. For example, one sample or reagent channel may have at least 85% of the fluidic resistance of another sample or reagent channel in fluid communication with the same sample or reagent inlet, e.g., at least 90, 95, or 99% or 100% of the fluidic resistance of the other channel, and no greater than 115% of the fluidic resistance of another sample or reagent channel in fluid communication with the same sample or reagent inlet, e.g., at most 110, 105, or 101% or 100% of the fluidic resistance of the other channel It will be understood, that all devices, methods, and systems described herein may be adapted to be compatible with a multi well plate layout, by making the inlets and reservoirs appropriately sized and spaced to be in a linear sequence according to a row or column of a multi-well plate, and that a plurality of any one of, or a combination of, the flow paths described herein can be arranged according to the multi well plate layout.

It will be understood that all methods described herein may produce droplets including particles and/or cells. In any aspect of the invention the first and/or third liquids can be aqueous, and the second liquid can be an oil. In any aspect of the invention, the first and/or third liquids can include a sample (e.g., cells) or particles. For example, either the first or third liquid can include cells, and the other liquid can include particles. Cells and particles can be combined in a droplet at the droplet formation regions in any fashion, e.g., 1:1, 1:2. 1:3, or in non-integer ratios as an average for a distribution of droplets. In some embodiments, the droplets include particles and cells in a 1:1 ratio.

Definitions

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "about" means ±10%.

The terms "adaptor(s)", "adapter(s)" and "tag(s)" may be used synonymously. An adaptor or tag can be coupled to a polynucleotide sequence to be "tagged" by any approach including ligation, hybridization, or other approaches.

The term "barcode," as used herein, generally refers to a label, or identifier, that conveys or is capable of conveying information about an analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "bead," as used herein, generally refers to a generally spherical or ellipsoid particle that is not a biological particle. The bead may be a solid or semi-solid particle. The bead may be a gel bead (e.g., a hydrogel bead). The bead may be formed of a polymeric material. The bead may be magnetic or non-magnetic.

The term "biological particle," as used herein, generally refers to a discrete biological system derived from a biological sample, such as a cell or a particulate component of a cell, such as an organelle, exosome, or vesicle. The biological particle may be a rare cell from a population of cells. The biological particle may be any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix. Alternatively, the biological particle may be a virus.

The term "canted", as used herein, refers to a surface that is at an angle of less than 90° in relation to the horizontal plane.

The term "disposed radially about," as used herein, refers to the location of two elements in relation to each other with a third element as a reference, such that the angle between the two elements is at least 5.0° (e.g., at least 8°, at least 10°, at least 15°, at least 20°, at least 30°, at least 40°, at least 50°, at least 60°, at least 70°, at least 80°, at least 90°, at least 100°, at least 110°, at least 120°, at least 130°, at least 140°, at least 150°, at least 160°, at least 170°, or 180°). In some instances, an angle between the two or more elements is between about 5° and about 180° (e.g., between about 10° and about 40°, between about 30° and about 70°, between about 50° and about 90°, between about 70° and about 110°, between about 90° and about 130°, between about 110° and about 150°, between about 130° and about 170°, or between about 135° and about 180°). In some instance, the two or more elements are substantially in line, i.e., within 5° radially.

The term "flow path," as used herein, refers to a path of channels and other structures for liquid flow from at least one inlet to at least one outlet. A flow path may include branches and may connect to adjacent flow paths, e.g., by a common inlet or a connecting channel.

The term "fluidically connected", as used herein, refers to a direct connection between at least two device elements, e.g., a channel, reservoir, etc., that allows for fluid to move between such device elements without passing through an intervening element.

The term "fluidically disposed between", as used herein, refers to the location of one element between two other elements so that fluid can flow through the three elements in one direction of flow.

The term "funnel," as used herein, refers to a channel portion having an inlet and an outlet in fluid communication with the inlet, and at least one cross-sectional dimension (e.g., width) between the inlet and outlet that is greater than the corresponding cross-sectional dimension (e.g., width) of the outlet. Funnels of the invention may be conical or pear-shaped (e.g., having an in-plane longitudinal cross-section of an isosceles trapezoid or hexagon). Funnels of the invention may have, e.g., an in-plane longitudinal cross-section of a trapezoid (e.g., an isosceles trapezoid), in which the smaller of the two bases corresponds to the funnel outlet. Alternatively, funnels of the invention may have, e.g., an in-plane longitudinal cross-section of a hexagon (e.g., a hexagon corresponding to two trapezoids fused at the greater of their bases, where the smaller of their bases correspond to the funnel inlet and outlet). For example, the leg of one trapezoid may be longer (e.g., at least 50% longer, at least 100% longer, at least 200% longer, at least 300% longer, at least 400% longer, or at least 500% longer; e.g., 1000% longer or less) than the leg of the other trapezoid in a funnel having an in-plane longitudinal cross-section of a hexagon. The sides in the trapezoid(s) may be straight or curved. The vertices of the trapezoid(s) may be sharp or rounded. Preferably, a funnel has two cross-sectional dimensions (e.g., width and depth) between the inlet and outlet that are greater than each of the corresponding cross-sectional dimensions (e.g., width and depth) of the outlet. Preferably, within a funnel, the maximum funnel width and the maximum funnel depth are located at the same distance from the inlet. Preferably, the depth and/or width maxima are closer to the funnel inlet than to the funnel outlet. A funnel may be a rectifier or mini-rectifier. Rectifiers are funnels having a length (i.e., the distance from the inlet to the outlet) of at least 10 times (e.g., at least 20 times, or at least 25 times) the smaller of the funnel outlet width, funnel outlet depth, funnel inlet width, and funnel inlet depth. Typically, a rectifier has a length that is 1,500% to 4,000% (e.g., 1,500% to 3,000%, 2,000% to 3,000%, or 2,500% to 3,000%) of the smaller of the funnel outlet width, funnel outlet depth, funnel inlet width, and funnel inlet depth. Mini-rectifiers are funnels having a length (i.e., the distance from the inlet to the outlet) of 10 times or less of the smaller of the funnel outlet width, funnel outlet depth, funnel inlet width, and funnel inlet depth. Typically, a mini-rectifier has a length that is 500% to 1,000% of the smaller of the funnel outlet width, funnel outlet depth, funnel inlet width, and funnel inlet depth.

The term "genome," as used herein, generally refers to genomic information from a subject, which may be, for example, at least a portion or an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The term "hurdle," as used herein, refers to a partial blockage of a channel or funnel that maintains the fluid communication between sides of the channel or funnel surrounding the blockage. Non-limiting examples of hurdles are pegs, barriers, and their combinations. A peg, or a row of pegs, is a hurdle having a height, width, and length, where the height is the greatest of the dimensions. A peg may be, for example, cylindrical. A barrier is a hurdle having a height, width, and length, where the width or length is the greatest of the dimensions. A barrier may be, for example, trapezoidal. In some embodiments, a peg has the same height as the channel or funnel, in which the peg is disposed. In certain embodiments, a barrier has the same width as the channel or funnel, in which the barrier is disposed. In particular embodiments, a barrier has the same length as the funnel, in which the barrier is disposed.

The term "in fluid communication with", as used herein, refers to a connection between at least two device elements, e.g., a channel, reservoir, etc., that allows for fluid to move between such device elements with or without passing through one or more intervening device elements. When two compartments in fluid communication are directly connected, i.e., connected in a manner allowing fluid exchange without necessity for the fluid to pass through any other intervening compartment, the two compartments are deemed to be fluidically connected.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA or a DNA molecule. The macromolecular constituent may comprise RNA or an RNA molecule. The RNA may be coding or non-coding. The RNA may be messenger RNA (mRNA), ribosomal RNA (rRNA) or transfer RNA (tRNA), for example. The RNA may be a transcript. The RNA molecule may be (i) a clustered regularly interspaced short palindromic (CRISPR) RNA molecule (crRNA) or (ii) a single guide RNA (sgRNA) molecule. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide or a protein. The polypeptide or protein may be an extracellular or an intracellular polypeptide or protein. The macromolecular constituent may also comprise a metabolite. These and other suitable macromolecular constituents (also referred to as analytes) will be appreciated by those skilled in the art (see U.S. Pat. Nos. 10,011,872 and 10,323,278, and WO/2019/157529 each of which is incorporated herein by reference in its entirety).

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise an oligonucleotide or polypeptide sequence. The molecular tag may comprise a DNA aptamer. The molecular tag may be or comprise a primer. The molecular tag may be or comprise a protein. The molecular tag may comprise a polypeptide. The molecular tag may be a barcode.

The term "oil," as used herein, generally refers to a liquid that is not miscible with water. An oil may have a density higher or lower than water. An oil may have a viscosity higher or lower than water.

The term "pitch," as used herein, refers to a linear dimension in the plane of channels in a device from the center of the shortest dimension of one flow path to the center of the shortest dimension of an adjacent flow path.

The term "sample," as used herein, generally refers to a biological sample of a subject. The biological sample may be a nucleic acid sample or protein sample. The biological sample may be derived from another sample. The sample may be a tissue sample, such as a biopsy, core biopsy, needle aspirate, or fine needle aspirate. The sample may be a liquid sample, such as a blood sample, urine sample, or saliva sample. The sample may be a skin sample. The sample may be a cheek swap. The sample may be a plasma or serum sample. The sample may include a biological particle, e.g., a cell or virus, or a population thereof, or it may alternatively be free of biological particles. A cell-free sample may include polynucleotides. Polynucleotides may be isolated from a bodily sample that may be selected from the group consisting of blood, plasma, serum, urine, saliva, mucosal excretions, sputum, stool and tears.

The term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina, Pacific Biosciences, Oxford Nanopore, or Life Technologies (Ion Torrent). As an alternative, sequencing may be performed using nucleic acid amplification, polymerase chain reaction (PCR) (e.g., digital PCR, quantitative PCR, or real time PCR) or isothermal amplification. Such devices may provide a plurality of raw genetic data corresponding to the genetic information of a subject (e.g., human), as generated by the device from a sample provided by the subject. In some situations, systems and methods provided herein may be used with proteomic information.

The term "side-channel," as used herein, refers to a channel in fluid communication with, but not fluidically connected to, a droplet formation region.

The term "subject," as used herein, generally refers to an animal, such as a mammal (e.g., human) or avian (e.g., bird), or other organism, such as a plant. The subject can be a vertebrate, a mammal, a mouse, a primate, a simian or a human. Animals may include, but are not limited to, farm animals, sport animals, and pets. A subject can be a healthy or asymptomatic individual, an individual that has or is suspected of having a disease (e.g., cancer) or a predisposition to the disease, or an individual that is in need of therapy or suspected of needing therapy. A subject can be a patient.

The term "substantially linearly" means that a single, straight line can be drawn through the elements. The term does not require that the elements are centered with respect to the line that can be drawn.

The term "substantially stationary", as used herein with respect to droplet formation, generally refers to a state when motion of formed droplets in the continuous phase is passive, e.g., resulting from the difference in density between the dispersed phase and the continuous phase.

By a "trough connecting" or similar language refers to a single fluidic chamber, i.e., the trough, that is in fluidic communication with the elements being connected. Thus, a single volume of liquid in a trough is divided, not necessarily equally, among the elements the trough connects. Furthermore, a trough may be disposed to be controllable by one or more pressure sources.

BRIEF DESCRIPTION OF THE DRAWINGS

FIG. 9A is top view of a device of the invention with reservoirs. FIG. 9B is a micrograph of a first channel intersected by a second channel adjacent a droplet formation region.

FIGS. 10A-10E are views of droplet formation regions including shelf regions.

FIGS. 13A-13B are views of a device of the invention. FIG. 13A is an overview of a device with four droplet formation regions. FIG. 13B is a zoomed in view of an exemplary droplet formation region within the dotted line box in FIG. 13A.

FIG. 14A shows a device with three reservoirs employed in droplet formation. FIG. 14B is a device of the invention with four reservoirs employed in the droplet formation.

FIG. 16A is a top view of a device having two liquid channels that meet adjacent to a droplet formation region. FIG. 16B is a zoomed in view of the droplet formation region showing the individual droplet formations regions.

FIG. 17A is an overview of the method, and FIG. 17B is a micrograph showing the use of a blocking fluid to protect a channel from a coating agent.

FIG. 18A shows the piezoelectric element in a first state. FIG. 18B shows the piezoelectric element in a second state.

FIG. 27A is an image showing the top view of an exemplary device of the invention. The device includes two first channels 2700, each first channel having two funnels 2701 and two mini-rectifiers 2704; first reservoir 2702; two second channels 2740 fluidically connected to the same second reservoir 2742; two droplet formation regions 2750; and one droplet collection region 2760. The proximal funnel 2701 on the left includes one barrier 2705 as a hurdle. The proximal funnel 2701 on the right includes three rows of pegs 2703 as hurdles. Droplet collection region 2760 is in fluid communication with first reservoir 2702 and second reservoir 2742. Barrier 2705 has a height of 30 µm, and pegs 2703 are spaced at 100 µm intervals.

FIG. 27B is an image focused on the combination of two proximal funnels 2701 and first reservoir 2702. Proximal funnel 2701 on the left is fluidically connected to first reservoir 2702 and includes one barrier 2705 as a hurdle. Proximal funnel 2701 on the right is fluidically connected to first reservoir 2702 includes three rows of pegs 2703 as hurdles.

FIG. 29A is an image showing the top view of an exemplary device of the invention. The device includes two first channels 2900, each first channel having two funnels 2901 and two mini-rectifiers 2904; first reservoir 2902; two second channels 2940 fluidically connected to the same second reservoir 2942; two droplet formation regions 2950; and one droplet collection region 2960. Proximal funnel 2901 on the left includes a barrier with two rows of pegs disposed on top of the barrier as hurdle 2906. Proximal funnel 2901 on the right includes a barrier with three rows of pegs disposed on top of the barrier as hurdle 2906. Droplet collection region 2960 is in fluid communication with first reservoir 2902 and second reservoir 2942. Each hurdle 2906 is a 30 µm-tall barrier with pegs spaced at 100 µm.

FIG. 29B is an image focused on the combination of proximal funnels 2901 and first reservoir 2902. Proximal funnel 2901 on the left is fluidically connected to first reservoir 2902 and includes a barrier with two rows of pegs disposed on top of the barrier as hurdle 2906. Proximal funnel 2901 on the right is fluidically connected to first reservoir 2902 includes a barrier with three rows of pegs disposed on top of the barrier as hurdle 2906.

FIG. 30A is an image showing the top view of an exemplary device of the invention. The device includes two first channels 3000, each first channel having two funnels 3001; first reservoir 3002; two second channels 3040 fluidically connected to the same second reservoir 3042; two droplet formation regions 3050; and one droplet collection region 3060. Proximal funnel 3001 on the left includes two rows of pegs 3003 as hurdles. Pegs 3003 are spaced at 100 µm. Proximal funnel 3001 on the right includes a barrier with two rows of pegs disposed on top of the barrier as hurdle 3006. Hurdle 3006 is a 60 µm-tall barrier with pegs spaced at 65 µm. Distal funnel 3001 on the left is elongated having the length of 2 mm and an inlet sized 60 µm×60 µm. Droplet collection region 3060 is in fluid communication with first reservoir 3002 and second reservoir 3042.

FIG. 30B is an image focused on the combination of proximal funnels 3001 and first reservoir 3002. Proximal funnel 3001 on the left is fluidically connected to first reservoir 3002 and includes two rows of pegs 3003 as hurdles. Proximal funnel 3001 on the right is fluidically connected to first reservoir 3002 includes a barrier with two rows of pegs disposed on top of the barrier as hurdle 3006.

FIG. 31A is an image showing the top view of an exemplary device of the invention. The device includes two first channels 3100, each first channel having two funnels 3101, where first channel 3100 on the left includes two mini-rectifiers 3104, and first channel 3100 on the right does not; first reservoir 3102; two second channels 3140 fluidically connected to the same second reservoir 3142; two droplet formation regions 3150; and one droplet collection region 3160. First channel 3100 on the left has dimensions of 65×60 µm, and first channel 3100 on the right has dimensions of 70×65 µm. Each proximal funnel 3101 includes a barrier with two rows of pegs 3103 as hurdles. Droplet collection region 3160 is in fluid communication with first reservoir 3102 and second reservoir 3142.

FIG. 31B is an image focused on the combination of proximal funnels 3101 and first reservoir 3102. Each proximal funnel 3101 on the left is fluidically connected to first reservoir 3102 and includes two rows of pegs 3103 as hurdles.

FIG. 36A is an image showing the top view of an exemplary device of the invention. The device includes first channel 3600 fluidically connected to first reservoir 3602, first side channel 3610 including mixer 3680, second channel 3640 fluidically connected to second reservoir 3642 and to first side-channel 3610, droplet formation region 3650, and droplet collection region 3660. Droplet collection region 3660 is in fluid communication with first reservoir 3602 and second reservoir 3642.

FIG. 36B focuses on a portion of the device of FIG. 36A in use. A mixture of first liquid L1 and beads 3630 is carried through first channel 3600 in the proximal-to-distal direction. Excess first liquid L1 is diverted from first channel 3600 at intersection 3611 into first side-channel 3610. Excess L1 is then combined with L3 at the intersection of first side-channel 3610 and second channel 3640. The combination of first liquid L1 and third liquid L3 then enters mixer 3680 and, after mixing, is combined with beads 3630/first liquid L1 at intersection 3612. As shown in FIG. 36B, beads 3630 are unevenly spaced in the proximal portion of first channel 3600 before intersection 3611. Between intersections 3611 and 3612 beads 3630 are tightly packed in first channel 3600. After intersection 3612, beads 3630 are substantially evenly spaced.

FIG. 48 is a depiction of a multiplex flow path and a device incorporating multiple multiplex flow paths.

FIG. 53A is a depiction of a device comprising multiple collection reservoirs, multiple sample reservoirs, and multiple reagent reservoirs. FIG. 53B is a side view cross section of the reservoirs in the device. FIG. 53C is a side view cross section presenting i) a collection reservoir, ii) a sample reservoir, and iii) a reagent reservoir.

FIG. 54A is a depiction of a device having multiple collection reservoirs, multiple sample reservoirs, and multiple reagent reservoirs that are connected by a trough. FIG. 54B is a depiction of an alternative architecture of a device having multiple collection reservoirs, multiple sample reservoirs, and multiple reagent reservoirs that are connected by a trough.

FIGS. 55A and 55B are depictions of reservoirs in a multiplex device showing two different multiplex device architectures where the dividing wall is shorter than the one surrounding wall. FIG. 55C is a depiction of reservoirs in a multiplex device where a portion of the dividing wall is shorter than the one common wall.

FIG. 56A has twice as many sample reservoirs (5603) as depicted in FIG. 56B FIGS. 57A and 57B are depictions of reservoirs in a multiplex device of the invention.

FIG. 58A is a depiction of a device incorporating multiple multiplex flow paths. FIG. 58B is a depiction of an alternative multiplex flow path.

FIG. 61A shows an emulsion layer (6101) at the top of a partitioning oil (6102) within a droplet collection reservoir. FIG. 61B shows a drawing of a spacing liquid (e.g., mineral oil) added to the top of the collection reservoir. FIG. 61C shows the emulsion layer reentrainment into a reentrainment channel. FIG. 61D is a close-up view of droplets in a reentrainment channel including an oil flow to meter droplets and dilute concentrated droplets prior to detection.

FIG. 63A is a depiction of a plurality of multiplex flow paths in a 96-well multi well plate. FIG. 63B is a depiction of a plurality of multiplex flow paths in a 384-well multi well plate.

DETAILED DESCRIPTION

Figure 1:
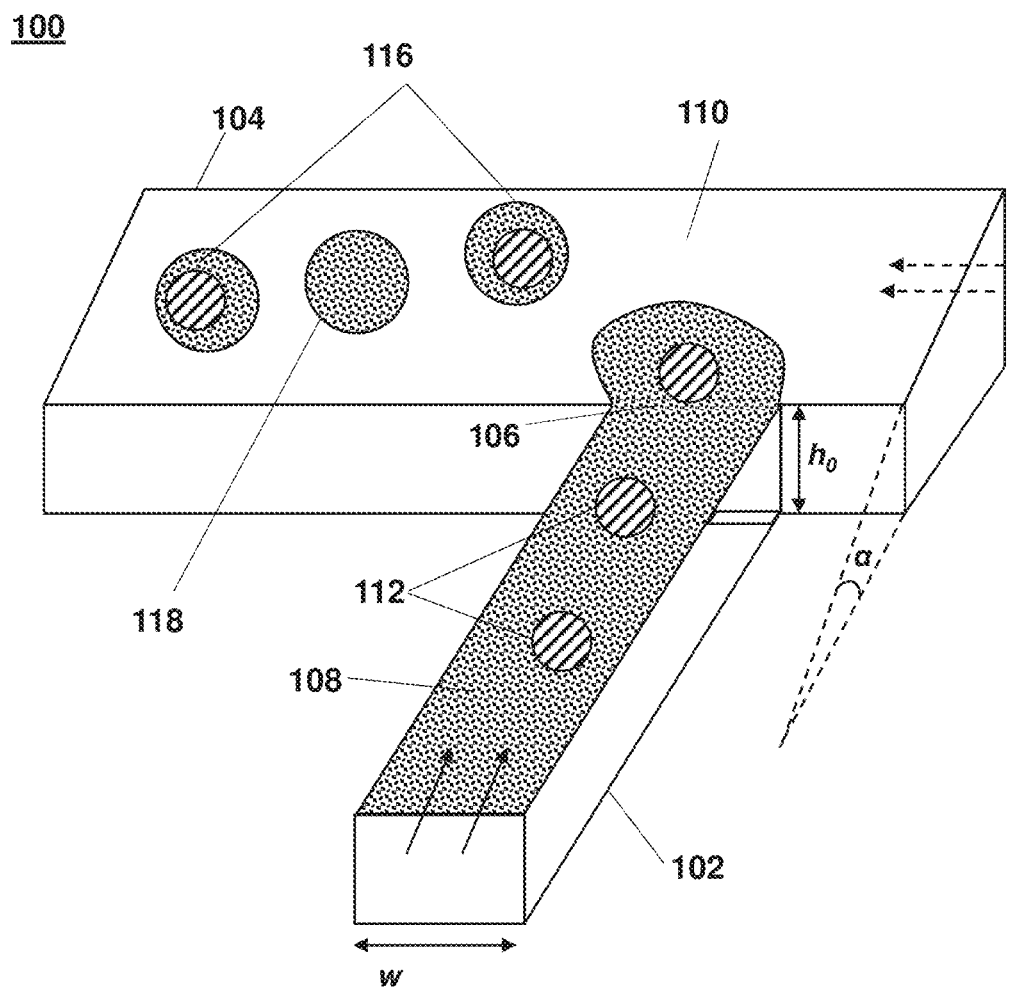
FIG. 1 shows an example of a microfluidic device for the introduction of particles, e.g., beads, into discrete droplets.

The invention provides devices, systems, and methods for efficiently producing and collecting droplets. For example, devices and methods of the invention may be beneficial for production and collection of droplets without the necessity to tilt the device at an angle to increase efficiency of droplet collection.

In certain commercial devices, efficient droplet collection requires that the device be tilted at an angle, e.g., a 45° angle, to increase recovery by a collection device, limiting throughput. Collection reservoirs including canted sidewalls, e.g., sidewalls canted at an angle between 89.5° and 4°, e.g., between 85° and 5°, may be beneficial for increasing throughput by removing the necessity of tilting the device for droplet recovery and increasing droplet recovery by a collection device, e.g., a pipette tip.

In addition, devices having multiplexed formats, e.g., those having multiple droplet formation regions, may be used to increase the rate of droplet production. The use of troughs to connect multiple inlets or collection reservoirs also provides advantages in terms of ease of loading or unloading, ease of controlling flow in parallel flow paths, e.g., by ensuring that all sample is consumed prior to ending use of the device, and the ability to process in multiple flow paths when one path becomes clogged or inoperative. A trough may connect at least two adjacent inlets or collection reservoirs, e.g., 3, 4, 5, 6, 7, 8, 9, 10, 11, 12, 13, 14, 15, or 16 inlets or collection reservoirs.

The devices, kits, systems, and methods of the invention may provide droplets with reduced droplet-to-droplet content variation and/or with improved droplet content uniformity. For example, the devices, systems, and methods of the invention may provide droplets having a single particle per droplet. This effect may be achieved through the use of one or more side-channels. Without wishing to be bound by theory, a side-channel may be used to take away excess liquid separating consecutive particles, thereby reducing the number of droplets lacking particles. Alternatively, a side-channel may be used to add liquid between consecutive particles to reduce the "bunching" effect, thereby reducing the number of droplets containing multiple particles of the same kind per droplet. The devices, kits, systems, and methods of the invention may provide a plurality of droplets, in which majority of droplets are occupied by no more than one particle of the same type. In some cases, fewer than 25% of the occupied droplets contain more than one particle of the same type, and in many cases, fewer than 20% of the occupied droplets have more than one particle of the same type. In some cases, fewer than 10% or even fewer than 5% of the occupied droplets include more than one particle of the same type. In some cases, the devices, kits, systems, and methods of the invention may provide a plurality of droplets, in which majority of droplets are occupied by no more than one particle of one type (e.g., a bead) and one particle of another type (e.g., a biological particle).

It may also be desirable to avoid the creation of excessive numbers of empty droplets, for example, from a cost perspective and/or efficiency perspective. However, while this may be accomplished by providing sufficient numbers of beads into the droplet formation region, the Poissonian distribution may expectedly increase the number of droplets that may include multiple particles of the same type. As such, at most about 95%, 90%, 85%, 80%, 75%, 70%, 65%, 60%, 55%, 50%, 45%, 40%, 35%, 30%, 25%, 20%, 15%, 10%, 5% or less of the generated droplets can be unoccupied. In some cases, the flow of one or more of the particles and/or liquids directed into the droplet formation region can be conducted such that, in many cases, no more than about 50% of the generated droplets, no more than about 25% of the generated droplets, or no more than about 10% of the generated droplets are unoccupied. These flows can be controlled, as described herein, so as to present non-Poissonian distribution of singly occupied droplets while providing lower levels of unoccupied droplets. The above noted ranges of unoccupied droplets can be achieved while still providing any of the single occupancy rates described above. For example, in many cases, the devices, kits, systems, and methods of the invention produce droplets that have multiple occupancy rates of the same type of less than about 25%, less than about 20%, less than about 15%, less than about 10%, and, in many cases, less than about 5%, while having unoccupied droplets of less than about 50%, less than about 40%, less than about 30%, less than about 20%, less than about 10%, less than about 5%, or less.

Figure 34A:
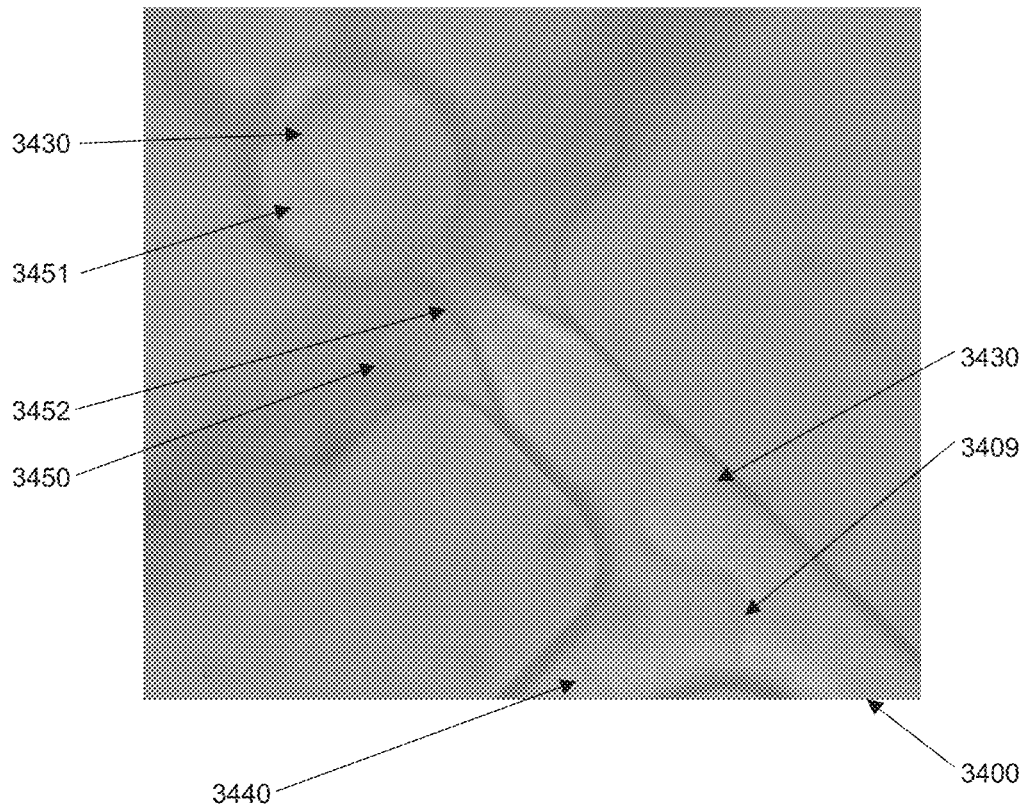
FIG. 34A is a brightfield image showing droplet generation in a device lacking a mixer. The brightfield image shows a portion of the device in use, the device including an intersection between first channel 3400 and second channel 3440; droplet formation region 3450; first, second, and third liquids; beads 3430; and forming droplet 3451 including bead 3430 and a combination of the first and third liquids. Interface 3409 is between the first and third liquids, and interface 3452 is between the second liquid and the combination of first and third liquids. In this device, first and third liquids are combined at an intersection of first channel 3400 and second channel 3440. The first liquid carries beads 3430. Forming droplet 3451 is surrounded by the second liquid. The first and third liquids are miscible, and the second liquid is not miscible with the first and third liquids.
Figure 34B:
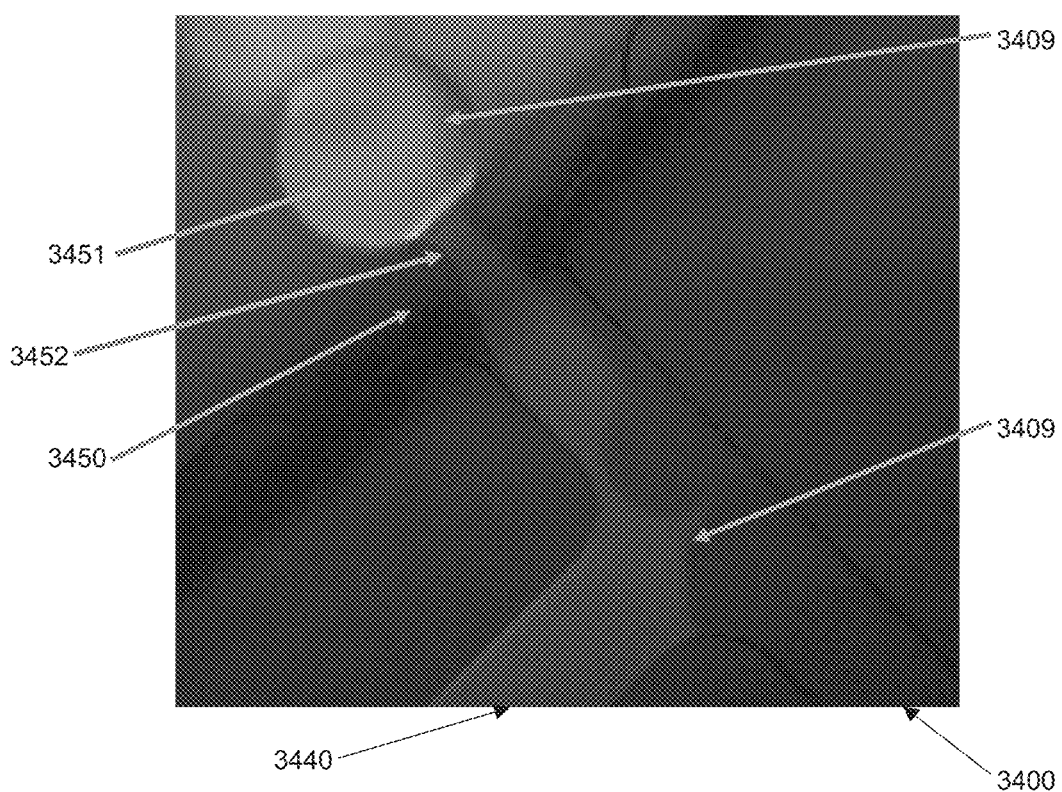
FIG. 34B is a fluorescent image showing droplet generation in the same device as that which is shown in FIG. 34A. The fluorescent image shows a portion of the device in use with a focus on the combination of first and third liquid at an intersection between first channel 3400 and second channel 3440. Interface 3409 between the first liquid (dark) and second liquid (light) extends from the channel intersection through droplet formation region 3450 into forming droplet 3451. The presence of interface 3409 in forming droplet 3451 indicates that the first liquid (dark) and the third liquid (light) are not homogeneously mixed at the channel intersection.

The devices, kits, systems, and methods of the invention may provide droplets having substantially uniform distribution of dissolved ingredients (e.g., lysing reagents). In applications requiring controlled cell lysis, the devices, systems, and methods of the invention may also be used to reduce premature cell lysis (e.g., to reduce the extent of cell lysis in channels). For example, non-uniform distribution of dissolved ingredients is illustrated in FIGS. 34A and 34B. In these figures, a combined stream of two partially unmixed liquids is formed by combining two liquids at a channel intersection. Without wishing to be bound by theory, the devices, kits, systems, and methods of the invention that include a mixer (e.g., a passive mixer) may pre-mix liquids (e.g., a third liquid and a fourth liquid or a third liquid and a first liquid) prior to droplet formation, thereby reducing localized high concentrations of dissolved ingredients (e.g., lysing reagents), which may cause premature cell lysis.

Additionally or alternatively, inclusion of funnels in sample channels (e.g., second channels) may improve distribution uniformity by reducing the amount of debris entering the sample channel from the sample. In particular, this reduction in the amount of debris may reduce pressure fluctuations at a channel intersection, thereby improving the consistency in the mix ratio between liquids at the channel intersection. Thus, inclusion of funnels in sample channels may reduce the droplet-to-droplet content variation.

Additionally or alternatively, inclusion of traps in channels (e.g., a first channel, second channel, or third channel) may improve uniformity by reducing the pressure fluctuations at a channel intersection by removing air bubbles from the liquid flow. Further, particle spacing uniformity may also be improved by removing air bubbles from the liquid flow. Thus, inclusion of traps in channels may reduce the droplet-to-droplet content variation.

The devices, kits, systems, and methods of the invention may be used to form droplets of a size suitable for utilization as microscale chemical reactors, e.g., for genetic sequencing. In general, droplets are formed in a device by flowing a first liquid through a channel and into a droplet formation region including a second liquid, i.e., the continuous phase, which may or may not be externally driven. Thus, droplets can be formed without the need for externally driving the second liquid. Exemplary fluidic configurations for generating droplets are described herein and shown in the devices of Examples 1-22.

Additionally, devices, kits, systems, and methods of the invention may allow for control over the size of the droplets with lower sensitivity to changes in liquid properties. For example, the size of the generated droplets is less sensitive to the dispersed phase flow rate. Adding multiple formation regions is also significantly easier from a layout and manufacturing standpoint. The addition of further formation regions allows for formation of droplets even in the event that one droplet formation region becomes blocked. Droplet formation can be controlled by adjusting one or more geometric features of fluidic channel architecture, such as a width, depth, and/or expansion angle of one or more fluidic channels. For example, droplet size and speed of droplet formation may be controlled. In some instances, the number of regions of formation at a driven pressure can be increased to increase the throughput of droplet formation.

Devices and Systems

A device or system of the invention include channels having a depth, a width, a proximal end, and a distal end. The proximal end is or is configured to be in fluid communication with a source of liquid, e.g., a reservoir integral to the device or coupled to the device, e.g., by tubing. The distal end is in fluid communication with, e.g., fluidically connected to, a droplet formation region.

In general, the components of a device or system, e.g., channels, may have certain geometric features that at least partly determine the sizes and/or content of the droplets. For example, any of the channels described herein have a depth (a height), $h_0$, and width, w. The droplet formation region may have an expansion angle, $\alpha$. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

As a non-limiting example, for a channel with w=21 µm, h=21 µm, and $\alpha=3°$, the predicted droplet size is 121 µm. In another example, for a channel with w=25 µm, h=25 µm, and $\alpha=5°$, the predicted droplet size is 123 µm. In yet another example, for a channel with w=28 µm, h=28 µm, and $\alpha=7°$, the predicted droplet size is 124 µm. In some instances, the expansion angle may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

The depth and width of the channel may be the same, or one may be larger than the other, e.g., the width is larger than the depth, or depth is larger than the width. In some embodiments, the depth and/or width is between about 0.1 µm and 1000 µm. In some embodiments, the depth and/or width of the channel is from 1 to 750 µm, 1 to 500 µm, 1 to 250 µm, 1 to 100 µm, 1 to 50 µm, or 3 to 40 µm. In certain embodiments, the depth and/or width of the channel is 10 µm to 100 µm. In some cases, when the width and length differ, the ratio of the width to depth is, e.g., from 0.1 to 10, e.g., 0.5 to 2 or greater than 3, such as 3 to 10, 3 to 7, or 3 to 5. The width and depths of the first channel may or may not be constant over its length. In particular, the width may increase or decrease adjacent the distal end. In general, channels may be of any suitable cross section, such as a rectangular, triangular, or circular, or a combination thereof. In particular embodiments, a channel may include a groove along the bottom surface. The width or depth of the channel may also increase or decrease, e.g., in discrete portions, to alter the rate of flow of liquid or particles or the alignment of particles.

Devices and systems of the invention may include additional channels that intersect the first channel between its proximal and distal ends, e.g., one or more side-channels (e.g., a first side-channel and optionally a second side-channel) and/or one or more additional channel (e.g., a second channel).

Funnels and/or side-channels may be used to control particle (e.g., bead) flow, e.g., to provide evenly spaced particles (e.g., beads).

In some cases, a particle channel (e.g., the first channel) may include one or more funnels, each funnel having a funnel proximal end, a funnel distal end, a funnel width, and a funnel depth, and each funnel proximal end has a funnel inlet, and each funnel distal end has a funnel outlet. In some cases, the particle channel (e.g., the first channel) includes 1 to 5 (e.g., 1 to 4, 1 to 3, 1 to 2, or 1) funnel(s). For example, the particle channel (e.g., the first channel) may include 1, 2, 3, 4, or 5 funnel(s). In some cases, at least one funnel is a mini-rectifier. In some cases, at least one funnel is a rectifier. For example, the particle channel (e.g., the first channel) may include 1, 2, or 3 rectifiers and 1, 2, or 3 mini-rectifiers. In some cases, the first channel may include a funnel (e.g., a rectifier) between the first reservoir and the proximal channel intersection (e.g., a proximal intersection of the first channel and the first side-channel, or an intersection of the first channel and the second channel). In some cases, the first channel may include a funnel (e.g., a rectifier) in its proximal portion, e.g., the funnel (e.g., the rectifier) inlet may be fluidically connected to the first reservoir. In some cases, the first channel may include a funnel (e.g., a rectifier) in its distal portion, e.g., the funnel (e.g., the rectifier) outlet may be fluidically connected to the distal channel intersection (e.g., a distal intersection of the first channel and the first side-channel, or an intersection of the first channel and the second channel). In some cases, the first channel may include one or more (e.g., 1, 2, or 3) funnels (e.g., mini-rectifiers) in its middle portion, e.g., between a distal funnel inlet and a proximal funnel outlet or a proximal intersection of the first channel and the first side-channel.

In some cases, a sample channel (e.g., the second channel) may include one or more funnels, each funnel having a funnel proximal end, a funnel distal end, a funnel width, and a funnel depth, and each funnel proximal end has a funnel inlet, and each funnel distal end has a funnel outlet. In some cases, the sample channel (e.g., the second channel) includes 1 to 5 (e.g., 1 to 4, 1 to 3, 1 to 2, or 1) funnel(s). For example, the sample channel (e.g., the second channel) may include 1, 2, 3, 4, or 5 funnel(s). In some cases, at least one funnel is a mini-rectifier. In some cases, at least one funnel is a rectifier. For example, the sample channel (e.g., the second channel) may include 1, 2, or 3 rectifiers and 1, 2, or 3 mini-rectifiers. In some cases, the second channel may include a funnel (e.g., a rectifier) between the second reservoir and a channel intersection (e.g., an intersection of the first channel and the second channel, an intersection of the second channel and the first side-channel, or an intersection of the second channel and the third channel). In some cases, the second channel may include a funnel (e.g., a rectifier) in its proximal portion, e.g., the funnel (e.g., the rectifier) inlet may be fluidically connected to the second reservoir. In some cases, the second channel may include a funnel (e.g., a rectifier) in its distal portion, e.g., the funnel (e.g., the rectifier) outlet may be fluidically connected to the channel intersection (e.g., an intersection of the first channel and the second channel, an intersection of the second channel and the first side-channel, or an intersection of the second channel and the third channel). In some cases, the second channel may include one or more (e.g., 1, 2, or 3) funnels (e.g., mini-rectifiers) in its middle portion, e.g., between a distal funnel inlet and a proximal funnel outlet or a channel intersection (e.g., an intersection of the first channel and the second channel, an intersection of the second channel and the first side-channel, or an intersection of the second channel and the third channel).

One or more funnels may include hurdle(s) (e.g., 1, 2, or 3 hurdles in one funnel). The hurdle may be a row of pegs, a barrier, or a combination thereof. The hurdles may be disposed anywhere within the funnel, e.g., closer to the funnel inlet, closer to the funnel outlet, or in the middle. Typically, when rows of pegs are included in the funnel, at least two rows of pegs are included. Pegs may have a diameter of 40 µm to 100 µm (e.g., 50 µm to 100 µm, 60 µm to 100 µm, 70 µm to 100 µm, 80 µm to 100 µm, 90 µm to 100 µm, 40 µm to 90 µm, 50 µm to 90 µm, 60 µm to 90 µm, 70 µm to 90 µm, 80 µm to 90 µm, 40 µm to 80 µm, 50 µm to 80 µm, 60 µm to 80 µm, 70 µm to 80 µm, 40 µm to 70 µm, 50 µm to 70 µm, or 60 µm to 70 µm). Pegs may have a width of 40 µm to 100 µm (e.g., 50 µm to 100 µm, 60 µm to 100 µm, 70 µm to 100 µm, 80 µm to 100 µm, 90 µm to 100 µm, 40 µm to 90 µm, 50 µm to 90 µm, 60 µm to 90 µm, 70 µm to 90 µm, 80 µm to 90 µm, 40 µm to 80 µm, 50 µm to 80 µm, 60 µm to 80 µm, 70 µm to 80 µm, 40 µm to 70 µm, 50 µm to 70 µm, or 60 µm to 70 µm). Pegs may have a peg length and a peg width, and the peg length may be greater than the peg width (e.g., the peg length may be at least 10%, 25%, 50%, 75%, 100%, 150%, 200%, or 300% greater than the peg width; e.g., the peg length may be 10% to 1000%, 10% to 900%, 10% to 800%, 10% to 700%, 10% to 600%, 50% to 1000%, 50% to 900%, 50% to 800%, 50% to 700%, 50% to 600%, 100% to 1000%, 100% to 900%, 100% to 800%, 100% to 700%, 100% to 600%, 200% to 1000%, 200% to 900%, 200% to 800%, 200% to 700%, or 200% to 600% greater than the peg width). Individual pegs may be spaced at a distance sized to allow at least one particle through the row of pegs (e.g., the distance between individual pegs may be 100% to 500% of the particle diameter). For example, the distance between individual pegs may be at least same as the diameter of a particle (e.g., 100% to 1000% of the particle diameter, 100% to 900% of the particle diameter, 100% to 800% of the particle diameter, 100% to 700% of the particle diameter, 100% to 600% of the particle diameter, or 100% to 500% of the particle diameter), for which the funnel is configured. For example, individual pegs may be spaced at 50 µm to 100 µm (e.g., 60 µm to 100 µm, 70 µm to 100 µm, 80 µm to 100 µm, 90 µm to 100 µm, 50 µm to 90 µm, 60 µm to 90 µm, 70 µm to 90 µm, 80 µm to 90 µm, 50 µm to 80 µm, 60 µm to 80 µm, 70 µm to 80 µm, 50 µm to 70 µm, 60 µm to 70 µm, or 50 µm to 60 µm) from each other. A barrier may have a height that leaves space between the barrier and the opposite funnel wall sized to permit a particle through the space (e.g., the height between the barrier and the funnel wall may be 50% to 400% of the particle diameter). For example, the height between the barrier and the funnel wall may be at least 50% of the particle diameter, for which the funnel is configured (e.g., at least 60%, at least 70%, at least 80%, at least 90%, at least 100% of the particle diameter; e.g., 400% or less, 300% or less, 200% or less of the particle diameter). The barrier may have a height that is at least 100% of the particle diameter, for which the funnel is configured (e.g., at least 200%, at least 300%, at least 400%, at least 500%, at least 600%, or at least 700% of the particle diameter; 800% or less, 700% or less, 600% or less, 500% or less, 400% or less, 300% or less, 200% or less of the particle diameter). A barrier may have a height of at least 20 µm (e.g., at least 30 µm, at least 40 µm, at least 50 µm, or at least 60 µm). For example, a barrier may have a height of 20 µm to 70 µm (e.g., 30 µm to 70 µm, 40 µm to 70 µm, 50 µm to 70 µm, 60 µm to 70 µm, 20 µm to 60 µm, 30 µm to 60 µm, 40 µm to 60 µm, 50 µm to 60 µm, 20 µm to 50 µm, 30 µm to 50 µm, 40 µm to 50 µm, 20 µm to 40 µm, 30 µm to 40 µm, or 20 µm to 30 µm).

In some cases, a reagent channel (e.g., the first channel) may intersect one or more side-channels (e.g., a first side-channel and optionally a second side-channel). In the devices and systems of the invention including a first side-channel, the first side-channel has a first side-channel depth, a first side-channel width, a first side-channel proximal end, and a first side-channel distal end. The first side-channel proximal end is fluidically connected to the first channel at a first proximal intersection between the first proximal end and the first distal end, and the first side-channel distal end is fluidically connected to the first channel at a first distal intersection between the first proximal intersection and the first distal end. The first side-channel includes a proximal end including one or more first side-channel inlets, and the first side-channel distal end includes one or more first side-channel outlets. The first side-channel may further include a first side-channel reservoir configured for holding a liquid. The first side-channel may be sized at its inlet to substantially prevent ingress of particles from the first channel. Accordingly, each of the one or more first side-channel inlets may have at least one dimension smaller than the smaller of the first depth and the first width. Each of the one or more first side-channel outlets may have at least one dimension smaller than the smaller of the first depth and the first width. For example, the first side-channel depth may be at least 25% (e.g., at least 50%) smaller than the first depth. Alternatively, the first side-channel may include a filter at its inlet and optionally at its outlet. The filter may be a row of spaced pegs disposed across the first side-channel inlet.

Additionally, in the devices and systems of the invention including a second side-channel, the second side-channel has a second side-channel depth, a second side-channel width, a second side-channel proximal end, and a second side-channel distal end. When the device or system of the invention includes the second side-channel, the second side-channel proximal end is fluidically connected to the first channel at a second proximal intersection between the first proximal end and the first distal end, and the second side-channel distal end is fluidically connected to the first channel at a second distal intersection between the second proximal intersection and the first distal end. The second side-channel optionally includes a reservoir configured for holding a liquid. Preferably, the first proximal intersection is substantially opposite the second proximal intersection. Also preferably, the first distal intersection is substantially opposite the second distal intersection. The arrangement of first and second (e.g., proximal and/or distal) intersections being substantially opposite each other may be particularly advantageous for reducing the amount of excess liquid between consecutive particles or for reducing the bunching of consecutive particles. The second side-channel at its inlet may further include a second side-channel reservoir configured for holding a liquid. The second side-channel may be sized to substantially prevent ingress of particles from the first channel. Accordingly, each of the one or more second side-channel inlets may have at least one dimension smaller than the smaller of the first depth and the first width. Each of the one or more second side-channel outlets may have at least one dimension smaller than the smaller of the first depth and the first width. For example, the second side-channel depth may be at least 25% (e.g., at least 50%) smaller than the first depth. Alternatively, the second side-channel may include a filter at its inlet and optionally at its outlet. The filter may be a row of spaced pegs disposed across the second side-channel inlet.

The side-channel reservoirs (e.g., the first side-channel reservoir and/or the second side-channel reservoir), when present, may be configured for controlling pressure in the side-channels to improve control over spacing between particles, thereby further enhancing droplet-to-droplet content uniformity (e.g., uniformity in the number of particles from the same source (e.g., of the same kind)). For example, a third liquid may be included in the side-channel reservoir, and the amount of the third liquid may control the pressure in the side-channels. Alternatively, the pressure control in the side-channel may be active or passive. Pressure control may be achieved using channel reservoirs. For example, the channel pressure may be passively controlled by controlling the amount of liquid in a reservoir, as the height level of the liquid may control the hydrostatic pressure exerted on the channel. Alternatively, the channel pressure may be actively controlled using a pump connected to the reservoir such that the pump applies a predetermined pressure to the liquid in the reservoir.

Additionally or alternatively, devices and systems of the invention may include one or more second channels having a second depth, a second width, a second proximal end, and a second distal end. Each of the first proximal end and second proximal ends are or are configured to be in fluid communication with, e.g., fluidically connected to, a source of liquid, e.g., a reservoir integral to the device or coupled to the device, e.g., by tubing.

The inclusion of one or more intersection channels allows for splitting liquid from the first channel or introduction of liquids into the first channel, e.g., that combine with the liquid in the first channel or do not combine with the liquid in the first channel, e.g., to form a sheath flow. Channels can intersect the first channel at any suitable angle, e.g., between 5° and 135° relative to the centerline of the first channel, such as between 75° and 115° or 85° and 95°. Additional channels may similarly be present to allow introduction of further liquids or additional flows of the same liquid. Multiple channels can intersect the first channel on the same side or different sides of the first channel. When multiple channels intersect on different sides, the channels may intersect along the length of the first channel to allow liquid introduction at the same point. Alternatively, channels may intersect at different points along the length of the first channel. In some instances, a channel configured to direct a liquid comprising a plurality of particles may comprise one or more grooves in one or more surface of the channel to direct the plurality of particles towards the droplet formation fluidic connection. For example, such guidance may increase single occupancy rates of the generated droplets. These additional channels may have any of the structural features discussed above for the first channel.

Devices may include multiple first channels, e.g., to increase the rate of droplet formation. In general, throughput may significantly increase by increasing the number of droplet formation regions of a device. For example, a device having five droplet formation regions may generate five times as many droplets than a device having one droplet formation region, provided that the liquid flow rate is substantially the same. A device may have as many droplet formation regions as is practical and allowed for the size of the source of liquid, e.g., reservoir. For example, the device may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 2000 or more droplet formation regions. Inclusion of multiple droplet formation regions may require the inclusion of channels that traverse but do not intersect, e.g., the flow path is in a different plane. Multiple first channel may be in fluid communication with, e.g., fluidically connected to, a separate source reservoir and/or a separate droplet formation region. In other embodiments, two or more first channels are in fluid communication with, e.g., fluidically connected to, the same fluid source, e.g., where the multiple first channels branch from a single, upstream channel. The droplet formation region may include a plurality of inlets in fluid communication with the first proximal end and a plurality of outlets (e.g., plurality of outlets in fluid communication with a collection region) (e.g., fluidically connected to the first proximal end and in fluid communication with a plurality of outlets). The number of inlets and the number of outlets in the droplet formation region may be the same (e.g., there may be 3-10 inlets and/or 3-10 outlets). Alternatively or in addition, the throughput of droplet formation can be increased by increasing the flow rate of the first liquid, third liquid (when present), and/or fourth liquid (when present). In some cases, the throughput of droplet formation can be increased by having a plurality of single droplet forming devices, e.g., devices with a first channel and a droplet formation region, in a single device, e.g., parallel droplet formation.

The devices, kits, systems, and methods of the invention may include a mixer. The mixer may be included downstream of an intersection where two different liquids from two intersecting channels are combined.

A second channel may include a mixer, e.g., a passive mixer (e.g., a chaotic advection mixer). The mixer may be included downstream of an intersection between the second and third channels. In this configuration, a third liquid may be combined with a fourth liquid at the intersection. The combined second and third liquids may be mixed in the second channel mixer. The mixed second and third liquids may then be combined with a first liquid at an intersection between the first and second channels downstream from the mixer.

Alternatively, the first side-channel may include a mixer, e.g., a passive mixer (e.g., a chaotic advection mixer). For example, a mixer may be included in the first side-channel between an intersection of the first side-channel with the second channel and an intersection of the first side-channel with the first channel. In this configuration, a first liquid flowing through the first side-channel may be first combined with the third liquid at the intersection of the first side-channel with the second channel. The combined first and third liquids may be mixed in the first side-channel mixer and are then combined with the liquid in the first channel.

Mixers that may be included in the devices and systems of the invention are known in the art. Non-limiting examples of mixers include a herringbone mixer, connected-groove mixer, modified staggered herringbone mixer, wavy-wall channel mixer, chessboard mixer, alternate-injection mixer with an increased cross-section chamber, serpentine laminating micromixer, two-layer microchannel mixer, connected-groove micromixer, and SAR mixer. Non-limiting examples of mixers are described in Suh and Kang, *Micromachines*, 1:82-111, 2010; Lee et al., *Int. J. Mol. Sci.*, 12:3263-3287, 2011; and Lee et al., *Chem. Eng. J.*, 288: 146-160, 2016. Typically, the mixer may be sized to accommodate particles passing through (e.g., biological particles, such as cells). The mixer may have a length of 2-15 mm (e.g., 2, 3, 4, 5, 6, 7, 8, 9, 10, 11, 12, 13, 14, or 15 mm).

Alternatively or additionally, the device may include one or more traps in channels. The traps may be included in channels in a configuration that permits air buoyancy to raise any bubbles away from the liquid flow. Thus, a trap typically has a trap depth that is greater than the depth of the channel, in which the trap is disposed. One of skill in the art will recognize that the terms depth and height may be used interchangeably to indicate the same dimension.

Droplets may be formed in a device by flowing a first liquid through a channel and into a droplet formation region including a second liquid, i.e., the continuous phase, which may or may not be externally driven. Thus, droplets can be formed without the need for externally driving the second liquid. The size of the generated droplets is significantly less sensitive to changes in liquid properties. For example, the size of the generated droplets is less sensitive to the dispersed phase flow rate. Adding multiple formation regions is also significantly easier from a layout and manufacturing standpoint. The addition of further formation regions allows for formation of droplets even in the event that one droplet formation region becomes blocked. Droplet formation can be controlled by adjusting one or more geometric features of fluidic channel architecture, such as a width, depth, and/or expansion angle of one or more fluidic channels. For example, droplet size and speed of droplet formation may be controlled. In some instances, the number of regions of formation at a driven pressure can be increased to increase the throughput of droplet formation.

Droplets may be formed by any suitable method known in the art. In general, droplet formation includes two liquid phases. The two phases may be, for example, an aqueous phase and an oil phase. During droplet formation, a plurality of discrete volume droplets is formed.

The droplets may be formed by shaking or stirring a liquid to form individual droplets, creating a suspension or an emulsion containing individual droplets, or forming the droplets through pipetting techniques, e.g., with needles, or the like. The droplets may be formed made using a micro-, or nanofluidic droplet maker. Examples of such droplet makers include, e.g., a T-junction droplet maker, a Y-junction droplet maker, a channel-within-a-channel junction droplet maker, a cross (or "X") junction droplet maker, a flow-focusing junction droplet maker, a micro-capillary droplet maker (e.g., co-flow or flow-focus), and a three-dimensional droplet maker. The droplets may be produced using a flow-focusing device, or with emulsification systems, such as homogenization, membrane emulsification, shear cell emulsification, and fluidic emulsification.

Discrete liquid droplets may be encapsulated by a carrier fluid that wets the microchannel. These droplets, sometimes known as plugs, form the dispersed phase in which the reactions occur. Systems that use plugs differ from segmented-flow injection analysis in that reagents in plugs do not come into contact with the microchannel. In T junctions, the disperse phase and the continuous phase are injected from two branches of the "T". Droplets of the disperse phase are produced as a result of the shear force and interfacial tension at the fluid-fluid interface. The phase that has lower interfacial tension with the channel wall is the continuous phase. To generate droplets in a flow-focusing configuration, the continuous phase is injected through two outside channels and the disperse phase is injected through a central channel into a narrow orifice. Other geometric designs to create droplets would be known to one of skill in the art. Methods of producing droplets are disclosed in Song et al. *Angew. Chem.* 45: 7336-7356, 2006, Mazutis et al. *Nat. Protoc.* 8(5):870-891, 2013, U.S. Pat. No. 9,839,911; U.S. Pub. Nos. 2005/0172476, 2006/0163385, and 2007/0003442, PCT Pub. Nos. WO 2009/005680 and WO 2018/009766. In some cases, electric fields or acoustic waves may be used to produce droplets, e.g., as described in PCT Pub. No. WO 2018/009766.

In some cases, a droplet formation region may allow liquid from the first channel to expand in at least one dimension, leading to droplet formation under appropriate conditions as described herein. A droplet formation region can be of any suitable geometry. In one embodiment, the droplet formation region includes a shelf region that allows liquid to expand substantially in one dimension, e.g., perpendicular to the direction of flow. The width of the shelf region is greater than the width of the first channel at its distal end. In certain embodiments, the first channel is a channel distinct from a shelf region, e.g., the shelf region widens or widens at a steeper slope or curvature than the distal end of the first channel. In other embodiments, the first channel and shelf region are merged into a continuous flow path, e.g., one that widens linearly or non-linearly from its proximal end to its distal end; in these embodiments, the distal end of the first channel can be considered to be an arbitrary point along the merged first channel and shelf region. In another embodiment, the droplet formation region includes a step region, which provides a spatial displacement and allows the liquid to expand in more than one dimension. The spatial displacement may be upward or downward or both relative to the channel. The choice of direction may be made based on the relative density of the dispersed and continuous phases, with an upward step employed when the dispersed phase is less dense than the continuous phase and a downward step employed when the dispersed phase is denser than the continuous phase. Droplet formation regions may also include combinations of a shelf and a step region, e.g., with the shelf region disposed between the channel and the step region.

Without wishing to be bound by theory, droplets of a first liquid can be formed in a second liquid in the devices of the invention by flow of the first liquid from the distal end into the droplet formation region. In embodiments with a shelf region and a step region, the stream of first liquid expands laterally into a disk-like shape in the shelf region. As the stream of first liquid continues to flow across the shelf region, the stream passes into the step region wherein the droplet assumes a more spherical shape and eventually detaches from the liquid stream. As the droplet is forming, passive flow of the continuous phase around the nascent droplet occurs, e.g., into the shelf region, where it reforms the continuous phase as the droplet separates from its liquid stream. Droplet formation by this mechanism can occur without externally driving the continuous phase, unlike in other systems. It will be understood that the continuous phase may be externally driven during droplet formation, e.g., by gently stirring or vibration but such motion is not necessary for droplet formation.

Passive flow of the continuous phase may occur simply around the nascent droplet. The droplet formation region may also include one or more channels that allow for flow of the continuous phase to a location between the distal end of the first channel and the bulk of the nascent droplet. These channels allow for the continuous phase to flow behind a nascent droplet, which modifies (e.g., increase or decreases) the rate of droplet formation. Such channels may be fluidically connected to a reservoir of the droplet formation region or to different reservoirs of the continuous phase. Although externally driving the continuous phase is not necessary, external driving may be employed, e.g., to pump continuous phase into the droplet formation region via additional channels. Such additional channels may be to one or both lateral sides of the nascent droplet or above or below the plane of the nascent droplet.

The width of a shelf region may be from 0.1 µm to 1000 µm. In particular embodiments, the width of the shelf is from 1 to 750 µm, 10 to 500 µm, 10 to 250 µm, or 10 to 150 µm. The width of the shelf region may be constant along its length, e.g., forming a rectangular shape. Alternatively, the width of the shelf region may increase along its length away from the distal end of the first channel. This increase may be linear, nonlinear, or a combination thereof. In certain embodiments, the shelf widens 5% to 10,000%, e.g., at least 300%, (e.g., 10% to 500%, 100% to 750%, 300% to 1000%, or 500% to 1000%) relative to the width of the distal end of the first channel. The depth of the shelf can be the same as or different from the first channel. For example, the bottom of the first channel at its distal end and the bottom of the shelf region may be co-planar. Alternatively, a step or ramp may be present where the distal end meets the shelf region. The depth of the distal end may also be greater than the shelf region, such that the first channel forms a notch in the shelf region. The depth of the shelf may be from 0.1 to 1000 µm, e.g., 1 to 750 µm, 1 to 500 µm, 1 to 250 µm, 1 to 100 µm, 1 to 50 µm, or 3 to 40 µm. In some embodiments, the depth is substantially constant along the length of the shelf. Alternatively, the depth of the shelf slopes, e.g., downward or upward, from the distal end of the liquid channel to the step region. The final depth of the sloped shelf may be, for example, from 5% to 1000% greater than the shortest depth, e.g., 10 to 750%, 10 to 500%, 50 to 500%, 60 to 250%, 70 to 200%, or 100 to 150%. The overall length of the shelf region may be from at least about 0.1 µm to about 1000 µm, e.g., 0.1 to 750 µm, 0.1 to 500 µm, 0.1 to 250 µm, 0.1 to 150 µm, 1 to 150 µm, 10 to 150 µm, 50 to 150 µm, 100 to 150 µm, 10 to 80 µm, or 10 to 50 µm. In certain embodiments, the lateral walls of the shelf region, i.e., those defining the width, may be not parallel to one another. In other embodiments, the walls of the shelf region may narrower from the distal end of the first channel towards the step region. For example, the width of the shelf region adjacent the distal end of the first channel may be sufficiently large to support droplet formation. In other embodiments, the shelf region is not substantially rectangular, e.g., not rectangular or not rectangular with rounded or chamfered corners.

A step region includes a spatial displacement (e.g., depth). Typically, this displacement occurs at an angle of approximately 90°, e.g., between 85° and 95°. Other angles are possible, e.g., 10-90°, e.g., 20 to 90°, 45 to 90°, or 70 to 90°. The spatial displacement of the step region may be any suitable size to be accommodated on a device, as the ultimate extent of displacement does not affect performance of the device. Preferably the displacement is several times the diameter of the droplet being formed. In certain embodiments, the displacement is from about 1 µm to about 10 cm, e.g., at least 10 µm, at least 40 µm, at least 100 µm, or at least 500 µm, e.g., 40 µm to 600 µm. In some embodiments, the displacement is at least 40 µm, at least 45 µm, at least 50 µm, at least 55 µm, at least 60 µm, at least 65 µm, at least 70 µm, at least 75 µm, at least 80 µm, at least 85 µm, at least 90 µm, at least 95 µm, at least 100 µm, at least 110 µm, at least 120 µm, at least 130 µm, at least 140 µm, at least 150 µm, at least 160 µm, at least 170 µm, at least 180 µm, at least 190 µm, at least 200 µm, at least 220 µm, at least 240 µm, at least 260 µm, at least 280 µm, at least 300 µm, at least 320 µm, at least 340 µm, at least 360 µm, at least 380 µm, at least 400 µm, at least 420 µm, at least 440 µm, at least 460 µm, at least 480 µm, at least 500 µm, at least 520 µm, at least 540 µm, at least 560 µm, at least 580 µm, or at least 600 µm. In some cases, the depth of the step region is substantially constant. Alternatively, the depth of the step region may increase away from the shelf region, e.g., to allow droplets that sink or float to roll away from the spatial displacement as they are formed. The step region may also increase in depth in two dimensions relative to the shelf region, e.g., both above and below the plane of the shelf region. The reservoir may have an inlet and/or an outlet for the addition of continuous phase, flow of continuous phase, or removal of the continuous phase and/or droplets.

While dimension of the devices may be described as width or depths, the channels, shelf regions, and step regions may be disposed in any plane. For example, the width of the shelf may be in the x-y plane, the x-z plane, the y-z plane or any plane therebetween. In addition, a droplet formation region, e.g., including a shelf region, may be laterally spaced in the x-y plane relative to the first channel or located above or below the first channel. Similarly, a droplet formation region, e.g., including a step region, may be laterally spaced in the x-y plane, e.g., relative to a shelf region or located above or below a shelf region. The spatial displacement in a step region may be oriented in any plane suitable to allow the nascent droplet to form a spherical shape. The fluidic components may also be in different planes so long as connectivity and other dimensional requirements are met.

The device may also include reservoirs for liquid reagents. For example, the device may include a reservoir for the liquid to flow in the first channel and/or a reservoir for the liquid into which droplets are formed. In some cases, devices of the invention include a collection region, e.g., a volume for collecting formed droplets. A droplet collection region may be a reservoir that houses continuous phase or can be any other suitable structure, e.g., a channel, a shelf, a chamber, or a cavity, on or in the device. For reservoirs or other elements used in collection, the walls may be smooth and not include an orthogonal element that would impede droplet movement. For example, the walls may not include any feature that at least in part protrudes or recedes from the surface. It will be understood, however, that such elements may have a ceiling or floor. The droplets that are formed may be moved out of the path of the next droplet being formed by gravity (either upward or downward depending on the relative density of the droplet and continuous phase). Alternatively or in addition, formed droplets may be moved out of the path of the next droplet being formed by an external force applied to the liquid in the collection region, e.g., gentle stirring, flowing continuous phase, or vibration. Similarly, a reservoir for liquids to flow in additional channels, such as those intersecting the first channel may be present. A single reservoir may also be connected to multiple channels in a device, e.g., when the same liquid is to be introduced at two or more different locations in the device. Waste reservoirs or overflow reservoirs may also be included to collect waste or overflow when droplets are formed. Alternatively, the device may be configured to mate with sources of the liquids, which may be external reservoirs such as vials, tubes, or pouches. Similarly, the device may be configured to mate with a separate component that houses the reservoirs. Reservoirs may be of any appropriate size, e.g., to hold 10 µL to 500 mL, e.g., 10 µL to 300 mL, 25 µL to 10 mL, 100 µL to 1 mL, 40 µL to 300 µL, 1 mL to 10 mL, or 10 mL to 50 mL. When multiple reservoirs are present, each reservoir may have the same or a different size.

Figure 53A:
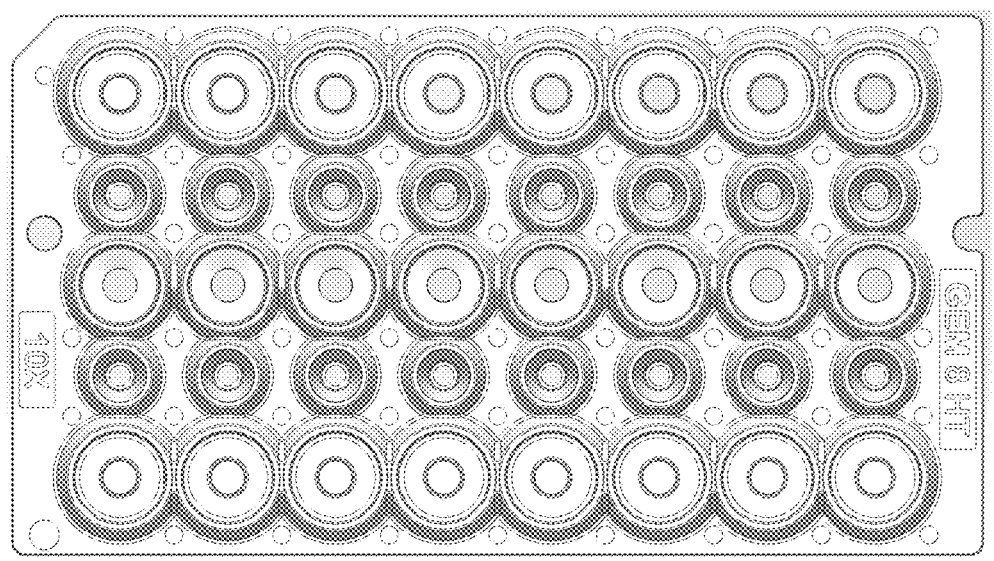
FIGS. 53A-53C are depictions of reservoirs in a multiplex device of the invention.
Figure 53B:
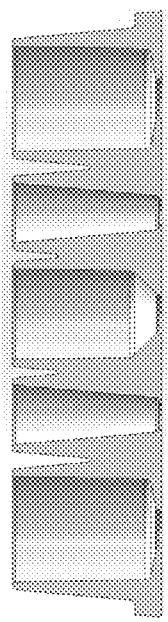
Figure 53C:
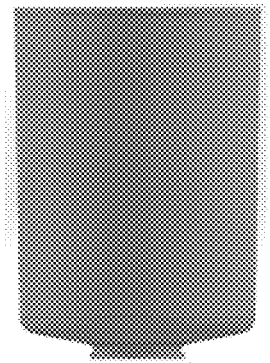
Figure 53C:
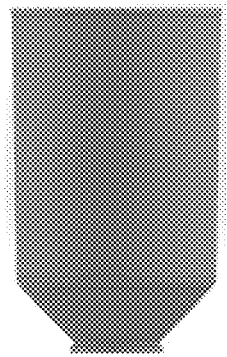
Figure 53C:
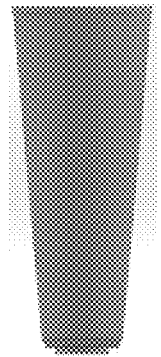

In some instances, reservoirs, e.g., collection reservoirs, sample reservoirs, and/or reagent reservoirs, may hold about 10 µL to about 1 ml, e.g., about 10 µL to about 500 µL, about 10 µL to about 750 µL, about 10 µL to about 50 µL, about 40 µL to about 80 µL, about 20 µL to about 100 µL, about 70 µL to about 100 µL, about 90 µL to about 120 µL, about 110 µL to about 150 µL, about 140 µL to about 190 about µL, about 180 µL to about 220 µL, about 210 µL to about 250 µL, about 240 µL to about 280 µL, about 270 µL to about 340 µL, about 330 µL to about 345 µL, about 340 µL to about 375 µL, about 370 µL to about 420 µL, about 410 µL to about 470 µL, or about 460 µL to about 500 µL. In some instances, the reservoirs may hold about 480 µL, about 340 µL, about 280 µL, about 220 µL, about 110 µL or about 80 µL. Typically, the volume of the collection reservoir is equal to or greater than the volumes of the sample and reagent reservoirs (or portions thereof) that empty into it. An exemplary device reservoir design is depicted in FIGS. 53A-53C.

In some instances, the reservoirs are filled between 20% and 98% of the volume, e.g., about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, or 98%. In some instances, the reservoirs are filled between 20% and 35%, between 30% and 45%, between 40% and 55%, between 50% and 65%, between 60% and 75%, between 70% and 85%, between 80% and 95%, or between 90% and 98%.

Alternatively or in addition, reservoirs, e.g., collection reservoirs, sample reservoirs, and/or reagent reservoirs, may include a side wall canted between a 89.5° and 4° angle, e.g., between a 85° and 5° angle, e.g., about a 89°, 88°, 87°, 86°, 85°, 84°, 83°, 82°, 81°, 80°, 79°, 78°, 77°, 76°, 75°, 74°, 73°, 72°, 71°, 70°, 69°, 68°, 67°, 66°, 65°, 64°, 63°, 62°, 61°, 60°, 59°, 58°, 57°, 56°, 55°, 54°, 53°, 52°, 51°, 50°, 49°, 48°, 47°, 46°, 45°, 44°, 43°, 42°, 41°, 40°, 39°, 38°, 37°, 36°, 35°, 34°, 33°, 32°, 31°, 30°, 29°, 28°, 27°, 26°, 25°, 24°, 23°, 22°, 21°, 20°, 19°, 18°, 17°, 16°, 15°, 14°, 13°, 12°, 11°, 10°, 9°, 8°, 7°, 6°, or 5° angle. In some instances, the side wall is canted between 85° and 70°, between 75° and 60°, between 65° and 50°, between 55° and 48°, between 50° and 43°, between 46° and 44°, between 44° and 35°, between 37° and 25°, between 30° and 15°, or between 20° and 5°. In certain embodiments, the side wall may be canted at two or more angles at various vertical heights. In other embodiments, the side wall is canted for a portion of the height and vertical for a portion of the height. For example, the side wall may be canted for 5-100% of the height, e.g., for 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. In some instances, the side wall may be canted for between 100% and 85%, between 100% and 75%, between 100% and 50%, between 90% and 75%, between 80% and 65%, between 70% and 55%, between 60% and 45%, between 50% and 35%, between 50% and 5%, between 40% and 25%, between 30% and 15%, or between 20% and 5%. When the side wall is canted at two or more angles, the canted portions may have the same vertical height or different vertical heights. For example, for two canted portions, the higher angled portion may be between 5 to 95% of the canted portion of the side wall, e.g., 5 to 75% 5 to 50%, 5 to 25%, 50 to 95%, 50 to 75%, 75 to 95%, 25 to 75%, 25 to 50%, or 40 to 60%.

Alternatively, or in addition, reservoirs, e.g., collection reservoirs, sample reservoirs, and/or reagent reservoirs, may include canted sidewalls, slots, and slots with protrusions, i.e., expanding the opening of the slot, at the interface between the reservoir and the channel. In some embodiments, the canted sidewalls are an oblique circular cone shape, a circular cone that tapers to a slot, or a circular cone that tapers to a slot with protrusions at the interface between the reservoir and the channel. Exemplary device reservoir designs are depicted in FIGS. 64-67.

The vertical height of a reservoir, e.g., collection reservoir, sample reservoir, and/or reagent reservoir, may be between 1 and 20 mm, e.g., 1 to 5 mm, 1 to 10 mm, 1 to 15 mm, 5 to 10 mm, 5 to 15 mm, 10 to 22 mm, 2 to 7 mm, 7 to 13 mm, 12 to 18 mm or at least 5, at least 10, or at least 15 mm.

In addition to the components discussed above, devices of the invention can include additional components. For example, channels may include filters to prevent introduction of debris into the device. In some cases, the microfluidic systems described herein may comprise one or more liquid flow units to direct the flow of one or more liquids, such as the aqueous liquid and/or the second liquid immiscible with the aqueous liquid. In some instances, the liquid flow unit may comprise a compressor to provide positive pressure at an upstream location to direct the liquid from the upstream location to flow to a downstream location. In some instances, the liquid flow unit may comprise a pump to provide negative pressure at a downstream location to direct the liquid from an upstream location to flow to the downstream location. In some instances, the liquid flow unit may comprise both a compressor and a pump, each at different locations. In some instances, the liquid flow unit may comprise different devices at different locations. The liquid flow unit may comprise an actuator. In some instances, where the second liquid is substantially stationary, the reservoir may maintain a constant pressure field at or near each droplet formation region. Devices may also include various valves to control the flow of liquids along a channel or to allow introduction or removal of liquids or droplets from the device. Suitable valves are known in the art. Valves useful for a device of the present invention include diaphragm valves, solenoid valves, pinch valves, or a combination thereof. Valves can be controlled manually, electrically, magnetically, hydraulically, pneumatically, or by a combination thereof. The device may also include integral liquid pumps or be connectable to a pump to allow for pumping in the first channels and any other channels requiring flow. Examples of pressure pumps include syringe, peristaltic, diaphragm pumps, and sources of vacuum. Other pumps can employ centrifugal or electrokinetic forces. Alternatively, liquid movement may be controlled by gravity, capillarity, or surface treatments. Multiple pumps and mechanisms for liquid movement may be employed in a single device. The device may also include one or more vents to allow pressure equalization, and one or more filters to remove particulates or other undesirable components from a liquid. The device may also include one or more inlets and or outlets, e.g., to introduce liquids and/or remove droplets. Such additional components may be actuated or monitored by one or more controllers or computers operatively coupled to the device, e.g., by being integrated with, physically connected to (mechanically or electrically), or by wired or wireless connection.

Alternatively or in addition to controlling droplet formation via microfluidic channel geometry, droplet formation may be controlled using one or more piezoelectric elements. Piezoelectric elements may be positioned inside a channel (i.e., in contact with a fluid in the channel), outside the channel (i.e., isolated from the fluid), or a combination thereof. In some cases, the piezoelectric element may be at the exit of a channel, e.g., where the channel connects to a reservoir or other channel, that serves as a droplet generation point. For example, the piezoelectric element may be integrated with the channel or coupled or otherwise fastened to the channel. Examples of fastenings include, but are not limited to, complementary threading, form-fitting pairs, hooks and loops, latches, threads, screws, staples, clips, clamps, prongs, rings, brads, rubber bands, rivets, grommets, pins, ties, snaps, adhesives (e.g., glue), tapes, vacuum, seals, magnets, or a combination thereof. In some instances, the piezoelectric element can be built into the channel. Alternatively or in addition, the piezoelectric element may be connected to a reservoir or channel or may be a component of a reservoir or channel, such as a wall. In some cases, the piezoelectric element may further include an aperture therethrough such that liquids can pass upon actuation of the piezoelectric element, or the device may include an aperture operatively coupled to the piezoelectric element.

The piezoelectric element can have various shapes and sizes. The piezoelectric element may have a shape or cross-section that is circular, triangular, square, rectangular, or partial shapes or combination of shapes thereof. The piezoelectric element can have a thickness from about 100 micrometers (μm) to about 100 millimeters (mm). The piezoelectric element can have a dimension (e.g., cross-section) of at least about 1 mm. The piezoelectric element can be formed of, for example, lead zirconate titanate, zinc oxide, barium titanate, potassium niobate, sodium tungstate, $Ba_2NaNb_5O_5$, and $Pb_2KNb_5O_{15}$. The piezoelectric element, for example, can be a piezo crystal. The piezoelectric element may contract when a voltage is applied and return to its original state when the voltage is unapplied. Alternatively, the piezoelectric element may expand when a voltage is applied and return to its original state when the voltage is unapplied. Alternatively or in addition, application of a voltage to the piezoelectric element can cause mechanical stress, vibration, bending, deformation, compression, decompression, expansion, and/or a combination thereof in its structure, and vice versa (e.g., applying some form of mechanical stress or pressure on the piezoelectric element may produce a voltage). In some instances, the piezoelectric element may include a composite of both piezoelectric material and non-piezoelectric material.

In some instances, the piezoelectric element may be in a first state when no electrical charge is applied, e.g., an equilibrium state. When an electrical charge is applied to the piezoelectric element, the piezoelectric element may bend backwards, pulling a part of the first channel outwards, and drawing in more of the first fluid into the first channel via negative pressure, such as from a reservoir of the first fluid. When the electrical charge is altered, the piezoelectric element may bend in another direction (e.g., inwards towards the contents of the channel), pushing a part of the first channel inwards, and propelling (e.g., at least partly via displacement) a volume of the first fluid, thereby generating a droplet of the first fluid in a second fluid. After the droplet is propelled, the piezoelectric element may return to the first state. The cycle can be repeated to generate more droplets. In some instances, each cycle may generate a plurality of droplets (e.g., a volume of the first fluid propelled breaks off as it enters the second fluid to form a plurality of discrete droplets). A plurality of droplets can be collected in a second channel for continued transportation to a different location (e.g., reservoir), direct harvesting, and/or storage.

While the above non-limiting example describes bending of the piezoelectric element in response to application of an electrical charge, the piezoelectric may undergo or experience vibration, bending, deformation, compression, decompression, expansion, other mechanical stress and/or a combination thereof upon application of an electrical charge, which movement may be translated to the first channel.

In some cases, a channel may include a plurality of piezoelectric elements working independently or cooperatively to achieve the desired formation (e.g., propelling) of droplets. For example, a first channel of a device can be coupled to at least 1, 2, 3, 4, 5, 6, 7, 8, 9, 10, 20, 30, 40, 50, 60, 70, 80, 90, 100, 200, 300, 400, or 500 piezoelectric elements. In an example, a separate piezoelectric element may be operatively coupled to (or be integrally part of) each side wall of a channel. In another example, multiple piezoelectric elements may be positioned adjacent to one another along an axis parallel to the direction of flow in the first channel. Alternatively or in addition, multiple piezoelectric elements may circumscribe the first channel. For example, a plurality of piezoelectric elements may each be in electrical communication with the same controller or one or more different controllers. The throughput of droplet generation can be increased by increasing the points of generation, such as increasing the number of junctions between first fluid channels and the second fluid channel. For example, each of the first fluid channels may comprise a piezoelectric element for controlled droplet generation at each point of generation. The piezoelectric element may be actuated to facilitate droplet formation and/or flow of the droplets.

The frequency of application of electrical charge to the piezoelectric element may be adjusted to control the speed of droplet generation. For example, the frequency of droplet generation may increase with the frequency of alternating electrical charge. Additionally, the material of the piezoelectric element, number of piezoelectric elements in the channel, the location of the piezoelectric elements, strength of the electrical charge applied, hydrodynamic forces of the respective fluids, and other factors may be adjusted to control droplet generation and/or size of the droplets generated. For example, without wishing to be bound by a particular theory, if the strength of the electrical charge applied is increased, the mechanical stress experienced by the piezoelectric element may be increased, which can increase the impact on the structural deformation of the first channel, increasing the volume of the first fluid propelled, resulting in an increased droplet size.

In a non-limiting example, the first channel can carry a first fluid (e.g., aqueous) and the second channel can carry a second fluid (e.g., oil) that is immiscible with the first fluid. The two fluids can communicate at a junction. In some instances, the first fluid in the first channel may include suspended particles. The particles may be beads, biological particles, cells, cell beads, or any combination thereof (e.g., a combination of beads and cells or a combination of beads and cell beads, etc.). A discrete droplet generated may include a particle, such as when one or more particles are suspended in the volume of the first fluid that is propelled into the second fluid. Alternatively, a discrete droplet generated may include more than one particle. Alternatively, a discrete droplet generated may not include any particles. For example, in some instances, a discrete droplet generated may contain one or more biological particles where the first fluid in the first channel includes a plurality of biological particles.

Alternatively or in addition, one or more piezoelectric elements may be used to control droplet formation acoustically.

The piezoelectric element may be operatively coupled to a first end of a buffer substrate (e.g., glass). A second end of the buffer substrate, opposite the first end, may include an acoustic lens. In some instances, the acoustic lens can have a spherical, e.g., hemispherical, cavity. In other instances, the acoustic lens can be a different shape and/or include one or more other objects for focusing acoustic waves. The second end of the buffer substrate and/or the acoustic lens can be in contact with the first fluid in the first channel. Alternatively, the piezoelectric element may be operatively coupled to a part (e.g., wall) of the first channel without an intermediary substrate. The piezoelectric element can be in electrical communication with a controller. The piezoelectric element can be responsive to (e.g., excited by) an electric voltage driven at RF frequency. In some embodiments, the piezoelectric element can be made from zinc oxide (ZnO).

The frequency that drives the electric voltage applied to the piezoelectric element may be from about 5 to about 300 megahertz (MHz). e.g., about 5 MHz, about 6 MHz, about 7 MHz, about MHz, about 9 MHz, about 10 MHz, about 20 MHz, about 30 MHz, about 40 MHz, about 50 MHz, about 60 MHz, about 70 MHz, about 80 MHz, about 90 MHz, about 100 MHz, about 110 MHz, about 120 MHz, about 130 MHz, about 140 MHz, about 150 MHz, about 160 MHz, about 170 MHz, about 180 MHz, about 190 MHz, about 200 MHz, about 210 MHz, about 220 MHz, about 230 MHz, about 240 MHz, about 250 MHz, about 260 MHz, about 270 MHz, about 280 MHz, about 290 MHz, or about 300 MHz. Alternatively, the RF energy may have a frequency range of less than about 5 MHz or greater than about 300 MHz. As will be appreciated, the necessary voltage and/or the RF frequency driving the electric voltage may change with the properties of the piezoelectric element (e.g., efficiency).

Before an electric voltage is applied to a piezoelectric element, the first fluid and the second fluid may remain separated at or near the junction via an immiscible barrier. When the electric voltage is applied to the piezoelectric element, it can generate acoustic waves (e.g., sound waves) that propagate in the buffer substrate. The buffer substrate, such as glass, can be any material that can transfer acoustic waves. The acoustic lens of the buffer substrate can focus the acoustic waves towards the immiscible interface between the two immiscible fluids. The acoustic lens may be located such that the interface is located at the focal plane of the converging beam of the acoustic waves. Upon impact of the sound burst on the barrier, the pressure of the acoustic waves may cause a volume of the first fluid to be propelled into the second fluid, thereby generating a droplet of the volume of the first fluid in the second fluid. In some instances, each propelling may generate a plurality of droplets (e.g., a volume of the first fluid propelled breaks off as it enters the second fluid to form a plurality of discrete droplets). After ejection of the droplet, the immiscible interface can return to its original state. Subsequent applications of electric voltage to the piezoelectric element can be repeated to subsequently generate more droplets. A plurality of droplets can be collected in the second channel for continued transportation to a different location (e.g., reservoir), direct harvesting, and/or storage. Beneficially, the droplets generated can have substantially uniform size, velocity (when ejected), and/or directionality.

In some cases, a device may include a plurality of piezoelectric elements working independently or cooperatively to achieve the desired formation (e.g., propelling) of droplets. For example, the first channel can be coupled to at least 1, 2, 3, 4, 5, 6, 7, 8, 9, 10, 20, 30, 40, 50, 60, 70, 80, 90, 100, 200, 300, 400, or 500 piezoelectric elements. In an example, multiple piezoelectric elements may be positioned adjacent to one another along an axis parallel of the first channel. Alternatively or in addition, multiple piezoelectric elements may circumscribe the first channel. In some instances, the plurality of piezoelectric elements may each be in electrical communication with the same controller or one or more different controllers. The plurality of piezoelectric elements may each transmit acoustic waves from the same buffer substrate or one or more different buffer substrates. In some instances, a single buffer substrate may comprise a plurality of acoustic lenses at different locations.

In some instances, the first channel may be in communication with a third channel. The third channel may carry the first fluid to the first channel such as from a reservoir of the first fluid. The third channel may include one or more piezoelectric elements, for example, as described herein in the described devices. As described elsewhere herein, the third channel may carry first fluid with one or more particles (e.g., beads, biological particles, etc.) and/or one or more reagents suspended in the fluid. Alternatively or in addition, the device may include one or more other channels communicating with the first channel and/or the second channel.

The number and duration of electric voltage pulses applied to the piezoelectric element may be adjusted to control the speed of droplet generation. For example, the frequency of droplet generation may increase with the number of electric voltage pulses. Additionally, the material and size of the piezoelectric element, material and size of the buffer substrate, material, size, and shape of the acoustic lens, number of piezoelectric elements, number of buffer substrates, number of acoustic lenses, respective locations of the one or more piezoelectric elements, respective locations of the one or more buffer substrates, respective locations of the one or more acoustic lenses, dimensions (e.g., length, width, depth, expansion angle) of the respective channels, level of electric voltage applied to the piezoelectric element, hydrodynamic forces of the respective fluids, and other factors may be adjusted to control droplet generation speed and/or size of the droplets generated.

A discrete droplet generated may include a particle, such as when one or more beads are suspended in the volume of the first fluid that is propelled into the second fluid. Alternatively, a discrete droplet generated may include more than one particle. Alternatively, a discrete droplet generated may not include any particles. For example, in some instances, a discrete droplet generated may contain one or more biological particles where the first fluid in the first channel further includes a suspension of a plurality of biological particles.

In some cases, the droplets formed using a piezoelectric element may be collected in a collection reservoir that is disposed below the droplet generation point. The collection reservoir may be configured to hold a source of fluid to keep the formed droplets isolated from one another. The collection reservoir used after piezoelectric or acoustic element-assisted droplet formation may contain an oil that is continuously circulated, e.g., using a paddle mixer, conveyor system, or a magnetic stir bar. Alternatively, the collection reservoir may contain one or more reagents for chemical reactions that can provide a coating on the droplets to ensure isolation, e.g., polymerization, e.g., thermal- or photo-initiated polymerization.

Droplets or particles may be first formed in a larger volume, such as in a reservoir, and then reentrained into a channel, e.g., for unit operations, such as trapping, holding, incubation, reaction, emulsion breaking, sorting, and/or detection. A device may include a first region in fluid communication with (e.g., fluidically connected to) a second region, e.g., with at least one (e.g., each) cross-sectional dimension smaller than the corresponding cross-sectional dimension of the first region. For example, the droplets or particles may be formed or provided in a region in which each cross-sectional dimension of the sorting region may have a length of at least 1 mm (e.g., 2 mm, 3 mm, 4 mm, 5 mm, 6 mm, 7 mm, 8 mm, 9 mm, 10 mm, or more). Following formation or provision, the droplets or particles may be reentrained into a second region (e.g., a channel) in which each cross-section dimension is less than about 1 mm (e.g., less than about 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, 5 nm, 1 nm, 900 μm, 800 μm, 700 μm, 600 μm, 500 μm, 400 μm, 300 μm, 200 μm, 100 μm, 50 μm, 10 μm, 5 μm, 2 μm, 1 μm, or less). Manipulations may be employed in the first region and/or the second region or a subsequent region downstream. This method may include detecting the droplets, e.g., as they are formed or provided in the first region, reentrained in the second region, or while traversing a subsequent region downstream. The device may further include additional regions, e.g., reservoirs, for manipulation, e.g., holding, incubation, reaction, or deemulsification. Any suitable mechanism for reentraining droplets may be employed. Examples include the use of magnetic, electric, dielectrophoretic, or optical energy, differences in density, advection, and pressure. In one example, droplets are produced in a ferrofluid, the magnetic actuation of which can be used to direct droplets to a reentrainment channel. Devices may include features in a reservoir to aid direction of droplets to a reentrainment channel. For example, a reservoir in which droplets are produced or held may have a funnel feature connecting to a reentrainment channel, e.g., sized to allow droplets to pass one by one into the reentrainment channel. In embodiments, droplets are produced in a channel in which they can be transported. In certain embodiments, the reentrainment channel is in fluid communication with one or more additional reservoirs, e.g., for any of the unit operations described herein.

Droplets or particles may be formed in a larger volume, such as a reservoir (e.g., a reservoir containing a ferrofluid (e.g., a colloidal suspension of small magnetic particles (e.g., iron oxide, nickel, cobalt, etc.) in a liquid (e.g., an aqueous liquid or an oil)), and then manipulated using a magnetic actuator. Droplets or particles in a ferrofluid may be reentrained into a channel using a magnetic actuator, e.g., for unit operations, such as trapping, holding, incubation, reaction, emulsion, breaking, sorting, and/or detection. A device may include a first region in fluid communication with (e.g., fluidically connected to) a second region, e.g., with at least one (e.g., each) cross-sectional dimension smaller than the corresponding cross-sectional dimension of the first region. For example, the droplets or particles may be formed or provided in a region containing a ferrofluid, and a magnetic actuator may alter the magnetic field, manipulating the droplets (e.g., the droplets may be separated based on size or the droplets may be directed above or below the ferrofluid). Following formation or provision, the droplets or particles may be reentrained into a second region (e.g., a channel) by activating the magnetic actuator. Manipulations may be employed in the first region and/or the second region or a subsequent region downstream. This method may include detecting the droplets, e.g., as they are formed or provided in the first region, reentrained in the second region, or while traversing a subsequent region downstream. The device may further include additional regions, e.g., reservoirs, for manipulation, e.g., holding, incubation, reaction, or deemulsification. The magnetic actuator can also be used to heat the ferrofluid and the droplets or particles by altering the magnetic field.

Multiplex Devices

Devices of the invention may be in multiplex format. Multiplex formats include devices having multiple droplet formation regions downstream from a single sample inlet, multiple parallel flow paths with a sample inlet and a droplet formation, and combinations thereof. The flow paths, e.g., channels, funnels, filters, and droplet formation regions, may be any as described herein. Inlets in multiplex devices may include a simple opening to allow introduction of fluid, or an inlet may be a chamber or reservoir housing a volume of fluid to be distributed (e.g., corresponding to a first or second reservoir or sample, reagent, or collection reservoir as described herein).

Figure 51:
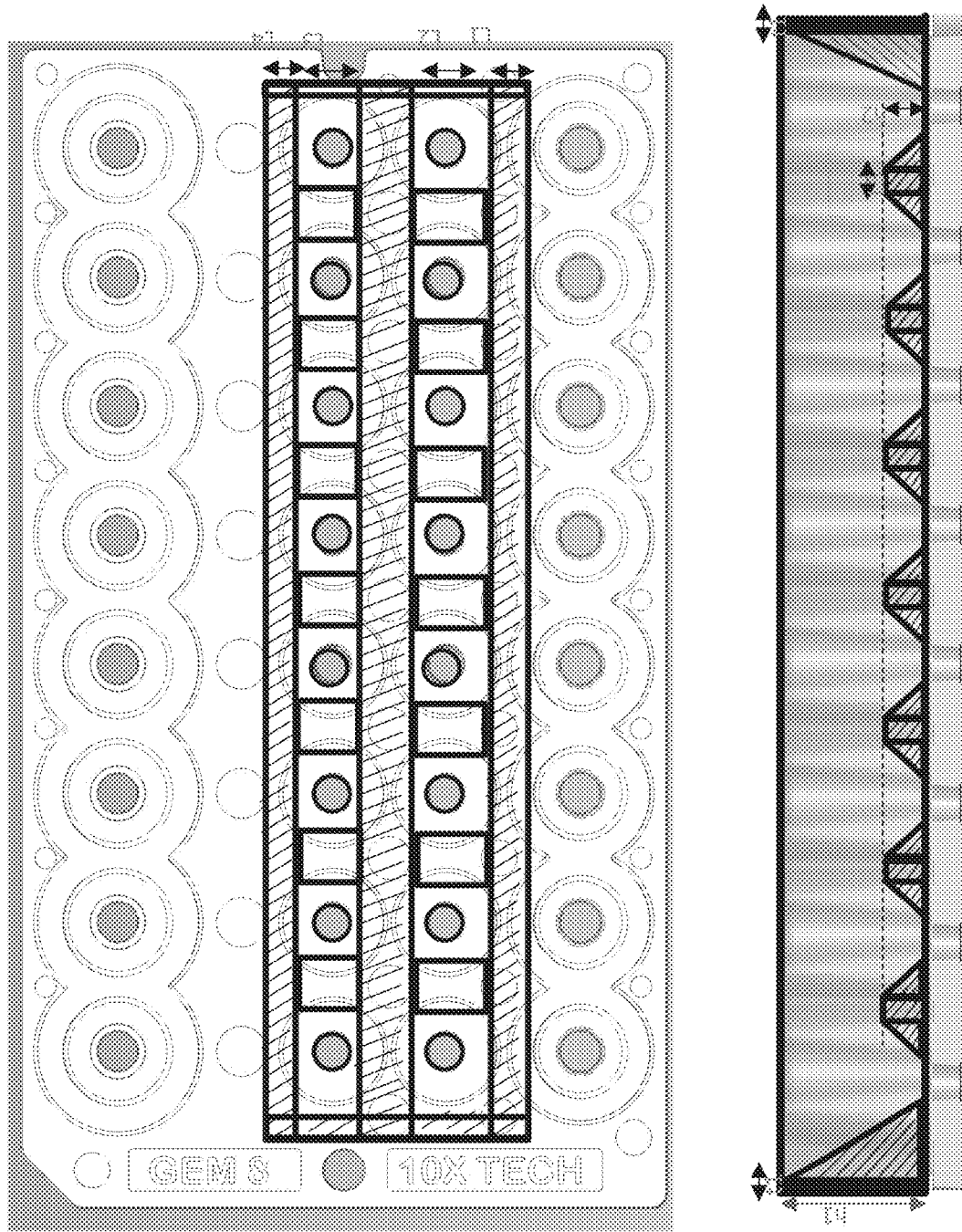
FIG. 51 is a depiction of a trough.

In certain embodiments, multiple inlets of a single type, e.g., sample or reagent (e.g., for particles such as gel beads) may be connected to a trough, allowing for loading using a single pipette or other transfer device. An exemplary trough design is shown in FIG. 51. Troughs may be of any appropriate volume, e.g., at least the combined volumes of any reservoirs that would otherwise be present. For example, the volumes may be 2 to 50 times, e.g., 2 to 20 times, 2 to 10 times, or 2, 3, 4, 5, 6, 7, 8, 9, 10, 11, 12, 13, 14, 15, or 16 times, the volume of a reservoir as described herein.

In one embodiment, the multiplex devices include one or more sample inlets, one or more reagent inlets, and one or more collection reservoirs. The one or more sample inlets, one or more reagent inlets, and one or more collection reservoirs are placed in fluid communication by channels. A channel from the sample inlet intersects a channel from the reagent inlet at an intersection. Fluids flowing from the sample and reagent inlets combine at the intersection. A droplet formation region is fluidically disposed between the intersection and the collection reservoir, and the combined sample and reagent fluids are formed into droplets. A single channel coming from an inlet may split into two or more branches, each of which may intersect another channel (or branch). Exemplary droplet formation regions include a shelf and a step as described herein. Sample channels may correspond to first and/or second channels as described herein, and reagent channels may correspond to first and/or second channels as described herein.

Multiplex devices may include multiple multiplex flow paths. Each multiplex flow path may be fluidically distinct or connected to other flow paths. In certain embodiments, a single reagent inlet delivers, via different reagent channels or different branches of a reagent channel, reagent to intersections with sample channels from different sample inlets. In the alternative or in addition, sample and/or reagent inlets may be connected by troughs. In some instances, devices described herein contain between 1 and 30 flow paths (e.g., at least 2, at least 4, at least 8, or 1, 2, 3, 4, 5, 6, 7, 8, 9, 10, 11, 12, 13, 14, or 15 flow paths). In some instances, devices described herein may feature troughs that connect inlets or collection reservoirs, e.g., a trough may connect between 1 and 30 inlets or collection reservoirs of the same and/or different flow paths (e.g., at least 2, at least 4, at least 8, or 1, 2, 3, 4, 5, 6, 7, 8, 9, 10, 11, 12, 13, 14, or 15 inlets or collection reservoirs of multiple flow paths).

For multiplex devices including multiple multiplex flow paths, the same or different samples can be introduced in different flow paths, and/or the same or different reagents can be introduced in different flow paths. For devices including flow paths, wherein the flow paths include multiple sample or reagent inlets, the same or different samples and/or reagents can be introduced in the inlets.

Combinations of different flow paths may be combined in a single multiplex device. Multiplex devices may also include common inlets, which may be a sample inlet, a reagent inlet, or a collection reservoir. In such devices, additional inlets are disposed around the common inlet. For example, the common inlet may be centrally located, with additional inlets arranged radially around the common inlet.

Inlets of the same type and/or collection reservoirs may be arranged substantially linearly, e.g., for ease of deliver or removal of fluids from the device by a multichannel pipette. Linear arrangement also allows for a more compact trough design when employed.

Multiplex devices may include a plurality of inlets surrounded by at least one common wall and have a dividing wall that has at least a portion of the dividing wall that is shorter than the one common wall. This arraignment allows a single pressure source to control fluid flow in two different inlets.

Multiplex devices may include multiplex flow path having either i) a connecting channel in fluid communication with two or more inlets or two or more reagent channels, or ii) one reagent channel that combines with another reagent channel for a distance before splitting into two separate reagent channels, as described herein.

Multiplex devices for producing droplets may include i) one or more sample inlets, ii) one or more sample channels in fluid communication with the one or more sample inlets; iii) one or more reagent inlets, iv) one or more reagent channels in fluid communication with the one or more reagent inlets and where the one or more reagent channels intersect with the one or more sample channels to form one or more intersections, vi) one or more droplet formation regions, and vii) one or more collection reservoirs, where the one or more droplet formation regions are fluidically disposed between the one or more intersections and the one or more collection reservoirs, and provided that the one or more sample inlets includes at least two sample inlets or the one or more reagent inlets includes at least two reagents inlets, where the maximum cross sectional dimension of the sample channels is 250 µm, e.g., about 1 µm, about 5 µm, about 10 µm, about 20 µm, about 30 µm, about 40 µm, about 50 µm, about 60 µm, about 70 µm, about 80 µm, about 90 µm, about 100 µm, about 105 µm, about 110 µm, about 115 µm, about 120 µm, about 125 µm, about 130 µm, about 135 µm, about 140 µm, about 145 µm, about 150 µm, about 155 µm, about 160 µm, about 165 µm, about 170 µm, about 175 µm, about 180 µm, about 185 µm, about 190 µm, about 195 µm, about 200 µm, about 205 µm, about 210 µm, about 215 µm, about 220 µm, about 225 µm, about 230 µm, about 235 µm, about 240 µm, about 245 µm, about 247 µm, about 248 µm, about 249 µm, e.g., between about 1 µm to about 20 µm, about 10 µm to about 30 µm, about 20 µm to about 40 µm, about 30 µm to about 50 µm, about 40 µm to about 60 µm, about 50 µm to about 70 µm, about 60 µm to about 80 µm, about 70 µm to about 90 µm, about 80 µm to about 100 µm, about 90 µm to about 110 µm, about 100 µm to about 120 µm, about 110 µm to about 130 µm, about 120 µm to about 140 µm, about 130 µm to about 150 µm, about 140 µm to about 160 µm, about 150 µm to about 170 µm, about 160 µm to about 180 µm, about 170 µm to about 190 µm, about 180 µm to about 200 µm, about 190 µm to about 210 µm, about 200 µm to about 220 µm, about 210 µm to about 230 µm, about 220 µm to about 240 µm, or about 230 µm to about 245 µm. In some instances, the maximum cross-sectional dimension of the reagent channels is about 250 µm, e.g., about 1 µm, about 5 µm, about 10 µm, about 20 µm, about 30 µm, about 40 µm, about 50 µm, about 60 µm, about 70 µm, about 80 µm, about 90 µm, about 100 µm, 1 about 05 µm, about 110 µm, about 115 µm, about 120 µm, about 125 µm, about 130 µm, about 135 µm, about 140 µm, about 145 µm, about 150 µm, about 155 µm, about 160 µm, about 165 µm, about 170 µm, about 175 µm, about 180 µm, about 185 µm, about 190 µm, about 195 µm, about 200 µm, about 205 µm, about 210 µm, about 215 µm, about 220 µm, about 225 µm, about 230 µm, about 235 µm, about 240 µm, about 245 µm, about 247 µm, about 248 µm, about 249 µm, e.g., between about 1 µm to about 20 µm, about 10 µm to about 30 µm, about 20 µm to about 40 µm, about 30 µm to about 50 µm, about 40 µm to about 60 µm, about 50 µm to about 70 µm, about 60 µm to about 80 µm, about 70 µm to about 90 µm, about 80 µm to about 100 µm, about 90 µm to about 110 µm, about 100 µm to about 120 µm, about 110 µm to about 130 µm, about 120 µm to about 140 µm, about 130 µm to about 150 µm, about 140 µm to about 160 µm, about 150 µm to about 170 µm, about 160 µm to about 180 µm, about 170 µm to about 190 µm, about 180 µm to about 200 µm, about 190 µm to about 210 µm, about 200 µm to about 220 µm, about 210 µm to about 230 µm, about 220 µm to about 240 µm, or about 230 µm to about 245 µm. In some instances, the maximum cross-sectional dimension of the reagent channels is between about 10 µm and about 150 µm, between about 50 µm and about 150 µm, between about 80 µm and about 200 µm, or between about 100 µm and about 250 µm. In some instances, the number of droplet formation regions per collection reservoir is at least 4, e.g., where the pitch is no greater than 20 mm per collection reservoir. For example, there may be 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 2000 or more droplet formation regions per collection reservoir, e.g. 2 to 16, such as 2, 3, 4, 5, 6, 7, 8, 9, 10, 11, 12, 13, 14, 15, or 16, e.g., 2 to 8. For example, the pitch may be about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, or about 19.5 mm.

Figure 63A:
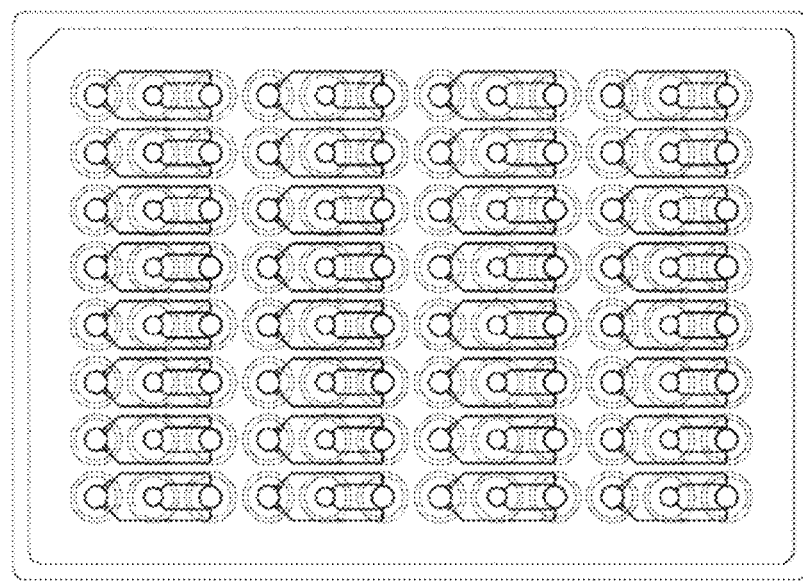
FIGS. 63A-63B are depictions of multiplex flow paths.
Figure 63B:
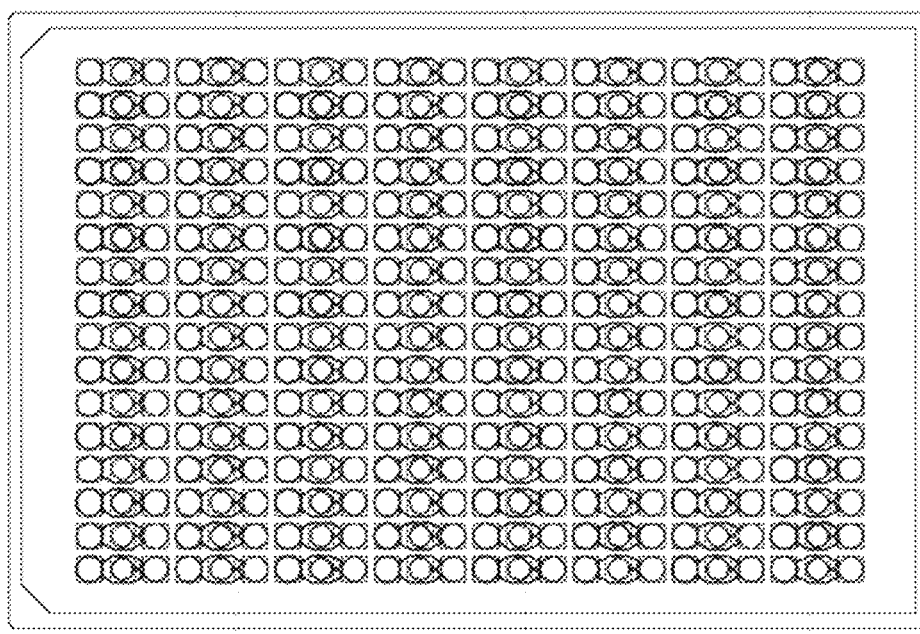
Figure 63C:
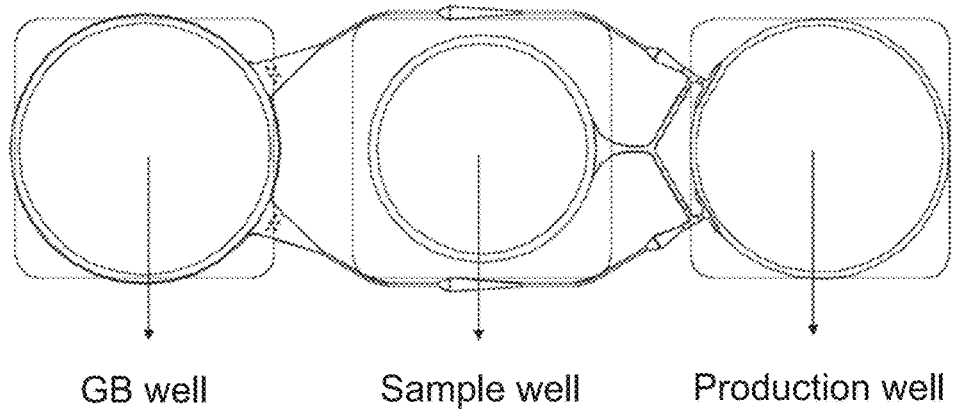
FIG. 63C is a close-up depiction of a flow path from FIG. 63B.

Advantageously, multiplexed devices of the invention may be compatible with equipment for use with multi-well plates, e.g., 96 well plates, 384 well plates, or 1536 well plates (see, e.g., FIGS. 63A-63C). Sizing and spacing the inlets and reservoirs of the multiplexed devices described herein to be in a linear sequence according to a row or column of a multi well plate allows the inlets to be filled or collection reservoirs emptied using multichannel pipettors, improving the efficiency of these steps. In another advantage, the multiplexed devices being sized and spaced to be in a linear sequence according to a row or column of a multi-well plate allow integration with robotic laboratory automation such as robotic plate handlers, samplers, analyzers, and other high-throughput systems adapted for multi well plate operations. Multiplexed devices of the invention can be disposed to fit a 96 well plate, a 384 well plate, or a 1536 well plate format. While it is preferable that the inlets and reservoirs of the multiplexed devices are arranged substantially linearly in order to maximize packing of flow paths into the area of a multi well plate, it is also possible for non-linear flow paths, and other non-linear arrangements of inlets and reservoirs, as described herein to be adapted to fit into a multi well plate format. In some embodiments, the number of flow paths possible in a multi well plate format is the number of wells of the multi well plate divided by the sum of the reservoirs and inlets in the flow path, provided the reservoirs and inlets are arranged substantially linearly. For example, for a flow path with two inlets and one collection reservoir, arranged substantially linearly, in a 96 well plate format the number of flow paths is 32. In some instances, the multiplexed devices described herein contain between 1 and 32 flow paths (e.g., up to 12, up to 13, up to 16, up to 19, or up to 24). In some instances, the multiplexed devices described herein contain between 1 and 128 flow paths (e.g., up to 48, up to 54, up to 64, up to 76, or up to 96). In some instances, the multiplexed devices described herein contain between 1 and 512 flow paths (e.g., up to 192, up to 219, up to 256, up to 307, or up to 384). Arrangements of multiple flow paths in other arrays is also within the scope of the invention.

Surface Properties

A surface of the device may include a material, coating, or surface texture that determines the physical properties of the device. In particular, the flow of liquids through a device of the invention may be controlled by the device surface properties (e.g., wettability of a liquid-contacting surface). In some cases, a device portion (e.g., a region, channel, or sorter) may have a surface having a wettability suitable for facilitating liquid flow (e.g., in a channel) or assisting droplet formation (e.g., in a channel), e.g., if droplet formation is performed.

Wetting, which is the ability of a liquid to maintain contact with a solid surface, may be measured as a function of a water contact angle. A water contact angle of a material can be measured by any suitable method known in the art, such as the static sessile drop method, pendant drop method, dynamic sessile drop method, dynamic Wilhelmy method, single-fiber Wilhelmy method, single-fiber meniscus method, and Washburn's equation capillary rise method. The wettability of each surface may be suited to producing droplets.

For example, portions of the device carrying aqueous phases (e.g., a channel) may have a surface material or coating that is hydrophilic or more hydrophilic than another region of the device, e.g., include a material or coating having a water contact angle of less than or equal to about 90°, and/or the other region of the device may have a surface material or coating that is hydrophobic or more hydrophobic than the channel, e.g., include a material or coating having a water contact angle of greater than 70° (e.g., greater than 90°, greater than 95°, greater than 100° (e.g., 95°-120° or 100°-10°)). In certain embodiments, a region of the device may include a material or surface coating that reduces or prevents wetting by aqueous phases. The device can be designed to have a single type of material or coating throughout. Alternatively, the device may have separate regions having different materials or coatings.

The device surface properties may be those of a native surface (i.e., the surface properties of the bulk material used for the device fabrication) or of a surface treatment. Non-limiting examples of surface treatments include, e.g., surface coatings and surface textures. In one approach, the device surface properties are attributable to one or more surface coatings present in a device portion. Hydrophobic coatings may include fluoropolymers (e.g., AQUAPEL® glass treatment), silanes, siloxanes, silicones, or other coatings known in the art. Other coatings include those vapor deposited from a precursor such as henicosyl-1,1,2,2-tetrahydrododecyldimethyltris(dimethylaminosilane); henicosyl-1,1,2,2-tetrahydrododecyltrichlorosilane (C12); heptadecafluoro-1,1,2,2-tetrahydrodecyltrichlorosilane (C10); nonafluoro-1,1,2,2-tetrahydrohexyltris(dimethylamino)silane; 3,3,3,4,4,5,5,6,6-nonafluorohexyltrichlorosilane; tridecafluoro-1,1,2,2-tetrahydrooctyltrichlorosilane (C8); bis(tridecafluoro-1,1,2,2-tetrahydrooctyl)dimethylsiloxymethylchlorosilane; nonafluorohexyltriethoxysilane (C6); dodecyltrichlorosilane (DTS); dimethyldichlorosilane (DDMS); or 10-undecenyl-trichlorosilane (V11); pentafluorophenylpropyltrichlorosilane (C5). Hydrophilic coatings include polymers such as polysaccharides, polyethylene glycol, polyamines, and polycarboxylic acids. Hydrophilic surfaces may also be created by oxygen plasma treatment of certain materials.

A coated surface may be formed by depositing a metal oxide onto a surface of the device. Example metal oxides useful for coating surfaces include, but are not limited to, $Al_2O_3$, $TiO_2$, $SiO_2$, or a combination thereof. Other metal oxides useful for surface modifications are known in the art. The metal oxide can be deposited onto a surface by standard deposition techniques, including, but not limited to, atomic layer deposition (ALD), physical vapor deposition (PVD), e.g., sputtering, chemical vapor deposition (CVD), or laser deposition. Other deposition techniques for coating surfaces, e.g., liquid-based deposition, are known in the art. For example, an atomic layer of $Al_2O_3$ can be deposited on a surface by contacting it with trimethylaluminum (TMA) and water.

In another approach, the device surface properties may be attributable to surface texture. For example, a surface may have a nanotexture, e.g., have a surface with nanometer surface features, such as cones or columns, that alters the wettability of the surface. Nanotextured surface may be hydrophilic, hydrophobic, or superhydrophobic, e.g., have a water contact angle greater than 150°. Exemplary superhydrophobic materials include Manganese Oxide Polystyrene ($MnO_2$/PS) nano-composite, Zinc Oxide Polystyrene (ZnO/PS) nano-composite, Precipitated Calcium Carbonate, Carbon nano-tube structures, and a silica nano-coating. Superhydrophobic coatings may also include a low surface energy material (e.g., an inherently hydrophobic material) and a surface roughness (e.g., using laser ablation techniques, plasma etching techniques, or lithographic techniques in which a material is etched through apertures in a patterned mask). Examples of low surface energy materials include fluorocarbon materials, e.g., polytetrafluoroethylene (PTFE), fluorinated ethylene propylene (FEP), ethylene tetrafluoroethylene (ETFE), ethylene chloro-trifluoroethylene (ECTFE), perfluoro-alkoxyalkane (PFA), poly(chloro-trifluoro-ethylene) (CTFE), perfluoro-alkoxyalkane (PFA), and poly(vinylidene fluoride) (PVDF). Other superhydrophobic surfaces are known in the art.

In some cases, the water contact angle of a hydrophilic or more hydrophilic material or coating is less than or equal to about 90°, e.g., less than 80°, 70°, 60°, 50°, 40°, 30°, 20°, or 10°, e.g., 90°, 85°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, or 0°. In some cases, the water contact angle of a hydrophobic or more hydrophobic material or coating is at least 70°, e.g., at least 80°, at least 85°, at least 90°, at least 95°, or at least 100° (e.g., about 100°, 101°, 102°, 103°, 104°, 105°, 106°, 107°, 108°, 109°, 110°, 115°, 120°, 125°, 130°, 135°, 140°, 145°, or about 150°).

The difference in water contact angles between that of a hydrophilic or more hydrophilic material or coating and a hydrophobic or more hydrophobic material or coating may be 5° to 100°, e.g., 5° to 80°, 5° to 60°, 5° to 50°, 5° to 40°, 5° to 30°, 5° to 20°, 10° to 75°, 15° to 70°, 20° to 65°, 25° to 60°, 30 to 50°, 35° to 45°, e.g., 5°, 6°, 7°, 8°, 9°, 10°, 15°, 20°, 25°, 30°, 35°, 40°, 45°, 50°, 55°, 60, 65°, 70°, 75°, 80°, 85°, 90°, 95°, or 100°.

The above discussion centers on the water contact angle. It will be understood that liquids employed in the devices and methods of the invention may not be water, or even aqueous. Accordingly, the actual contact angle of a liquid on a surface of the device may differ from the water contact angle. Furthermore, the determination of a water contact angle of a material or coating can be made on that material or coating when not incorporated into a device of the invention.

Particles

The invention includes devices, systems, and kits having particles, e.g., for use in analyte detection. For example, particles configured with analyte detection moieties (e.g., barcodes, nucleic acids, binding molecules (e.g., proteins, peptides, aptamers, antibodies, or antibody fragments), enzymes, substrates, etc.) can be included in a droplet containing an analyte to modify the analyte and/or detect the presence or concentration of the analyte. In some embodiments, particles are synthetic particles (e.g., beads, e.g., gel beads).

For example, a droplet may include one or more analyte-detection moieties, e.g., unique identifiers, such as barcodes. Analyte-detection moieties, e.g., barcodes, may be introduced into droplets previous to, subsequent to, or concurrently with droplet formation. The delivery of the analyte-detection moieties, e.g., barcodes, to a particular droplet allows for the later attribution of the characteristics of an individual sample (e.g., biological particle) to the particular droplet. Analyte-detection moieties, e.g., barcodes, may be delivered, for example on a nucleic acid (e.g., an oligonucleotide), to a droplet via any suitable mechanism. Analyte-detection moieties, e.g., barcoded nucleic acids (e.g., oligonucleotides), can be introduced into a droplet via a particle, such as a microcapsule. In some cases, analyte-detection moieties, e.g., barcoded nucleic acids (e.g., oligonucleotides), can be initially associated with the particle (e.g., microcapsule) and then released upon application of a stimulus which allows the analyte-detection moieties, e.g., nucleic acids (e.g., oligonucleotides), to dissociate or to be released from the particle.

A particle, e.g., a bead, may be porous, non-porous, hollow (e.g., a microcapsule), solid, semi-solid, semi-fluidic, fluidic, and/or a combination thereof. In some instances, a particle, e.g., a bead, may be dissolvable, disruptable, and/or degradable. In some cases, a particle, e.g., a bead, may not be degradable. In some cases, the particle, e.g., a bead, may be a gel bead. A gel bead may be a hydrogel bead. A gel bead may be formed from molecular precursors, such as a polymeric or monomeric species. A semi-solid particle, e.g., a bead, may be a liposomal bead. Solid particles, e.g., beads, may comprise metals including iron oxide, gold, and silver. In some cases, the particle, e.g., the bead, may be a silica bead. In some cases, the particle, e.g., a bead, can be rigid. In other cases, the particle, e.g., a bead, may be flexible and/or compressible.

A particle, e.g., a bead, may comprise natural and/or synthetic materials. For example, a particle, e.g., a bead, can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, poly ethylene terephthalate, poly(chlorotrifluoroethylene), poly (ethylene oxide), poly(ethylene terephthalate), polyethylene, polyisobutylene, poly(methyl methacrylate), poly(oxymethylene), polyformaldehyde, polypropylene, polystyrene, poly (tetrafluoroethylene), poly(vinyl acetate), poly(vinyl alcohol), poly(vinyl chloride), poly(vinylidene dichloride), poly (vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the particle, e.g., the bead, may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the particle, e.g., the bead, may comprise prepolymers, which are oligomers capable of further polymerization. For example, polyurethane beads may be prepared using prepolymers. In some cases, the particle, e.g., the bead, may contain individual polymers that may be further polymerized together. In some cases, particles, e.g., beads, may be generated via polymerization of different precursors, such that they comprise mixed polymers, co-polymers, and/or block co-polymers. In some cases, the particle, e.g., the bead, may comprise covalent or ionic bonds between polymeric precursors (e.g., monomers, oligomers, linear polymers), oligonucleotides, primers, and other entities. In some cases, the covalent bonds can be carbon-carbon bonds or thioether bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

Particles, e.g., beads, may be of uniform size or heterogeneous size. In some cases, the diameter of a particle, e.g., a bead, may be at least about 1 micrometer ($\mu m$), 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or greater. In some cases, a particle, e.g., a bead, may have a diameter of less than about 1 $\mu m$, 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or less. In some cases, a particle, e.g., a bead, may have a diameter in the range of about 40-75 $\mu m$, 30-75 $\mu m$, 20-75 $\mu m$, 40-85 $\mu m$, 40-95 $\mu m$, 20-100 $\mu m$, 10-100 $\mu m$, 1-100 $\mu m$, 20-250 $\mu m$, or 20-500 $\mu m$. The size of a particle, e.g., a bead, e.g., a gel bead, used to produce droplets is typically on the order of a cross section of the first channel (width or depth). In some cases, the gel beads are larger than the width and/or depth of the first channel and/or shelf, e.g., at least 1.5×, 2×, 3×, or 4× larger than the width and/or depth of the first channel and/or shelf.

In certain embodiments, particles, e.g., beads, can be provided as a population or plurality of particles, e.g., beads, having a relatively monodisperse size distribution. Where it may be desirable to provide relatively consistent amounts of reagents within droplets, maintaining relatively consistent particle, e.g., bead, characteristics, such as size, can contribute to the overall consistency. In particular, the particles, e.g., beads, described herein may have size distributions that have a coefficient of variation in their cross-sectional dimensions of less than 50%, less than 40%, less than 30%, less than 20%, and in some cases less than 15%, less than 10%, less than 5%, or less.

Particles may be of any suitable shape. Examples of particles, e.g., beads, shapes include, but are not limited to, spherical, non-spherical, oval, oblong, amorphous, circular, cylindrical, and variations thereof.

A particle, e.g., bead, injected or otherwise introduced into a droplet may comprise releasably, cleavably, or reversibly attached analyte detection moieties (e.g., barcodes). A particle, e.g., bead, injected or otherwise introduced into a droplet may comprise activatable analyte detection moieties (e.g., barcodes). A particle, e.g., bead, injected or otherwise introduced into a droplet may be a degradable, disruptable, or dissolvable particle, e.g., dissolvable bead.

Particles, e.g., beads, within a channel may flow at a substantially regular flow profile (e.g., at a regular flow rate). Such regular flow profiles can permit a droplet, when formed, to include a single particle (e.g., bead) and a single cell or other biological particle. Such regular flow profiles may permit the droplets to have an dual occupancy (e.g., droplets having at least one bead and at least one cell or other biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99% of the population. In some embodiments, the droplets have a 1:1 dual occupancy (i.e., droplets having exactly one particle (e.g., bead) and exactly one cell or other biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99% of the population. Such regular flow profiles and devices that may be used to provide such regular flow profiles are provided, for example, in U.S. Patent Publication No. 2015/0292988, which is entirely incorporated herein by reference.

As discussed above, analyte-detection moieties (e.g., barcodes) can be releasably, cleavably or reversibly attached to the particles, e.g., beads, such that analyte detection moieties (e.g., barcodes) can be released or be releasable through cleavage of a linkage between the barcode molecule and the particle, e.g., bead, or released through degradation of the particle (e.g., bead) itself, allowing the barcodes to be accessed or be accessible by other reagents, or both. Releasable analyte-detection moieties (e.g., barcodes) may sometimes be referred to as activatable analyte-detection moieties (e.g., activatable barcodes), in that they are available for reaction once released. Thus, for example, an activatable analyte detection-moiety (e.g., activatable barcode) may be activated by releasing the analyte detection moiety (e.g., barcode) from a particle, e.g., bead (or other suitable type of droplet described herein). Other activatable configurations are also envisioned in the context of the described methods and systems.

In addition to, or as an alternative to the cleavable linkages between the particles, e.g., beads, and the associated antigen detection moieties, such as barcode containing nucleic acids (e.g., oligonucleotides), the particles, e.g., beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a particle, e.g., bead, may be dissolvable, such that material components of the particle, e.g., bead, are degraded or solubilized when exposed to a particular chemical species or an environmental change, such as a change temperature or a change in pH. In some cases, a gel bead can be degraded or dissolved at elevated temperature and/or in basic conditions. In some cases, a particle, e.g., bead, may be thermally degradable such that when the particle, e.g., bead, is exposed to an appropriate change in temperature (e.g., heat), the particle, e.g., bead, degrades. Degradation or dissolution of a particle (e.g., bead) bound to a species (e.g., a nucleic acid, e.g., an oligonucleotide, e.g., barcoded oligonucleotide) may result in release of the species from the particle, e.g., bead. As will be appreciated from the above disclosure, the degradation of a particle, e.g., bead, may refer to the disassociation of a bound or entrained species from a particle, e.g., bead, both with and without structurally degrading the physical particle, e.g., bead, itself. For example, entrained species may be released from particles, e.g., beads, through osmotic pressure differences due to, for example, changing chemical environments. By way of example, alteration of particle, e.g., bead, pore sizes due to osmotic pressure differences can generally occur without structural degradation of the particle, e.g., bead, itself. In some cases, an increase in pore size due to osmotic swelling of a particle, e.g., bead or microcapsule (e.g., liposome), can permit the release of entrained species within the particle. In other cases, osmotic shrinking of a particle may cause the particle, e.g., bead, to better retain an entrained species due to pore size contraction.

A degradable particle, e.g., bead, may be introduced into a droplet, such that the particle, e.g., bead, degrades within the droplet and any associated species (e.g., nucleic acids, oligonucleotides, or fragments thereof) are released within the droplet when the appropriate stimulus is applied. The free species (e.g., nucleic acid, oligonucleotide, or fragment thereof) may interact with other reagents contained in the droplet. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in particle, e.g., bead, degradation and release of the barcode sequence into the aqueous, inner environment of the droplet. In another example, heating of a droplet comprising a particle-, e.g., bead-, bound analyte-detection moiety (e.g., barcode) in basic solution may also result in particle, e.g., bead, degradation and release of the attached barcode sequence into the aqueous, inner environment of the droplet.

Any suitable number of analyte-detection moieties (e.g., molecular tag molecules (e.g., primer, barcoded oligonucleotide, etc.)) can be associated with a particle, e.g., bead, such that, upon release from the particle, the analyte detection moieties (e.g., molecular tag molecules (e.g., primer, e.g., barcoded oligonucleotide, etc.)) are present in the droplet at a pre-defined concentration. Such pre-defined concentration may be selected to facilitate certain reactions for generating a sequencing library, e.g., amplification, within the droplet. In some cases, the pre-defined concentration of a primer can be limited by the process of producing oligonucleotide-bearing particles, e.g., beads.

Additional reagents may be included as part of the particles (e.g., analyte-detection moieties) and/or in solution or dispersed in the droplet, for example, to activate, mediate, or otherwise participate in a reaction, e.g., between the analyte and analyte-detection moiety.

Biological Samples

A droplet of the invention may include biological particles (e.g., cells) and/or macromolecular constituents thereof (e.g., components of cells (e.g., intracellular or extracellular proteins, nucleic acids, glycans, or lipids) or products of cells (e.g., secretion products)). An analyte from a biological particle, e.g., component or product thereof, may be considered to be a bioanalyte. In some embodiments, a biological particle, e.g., cell, or product thereof is included in a droplet, e.g., with one or more particles (e.g., beads) having an analyte detection moiety. A biological particle, e.g., cell, and/or components or products thereof can, in some embodiments, be encased inside a gel, such as via polymerization of a droplet containing the biological particle and precursors capable of being polymerized or gelled.

In the case of encapsulated biological particles (e.g., cells), a biological particle may be included in a droplet that contains lysis reagents in order to release the contents (e.g., contents containing one or more analytes (e.g., bioanalytes)) of the biological particles within the droplet. In such cases, the lysis agents can be contacted with the biological particle suspension concurrently with, or immediately prior to the introduction of the biological particles into the droplet formation region, for example, through an additional channel or channels upstream or proximal to a second channel or a third channel that is upstream or proximal to a second droplet formation region. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be contained in a droplet with the biological particles (e.g., cells) to cause the release of the biological particles' contents into the droplets. For example, in some cases, surfactant based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). In some embodiments, lysis solutions are hypotonic, thereby lysing cells by osmotic shock. Electroporation, thermal, acoustic or mechanical cellular disruption may also be used in certain cases, e.g., non-emulsion based droplet formation such as encapsulation of biological particles that may be in addition to or in place of droplet formation, where any pore size of the encapsulate is sufficiently small to retain nucleic acid fragments of a desired size, following cellular disruption.

In addition to the lysis agents, other reagents can also be included in droplets with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles (e.g., cells), the biological particles may be exposed to an appropriate stimulus to release the biological particles or their contents from a microcapsule within a droplet. For example, in some cases, a chemical stimulus may be included in a droplet along with an encapsulated biological particle to allow for degradation of the encapsulating matrix and release of the cell or its contents into the larger droplet. In some cases, this stimulus may be the same as the stimulus described elsewhere herein for release of analyte detection moieties (e.g., oligonucleotides) from their respective particle (e.g., bead). In alternative aspects, this may be a different and non-overlapping stimulus, in order to allow an encapsulated biological particle to be released into a droplet at a different time from the release of analyte detection moieties (e.g., oligonucleotides) into the same droplet.

Additional reagents may also be included in droplets with the biological particles, such as endonucleases to fragment a biological particle's DNA, DNA polymerase enzymes and dNTPs used to amplify the biological particle's nucleic acid fragments and to attach the barcode molecular tags to the amplified fragments. Other reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyinosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250 nucleotides or longer.

In some cases, the length of a switch oligo may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective droplets, the macromolecular components (e.g., macromolecular constituents of biological particles, such as RNA, DNA, or proteins) contained therein may be further processed within the droplets.

As described above, the macromolecular components (e.g., bioanalytes) of individual biological particles (e.g., cells) can be provided with unique identifiers (e.g., barcodes) such that upon characterization of those macromolecular components, at which point components from a heterogeneous population of cells may have been mixed and are interspersed or solubilized in a common liquid, any given component (e.g., bioanalyte) may be traced to the biological particle (e.g., cell) from which it was obtained. The ability to attribute characteristics to individual biological particles or groups of biological particles is provided by the assignment of unique identifiers specifically to an individual biological particle or groups of biological particles. Unique identifiers, for example, in the form of nucleic acid barcodes, can be assigned or associated with individual biological particles (e.g., cells) or populations of biological particles (e.g., cells), in order to tag or label the biological particle's macromolecular components (and as a result, its characteristics) with the unique identifiers. These unique identifiers can then be used to attribute the biological particle's components and characteristics to an individual biological particle or group of biological particles. This can be performed by forming droplets including the individual biological particle or groups of biological particles with the unique identifiers (via particles, e.g., beads), as described in the systems and methods herein.

In some aspects, the unique identifiers are provided in the form of oligonucleotides that comprise nucleic acid barcode sequences that may be attached to or otherwise associated with the nucleic acid contents of individual biological particle, or to other components of the biological particle, and particularly to fragments of those nucleic acids. The oligonucleotides are partitioned such that as between oligonucleotides in a given droplet, the nucleic acid barcode sequences contained therein are the same, but as between different droplets, the oligonucleotides can, and do have differing barcode sequences, or at least represent a large number of different barcode sequences across all of the droplets in a given analysis. In some aspects, only one nucleic acid barcode sequence can be associated with a given droplet, although in some cases, two or more different barcode sequences may be present.

The nucleic acid barcode sequences can include from 6 to about 20 or more nucleotides within the sequence of the oligonucleotides. In some cases, the length of a barcode sequence may be 6, 7, 8, 9, 10, 11, 12, 13, 14, 15, 16, 17, 18, 19, 20 nucleotides or longer. In some cases, the length of a barcode sequence may be at least 6, 7, 8, 9, 10, 11, 12, 13, 14, 15, 16, 17, 18, 19, 20 nucleotides or longer. In some cases, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be 4, 5, 6, 7, 8, 9, 10, 11, 12, 13, 14, 15, 16 nucleotides or longer. In some cases, the barcode subsequence may be at least 4, 5, 6, 7, 8, 9, 10, 11, 12, 13, 14, 15, 16 nucleotides or longer. In some cases, the barcode subsequence may be at most 4, 5, 6, 7, 8, 9, 10, 11, 12, 13, 14, 15, 16 nucleotides or shorter.

Analyte-detection moieties (e.g., oligonucleotides) in droplets can also include other functional sequences useful in processing of nucleic acids from biological particles contained in the droplet. These sequences include, for example, targeted or random/universal amplification primer sequences for amplifying the genomic DNA from the individual biological particles within the droplets while attaching the associated barcode sequences, sequencing primers or primer recognition sites, hybridization or probing sequences, e.g., for identification of presence of the sequences or for pulling down barcoded nucleic acids, or any of a number of other potential functional sequences.

Other mechanisms of forming droplets containing oligonucleotides may also be employed, including, e.g., coalescence of two or more droplets, where one droplet contains oligonucleotides, or microdispensing of oligonucleotides into droplets, e.g., droplets within microfluidic systems.

In an example, particles (e.g., beads) are provided that each include large numbers of the above described barcoded oligonucleotides releasably attached to the beads, where all of the oligonucleotides attached to a particular bead will include the same nucleic acid barcode sequence, but where a large number of diverse barcode sequences are represented across the population of beads used. In some embodiments, hydrogel beads, e.g., beads having polyacrylamide polymer matrices, are used as a solid support and delivery vehicle for the oligonucleotides into the droplets, as they are capable of carrying large numbers of oligonucleotide molecules, and may be configured to release those oligonucleotides upon exposure to a particular stimulus, as described elsewhere herein. In some cases, the population of beads will provide a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of oligonucleotide molecules attached. In particular, the number of molecules of oligonucleotides including the barcode sequence on an individual bead can be at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules, or more.

Moreover, when the population of beads are included in droplets, the resulting population of droplets can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each droplet of the population can include at least about 1,000 oligonucleotide molecules, at least about 5,000 oligonucleotide molecules, at least about 10,000 oligonucleotide molecules, at least about 50,000 oligonucleotide molecules, at least about 100,000 oligonucleotide molecules, at least about 500,000 oligonucleotides, at least about 1,000,000 oligonucleotide molecules, at least about 5,000,000 oligonucleotide molecules, at least about 10,000,000 oligonucleotide molecules, at least about 50,000,000 oligonucleotide molecules, at least about 100,000,000 oligonucleotide molecules, and in some cases at least about 1 billion oligonucleotide molecules.

In some cases, it may be desirable to incorporate multiple different barcodes within a given droplet, either attached to a single or multiple particles, e.g., beads, within the droplet. For example, in some cases, mixed, but known barcode sequences set may provide greater assurance of identification in the subsequent processing, for example, by providing a stronger address or attribution of the barcodes to a given droplet, as a duplicate or independent confirmation of the output from a given droplet.

Oligonucleotides may be releasable from the particles (e.g., beads) upon the application of a particular stimulus. In some cases, the stimulus may be a photo-stimulus, e.g., through cleavage of a photo-labile linkage that releases the oligonucleotides. In other cases, a thermal stimulus may be used, where increase in temperature of the particle, e.g., bead, environment will result in cleavage of a linkage or other release of the oligonucleotides form the particles, e.g., beads. In still other cases, a chemical stimulus is used that cleaves a linkage of the oligonucleotides to the beads, or otherwise results in release of the oligonucleotides from the particles, e.g., beads. In one case, such compositions include the polyacrylamide matrices described above for encapsulation of biological particles, and may be degraded for release of the attached oligonucleotides through exposure to a reducing agent, such as dithiothreitol (DTT).

The droplets described herein may contain either one or more biological particles (e.g., cells), either one or more barcode carrying particles, e.g., beads, or both at least a biological particle and at least a barcode carrying particle, e.g., bead. In some instances, a droplet may be unoccupied and contain neither biological particles nor barcode-carrying particles, e.g., beads. As noted previously, by controlling the flow characteristics of each of the liquids combining at the droplet formation region(s), as well as controlling the geometry of the droplet formation region(s), droplet formation can be optimized to achieve a desired occupancy level of particles, e.g., beads, biological particles, or both, within the droplets that are generated.

Kits and Systems

Devices of the invention may be combined with various external components, e.g., pumps, reservoirs, or controllers, reagents, e.g., analyte detection moieties, liquids, particles (e.g., beads), and/or sample in the form of kits and systems.

Methods

The methods described herein to generate droplets, e.g., of uniform and predictable content, and with high throughput, may be used to greatly increase the efficiency of single cell applications and/or other applications receiving droplet-based input. Such single cell applications and other applications may often be capable of processing a certain range of droplet sizes. The methods may be employed to generate droplets for use as microscale chemical reactors, where the volumes of the chemical reactants are small (~pLs).

Methods of the invention include the step of allowing one or more liquids to flow from the channels (e.g., the first, second, and optional third channel) to the droplet formation region.

The methods disclosed herein may produce emulsions, generally, i.e., droplet of a dispersed phases in a continuous phase. For example, droplets may include a first liquid (and optionally a third liquid, and, further, optionally a fourth liquid), and the other liquid may be a second liquid. The first liquid may be substantially immiscible with the second liquid. In some instances, the first liquid may be an aqueous liquid or may be substantially miscible with water. Droplets produced according to the methods disclosed herein may combine multiple liquids. For example, a droplet may combine a first and third liquids. The first liquid may be substantially miscible with the third liquid. The second liquid may be an oil, as described herein.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

The methods described herein may allow for the production of one or more droplets containing a single particle, e.g., bead, and/or single biological particle (e.g., cell) with uniform and predictable droplet content. The methods described herein may allow for the production of one or more droplets containing a single particle, e.g., bead, and/or single biological particle (e.g., cell) with uniform and predictable droplet size. The methods may also allow for the production of one or more droplets comprising a single biological particle (e.g., cell) and more than one particle, e.g., bead, one or more droplets comprising more than one biological particle (e.g., cell) and a single particle, e.g., bead, and/or one or more droplets comprising more than one biological particle (e.g., cell) and more than one particle, e.g., beads. The methods may also allow for increased throughput of droplet formation.

Droplets are in general formed by allowing a first liquid, or a combination of a first liquid with a third liquid and optionally fourth liquid, to flow into a second liquid in a droplet formation region, where droplets spontaneously form as described herein. The droplet content uniformity may be controlled using, e.g., funnels (e.g., funnels including hurdles), side channels, and/or mixers.

Mixers can be used to mix two liquid streams, e.g., before the droplet formation. Mixing two liquids is advantageous for controlling content uniformity of liquid streams and of droplets formed from such liquid streams. For example, one liquid (e.g., a third or fourth liquid) and another liquid (e.g., a first, third, or fourth liquid) may be combined at an intersection of two channels (e.g., an intersection of a first side-channel and a second channel, or an intersection of a second channel and a third channel). The one liquid may contain a biological particle (e.g., a cell), and the other liquid may contain reagents. By using a mixer, the two liquids can be rapidly mixed, thereby reducing localized high concentrations of lysing reagents. Thus, biological particle lysis may be reduced or eliminated until the droplet formation.

The mixer may be included downstream of an intersection between the second and third channels. In this configuration, a third liquid may be combined with a fourth liquid at the intersection. The combined third and fourth liquids may be mixed in the second channel mixer. The mixed third and fourth liquids may then be combined with a first liquid at an intersection between the first and second channels downstream from the mixer.

Alternatively, the mixer may be included downstream of an intersection between a first side-channel and a second channel. For example, a mixer may be included in the first side-channel between an intersection of the first side-channel with the second channel and an intersection of the first side-channel with the first channel. In this configuration, a first liquid flowing through the first side-channel may be combined with the third liquid at the intersection of the first side-channel with the second channel. The combined first and third liquids may be mixed in the first side-channel mixer and are then combined with the liquid in the first channel.

In methods described herein, funnels and/or side-channels may be used to control particle (e.g., bead) flow, e.g., to provide evenly spaced particles (e.g., beads). The evenly spaced particles may be used for forming droplets containing a single particle. Methods described herein including a step of allowing a liquid (e.g., a first liquid) to flow from the first channel to the droplet formation region may include allowing the liquid to flow through the first side-channel and optionally through the second side-channel.

The droplets may comprise an aqueous liquid dispersed phase within a non-aqueous continuous phase, such as an oil phase. In some cases, droplet formation may occur in the absence of externally driven movement of the continuous phase, e.g., a second liquid, e.g., an oil. As discussed above, the continuous phase may nonetheless be externally driven, even though it is not required for droplet formation. Emulsion systems for creating stable droplets in non-aqueous (e.g., oil) continuous phases are described in detail in, for example, U.S. Pat. No. 9,012,390, which is entirely incorporated herein by reference for all purposes. Alternatively or in addition, the droplets may comprise, for example, microvesicles that have an outer barrier surrounding an inner liquid center or core. In some cases, the droplets may comprise a porous matrix that is capable of entraining and/or retaining materials within its matrix. A variety of different vessels are described in, for example, U.S. Patent Application Publication No. 2014/0155295, which is entirely incorporated herein by reference for all purposes. The droplets can be collected in a substantially stationary volume of liquid, e.g., with the buoyancy of the formed droplets moving them out of the path of nascent droplets (up or down depending on the relative density of the droplets and continuous phase). Alternatively or in addition, the formed droplets can be moved out of the path of nascent droplets actively, e.g., using a gentle flow of the continuous phase, e.g., a liquid stream or gently stirred liquid.

Allocating particles, e.g., beads (e.g., microcapsules carrying barcoded oligonucleotides) or biological particles (e.g., cells) to discrete droplets may generally be accomplished by introducing a flowing stream of particles, e.g., beads, in an aqueous liquid into a flowing stream or non-flowing reservoir of a non-aqueous liquid, such that droplets are generated. In some instances, the occupancy of the resulting droplets (e.g., number of particles, e.g., beads, per droplet) can be controlled by providing the aqueous stream at a certain concentration or frequency of particles, e.g., beads. In some instances, the occupancy of the resulting droplets can also be controlled by adjusting one or more geometric features at the point of droplet formation, such as a width of a fluidic channel carrying the particles, e.g., beads, relative to a diameter of a given particles, e.g., beads.

Where single particle-, e.g., bead-, containing droplets are desired, the relative flow rates of the liquids can be selected such that, on average, the droplets contain fewer than one particle, e.g., bead, per droplet in order to ensure that those droplets that are occupied are primarily singly occupied. In some embodiments, the relative flow rates of the liquids can be selected such that a majority of droplets are occupied, for example, allowing for only a small percentage of unoccupied droplets. The flows and channel architectures can be controlled as to ensure a desired number of singly occupied droplets, less than a certain level of unoccupied droplets and/or less than a certain level of multiply occupied droplets.

The methods described herein can be operated such that a majority of occupied droplets include no more than one biological particle per occupied droplet. In some cases, the droplet formation process is conducted such that fewer than 25% of the occupied droplets contain more than one biological particle (e.g., multiply occupied droplets), and in many cases, fewer than 20% of the occupied droplets have more than one biological particle. In some cases, fewer than 10% or even fewer than 5% of the occupied droplets include more than one biological particle per droplet.

It may be desirable to avoid the creation of excessive numbers of empty droplets, for example, from a cost perspective and/or efficiency perspective. However, while this may be accomplished by providing sufficient numbers of particles, e.g., beads, into the droplet formation region, the Poisson distribution may expectedly increase the number of droplets that may include multiple biological particles. As such, at most about 95%, 90%, 85%, 80%, 75%, 70%, 65%, 60%, 55%, 50%, 45%, 40%, 35%, 30%, 25%, 20%, 15%, 10%, 5% or less of the generated droplets can be unoccupied. In some cases, the flow of one or more of the particles, or liquids directed into the droplet formation region can be conducted using devices and systems of the invention (e.g., those including one or more side-channels and/or funnels) such that, in many cases, no more than about 50% of the generated droplets, no more than about 25% of the generated droplets, or no more than about 10% of the generated droplets are unoccupied. These flows can be controlled so as to present non-Poisson distribution of singly occupied droplets while providing lower levels of unoccupied droplets. The above noted ranges of unoccupied droplets can be achieved while still providing any of the single occupancy rates described above. For example, in many cases, the use of the systems and methods described herein creates resulting droplets that have multiple occupancy rates of less than about 25%, less than about 20%, less than about 15%, less than about 10%, and in many cases, less than about 5%, while having unoccupied droplets of less than about 50%, less than about 40%, less than about 30%, less than about 20%, less than about 10%, less than about 5%, or less.

The flow of the first fluid may be such that the droplets contain a single particle, e.g., bead. In certain embodiments, the yield of droplets containing a single particle is at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

As will be appreciated, the above-described occupancy rates are also applicable to droplets that include both biological particles (e.g., cells) and beads. The occupied droplets (e.g., at least about 10%, 20%, 30%, 40%, 50%, 60%, 70%, 80%, 90%, 95%, or 99% of the occupied droplets) can include both a bead and a biological particle. Particles, e.g., beads, within a channel (e.g., a particle channel) may flow at a substantially regular flow profile (e.g., at a regular flow rate; e.g., the flow profile being controlled by one or more side-channels and/or one or more funnels) to provide a droplet, when formed, with a single particle (e.g., bead) and a single cell or other biological particle. Such regular flow profiles may permit the droplets to have a dual occupancy (e.g., droplets having at least one bead and at least one cell or biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99%. In some embodiments, the droplets have a 1:1 dual occupancy (i.e., droplets having exactly one particle (e.g., bead) and exactly one cell or biological particle) greater than 5%, 10%, 20%, 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97% 98%, or 99%. Such regular flow profiles and devices that may be used to provide such regular flow profiles are provided, for example, in U.S. Patent Publication No. 2015/0292988, which is entirely incorporated herein by reference.

In some cases, additional particles may be used to deliver additional reagents to a droplet. In such cases, it may be advantageous to introduce different particles (e.g., beads) into a common channel (e.g., proximal to or upstream from a droplet formation region) or droplet formation intersection from different bead sources (e.g., containing different associated reagents) through different channel inlets into such common channel or droplet formation region. In such cases, the flow and/or frequency of each of the different particle, e.g., bead, sources into the channel or fluidic connections may be controlled to provide for the desired ratio of particles, e.g., beads, from each source, while optionally ensuring the desired pairing or combination of such particles, e.g., beads, are formed into a droplet with the desired number of biological particles.

The droplets described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less. For example, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where the droplets further comprise particles (e.g., beads or microcapsules), it will be appreciated that the sample liquid volume within the droplets may be less than about 90% of the above described volumes, less than about 80%, less than about 70%, less than about 60%, less than about 50%, less than about 40%, less than about 30%, less than about 20%, or less than about 10% the above described volumes (e.g., of a partitioning liquid), e.g., from 1% to 99%, from 5% to 95%, from 10% to 90%, from 20% to 80%, from 30% to 70%, or from 40% to 60%, e.g., from 1% to 5%, 5% to 10%, 10% to 15%, 15% to 20%, 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, 90% to 95%, or 95% to 100% of the above described volumes.

Any suitable number of droplets can be generated. For example, in a method described herein, a plurality of droplets may be generated that comprises at least about 1,000 droplets, at least about 5,000 droplets, at least about 10,000 droplets, at least about 50,000 droplets, at least about 100,000 droplets, at least about 500,000 droplets, at least about 1,000,000 droplets, at least about 5,000,000 droplets at least about 10,000,000 droplets, at least about 50,000,000 droplets, at least about 100,000,000 droplets, at least about 500,000,000 droplets, at least about 1,000,000,000 droplets, or more. Moreover, the plurality of droplets may comprise both unoccupied droplets (e.g., empty droplets) and occupied droplets.

The fluid to be dispersed into droplets may be transported from a reservoir to the droplet formation region. Alternatively, the fluid to be dispersed into droplets is formed in situ by combining two or more fluids in the device. For example, the fluid to be dispersed may be formed by combining one fluid containing one or more reagents with one or more other fluids containing one or more reagents. In these embodiments, the mixing of the fluid streams may result in a chemical reaction. For example, when a particle is employed, a fluid having reagents that disintegrates the particle may be combined with the particle, e.g., immediately upstream of the droplet generating region. In these embodiments, the particles may be cells, which can be combined with lysing reagents, such as surfactants. When particles, e.g., beads, are employed, the particles, e.g., beads, may be dissolved or chemically degraded, e.g., by a change in pH (acid or base), redox potential (e.g., addition of an oxidizing or reducing agent), enzymatic activity, change in salt or ion concentration, or other mechanism.

The first fluid is transported through the first channel at a flow rate sufficient to produce droplets in the droplet formation region. Faster flow rates of the first fluid generally increase the rate of droplet production; however, at a high enough rate, the first fluid will form a jet, which may not break up into droplets. Typically, the flow rate of the first fluid though the first channel may be between about 0.01 µL/min to about 100 µL/min, e.g., 0.1 to 50 µL/min, 0.1 to 10 µL/min, or 1 to 5 µL/min. In some instances, the flow rate of the first liquid may be between about 0.04 µL/min and about 40 µL/min. In some instances, the flow rate of the first liquid may be between about 0.01 µL/min and about 100 µL/min. Alternatively, the flow rate of the first liquid may be less than about 0.01 µL/min. Alternatively, the flow rate of the first liquid may be greater than about 40 µL/min, e.g., 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µL/min, or greater. At lower flow rates, such as flow rates of about less than or equal to 10 µL/min, the droplet radius may not be dependent on the flow rate of first liquid. Alternatively, or in addition, for any of the abovementioned flow rates, the droplet radius may be independent of the flow rate of the first liquid.

The typical droplet formation rate for a single channel in a device of the invention is between 0.1 Hz to 10,000 Hz, e.g., 1 to 1000 Hz or 1 to 500 Hz. The use of multiple first channels can increase the rate of droplet formation by increasing the number of locations of formation.

As discussed above, droplet formation may occur in the absence of externally driven movement of the continuous phase. In such embodiments, the continuous phase flows in response to displacement by the advancing stream of the first fluid or other forces. Channels may be present in the droplet formation region, e.g., including a shelf region, to allow more rapid transport of the continuous phase around the first fluid. This increase in transport of the continuous phase can increase the rate of droplet formation. Alternatively, the continuous phase may be actively transported. For example, the continuous phase may be actively transported into the droplet formation region, e.g., including a shelf region, to increase the rate of droplet formation; continuous phase may be actively transported to form a sheath flow around the first fluid as it exits the distal end; or the continuous phase may be actively transported to move droplets away from the point of formation.

Additional factors that affect the rate of droplet formation include the viscosity of the first fluid and of the continuous phase, where increasing the viscosity of either fluid reduces the rate of droplet formation. In certain embodiments, the viscosity of the first fluid and/or continuous is between 0.5 cP to 10 cP. Furthermore, lower interfacial tension results in slower droplet formation. In certain embodiments, the interfacial tension is between 0.1 and 100 mN/m, e.g., 1 to 100 mN/m or 2 mN/m to 60 mN/m. The depth of the shelf region can also be used to control the rate of droplet formation, with a shallower depth resulting in a faster rate of formation.

The methods may be used to produce droplets in range of 1 µm to 500 µm in diameter, e.g., 1 to 250 µm, 5 to 200 µm, 5 to 150 µm, or 12 to 125 µm. Factors that affect the size of the droplets include the rate of formation, the cross-sectional dimension of the distal end of the first channel, the depth of the shelf, and fluid properties and dynamic effects, such as the interfacial tension, viscosity, and flow rate.

The first liquid may be aqueous, and the second liquid may be an oil (or vice versa). Examples of oils include perfluorinated oils, mineral oil, and silicone oils. For example, a fluorinated oil may include a fluorosurfactant for stabilizing the resulting droplets, for example, inhibiting subsequent coalescence of the resulting droplets. Examples of particularly useful liquids and fluorosurfactants are described, for example, in U.S. Pat. No. 9,012,390, which is entirely incorporated herein by reference for all purposes. Specific examples include hydrofluoroethers, such as HFE 7500, 7300, 7200, or 7100. Suitable liquids are those described in US 2015/0224466 and U.S. 62/522,292, the liquids of which are hereby incorporated by reference. In some cases, liquids include additional components such as a particle, e.g., a cell or a gel bead. As discussed above, the first fluid or continuous phase may include reagents for carrying out various reactions, such as nucleic acid amplification, lysis, or bead dissolution. The first liquid or continuous phase may include additional components that stabilize or otherwise affect the droplets or a component inside the droplet. Such additional components include surfactants, antioxidants, preservatives, buffering agents, antibiotic agents, salts, chaotropic agents, enzymes, nanoparticles, and sugars.

Once formed, droplets may be manipulated, e.g., transported, detected, sorted, held, incubated, reacted, or demulsified. Droplets may be manipulated in a reservoir or reentrained into a channel for manipulation. Reentrainment may occur by any mechanism, e.g., pressure, magnetic, electric, dielectrophoretic, optical, etc. Various generally applicable methods for reentrainment are described herein.

Devices, systems, compositions, and methods of the invention may be used for various applications, such as, for example, processing a single analyte (e.g., bioanalytes, e.g., RNA, DNA, or protein) or multiple analytes (e.g., bioanalytes, e.g., DNA and RNA, DNA and protein, RNA and protein, or RNA, DNA and protein) from a single cell. For example, a biological particle (e.g., a cell or virus) can be formed in a droplet, and one or more analytes (e.g., bioanalytes) from the biological particle (e.g., cell) can be modified or detected (e.g., bound, labeled, or otherwise modified by an analyte detection moiety) for subsequent processing. The multiple analytes may be from the single cell. This process may enable, for example, proteomic, transcriptomic, and/or genomic analysis of the cell or population thereof (e.g., simultaneous proteomic, transcriptomic, and/or genomic analysis of the cell or population thereof).

Methods of modifying analytes include providing a plurality of particles (e.g., beads) in a liquid carrier (e.g., an aqueous carrier); providing a sample containing an analyte (e.g., as part of a cell, or component or product thereof) in a sample liquid; and using the device to combine the liquids and form an analyte detection droplet containing one or more particles and one or more analytes (e.g., as part of one or more cells, or components or products thereof). Such sequestration of one or more particles with analyte (e.g., bioanalyte associated with a cell) in a droplet enables labeling of discrete portions of large, heterologous samples (e.g., single cells within a heterologous population). Once labeled or otherwise modified, droplets can be combined (e.g., by breaking an emulsion), and the resulting liquid can be analyzed to determine a variety of properties associated with each of numerous single cells.

In particular embodiments, the invention features methods of producing analyte detection droplets using a device having a particle channel (e.g., a first channel) and a sample channel (e.g., a second channel or a first side-channel that intersects a second channel) that intersect upstream of a droplet formation region. Particles having an analyte-detection moiety in a liquid carrier flow proximal-to-distal (e.g., towards the droplet formation region) through the particle channel (e.g., a first channel) and a sample liquid containing an analyte flows in the proximal-to-distal direction (e.g., towards the droplet formation region) through the sample channel (e.g., a second channel or a first side-channel that intersects a second channel) until the two liquids meet and combine at the intersection of the sample channel and the particle channel, upstream (and/or proximal to) the droplet formation region. The combination of the liquid carrier with the sample liquid results in an analyte detection liquid. In some embodiments, the two liquids are miscible (e.g., they both contain solutes in water or aqueous buffer). The two liquids may be mixed in a mixer as described herein. The combination of the two liquids can occur at a controlled relative rate, such that the analyte detection liquid has a desired volumetric ratio of particle liquid to sample liquid, a desired numeric ratio of particles to cells, or a combination thereof (e.g., one particle per cell per 50 pL). As the analyte detection liquid flows through the droplet formation region into a partitioning liquid (e.g., a liquid which is immiscible with the analyte detection liquid, such as an oil), analyte detection droplets form. These analyte detection droplets may continue to flow through one or more channels. Alternatively or in addition, the analyte detection droplets may accumulate (e.g., as a substantially stationary population) in a droplet collection region. In some cases, the accumulation of a population of droplets may occur by a gentle flow of a fluid within the droplet collection region, e.g., to move the formed droplets out of the path of the nascent droplets.

Devices useful for analyte detection may feature any combination of elements described herein. For example, various droplet formation regions can be employed in the design of a device for analyte detection. In some embodiments, analyte detection droplets are formed at a droplet formation region having a shelf region, where the analyte detection liquid expands in at least one dimension as it passes through the droplet formation region. Any shelf region described herein can be useful in the methods of analyte detection droplet formation provided herein. Additionally or alternatively, the droplet formation region may have a step at or distal to an inlet of the droplet formation region (e.g., within the droplet formation region or distal to the droplet formation region). In some embodiments, analyte detection droplets are formed without externally driven flow of a continuous phase (e.g., by one or more crossing flows of liquid at the droplet formation region). Alternatively, analyte detection droplets are formed in the presence of an externally driven flow of a continuous phase.

A device useful for droplet formation, e.g., analyte detection, may feature multiple droplet formation regions (e.g., in or out of (e.g., as independent, parallel circuits) fluid communication with one another. For example, such a device may have 2-100, 3-50, 4-40, 5-30, 6-24, 8-18, or 9-12, e.g., 2-6, 6-12, 12-18, 18-24, 24-36, 36-48, or 48-96, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more droplet formation regions configured to produce analyte detection droplets).

Source reservoirs can store liquids prior to and during droplet formation. In some embodiments, a device useful in analyte detection droplet formation includes one or more particle reservoirs connected proximally to one or more particle channels. Particle suspensions can be stored in particle reservoirs (e.g., a first reservoir) prior to analyte detection droplet formation. Particle reservoirs can be configured to store particles containing an analyte detection moiety. For example, particle reservoirs can include, e.g., a coating to prevent adsorption or binding (e.g., specific or non-specific binding) of particles or analyte-detection moieties. Additionally or alternatively, particle reservoirs can be configured to minimize degradation of analyte detection moieties (e.g., by containing nuclease, e.g., DNAse or RNAse) or the particle matrix itself, accordingly.

Additionally, or alternatively, a device includes one or more sample reservoirs connected proximally to one or more sample channels. Samples containing cells and/or other reagents useful in analyte detection and/or droplet formation can be stored in sample reservoirs prior to analyte detection droplet formation. Sample reservoirs can be configured to reduce degradation of sample components, e.g., by including nuclease (e.g., DNAse or RNAse).

Methods of the invention may include adding a sample and/or particles to the device, for example, (a) by pipetting a sample liquid, or a component or concentrate thereof, into a sample reservoir (e.g., a second reservoir) and/or (b) by pipetting a liquid carrier (e.g., an aqueous carrier) and/or particles into a particle reservoir (e.g., a first reservoir). In some embodiments, the method involves first adding (e.g., pipetting) the liquid carrier (e.g., an aqueous carrier) and/or particles into the particle reservoir prior to adding (e.g., pipetting) the sample liquid, or a component or concentrate thereof, into the sample reservoir. In some embodiments, the liquid carrier added to the particle reservoir includes lysing reagents. Alternatively, the methods of the invention include adding a liquid (e.g., a fourth liquid) containing lysing reagent(s) to a lysing reagent reservoir (e.g., a third reservoir).

The sample reservoir and/or particle reservoir may be incubated in conditions suitable to preserve or promote activity of their contents until the initiation or commencement of droplet formation.

Formation of bioanalyte detection droplets, as provided herein, can be used for various applications. In particular, by forming bioanalyte detection droplets using the methods, devices, systems, and kits herein, a user can perform standard downstream processing methods to barcode heterogeneous populations of cells or perform single-cell nucleic acid sequencing.

In methods of barcoding a population of cells, an aqueous sample having a population of cells is combined with bioanalyte detection particles having a nucleic acid primer sequence and a barcode in an aqueous carrier at an intersection of the sample channel and the particle channel to form a reaction liquid. In some embodiments, the bioanalyte detection particles are in a liquid carrier including lysing reagents. For example, the liquid carrier including bioanalyte detection particles and a liquid carrier may be used in a device or system including a first side-channel intersection with a second channel. In some embodiments, the lysing reagents are included in a lysing liquid. For example, a lysing liquid may be used in a device or system including a second channel, a third channel, and an intersection between them. The lysing reagent(s) (e.g., in a first liquid or in a fourth liquid) may be combined with a sample liquid (e.g., a third liquid) at a channel intersection (e.g., an intersection between a first side-channel and a second channel or an intersection between a first channel and a second channel). The combined liquids can be mixed in a mixer disposed downstream of the intersection.

Upon passing through the droplet formation region, the reaction liquid meets a partitioning liquid (e.g., a partitioning oil) under droplet-forming conditions to form a plurality of reaction droplets, each reaction droplet having one or more of the particles and one or more cells in the reaction liquid. The reaction droplets are incubated under conditions sufficient to allow for barcoding of the nucleic acid of the cells in the reaction droplets. In some embodiments, the conditions sufficient for barcoding are thermally optimized for nucleic acid replication, transcription, and/or amplification. For example, reaction droplets can be incubated at temperatures configured to enable reverse transcription of RNA produced by a cell in a droplet into DNA, using reverse transcriptase. Additionally or alternatively, reaction droplets may be cycled through a series of temperatures to promote amplification, e.g., as in a polymerase chain reaction (PCR). Accordingly, in some embodiments, one or more nucleotide amplification reagents (e.g., PCR reagents) are included in the reaction droplets (e.g., primers, nucleotides, and/or polymerase). Any one or more reagents for nucleic acid replication, transcription, and/or amplification can be provided to the reaction droplet by the aqueous sample, the liquid carrier, or both. In some embodiments, one or more of the reagents for nucleic acid replication, transcription, and/or amplification are in the aqueous sample.

Also provided herein are methods of single-cell nucleic acid sequencing, in which a heterologous population of cells can be characterized by their individual gene expression, e.g., relative to other cells of the population. Methods of barcoding cells discussed above and known in the art can be part of the methods of single-cell nucleic acid sequencing provided herein. After barcoding, nucleic acid transcripts that have been barcoded are sequenced, and sequences can be processed, analyzed, and stored according to known methods. In some embodiments, these methods enable the generation of a genome library containing gene expression data for any single cell within a heterologous population.

Alternatively, the ability to sequester a single cell in a reaction droplet provided by methods herein enables bioanalyte detection for applications beyond genome characterization. For example, a reaction droplet containing a single cell and variety of analyte detection moieties capable of binding different proteins can allow a single cell to be detectably labeled to provide relative protein expression data. In some embodiments, analyte detection moieties are antigen-binding molecules (e.g., antibodies or fragments thereof), wherein each antibody clone is detectably labeled (e.g., with a fluorescent marker having a distinct emission wavelength). Binding of antibodies to proteins can occur within the reaction droplet, and cells can be subsequently analyzed for bound antibodies according to known methods to generate a library of protein expression. Other methods known in the art can be employed to characterize cells within heterologous populations after detecting analytes using the methods provided herein. In one example, following the formation or droplets, subsequent operations that can be performed can include formation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the droplet). An exemplary use for droplets formed using methods of the invention is in performing nucleic acid amplification, e.g., polymerase chain reaction (PCR), where the reagents necessary to carry out the amplification are contained within the first fluid. In the case where a droplet is a droplet in an emulsion, the emulsion can be broken and the contents of the droplet pooled for additional operations. Additional reagents that may be included in a droplet along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of poly-T sequence during sequencing and/or sequence the 5' end of a polynucleotide sequence. The amplification products, for example first amplification products and/or second amplification products, may be subject to sequencing for sequence analysis. In some cases, amplification may be performed using the Partial Hairpin Amplification for Sequencing (PHASE) method.

Methods of Device Manufacture

The microfluidic devices of the invention may be fabricated in any of a variety of conventional ways. For example, in some cases the devices comprise layered structures, where a first layer includes a planar surface into which is disposed a series of channels or grooves that correspond to the channel network in the finished device. A second layer includes a planar surface on one side, and a series of reservoirs defined on the opposing surface, where the reservoirs communicate as passages through to the planar layer, such that when the planar surface of the second layer is mated with the planar surface of the first layer, the reservoirs defined in the second layer are positioned in liquid communication with the termini of the channels on the first layer. Alternatively, both the reservoirs and the connected channels may be fabricated into a single part, where the reservoirs are provided upon a first surface of the structure, with the apertures of the reservoirs extending through to the opposing surface of the structure. The channel network is fabricated as a series of grooves and features in this second surface. A thin laminating layer is then provided over the second surface to seal, and provide the final wall of the channel network, and the bottom surface of the reservoirs.

These layered structures may be fabricated in whole or in part from polymeric materials, such as polyethylene or polyethylene derivatives, such as cyclic olefin copolymers (COC), polymethylmethacrylate (PMMA), polydimethylsiloxane (PDMS), polycarbonate, polystyrene, polypropylene, polyvinyl chloride, polytetrafluoroethylene, polyoxymethylene, polyether ether ketone, polycarbonate, polystyrene, or the like, or they may be fabricated in whole or in part from inorganic materials, such as silicon, or other silica based materials, e.g., glass, quartz, fused silica, borosilicate glass, metals, ceramics, and combinations thereof. Polymeric device components may be fabricated using any of a number of processes including soft lithography, embossing techniques, micromachining, e.g., laser machining, or in some aspects injection molding of the layer components that include the defined channels as well as other structures, e.g., reservoirs, integrated functional components, etc. In some aspects, the structure comprising the reservoirs and channels may be fabricated using, e.g., injection molding techniques to produce polymeric structures. In such cases, a laminating layer may be adhered to the molded structured part through readily available methods, including thermal lamination, solvent based lamination, sonic welding, or the like.

As will be appreciated, structures comprised of inorganic materials also may be fabricated using known techniques. For example, channels and other structures may be micromachined into surfaces or etched into the surfaces using standard photolithographic techniques. In some aspects, the microfluidic devices or components thereof may be fabricated using three-dimensional printing techniques to fabricate the channel or other structures of the devices and/or their discrete components.

Methods for Surface Modifications

The invention features methods for producing a microfluidic device that has a surface modification, e.g., a surface with a modified water contact angle. The methods may be employed to modify the surface of a device such that a liquid can "wet" the surface by altering the contact angle the liquid makes with the surface. An exemplary use of the methods of the invention is in creating a device having differentially coated surfaces to optimize droplet formation.

Devices to be modified with surface coating agents may be primed, e.g., pre-treated, before coating processes occur. In one embodiment, the device has a channel that is in fluid communication with a droplet formation region. In particular, the droplet formation region is configured to allow a liquid exiting the channel to expand in at least one dimension. A surface of the droplet formation region is contacted by at least one reagent that has an affinity for the primed surface to produce a surface having a first water contact angle of greater than about 90°, e.g., a hydrophobic or fluorophillic surface. In certain embodiments, the first contact angle is greater than the water contact angle of the primed surface. In other embodiments, the first contact angle is greater than the water contact angle of the channel surface. Thus, the method allows for the differential coating of surfaces within the microfluidic device.

A surface may be primed by depositing a metal oxide onto it. Example metal oxides useful for priming surfaces include, but are not limited to, $Al_2O_3$, $TiO_2$, $SiO_2$, or a combination thereof. Other metal oxides useful for surface modifications are known in the art. The metal oxide can be applied to the surface by standard deposition techniques, including, but not limited to, atomic layer deposition (ALD), physical vapor deposition (PVD), e.g., sputtering, chemical vapor deposition (CVD), or laser deposition. Other deposition techniques for coating surfaces, e.g., liquid-based deposition, are known in the art. For example, an atomic layer of $Al_2O_3$ can be prepared on a surface by depositing trimethylaluminum (TMA) and water.

In some cases, the coating agent may create a surface that has a water contact angle greater than 90°, e.g., hydrophobic or fluorophillic, or may create a surface with a water contact angle of less than 90°, e.g., hydrophilic. For example, a fluorophillic surface may be created by flowing fluorosilane (e.g., $H_3FSi$) through a primed device surface, e.g., a surface coated in a metal oxide. The priming of the surfaces of the device enhances the adhesion of the coating agents to the surface by providing appropriate surface functional groups. In some cases, the coating agent used to coat the primed surface may be a liquid reagent. For example, when a liquid coating agent is used to coat a surface, the coating agent may be directly introduced to the droplet formation region by a feed channel in fluid communication with the droplet formation region. In order to keep the coating agent localized to the droplet formation region, e.g., prevent ingress of the coating agent to another portion of the device, e.g., the channel, the portion of the device that is not to be coated can be substantially blocked by a substance that does not allow the coating agent to pass. For example, in order to prevent ingress of a liquid coating agent into the channel, the channel may be filled with a blocking liquid that is substantially immiscible with the coating agent. The blocking liquid may be actively transported through the portion of the device not to be coated, or the blocking liquid may be stationary. Alternatively, the channel may be filled with a pressurized gas such that the pressure prevents ingress of the coating agent into the channel. The coating agent may also be applied to the regions of interest external to the main device. For example, the device may incorporate an additional reservoir and at least one feed channel that connects to the region of interest such that no coating agent is passed through the device.

EXAMPLE

Examples 1-22 show various droplets formation regions and configurations that may be used in any device of the invention. It will be understood, that although channels, reservoirs, and inlets are labeled as "sample" and "reagent" herein, each channel, reservoir, and inlet may be for either a sample or a reagent being used.

Example 1

FIG. 1 shows an example of a microfluidic device for the controlled inclusion of particles, e.g., beads, into discrete droplets. A device 100 can include a channel 102 communicating at a fluidic connection 106 (or intersection) with a reservoir 104. The reservoir 104 can be a chamber. Any reference to "reservoir," as used herein, can also refer to a "chamber." In operation, an aqueous liquid 108 that includes suspended beads 112 may be transported along the channel 102 into the fluidic connection 106 to meet a second liquid 110 that is immiscible with the aqueous liquid 108 in the reservoir 104 to create droplets 116, 118 of the aqueous liquid 108 flowing into the reservoir 104. At the fluidic connection 106 where the aqueous liquid 108 and the second liquid 110 meet, droplets can form based on factors such as the hydrodynamic forces at the fluidic connection 106, flow rates of the two liquids 108, 110, liquid properties, and certain geometric parameters (e.g., w, $h_0$, α, etc.) of the device 100. A plurality of droplets can be collected in the reservoir 104 by continuously injecting the aqueous liquid 108 from the channel 102 through the fluidic connection 106.

In some instances, the second liquid 110 may not be subjected to and/or directed to any flow in or out of the reservoir 104. For example, the second liquid 110 may be substantially stationary in the reservoir 104. In some instances, the second liquid 110 may be subjected to flow within the reservoir 104, but not in or out of the reservoir 104, such as via application of pressure to the reservoir 104 and/or as affected by the incoming flow of the aqueous liquid 108 at the fluidic connection 106. Alternatively, the second liquid 110 may be subjected and/or directed to flow in or out of the reservoir 104. For example, the reservoir 104 can be a channel directing the second liquid 110 from upstream to downstream, transporting the generated droplets. Alternatively or in addition, the second liquid 110 in reservoir 104 may be used to sweep formed droplets away from the path of the nascent droplets.

While FIG. 1 illustrates the reservoir 104 having a substantially linear inclination (e.g., creating the expansion angle, α) relative to the channel 102, the inclination may be non-linear. The expansion angle may be an angle between the immediate tangent of a sloping inclination and the channel 102. In an example, the reservoir 104 may have a dome-like (e.g., hemispherical) shape. The reservoir 104 may have any other shape.

Example 2

Figure 2:
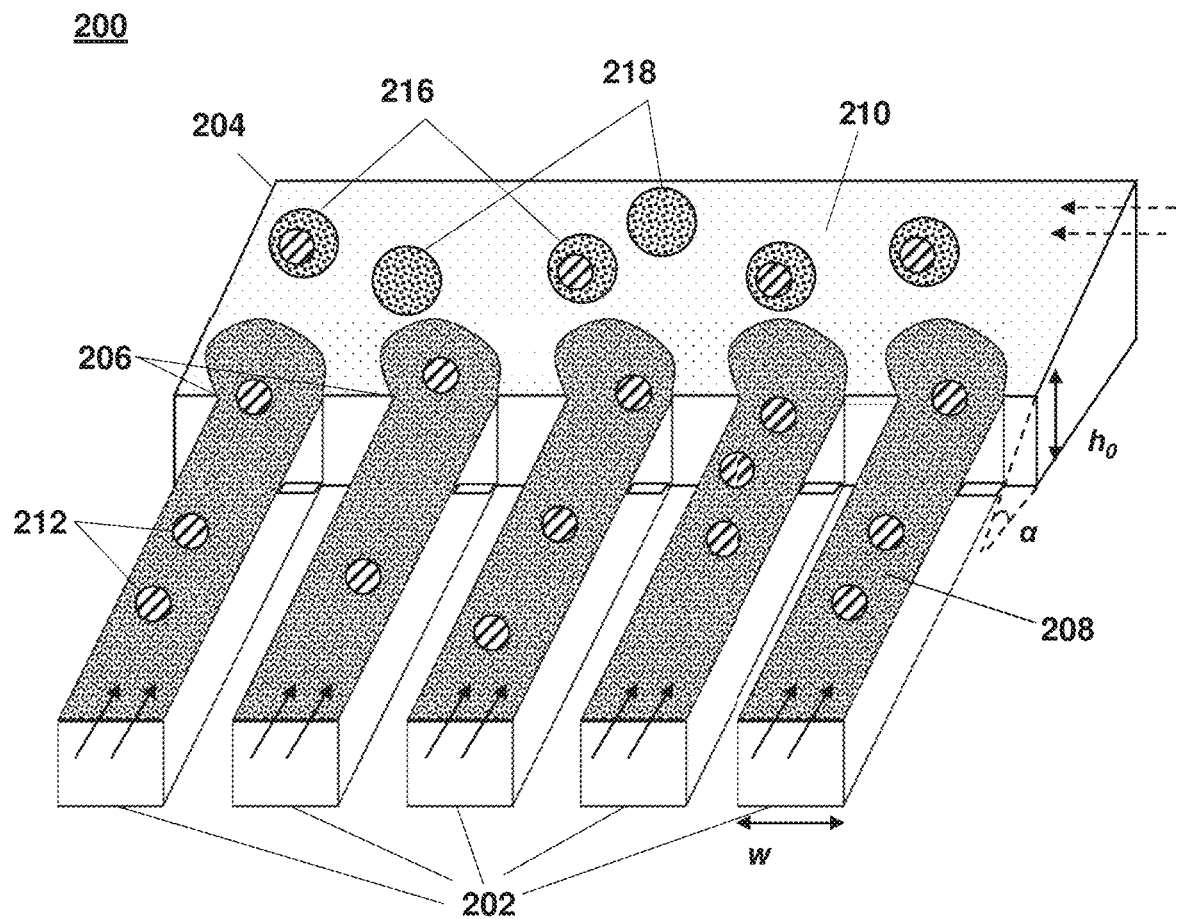
FIG. 2 shows an example of a microfluidic device for increased droplet formation throughput.

FIG. 2 shows an example of a microfluidic device for increased droplet formation throughput. A device 200 can comprise a plurality of channels 202 and a reservoir 204. Each of the plurality of channels 202 may be in fluid communication with the reservoir 204. The device 200 can comprise a plurality of fluidic connections 206 between the plurality of channels 202 and the reservoir 204. Each fluidic connection can be a point of droplet formation. The channel 102 from the device 100 in FIG. 1 and any description to the components thereof may correspond to a given channel of the plurality of channels 202 in device 200 and any description to the corresponding components thereof. The reservoir 104 from the device 100 and any description to the components thereof may correspond to the reservoir 204 from the device 200 and any description to the corresponding components thereof.

Each channel of the plurality of channels 202 may comprise an aqueous liquid 208 that includes suspended particles, e.g., beads, 212. The reservoir 204 may comprise a second liquid 210 that is immiscible with the aqueous liquid 208. In some instances, the second liquid 210 may not be subjected to and/or directed to any flow in or out of the reservoir 204. For example, the second liquid 210 may be substantially stationary in the reservoir 204. Alternatively or in addition, the formed droplets can be moved out of the path of nascent droplets using a gentle flow of the second liquid 210 in the reservoir 204. In some instances, the second liquid 210 may be subjected to flow within the reservoir 204, but not in or out of the reservoir 204, such as via application of pressure to the reservoir 204 and/or as affected by the incoming flow of the aqueous liquid 208 at the fluidic connections. Alternatively, the second liquid 210 may be subjected and/or directed to flow in or out of the reservoir 204. For example, the reservoir 204 can be a channel directing the second liquid 210 from upstream to downstream, transporting the generated droplets. Alternatively or in addition, the second liquid 210 in reservoir 204 may be used to sweep formed droplets away from the path of the nascent droplets.

In operation, the aqueous liquid 208 that includes suspended particles, e.g., beads, 212 may be transported along the plurality of channels 202 into the plurality of fluidic connections 206 to meet the second liquid 210 in the reservoir 204 to create droplets 216, 218. A droplet may form from each channel at each corresponding fluidic connection with the reservoir 204. At the fluidic connection where the aqueous liquid 208 and the second liquid 210 meet, droplets can form based on factors such as the hydrodynamic forces at the fluidic connection, flow rates of the two liquids 208, 210, liquid properties, and certain geometric parameters (e.g., w, $h_0$, α, etc.) of the device 200, as described elsewhere herein. A plurality of droplets can be collected in the reservoir 204 by continuously injecting the aqueous liquid 208 from the plurality of channels 202 through the plurality of fluidic connections 206. The geometric parameters, w, $h_0$, and α, may or may not be uniform for each of the channels in the plurality of channels 202. For example, each channel may have the same or different widths at or near its respective fluidic connection with the reservoir 204. For example, each channel may have the same or different height at or near its respective fluidic connection with the reservoir 204. In another example, the reservoir 204 may have the same or different expansion angle at the different fluidic connections with the plurality of channels 202. When the geometric parameters are uniform, beneficially, droplet size may also be controlled to be uniform even with the increased throughput. In some instances, when it is desirable to have a different distribution of droplet sizes, the geometric parameters for the plurality of channels 202 may be varied accordingly.

Example 3

Figure 3:
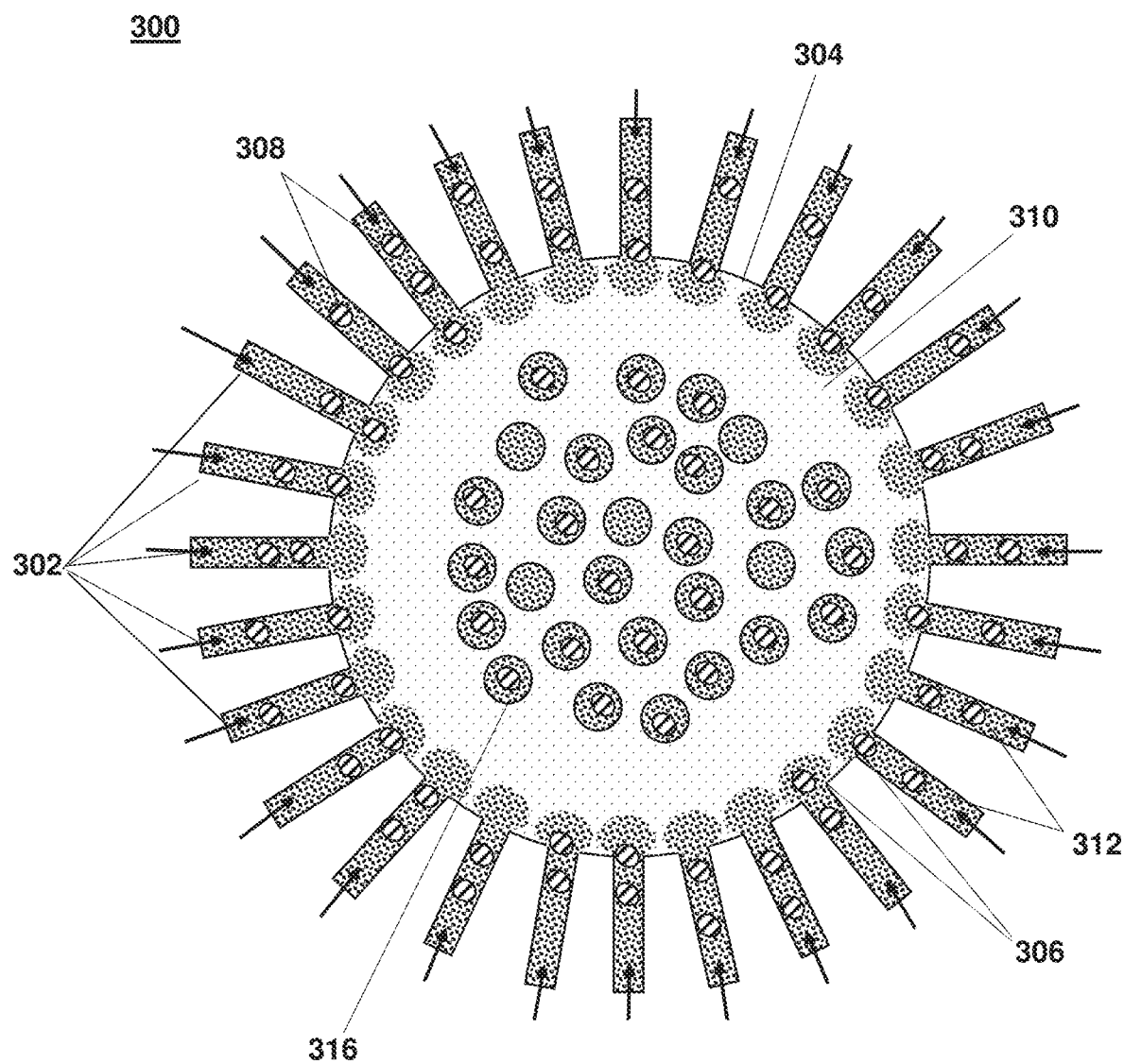
FIG. 3 shows another example of a microfluidic device for increased droplet formation throughput.

FIG. 3 shows another example of a microfluidic device for increased droplet formation throughput. A microfluidic device 300 can comprise a plurality of channels 302 arranged generally circularly around the perimeter of a reservoir 304. Each of the plurality of channels 302 may be in liquid communication with the reservoir 304. The device 300 can comprise a plurality of fluidic connections 306 between the plurality of channels 302 and the reservoir 304. Each fluidic connection can be a point of droplet formation. The channel 102 from the device 100 in FIG. 1 and any description to the components thereof may correspond to a given channel of the plurality of channels 302 in device 300 and any description to the corresponding components thereof. The reservoir 104 from the device 100 and any description to the components thereof may correspond to the reservoir 304 from the device 300 and any description to the corresponding components thereof.

Each channel of the plurality of channels 302 may comprise an aqueous liquid 308 that includes suspended particles, e.g., beads, 312. The reservoir 304 may comprise a second liquid 310 that is immiscible with the aqueous liquid 308. In some instances, the second liquid 310 may not be subjected to and/or directed to any flow in or out of the reservoir 304. For example, the second liquid 310 may be substantially stationary in the reservoir 304. In some instances, the second liquid 310 may be subjected to flow within the reservoir 304, but not in or out of the reservoir 304, such as via application of pressure to the reservoir 304 and/or as affected by the incoming flow of the aqueous liquid 308 at the fluidic connections. Alternatively, the second liquid 310 may be subjected and/or directed to flow in or out of the reservoir 304. For example, the reservoir 304 can be a channel directing the second liquid 310 from upstream to downstream, transporting the generated droplets. Alternatively or in addition, the second liquid 310 in reservoir 304 may be used to sweep formed droplets away from the path of the nascent droplets.

In operation, the aqueous liquid 308 that includes suspended particles, e.g., beads, 312 may be transported along the plurality of channels 302 into the plurality of fluidic connections 306 to meet the second liquid 310 in the reservoir 304 to create a plurality of droplets 316. A droplet may form from each channel at each corresponding fluidic connection with the reservoir 304. At the fluidic connection where the aqueous liquid 308 and the second liquid 310 meet, droplets can form based on factors such as the hydrodynamic forces at the fluidic connection, flow rates of the two liquids 308, 310, liquid properties, and certain geometric parameters (e.g., widths and heights of the channels 302, expansion angle of the reservoir 304, etc.) of the channel 300, as described elsewhere herein. A plurality of droplets can be collected in the reservoir 304 by continuously injecting the aqueous liquid 308 from the plurality of channels 302 through the plurality of fluidic connections 306.

Example 4

Figure 4:
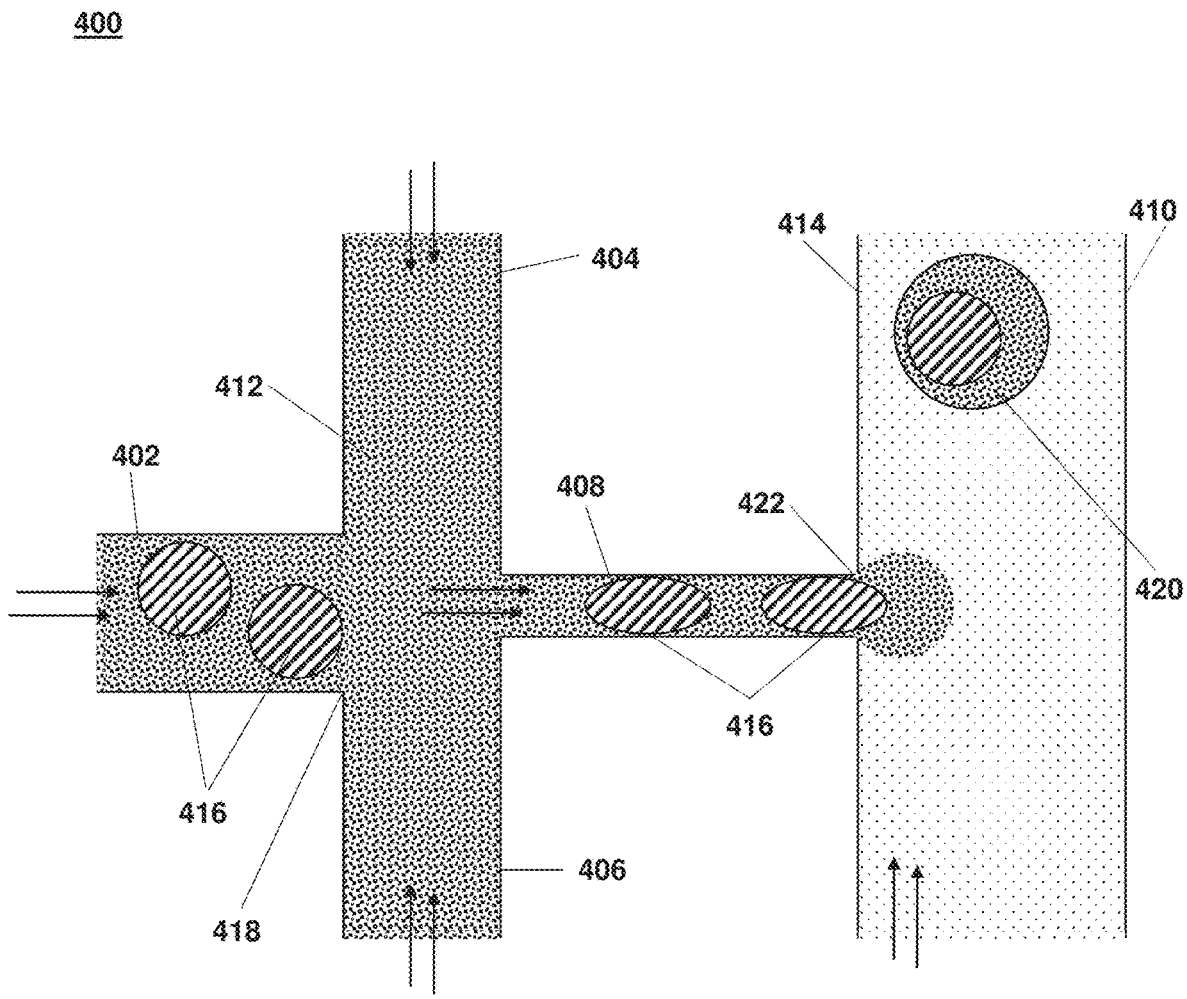
FIG. 4 shows another example of a microfluidic device for the introduction of particles, e.g., beads, into discrete droplets.

FIG. 4 shows another example of a microfluidic device for the introduction of beads into discrete droplets. A device 400 can include a first channel 402, a second channel 404, a third channel 404, a fourth channel 406, and a reservoir 410. The first channel 402, second channel 404, third channel 404, and fourth channel 406 can communicate at a first intersection 418. The fourth channel 406 and the reservoir 410 can communicate at a fluidic connection 422. In some instances, the fourth channel 406 and components thereof can correspond to the channel 102 in the device 100 in FIG. 1 and components thereof. In some instances, the reservoir 410 and components thereof can correspond to the reservoir 104 in the device 100 and components thereof.

In operation, an aqueous liquid 412 that includes suspended particles, e.g., beads, 416 may be transported along the first channel 402 into the intersection 418 at a first frequency to meet another source of the aqueous liquid 412 flowing along the second channel 404 and the third channel 406 towards the intersection 418 at a second frequency. In some instances, the aqueous liquid 412 in the second channel 404 and the third channel 406 may comprise one or more reagents. At the intersection, the combined aqueous liquid 412 carrying the suspended particles, e.g., beads, 416 (and/or the reagents) can be directed into the fourth channel 408. In some instances, a cross-section width or diameter of the fourth channel 408 can be chosen to be less than a cross-section width or diameter of the particles, e.g., beads, 416. In such cases, the particles, e.g., beads, 416 can deform and travel along the fourth channel 408 as deformed particles, e.g., beads, 420 towards the fluidic connection 422. At the fluidic connection 422, the aqueous liquid 412 can meet a second liquid 414 that is immiscible with the aqueous liquid 412 in the reservoir 410 to create droplets 420 of the aqueous liquid 412 flowing into the reservoir 410. Upon leaving the fourth channel 408, the deformed particles, e.g., beads, 420 may revert to their original shape in the droplets 420. At the fluidic connection 422 where the aqueous liquid 412 and the second liquid 414 meet, droplets can form based on factors such as the hydrodynamic forces at the fluidic connection 422, flow rates of the two liquids 412, 414, liquid properties, and certain geometric parameters (e.g., w, $h_0$, α, etc.) of the channel 400, as described elsewhere herein. A plurality of droplets can be collected in the reservoir 410 by continuously injecting the aqueous liquid 412 from the fourth channel 408 through the fluidic connection 422.

A discrete droplet generated may include a particle, e.g., a bead, (e.g., as in droplets 420). Alternatively, a discrete droplet generated may include more than one particle, e.g., bead. Alternatively, a discrete droplet generated may not include any particles, e.g., beads. In some instances, a discrete droplet generated may contain one or more biological particles, e.g., cells (not shown in FIG. 4).

In some instances, the second liquid 414 may not be subjected to and/or directed to any flow in or out of the reservoir 410. For example, the second liquid 414 may be substantially stationary in the reservoir 410. In some instances, the second liquid 414 may be subjected to flow within the reservoir 410, but not in or out of the reservoir 410, such as via application of pressure to the reservoir 410 and/or as affected by the incoming flow of the aqueous liquid 412 at the fluidic connection 422. In some instances, the second liquid 414 may be gently stirred in the reservoir 410. Alternatively, the second liquid 414 may be subjected and/or directed to flow in or out of the reservoir 410. For example, the reservoir 410 can be a channel directing the second liquid 414 from upstream to downstream, transporting the generated droplets. Alternatively or in addition, the second liquid 414 in reservoir 410 may be used to sweep formed droplets away from the path of the nascent droplets.

Example 5

Figure 5A:
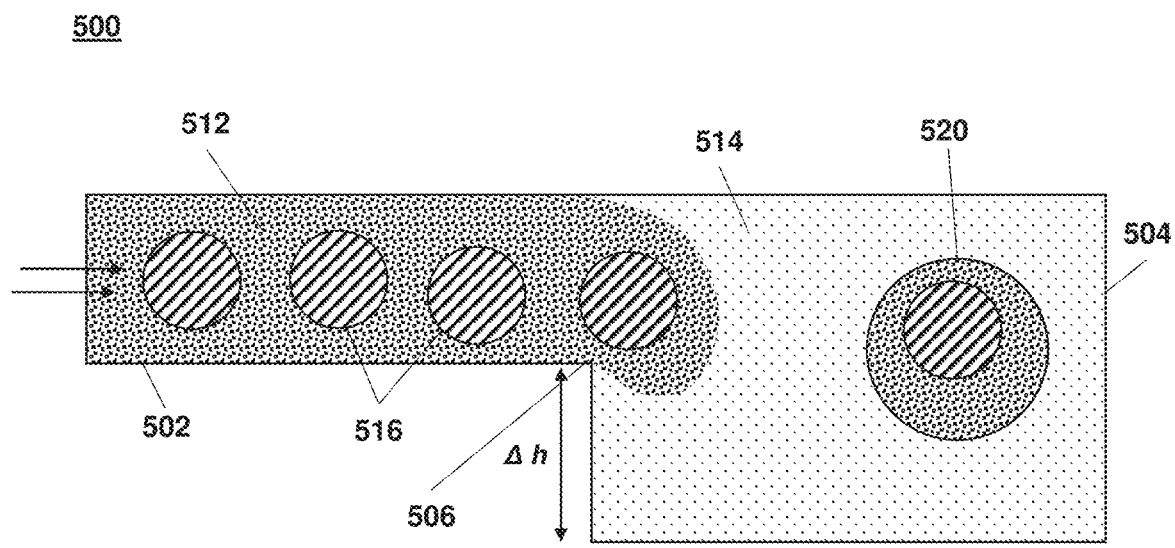
FIGS. 5A-5B show cross-section (FIG. 5A) and perspective (FIG. 5B) views an embodiment according to the invention of a microfluidic device with a geometric feature for droplet formation.

FIG. 5A shows a cross-section view of another example of a microfluidic device with a geometric feature for droplet formation. A device 500 can include a channel 502 communicating at a fluidic connection 506 (or intersection) with a reservoir 504. In some instances, the device 500 and one or more of its components can correspond to the device 100 and one or more of its components. FIG. 7B shows a perspective view of the device 500 of FIG. 7A.

An aqueous liquid 512 comprising a plurality of particles 516 may be transported along the channel 502 into the fluidic connection 506 to meet a second liquid 514 (e.g., oil, etc.) that is immiscible with the aqueous liquid 512 in the reservoir 504 to create droplets 520 of the aqueous liquid 512 flowing into the reservoir 504. At the fluidic connection 506 where the aqueous liquid 512 and the second liquid 514 meet, droplets can form based on factors such as the hydrodynamic forces at the fluidic connection 506, relative flow rates of the two liquids 512, 514, liquid properties, and certain geometric parameters (e.g., Δh, etc.) of the device 500. A plurality of droplets can be collected in the reservoir 504 by continuously injecting the aqueous liquid 512 from the channel 502 at the fluidic connection 506.

Figure 5B:
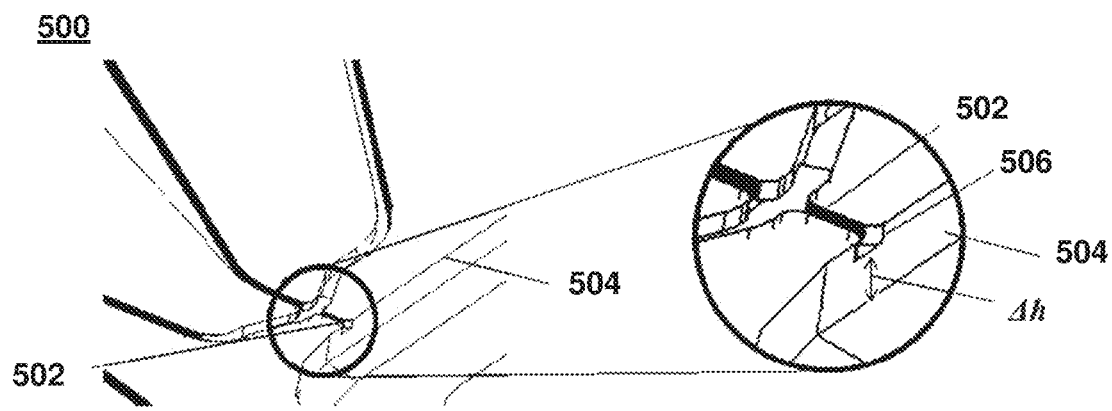

While FIGS. 5A and 5B illustrate the height difference, Δh, being abrupt at the fluidic connection 506 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the fluidic connection 506, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly.

Example 6

Figure 6A:
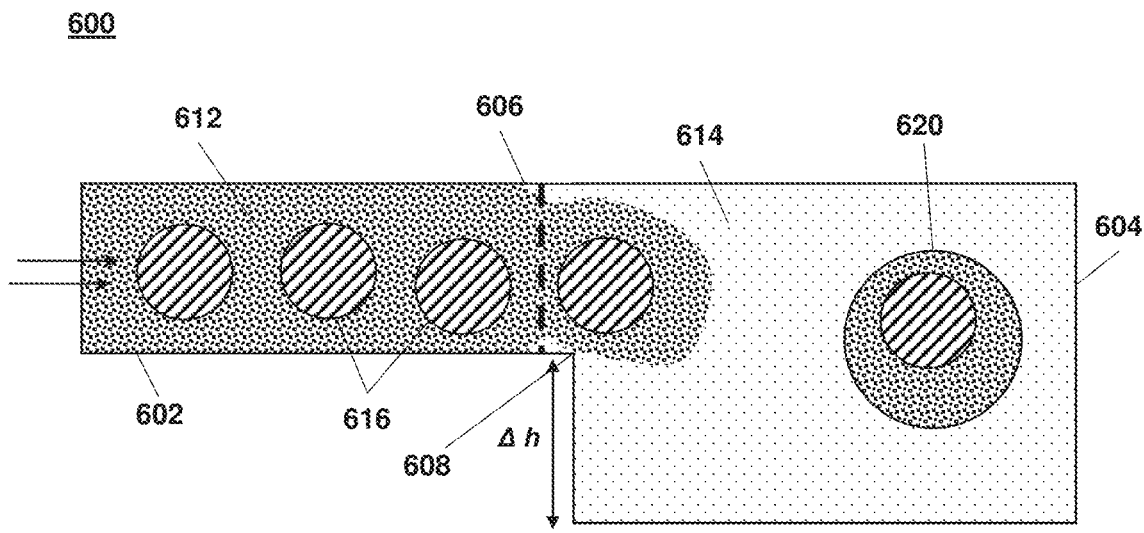
FIGS. 6A-6B show a cross-section view and a top view, respectively, of another example of a microfluidic device with a geometric feature for droplet formation.
Figure 6B:
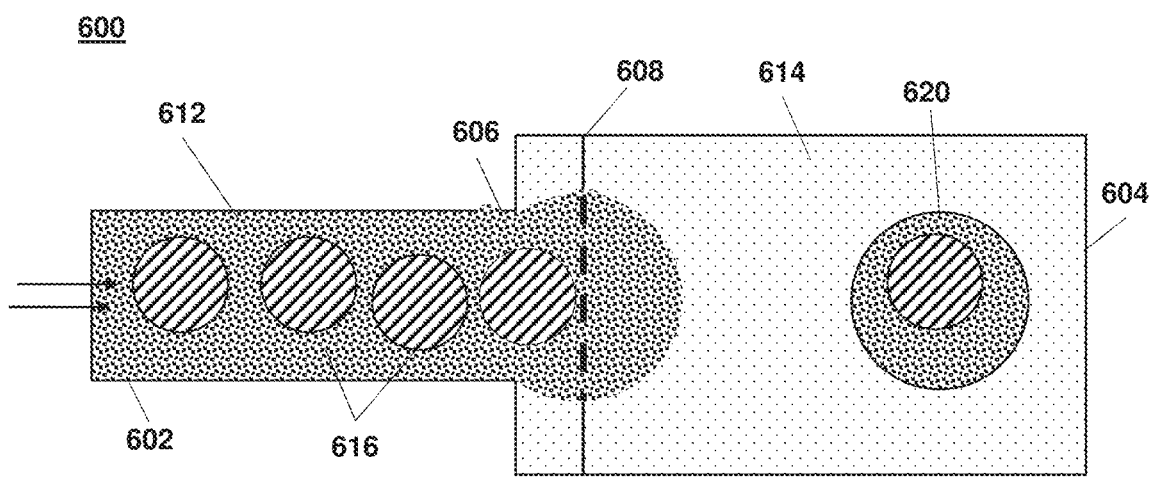

FIGS. 6A and 6B show a cross-section view and a top view, respectively, of another example of a microfluidic device with a geometric feature for droplet formation. A device 600 can include a channel 602 communicating at a fluidic connection 606 (or intersection) with a reservoir 604. In some instances, the device 600 and one or more of its components can correspond to the channel 500 and one or more of its components.

An aqueous liquid 612 comprising a plurality of particles 616 may be transported along the channel 602 into the fluidic connection 606 to meet a second liquid 614 (e.g., oil, etc.) that is immiscible with the aqueous liquid 612 in the reservoir 604 to create droplets 620 of the aqueous liquid 612 flowing into the reservoir 604. At the fluidic connection 606 where the aqueous liquid 612 and the second liquid 614 meet, droplets can form based on factors such as the hydrodynamic forces at the fluidic connection 606, relative flow rates of the two liquids 612, 614, liquid properties, and certain geometric parameters (e.g., Δh, ledge, etc.) of the channel 602. A plurality of droplets can be collected in the reservoir 604 by continuously injecting the aqueous liquid 612 from the channel 602 at the fluidic connection 606.

The aqueous liquid may comprise particles. The particles 616 (e.g., beads) can be introduced into the channel 602 from a separate channel (not shown in FIG. 6). In some instances, the particles 616 can be introduced into the channel 602 from a plurality of different channels, and the frequency controlled accordingly. In some instances, different particles may be introduced via separate channels. For example, a first separate channel can introduce beads and a second separate channel can introduce biological particles into the channel 602. The first separate channel introducing the beads may be upstream or downstream of the second separate channel introducing the biological particles.

While FIGS. 6A and 6B illustrate one ledge (e.g., step) in the reservoir 604, as can be appreciated, there may be a plurality of ledges in the reservoir 604, for example, each having a different cross-section height. For example, where there is a plurality of ledges, the respective cross-section height can increase with each consecutive ledge. Alternatively, the respective cross-section height can decrease and/or increase in other patterns or profiles (e.g., increase then decrease then increase again, increase then increase then increase, etc.).

While FIGS. 6A and 6B illustrate the height difference, Δh, being abrupt at the ledge 608 (e.g., a step increase), the height difference may increase gradually (e.g., from about 0 μm to a maximum height difference). In some instances, the height difference may decrease gradually (e.g., taper) from a maximum height difference. In some instances, the height difference may variably increase and/or decrease linearly or non-linearly. The same may apply to a height difference, if any, between the first cross-section and the second cross-section.

Example 7

Figure 7A:
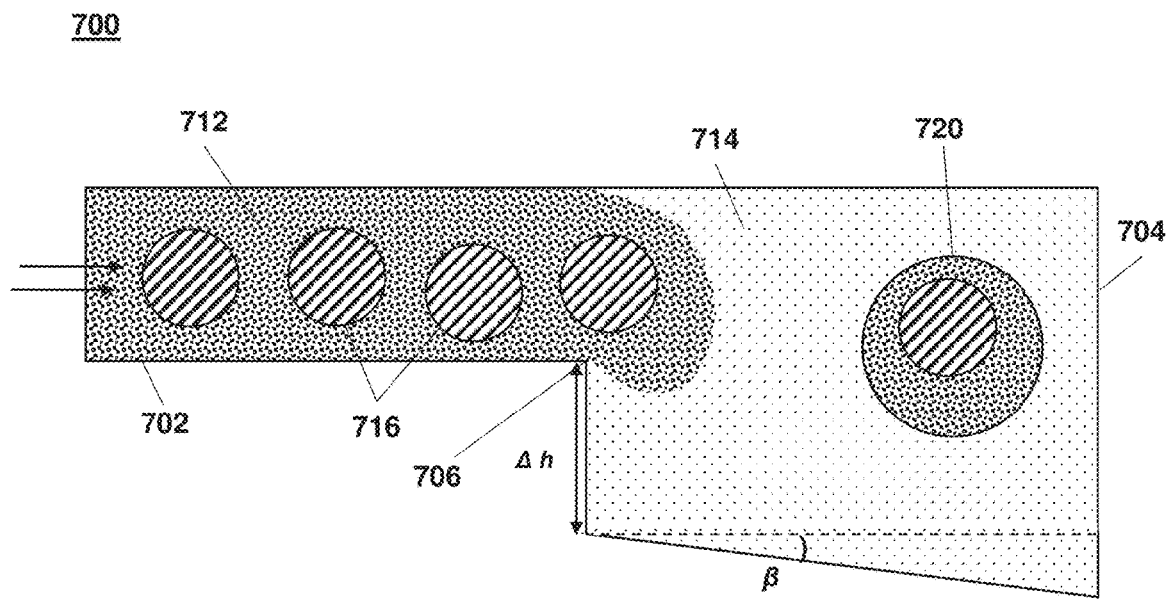
FIGS. 7A-7B show a cross-section view and a top view, respectively, of another example of a microfluidic device with a geometric feature for droplet formation.
Figure 7B:
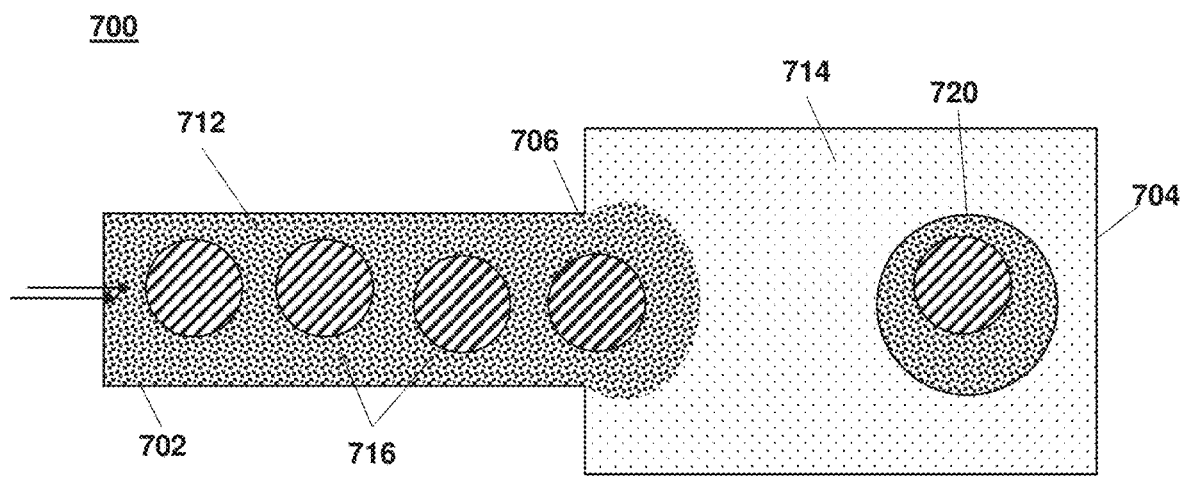

FIGS. 7A and 7B show a cross-section view and a top view, respectively, of another example of a microfluidic device with a geometric feature for droplet formation. A device 700 can include a channel 702 communicating at a fluidic connection 706 (or intersection) with a reservoir 704. In some instances, the device 700 and one or more of its components can correspond to the channel 600 and one or more of its components.

An aqueous liquid 712 comprising a plurality of particles 716 may be transported along the channel 702 into the fluidic connection 706 to meet a second liquid 714 (e.g., oil, etc.) that is immiscible with the aqueous liquid 712 in the reservoir 704 to create droplets 720 of the aqueous liquid 712 flowing into the reservoir 704. At the fluidic connection 706 where the aqueous liquid 712 and the second liquid 714 meet, droplets can form based on factors such as the hydrodynamic forces at the fluidic connection 706, relative flow rates of the two liquids 712, 714, liquid properties, and certain geometric parameters (e.g., Δh, etc.) of the device 700. A plurality of droplets can be collected in the reservoir 704 by continuously injecting the aqueous liquid 712 from the channel 702 at the fluidic connection 706.

In some instances, the second liquid 714 may not be subjected to and/or directed to any flow in or out of the reservoir 704. For example, the second liquid 714 may be substantially stationary in the reservoir 704. In some instances, the second liquid 714 may be subjected to flow within the reservoir 704, but not in or out of the reservoir 704, such as via application of pressure to the reservoir 704 and/or as affected by the incoming flow of the aqueous liquid 712 at the fluidic connection 706. Alternatively, the second liquid 714 may be subjected and/or directed to flow in or out of the reservoir 704. For example, the reservoir 704 can be a channel directing the second liquid 714 from upstream to downstream, transporting the generated droplets. Alternatively or in addition, the second liquid 714 in reservoir 704 may be used to sweep formed droplets away from the path of the nascent droplets.

The device 700 at or near the fluidic connection 706 may have certain geometric features that at least partly determine the sizes and/or shapes of the droplets formed by the device 700. The channel 702 can have a first cross-section height, $h_1$, and the reservoir 704 can have a second cross-section height, $h_2$. The first cross-section height, $h_1$, may be different from the second cross-section height $h_2$ such that at or near the fluidic connection 706, there is a height difference of Δh. The second cross-section height, $h_2$, may be greater than the first cross-section height, $h_1$. The reservoir may thereafter gradually increase in cross-section height, for example, the more distant it is from the fluidic connection 706. In some instances, the cross-section height of the reservoir may increase in accordance with expansion angle, β, at or near the fluidic connection 706. The height difference, Δh, and/or expansion angle, β, can allow the tongue (portion of the aqueous liquid 712 leaving channel 702 at fluidic connection 706 and entering the reservoir 704 before droplet formation) to increase in depth and facilitate decrease in curvature of the intermediately formed droplet. For example, droplet size may decrease with increasing height difference and/or increasing expansion angle.

While FIGS. 7A and 7B illustrate the height difference, Δh, being abrupt at the fluidic connection 706, the height difference may increase gradually (e.g., from about 0 μm to a maximum height difference). In some instances, the height difference may decrease gradually (e.g., taper) from a maximum height difference. In some instances, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

Example 8

Figure 8A:
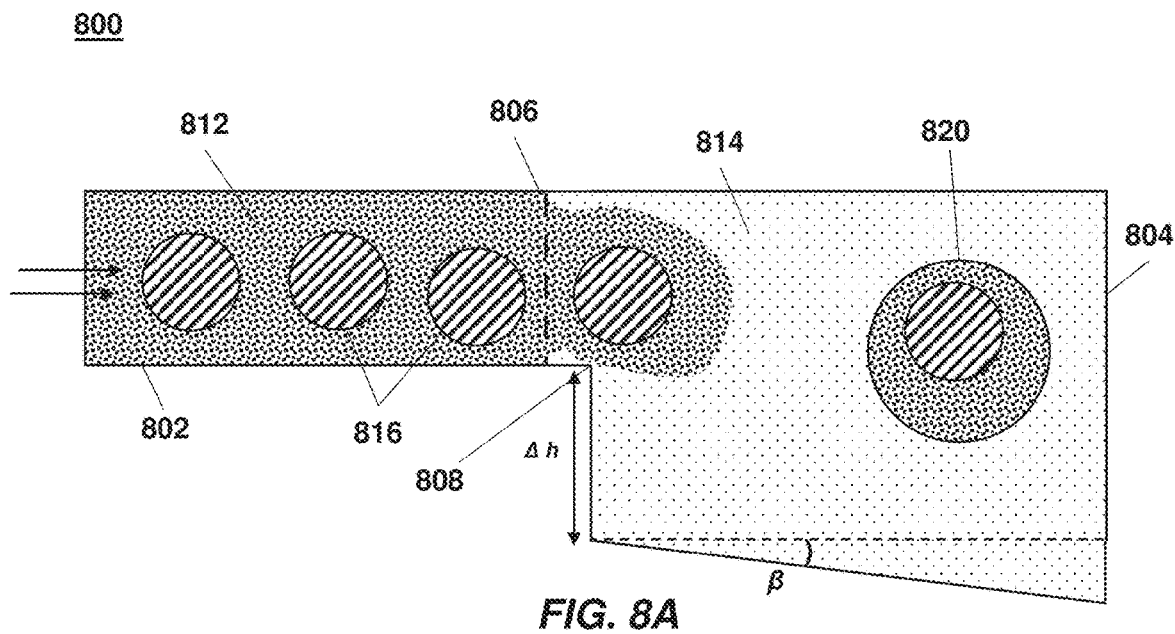
FIGS. 8A-8B show a cross-section view and a top view, respectively, of another example of a microfluidic device with a geometric feature for droplet formation.
Figure 8B:
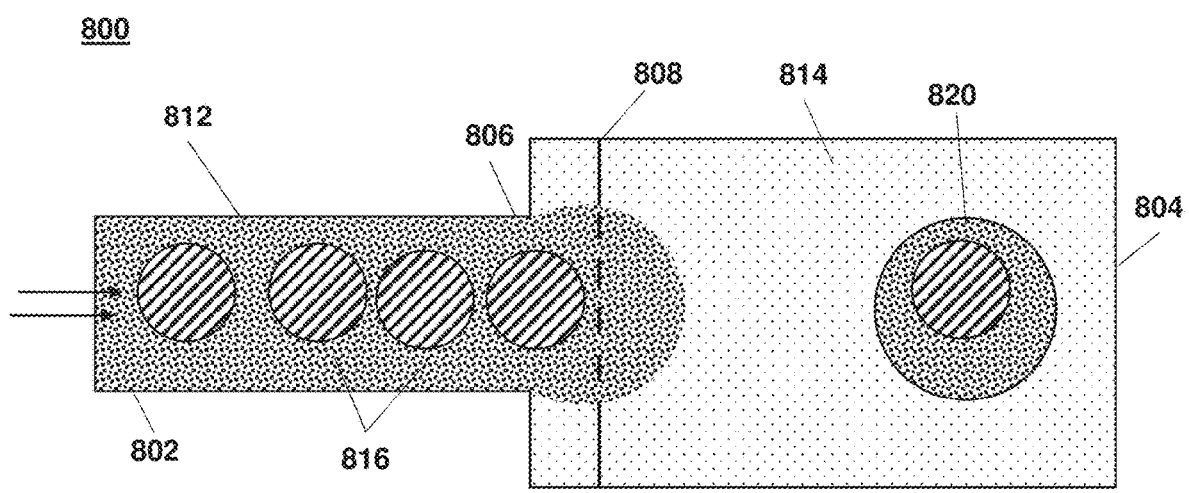

FIGS. 8A and 8B show a cross-section view and a top view, respectively, of another example of a microfluidic device with a geometric feature for droplet formation. A device 800 can include a channel 802 communicating at a fluidic connection 806 (or intersection) with a reservoir 804. In some instances, the device 800 and one or more of its components can correspond to the device 700 and one or more of its components and/or correspond to the device 600 and one or more of its components.

An aqueous liquid 812 comprising a plurality of particles 816 may be transported along the channel 802 into the fluidic connection 806 to meet a second liquid 814 (e.g., oil, etc.) that is immiscible with the aqueous liquid 812 in the reservoir 804 to create droplets 820 of the aqueous liquid 812 flowing into the reservoir 804. At the fluidic connection 806 where the aqueous liquid 812 and the second liquid 814 meet, droplets can form based on factors such as the hydrodynamic forces at the fluidic connection 806, relative flow rates of the two liquids 812, 814, liquid properties, and certain geometric parameters (e.g., Δh, etc.) of the device 800. A plurality of droplets can be collected in the reservoir 804 by continuously injecting the aqueous liquid 812 from the channel 802 at the fluidic connection 806.

A discrete droplet generated may comprise one or more particles of the plurality of particles 816. As described elsewhere herein, a particle may be any particle, such as a bead, cell bead, gel bead, biological particle, macromolecular constituents of biological particle, or other particles. Alternatively, a discrete droplet generated may not include any particles.

In some instances, the second liquid 814 may not be subjected to and/or directed to any flow in or out of the reservoir 804. For example, the second liquid 814 may be substantially stationary in the reservoir 804. In some instances, the second liquid 814 may be subjected to flow within the reservoir 804, but not in or out of the reservoir 804, such as via application of pressure to the reservoir 804 and/or as affected by the incoming flow of the aqueous liquid 812 at the fluidic connection 806. Alternatively, the second liquid 814 may be subjected and/or directed to flow in or out of the reservoir 804. For example, the reservoir 804 can be a channel directing the second liquid 814 from upstream to downstream, transporting the generated droplets. Alternatively or in addition, the second liquid 814 in reservoir 804 may be used to sweep formed droplets away from the path of the nascent droplets.

While FIGS. 8A and 8B illustrate one ledge (e.g., step) in the reservoir 804, as can be appreciated, there may be a plurality of ledges in the reservoir 804, for example, each having a different cross-section height. For example, where there is a plurality of ledges, the respective cross-section height can increase with each consecutive ledge. Alternatively, the respective cross-section height can decrease and/or increase in other patterns or profiles (e.g., increase then decrease then increase again, increase then increase then increase, etc.).

While FIGS. 8A and 8B illustrate the height difference, Δh, being abrupt at the ledge 808, the height difference may increase gradually (e.g., from about 0 μm to a maximum height difference). In some instances, the height difference may decrease gradually (e.g., taper) from a maximum height difference. In some instances, the height difference may variably increase and/or decrease linearly or non-linearly. While FIGS. 8A and 8B illustrate the expanding reservoir cross-section height as linear (e.g., constant expansion angle), the cross-section height may expand non-linearly. For example, the reservoir may be defined at least partially by a dome-like (e.g., hemispherical) shape having variable expansion angles. The cross-section height may expand in any shape.

Example 9

Figure 9A:
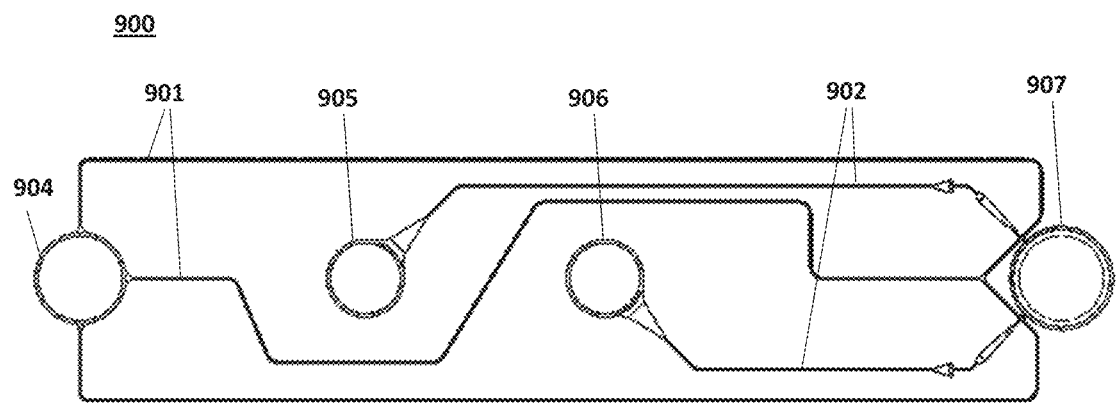
FIGS. 9A-9B are views of another device of the invention.
Figure 9B:
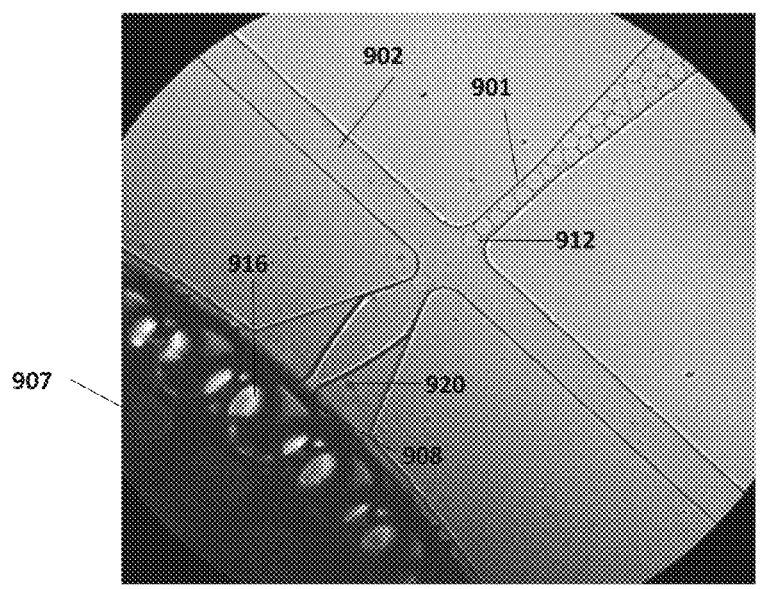
Figure 11A:
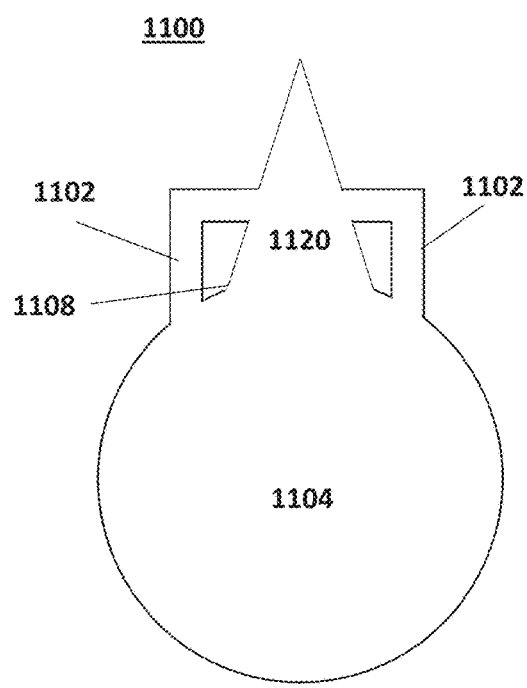
FIGS. 11A-11D are views of droplet formation regions including shelf regions including additional channels to deliver continuous phase.
Figure 11B:
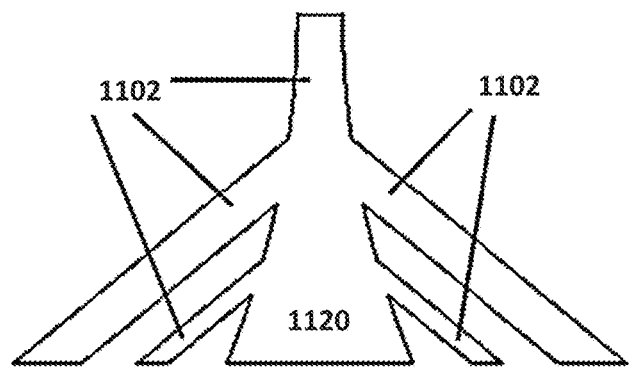
Figure 11C:
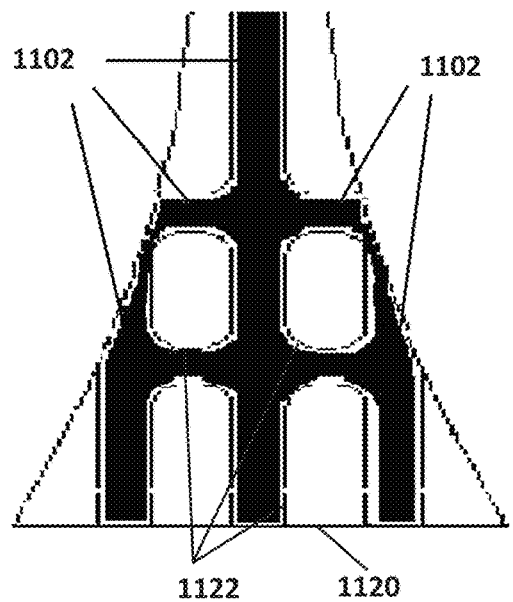
Figure 11D:
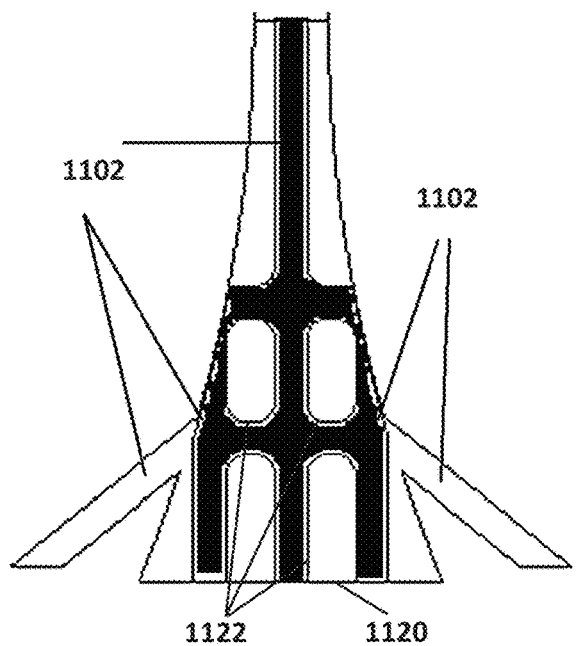

An example of a device according to the invention is shown in FIGS. 9A-9B. The device 900 includes four fluid reservoirs, 904, 905, 906, and 907, respectively. Reservoir 904 houses one liquid; reservoirs 905 and 906 house another liquid, and reservoir 907 houses continuous phase in the step region 908. This device 900 include two first channels 902 connected to reservoir 905 and reservoir 906 and connected to a shelf region 920 adjacent a step region 908. As shown, multiple channels 901 from reservoir 904 deliver additional liquid to the first channels 902. The liquids from reservoir 904 and reservoir 905 or 906 combine in the first channel 902 forming the first liquid that is dispersed into the continuous phase as droplets. In certain embodiments, the liquid in reservoir 905 and/or reservoir 906 includes a particle, such as a gel bead. FIG. 9B shows a view of the first channel 902 containing gel beads intersected by a second channel 901 adjacent to a shelf region 920 leading to a step region 908, which contains multiple droplets 916.

Example 10

Variations on shelf regions 1020 are shown in FIGS. 10A-10E. As shown in FIGS. 10A-10B, the width of the shelf region 1020 can increase from the distal end of a first channel 1002 towards the step region 1008, linearly as in 10A or non-linearly as in 10B. As shown in FIG. 10C, multiple first channels 1002 can branch from a single feed channel 1002 and introduce fluid into interconnected shelf regions 1020. As shown in FIG. 10D, the depth of the first channel 1002 may be greater than the depth of the shelf region 1020 and cut a path through the shelf region 1020. As shown in FIG. 10E, the first channel 1002 and shelf region 1020 may contain a grooved bottom surface. This device 1000 also includes a second channel 1002 that intersects the first channel 1002 proximal to its distal end.

Example 11

Continuous phase delivery channels 1102, shown in FIGS. 11A-11D, are variations on shelf regions 1120 including channels 1102 for delivery (passive or active) of continuous phase behind a nascent droplet. In one example in FIG. 11A, the device 1100 includes two channels 1102 that connect the reservoir 1304 of the step region 1108 to either side of the shelf region 1120. In another example in FIG. 11B, four channels 1102 provide continuous phase to the shelf region 1120. These channels 1102 can be connected to the reservoir 1104 of the step region 1108 or to a separate source of continuous phase. In a further example in FIG. 11C, the shelf region 1120 includes one or more channels 1102 (white) below the depth of the first channel 1102 (black) that connect to the reservoir 1104 of the step region 1108. The shelf region 1120 contains islands 1122 in black. In another example FIG. 11D, the shelf region 1120 of FIG. 11C includes two additional channels 1102 for delivery of continuous phase on either side of the shelf region 1120.

Example 12

Figure 12:
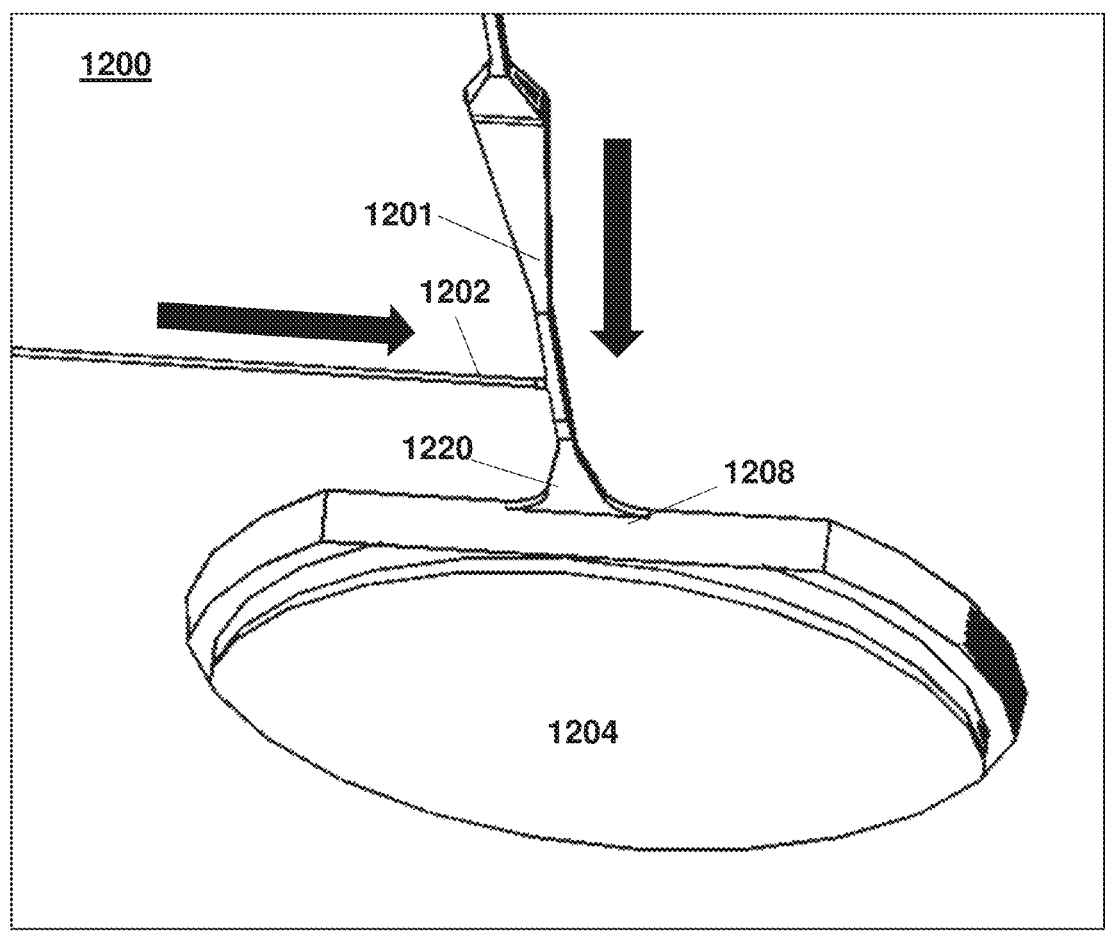
FIG. 12 is another device according to the invention having a pair of intersecting channels that lead to a droplet formation region and collection reservoir.

An embodiment of a device according to the invention is shown in FIG. 12. This device 1200 includes two channels 1201, 1202 that intersect upstream of a droplet formation region. The droplet formation region includes both a shelf region 1220 and a step region 1208 disposed between the distal end of the first channel 1201 and the step region 1208 that lead to a collection reservoir 1204. The black and white arrows show the flow of liquids through each of first channel 1201 and second channel 1202, respectively. In certain embodiments, the liquid flowing through the first channel 1201 or second channel 1202 includes a particle, such as a gel bead. As shown in the FIG. 12, the width of the shelf region 1220 can increase from the distal end of a first channel 1201 towards the step region 1208; in particular, the width of the shelf region 1220 in FIG. 12 increases non-linearly. In this embodiment, the shelf region extends from the edge of a reservoir to allow droplet formation away from the edge. Such a geometry allows droplets to move away from the droplet formation region due to differential density between the continuous and dispersed phase.

Example 13

An embodiment of a device according to the invention for multiplexed droplet formation is shown in FIGS. 13A-13B. This device 1300 includes four fluid reservoirs, 1304, 1305, 1306, and 1307, and the overall direction of flow within the device 1300 is shown by the black arrow in FIG. 13A. Reservoir 1304 and reservoir 1306 house one liquid; reservoir 1305 houses another liquid, and reservoir 1307 houses continuous phase and is a collection reservoir. Fluid channels 1301, 1303 directly connect reservoir 1304 and reservoir 1306, respectively, to reservoir 1307; thus, there are four droplet formation region in this device 1300. Each droplet formation region has a shelf region 1320 and a step region 1308. This device 1300 further has two channels 1302 from the reservoir 1305 where each of these channels splits into two separate channels at their distal ends. Each of the branches of the split channel intersects the first channels 1301 or 1303 upstream of their connection to the collection reservoir 1307. As shown in the zoomed in view of the dotted line box in FIG. 13B, second channel 1302, with its flow indicated by the white arrow, has its distal end intersecting a channel 1302 from reservoir 1304, with the flow of the channel indicated by the black arrow, upstream of the droplet formation region. The liquid from reservoir 1304 and reservoir 1306, separately, are introduced into channels 1301, 1303 and flow towards the collection reservoir 1307. The liquid from the second reservoir 1305 combines with the fluid from reservoir 1304 or reservoir 1306, and the combined fluid is dispersed into the droplet formation region and to the continuous phase. In certain embodiments, the liquid flowing through the first channel 1301 or 1303 or second channel 1302 includes a particle, such as a gel bead.

Example 14

Figure 14A:
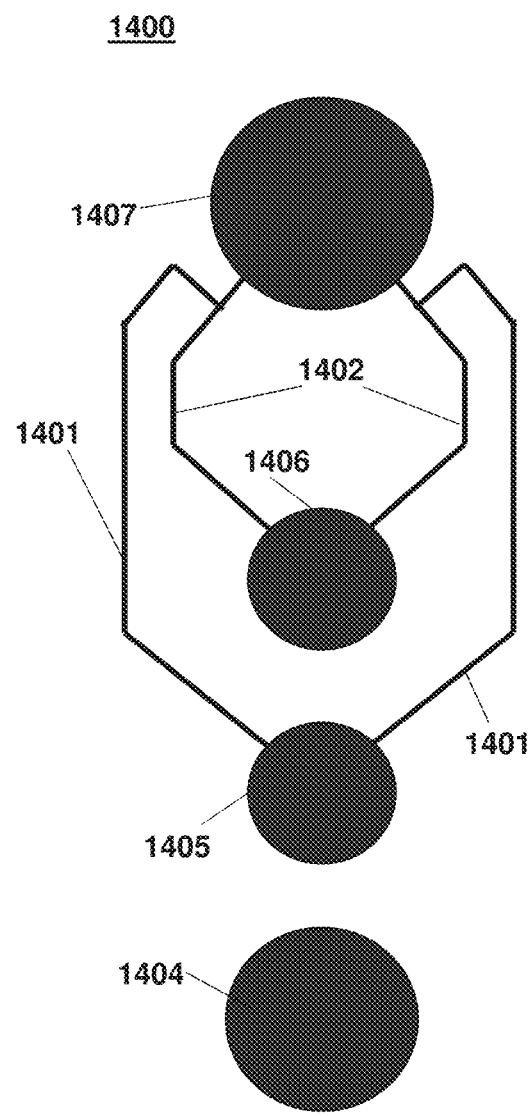
FIGS. 14A-14B are views of devices according to the invention.
Figure 14B:
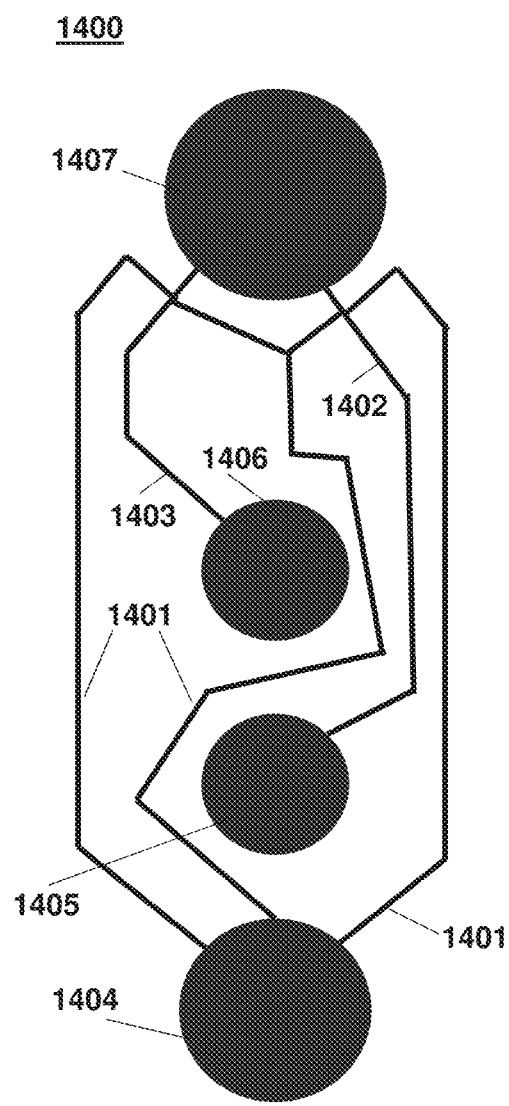

Examples of devices according to the invention that include two droplet formation regions are shown in FIGS. 14A-14B. The device 1400 of FIG. 14A includes three reservoirs, 1405, 1406, and 1407, and the device 1400 of FIG. 14B includes four reservoirs, 1404, 1405, 1406, and 1407. For the device 1400 of FIG. 14A, reservoir 1405 houses a portion of the first fluid, reservoir 1406 houses a different portion of the first fluid, and reservoir 1407 houses continuous phase and is a collection reservoir. In the device 1400 of FIG. 14B, reservoir 1404 houses a portion of the first fluid, reservoir 1405 and reservoir 1406 house different portions of the first fluid, and reservoir 1407 houses continuous phase and is a collection reservoir. In both devices 1400, there are two droplet formation regions. For the device 1400 of FIG. 14A, the connections to the collection reservoir 1407 are from the reservoir 1406, and the distal ends of the channels 1401 from reservoir 1405 intersect the channels 1402 from reservoir 1406 upstream of the droplet formation region. The liquids from reservoir 1405 and reservoir 1406 combine in the channels 1402 from reservoir 1406, forming the first liquid that is dispersed into the continuous phase in the collection reservoir 1407 as droplets. In certain embodiments, the liquid in reservoir 1405 and/or reservoir 1406 includes a particle, such as a gel bead.

In the device 1400 of FIG. 14B, each of reservoir 1405 and reservoir 1406 are connected to the collection reservoir 1407. Reservoir 1404 has three channels 1401, two of which have distal ends that intersect each of the channels 1402, 1403 from reservoir 1404 and reservoir 1406, respectively, upstream of the droplet formation region. The third channel 1401 from reservoir 1404 splits into two separate distal ends, with one end intersecting the channel 1402 from reservoir 1405 and the other distal end intersecting the channel 1403 from reservoir 1406, both upstream of droplet formation regions. The liquid from reservoir 1404 combines with the liquids from reservoir 1405 and reservoir 1406 in the channels 1402 from reservoir 1405 and reservoir 1406, forming the first liquid that is dispersed into the continuous phase in the collection reservoir 1407 as droplets. In certain embodiments, the liquid in reservoir 1404, reservoir 1405, and/or reservoir 1406 includes a particle, such as a gel bead.

Example 15

Figure 15:
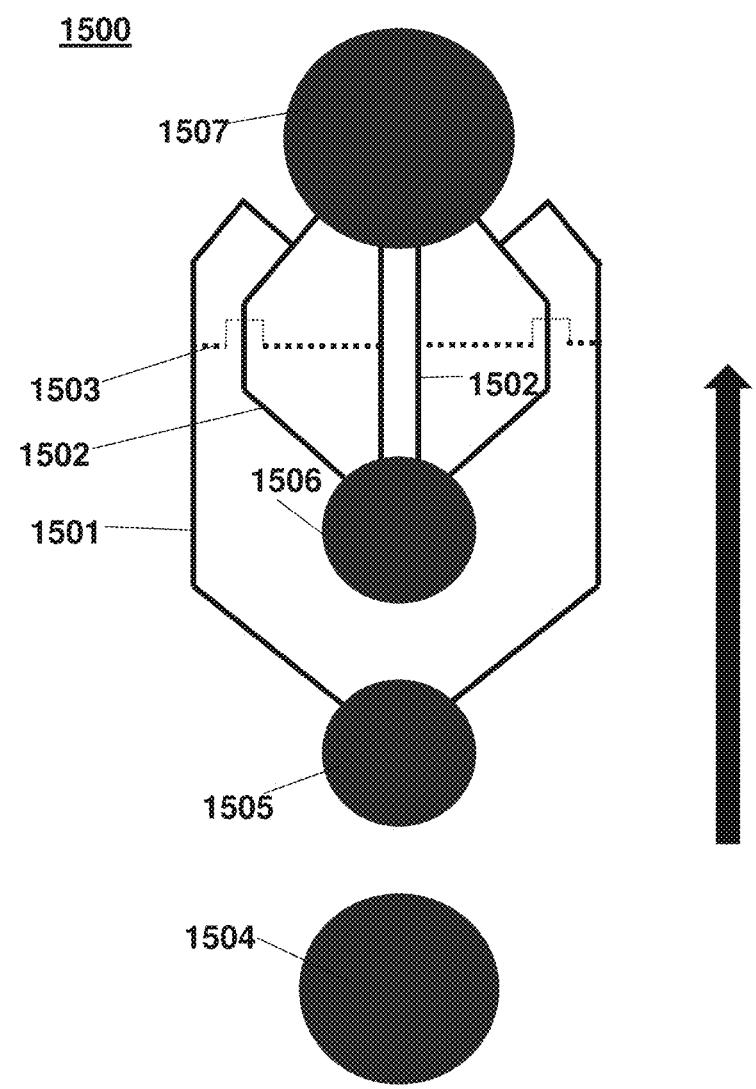
FIG. 15 is a view of a device according to the invention with four reservoirs.

An embodiment of a device according to the invention that has four droplet formation regions is shown in FIG. 15. The device 1500 of FIG. 15 includes four reservoirs, 1504, 1505, 1506, and 1507; the reservoir labeled 1504 is unused in this embodiment. In the device 1500 of FIG. 15, reservoir 1505 houses a portion of the first fluid, reservoir 1506 houses a different portion of the first fluid, and reservoir 1507 houses continuous phase and is a collection reservoir. Reservoir 1506 has four channels 1502 that connect to the collection reservoir 1507 at four droplet formation regions. The channels 1502 from originating at reservoir 1506 include two outer channels 1502 and two inner channels 1502. Reservoir 1505 has two channels 1501 that intersect the two outer channels 1502 from reservoir 1506 upstream of the droplet formation regions. Channels 1501 and the inner channels 1502 are connected by two channels 1503 that traverse, but do not intersect, the fluid paths of the two outer channels 1502. These connecting channels 1503 from channels 1501 pass over the outer channels 1502 and intersect the inner channels 1502 upstream of the droplet formation regions. The liquids from reservoir 1505 and reservoir 1506 combine in the channels 1502, forming the first liquid that is dispersed into the continuous phase in the collection reservoir 1507 as droplets. In certain embodiments, the liquid in reservoir 1505 and/or reservoir 1506 includes a particle, such as a gel bead.

Example 16

Figure 16A:
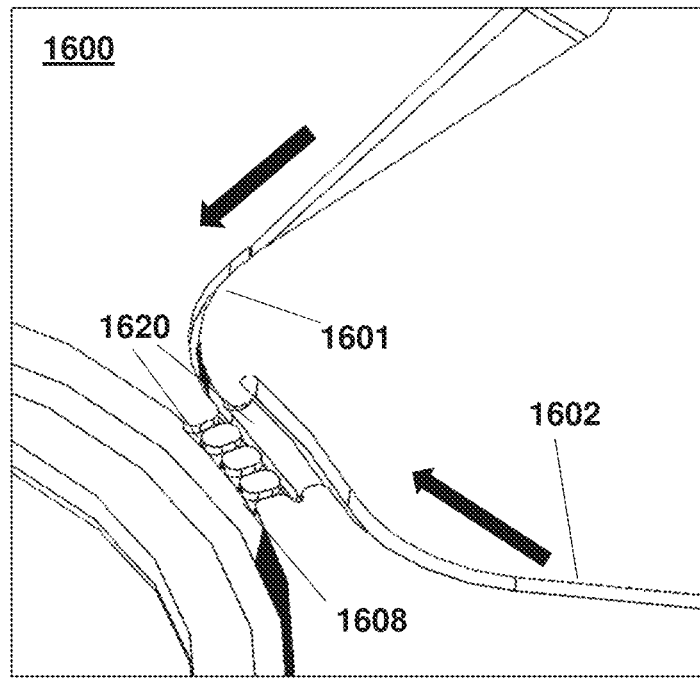
FIGS. 16A-16B are views of an embodiment according to the invention.
Figure 16B:
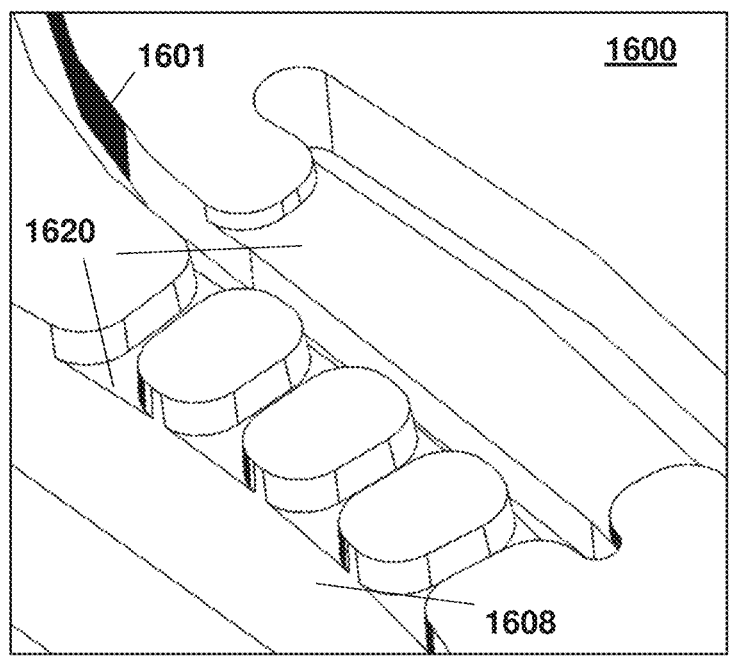

An embodiment of a device according to the invention that has a plurality of droplet formation regions is shown in FIGS. 16A-16B (FIG. 16B is a zoomed in view of FIG. 16A), with the droplet formation region including a shelf region 1620 and a step region 1608. This device 1600 includes two channels 1601, 1602 that meet at the shelf region 1620. As shown, after the two channels 1601, 1602 meet at the shelf region 1620, the combination of liquids is divided, in this example, by four shelf regions. In certain embodiments, the liquid with flow indicated by the black arrow includes a particle, such as a gel bead, and the liquid flow from the other channel, indicated by the white arrow, can move the particles into the shelf regions such that each particle can be introduced into a droplet.

Example 17

Figure 17A:
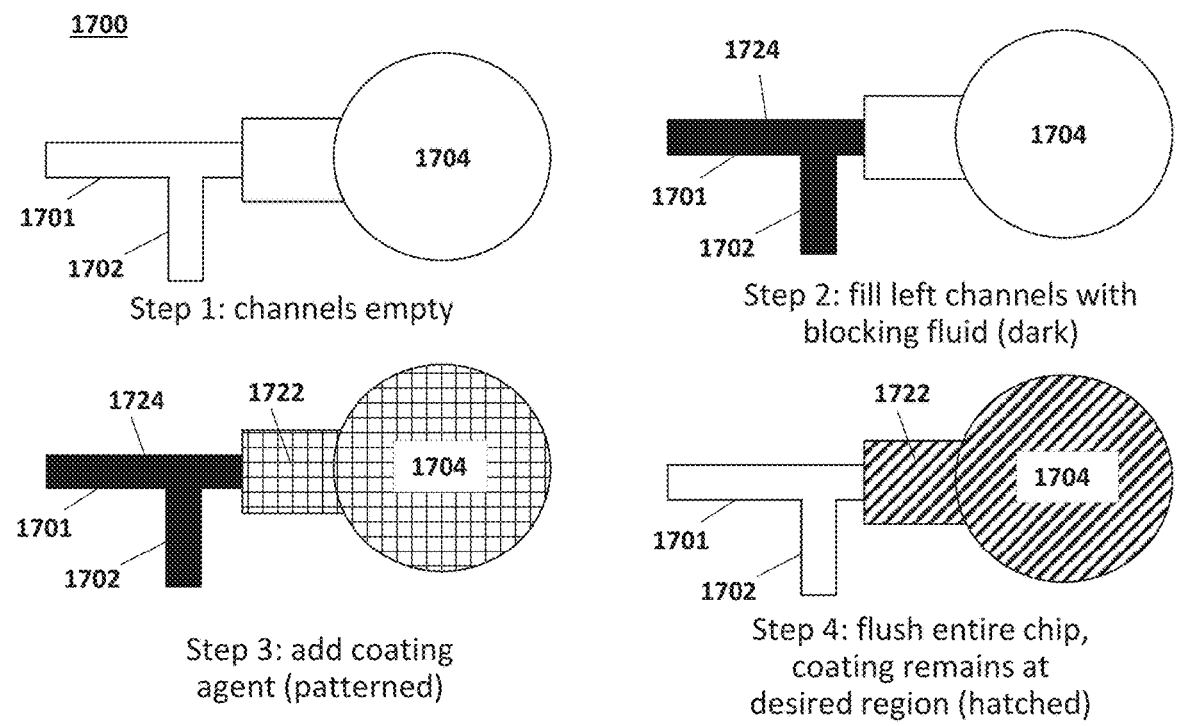
FIGS. 17A-17B are schematic representations of a method according to the invention for applying a differential coating to a surface of a device of the invention.
Figure 17B:
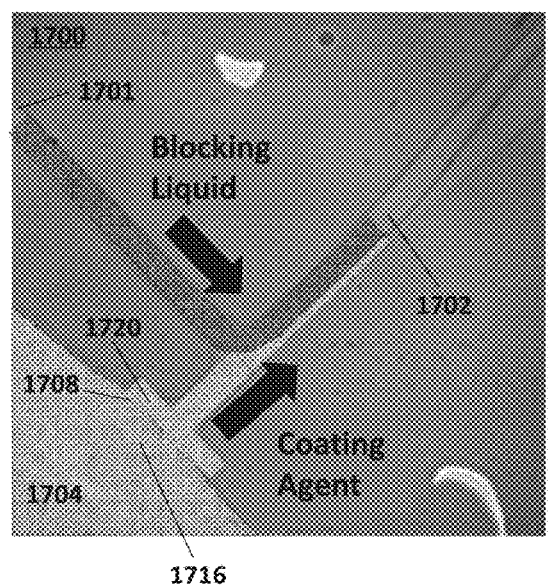

An embodiment of a method of modifying the surface of a device using a coating agent is shown in FIGS. 17A-17B. In this example, the surface of the droplet formation region of the device 1700, e.g., the rectangular area connected to the circular shaped collection reservoir 1704, is coated with a coating agent 1722 to modify its surface properties. To localize the coating agent to only the regions of interest, the first channel 1701 and second channel 1702 of the device 1700 are filled with a blocking liquid 1724 (Step 2 of FIG. 17A) such that the coating agent 1722 cannot contact the channels 1701, 1702. The device 1700 is then filled with the coating agent 1722 to fill the droplet formation region and the collection reservoir 1704 (Step 3 of FIG. 17A). After the coating process is complete, the device 1700 is flushed (Step 4 of FIG. 17A) to remove both the blocking liquid 1724 from the channels and the coating agent 1722 from the droplet formation region and the collection reservoir 1704. This leaves behind a layer of the coating agent 1722 only in the regions where it is desired. This is further exemplified in the micrograph of FIG. 17B, the blocking liquid (dark gray) fills the first channel 1701 and second channel 1702, preventing ingress of the coating agent 1722 (white) into either the first channel 1701 or the second channel 1702 while completely coating the droplet formation region and the collection reservoir 1704. In this example, the first channel 1701 is also acting as a feed channel for the blocking liquid 1724, shown by the arrow for flow direction in FIG. 17B.

Example 18

Figure 18A:
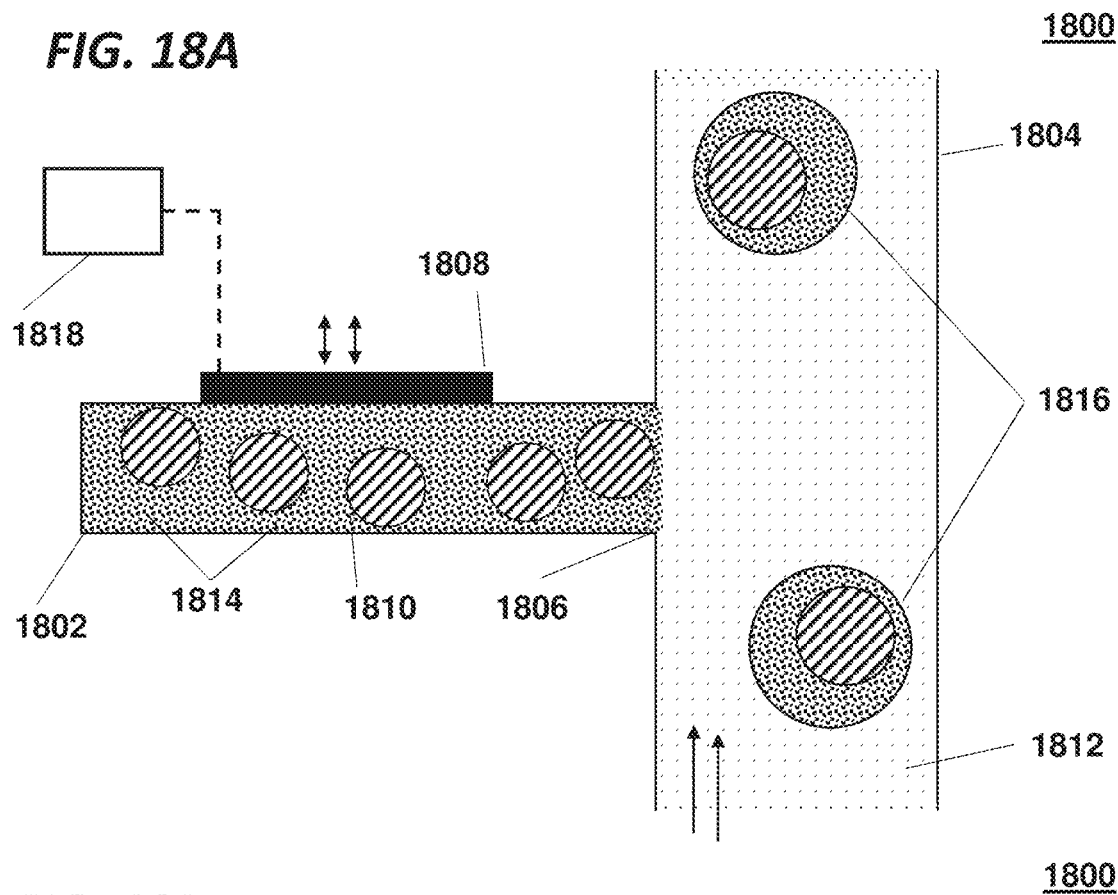
FIGS. 18A-18B are cross-sectional views of a microfluidic device including a piezoelectric element for droplet formation.
Figure 18B:
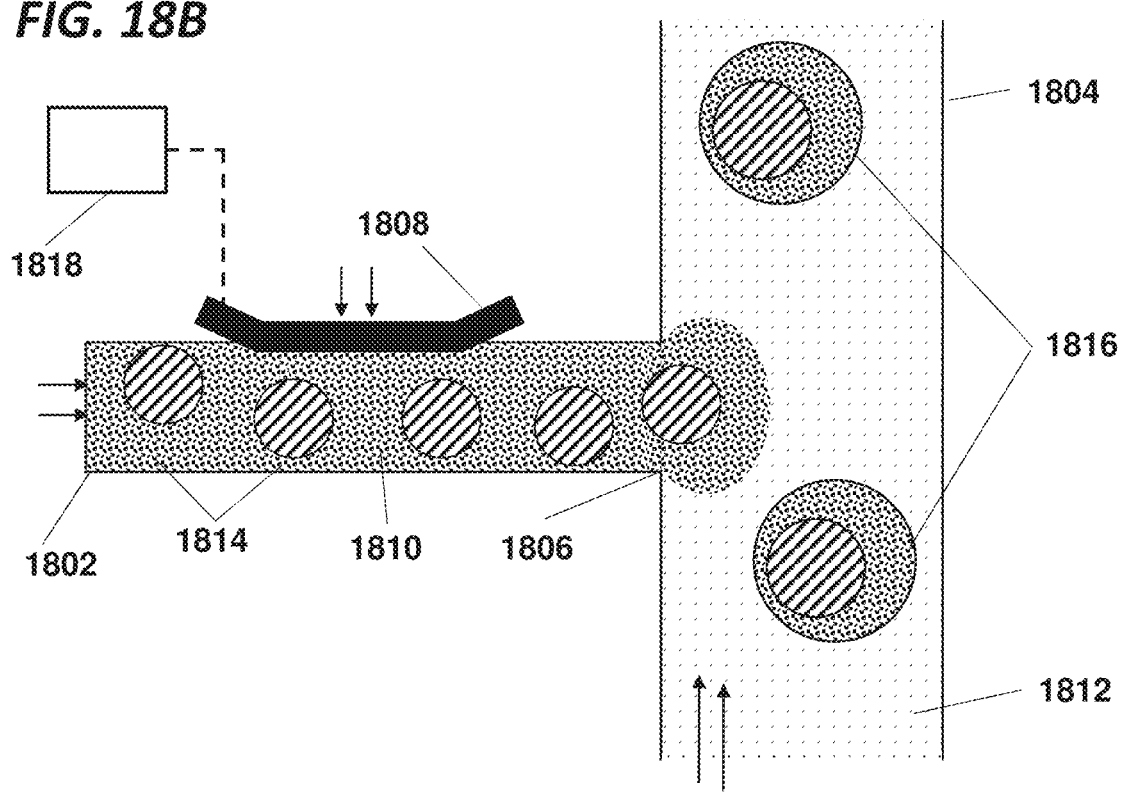

FIGS. 18A-18B show an embodiment of a device according to the invention that includes a piezoelectric element for droplet formation. A device 1800 includes a first channel 1802, a second channel 1804, and a piezoelectric element 1808. The first channel 1802 and the second channel 1804 are in fluid communication at a channel junction 1806. In some instances, the first channel 1802 and components thereof can correspond to the channel 102 in the device 100 in FIG. 1 and components thereof.

In this example, the first channel 1802 carries a first fluid 1810 (e.g., aqueous) and the second channel 1804 can carries second fluid 1812 (e.g., oil) that is immiscible with the first fluid 1810. The two fluids 1810, 1812 come in contact with one another at the junction 1806. In some instances, the first fluid 1810 in the first channel 1802 includes suspended particles 1814. The particles 1814 may be beads, biological particles, cells, cell beads, or any combination thereof (e.g., a combination of beads and cells or a combination of beads and cell beads, etc.). The piezoelectric element 1808 is operatively coupled to the first channel 1802 such that at least part of the first channel 1802 is capable of moving or deforming in response to movement of the piezoelectric element 1808. In some instances, the piezoelectric element 1808 is part of the first channel 1802, such as one or more walls of the first channel 1802. The piezoelectric element 1808 can be a piezoelectric plate. The piezoelectric element 1808 is responsive to electrical signals received from the controller 1818 and moves between at least a first state (as in FIG. 18A) and a second state (as in FIG. 18B). In the first state, the first fluid 1810 and the second fluid 1812 remain separated at or near the junction 1806 via an immiscible barrier. In the second state, the first fluid 1810 is directed towards the junction 1806 into the second fluid 1812 to create droplets 1816.

In some instances, the piezoelectric element 1808 is in the first state (shown in FIG. 18A) when no electrical charge, e.g., electric voltage, is applied. The first state can be an equilibrium state. When an electrical charge is applied to the piezoelectric element 1808, the piezoelectric element 1808 may bend backwards (not shown in FIG. 18A or 18B), pulling a part of the first channel 1802 outwards and drawing in more of the first fluid 1810 into the first channel 1802 such as from a reservoir of the first fluid 1810. When the electrical charge is altered, the piezoelectric element may bend in the other direction (e.g., inwards towards the contents of the channel 1802) (shown in FIG. 18B) pushing a part of the first channel 1802 inwards and propelling (e.g., at least partly via displacement) a volume of the first fluid 1810 into the second channel 1804, thereby generating a droplet of the first fluid 1810 in the second fluid 1812. After the droplet is propelled, the piezoelectric element 1808 may return to the first state (shown in FIG. 18A). The cycle can be repeated to generate more droplets. In some instances, each cycle may generate a plurality of droplets (e.g., a volume of the first fluid 1810 propelled breaks off as it enters the second fluid 1812 to form a plurality of discrete droplets). A plurality of droplets 1816 can be collected in the second channel 1804 for continued transportation to a different location (e.g., reservoir), direct harvesting, and/or storage.

Example 19

Figure 19:
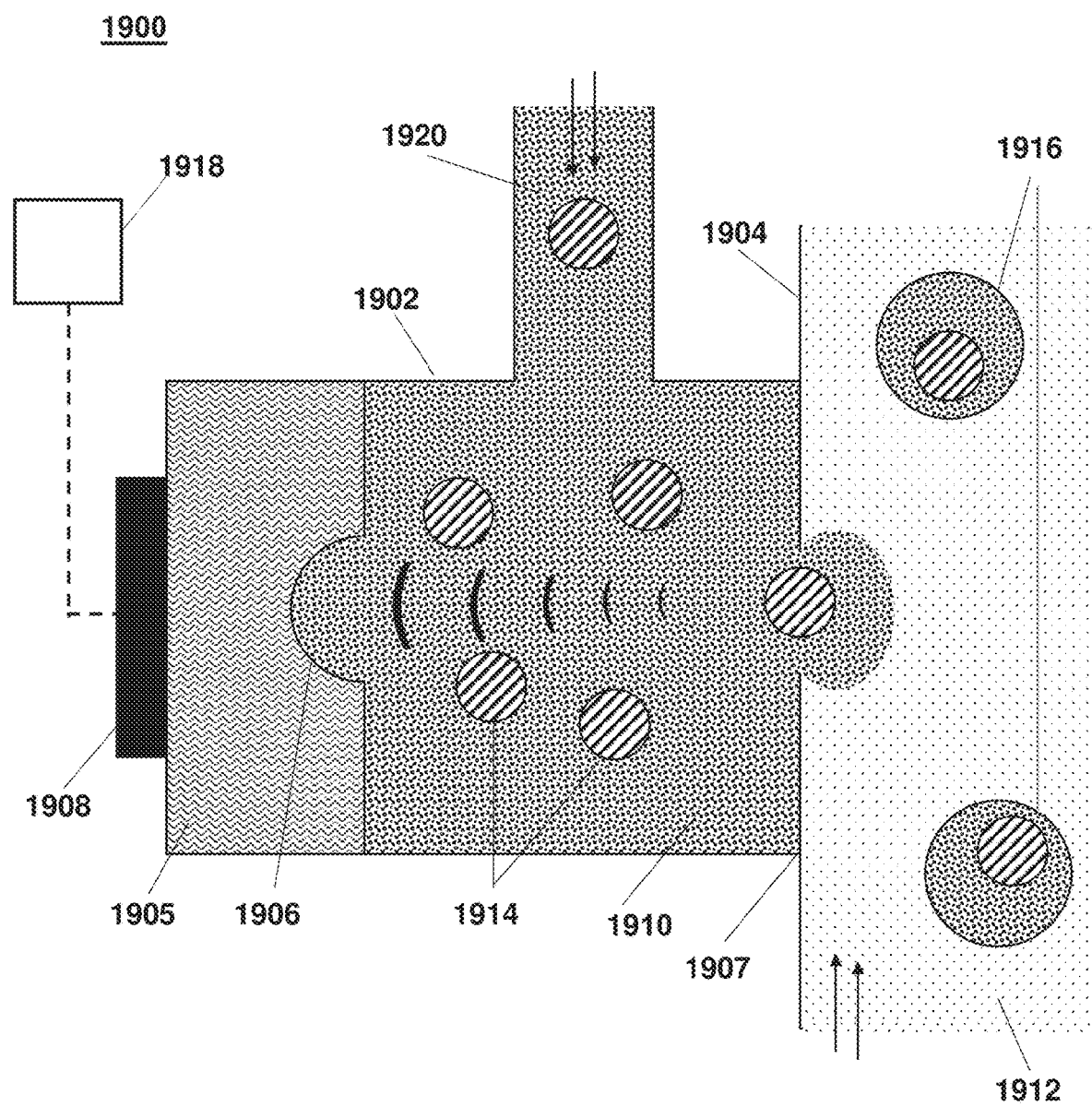
FIG. 19 is a scheme of a microfluidic device including a piezoelectric element for droplet formation.

FIG. 19 shows an embodiment of a device according to the invention that uses a piezoelectric, e.g., a piezoacoustic element, for droplet formation. A device 1900 includes a first channel 1902, a second channel 1904, a piezoelectric element 1908, and a buffer substrate 1905. The first channel 1902 and the second channel 1904 communicate at a channel junction 1907. In some instances, the first channel 1902 and components thereof can correspond to the channel 102 in the channel structure 100 in FIG. 1 and components thereof.

The first channel 1902 carries a first fluid 1910 (e.g., aqueous), and the second channel 1904 carries a second fluid 1912 (e.g., oil) that is immiscible with the first fluid 1910. In some instances, the first fluid 1910 in the first channel 1902 includes suspended particles 1914. The particles 1914 may be beads, biological particles, cells, cell beads, or any combination thereof (e.g., a combination of beads and cells or a combination of beads and cell beads, etc.). The piezoelectric element 1908 is operatively coupled to a buffer substrate 1905 (e.g., glass). The buffer substrate 1905 includes an acoustic lens 1906. In some instances, the acoustic lens 1906 is a substantially spherical cavity, e.g., a partially spherical cavity, e.g., hemispherical. In other instances, the acoustic lens 1906 is a different shape and/or includes one or more other objects for focusing acoustic waves. The buffer substrate 1905 and/or the acoustic lens 1906 can be in contact with the first fluid 1910 in the first channel 1902. Alternatively, the piezoelectric element 1908 is operatively coupled to a part (e.g., wall) of the first channel 1902 without an intermediary buffer substrate. The piezoelectric element 1908 is in electrical communication with a controller 1918. The piezoelectric element 1908 is responsive to a pulse of electric voltage driven at a particular frequent transmitted by the controller 1918. In some instances, the piezoelectric element 1908 and its properties can correspond to the piezoelectric element 1808 and its properties in FIGS. 18A-18B.

Before electric voltage is applied, the first fluid 1910 and the second fluid 1912 are separated at or near the junction 1907 via an immiscible barrier. When the electric voltage is applied to the piezoelectric element 1908, it generates acoustic waves that propagate in the buffer substrate 1905, from the first end to the second end. The acoustic lens 1906 at the second end of the buffer substrate 1905 focuses the acoustic waves towards the immiscible interface between the two fluids 1910, 1912. The acoustic lens 1906 may be located such that the immiscible interface is located at the focal plane of the converging beam of the acoustic waves. The pressure of the acoustic waves may cause a volume of the first fluid 1910 to be propelled into the second fluid 1912, thereby generating a droplet of the first fluid 1910 in the second fluid 1912. In some instances, each propelling may generate a plurality of droplets (e.g., a volume of the first fluid 1910 propelled breaks off as it enters the second fluid 1912 to form a plurality of discrete droplets). After ejection of the droplet, the immiscible interface can return to its original state. Subsequent bursts of electric voltage to the piezoelectric element 1908 can be repeated to generate more droplets 1916. A plurality of droplets 1916 can be collected in the second channel 1904 for continued transportation to a different location (e.g., reservoir), direct harvesting, and/or storage.

Example 20

Figure 20:
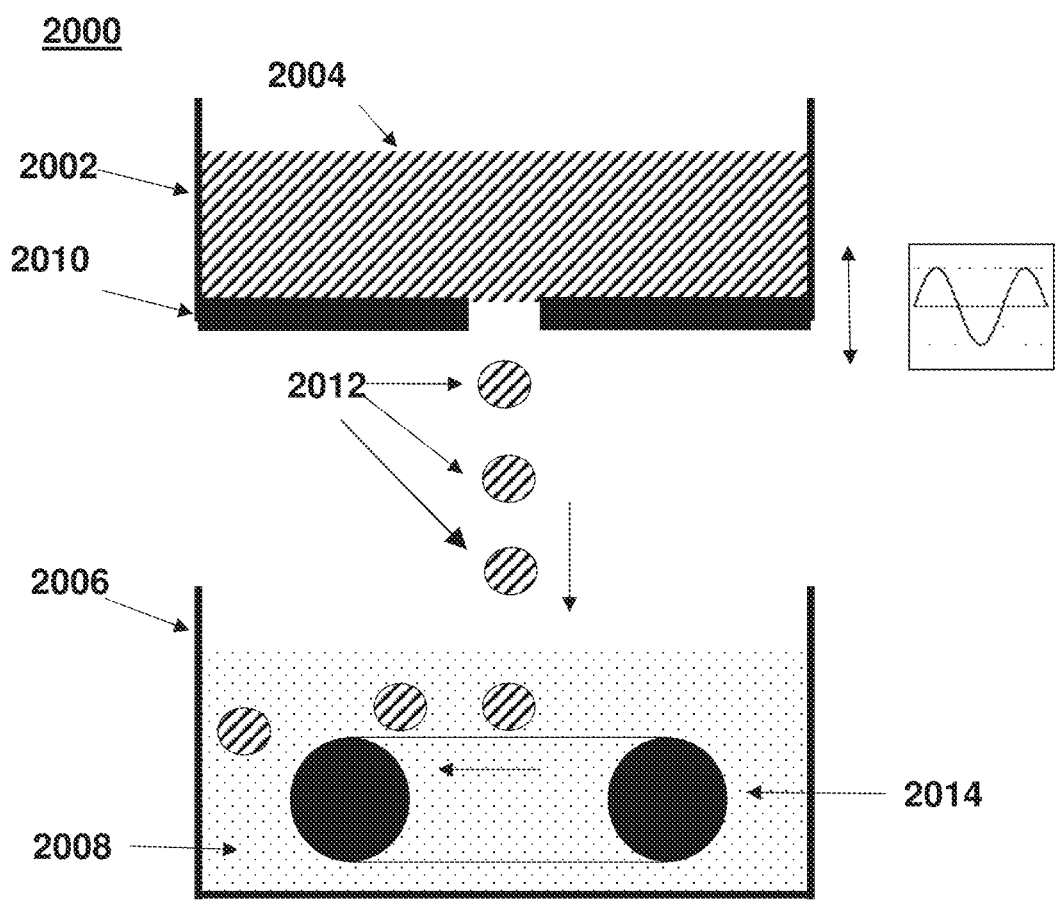
FIG. 20 is a scheme of a microfluidic device including a piezoelectric element for droplet formation. The droplets are collected in a circulating bath after formation.

FIG. 20 shows an embodiment of a device according to the invention that includes a piezoelectric element for droplet formation. The device 2000 includes a reservoir 2002 for holding first fluid 2004 and a collection reservoir 2006 for holding second fluid 2008, such as an oil. In one wall of the reservoir 2002 is a piezoelectric element 2010 operatively coupled to an aperture.

Upon actuation of the piezoelectric element 2010, the first fluid 2004 exits the aperture and forms a droplet 2012 that is collected in collection reservoir 2006. Collection reservoir 2006 includes a mechanism 2014 for circulating second fluid 2008 and moving formed droplets 2012 through the second fluid 2008. The signal applied to the piezoelectric element 2010 may be a sinusoidal signal as indicated in the inset photo.

Example 21

Figure 21:
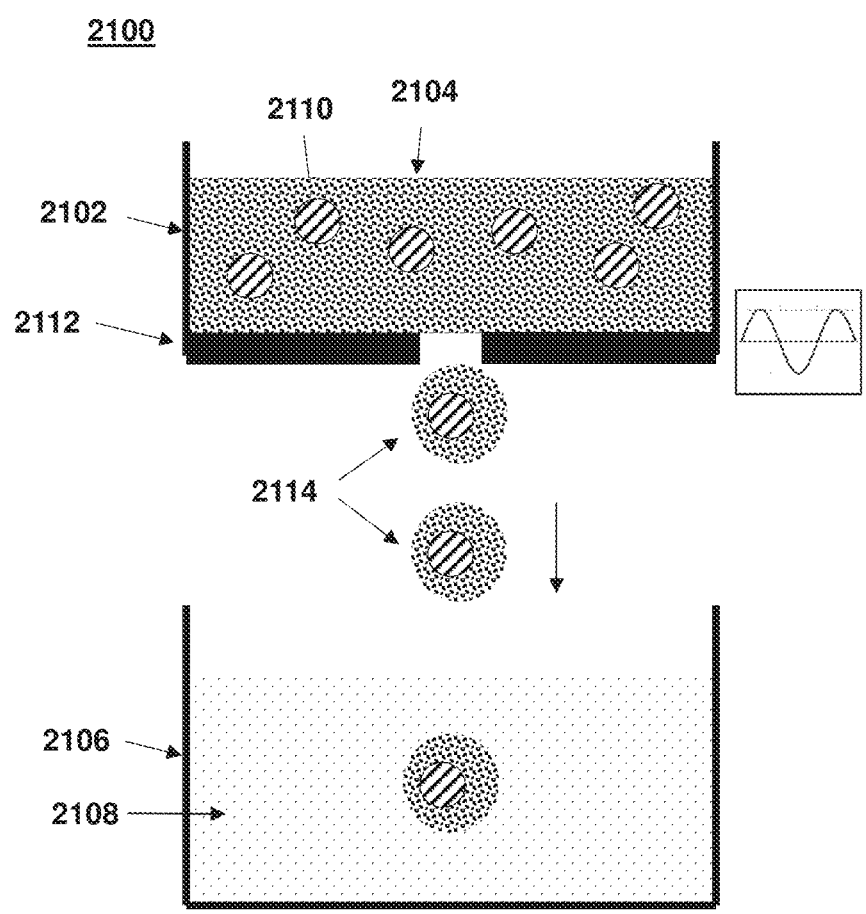
FIG. 21 is a scheme of a microfluidic device including a piezoelectric element for droplet formation including a particle. The droplets contain a particle and are collected in a bath after formation.

FIG. 21 shows an embodiment of a device according to the invention that includes a piezoelectric element for droplet formation. The device 2100 includes a reservoir 2102 for holding first fluid 2104 and a collection reservoir 2106 for holding second fluid 2108, such as an oil. The first fluid 2104 may contain particles 2110. In one wall of the reservoir 2102 is a piezoelectric element 2112 operatively couple to an aperture.

Upon operation of the piezoelectric element 2112 the first fluid 2104 and the particles 2110 exit the aperture and form a droplet 2114 containing the particle 2110. The droplet 2114 is collected in the second fluid 2108 held in the collection reservoir 2106. The second fluid 2108 may or may not be circulated. The signal applied to the piezoelectric element 2112 may be a sinusoidal signal as indicated in the inset photo.

Example 22

Figure 22:
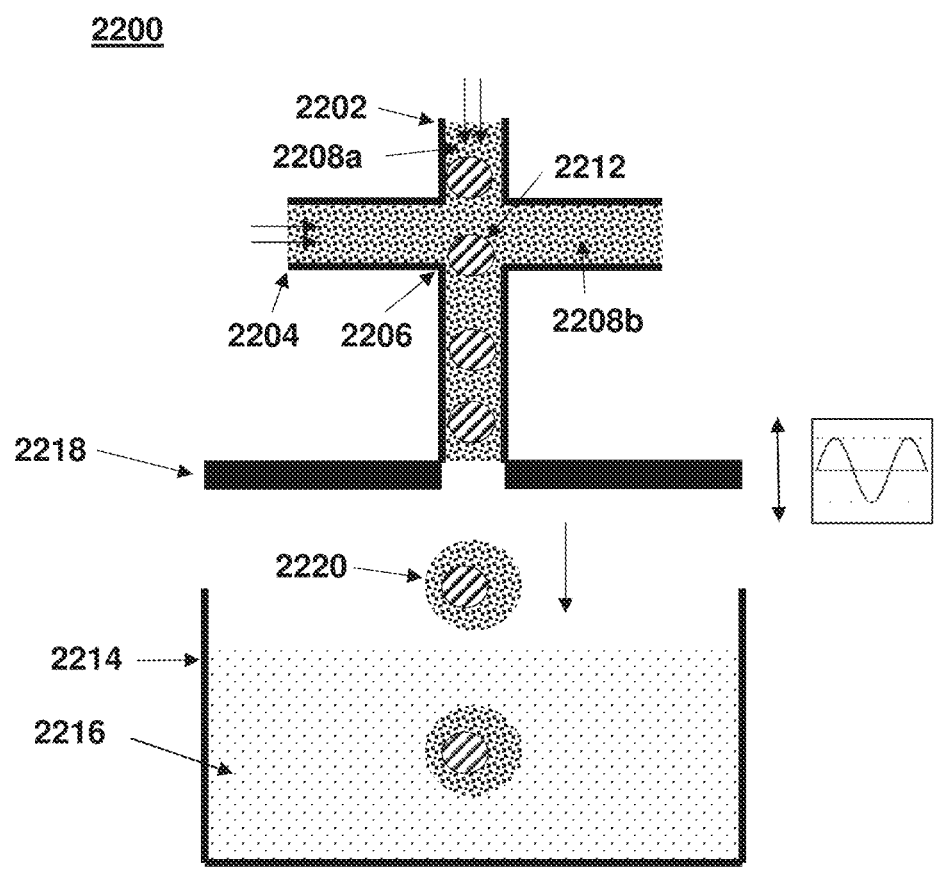
FIG. 22 is a scheme of a microfluidic device including a piezoelectric element for droplet formation. The droplets contain a particle and are collected in a bath after formation.

FIG. 22 shows an embodiment of a device according to the invention that includes a piezoelectric element for droplet formation. The device 2200 includes a first channel 2202 and a second channel 2204 that meet at junction 2206. The first channel 2202 carries a portion of first fluid 2208*a*, and the second channel 2204 carries another portion of first fluid 2208*b*. One of the portions of the first fluid 2208*a* or 2208*b* further includes a particle 2212. The device includes a collection reservoir 2214 for holding second fluid 2216, such as an oil. The distal end of the first channel includes a piezoelectric element 2218 operatively couple to an aperture.

The portion of first fluid 2208*a* flowing through the first channel 2202, e.g., carrying particles 2212, combines with the portion of the first fluid 2208*b* flowing through second channel 2204 to form the first fluid, and the first fluid continues to the distal end of the first channel 2202. Upon actuation of the piezoelectric element 2218 at the distal end of the first channel 2202, the first fluid and particles 2212 form a droplet 2220 containing a particle 2212. The droplet 2220 is collected in the second fluid 2216 in the collection reservoir 2214. The second fluid 2216 may or may not be circulated. The signal applied to the piezoelectric element 2218 may be a sinusoidal signal as indicated in the inset photo.

Example 23

Figure 23:
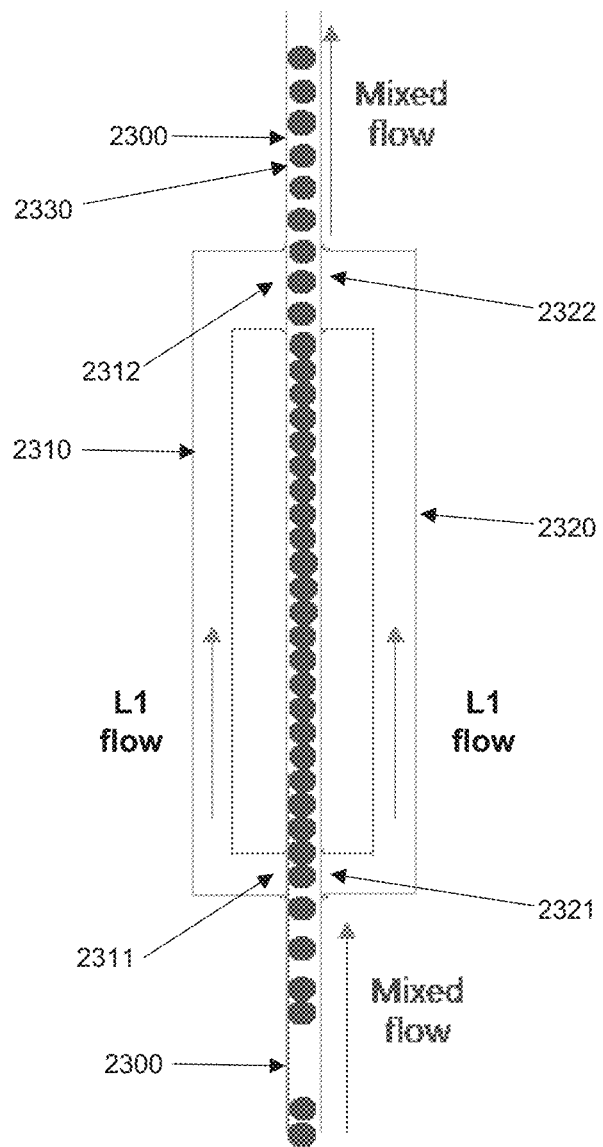
FIG. 23 illustrates the function of a combination of first channel 2300, first side-channel 2310, and second side-channel 2320. In this figure, particles 2330 propagate through channel 2300 in the direction of an arrow labeled "Mixed flow." Prior to proximal intersections 2311 and 2321, spacing between consecutive particles is non-uniform. At the proximal intersections, excess first liquid L1 escapes into side-channels 2310 and 2320. The inlets of side-channels 2310 and 2320 are sized to substantially prevent ingress of particles from first channel 2300. The liquid that escapes into side-channels 2310 and 2320 rejoins first channel 2300 at distal intersections 2312 and 2322.

FIG. 23 illustrates a device for converting a stream of unevenly spaced particles (e.g., beads) into a stream of evenly spaced particles. The device includes first channel 2300, first side-channel 2310, and second side-channel 2320. In the operating device, particles 2330 propagate through channel 2300 in the direction of an arrow labeled "Mixed flow." Prior to proximal intersections 2311 and 2321, spacing between consecutive particles is non-uniform. At the proximal intersections, excess first liquid L1 escapes into side-channels 2310 and 2320. Inlets of side-channels 2310 and 2320 are sized to substantially prevent ingress of particles from first channel 2300. The liquid that escapes into side-channels 2310 and 2320 rejoins first channel 2300 at distal intersections 2312 and 2322. Upon rejoining first channel 2300, liquid L1 separates consecutively packed particles 2330, thereby providing evenly spaced particles 2330.

Figure 24A:
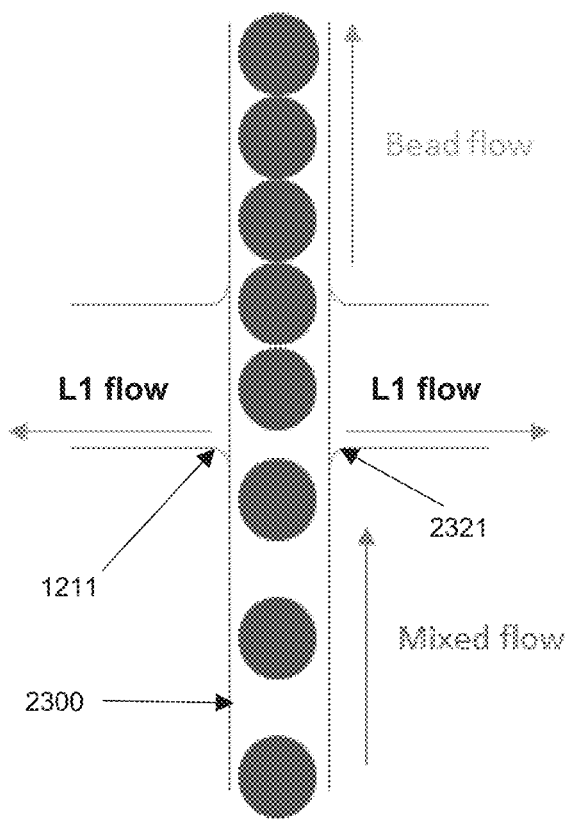
FIG. 24A illustrates the direction of the excess liquid flow from first channel 2300 into the side-channels at proximal intersections 2311 and 2321. In this figure, the side-channels have a depth sized to substantially prevent particle ingress from first channel 2300.
Figure 24B:
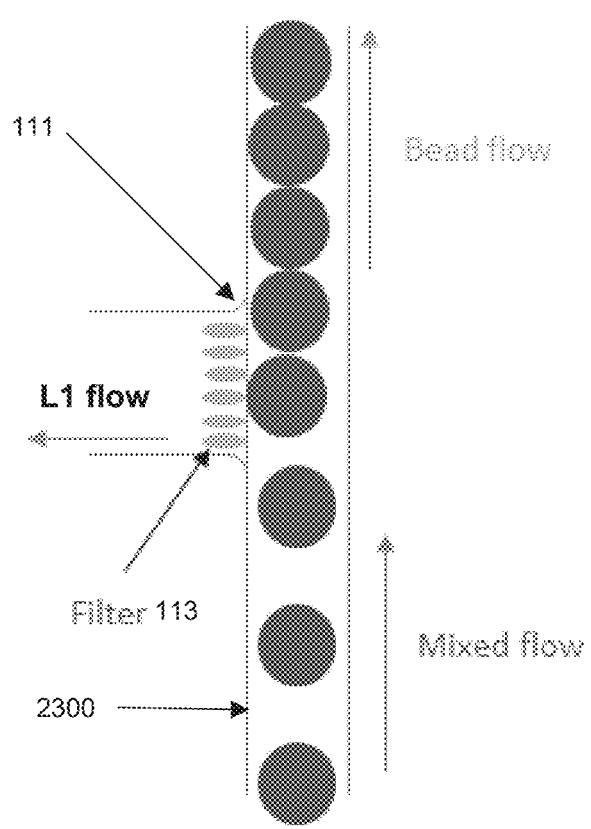
FIG. 24B illustrates the direction of the excess liquid flow from first channel 2300 into the side-channel at proximal intersection 2311. In this figure, the side-channel includes filter 2313 to substantially prevent particle ingress from first channel 2300.

FIG. 24A and FIG. 24B are alternative configurations of proximal intersections of first channel 2300 with first side-channel 2310 (FIG. 24A and FIG. 24B) and second side-channel 2320 (FIG. 24A).

FIG. 24A illustrates the direction of the excess liquid flow from first channel 2300 into the side-channels at proximal intersections 2311 and 2321. In this configuration, the side-channels have a depth sized to substantially prevent particle ingress from first channel 2300.

FIG. 24B illustrates the direction of the excess liquid flow from first channel 2300 into the side-channel at proximal intersection 2311. In this configuration, the side-channel includes filter 2313 to substantially prevent particle ingress from first channel 2300.

Example 24

Figure 25A:
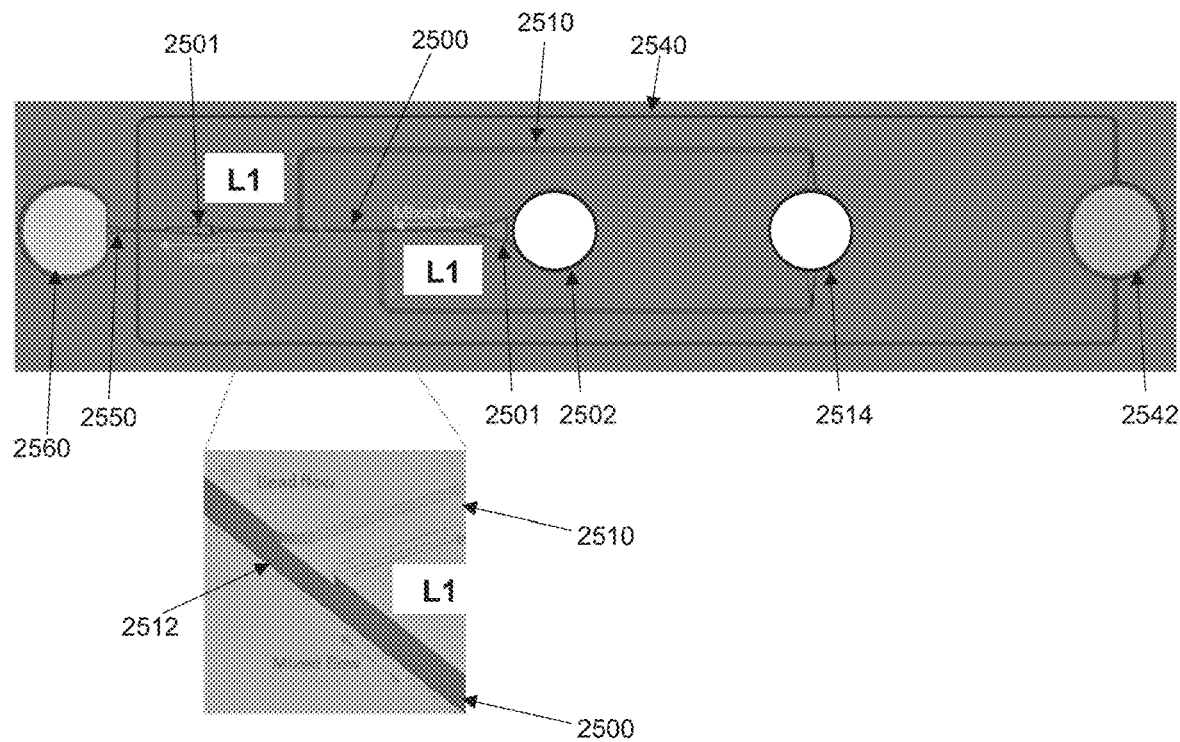
FIG. 25A is an image showing the top view of an exemplary device of the invention. The device includes first channel 2500 having two funnels 2501, first reservoir 2502, first side-channel 2510 including first side-channel reservoir 2514, two second channels 2540 fluidically connected to second reservoir 2542, droplet formation region 2550, and droplet collection region 2560. This device is adapted to control pressure in first channel 2500 through the use of first side-channel 2510. The inset shows an isometric view of the distal intersection 2512 with first-side channel 2510 having a first side-channel depth that is smaller than the first depth and a first side-channel width that is greater than the first width. Droplet collection region 2560 is in fluid communication with first reservoir 2502, first side-channel reservoir 2514, and second reservoir 2542. First channel 2500 has a depth of 60 µm, and first side-channel 2510 has a depth of 14 µm. This configuration may be used, e.g., with beads having a mean diameter of about 54 µm. In operation, beads flow with the first liquid L1 along first channel 2500, and excess first liquid L1 is removed through first side-channel 2510, and beads are sized to reduce or even substantially eliminate their ingress into first side-channel 2510.

FIG. 25A illustrates an exemplary device of the invention. The device includes first channel 2500 having two funnels 2501, first reservoir 2502, first side-channel 2510 including first side-channel reservoir 2514, two second channels 2540 fluidically connected to second reservoir 2542, droplet formation region 2550, and droplet collection region 2560. First channel 2500 has a depth of 60 µm, and first side-channel 2510 has a depth of 14 µm. This configuration may be used, e.g., with beads having a mean diameter of about 54 µm. This device is adapted to control pressure in first channel 2500 through the use of first side-channel 2510.

In use, beads and first liquid L1, preloaded into reservoir 2502, are allowed to flow from reservoir 2502 to droplet formation region 2550. The bead spacing is controlled by way of side-channel 2510, which includes side-channel reservoir 2514. In use, side-channel reservoir 2514 can be used for active control of the pressure in side-channel 2510. Thus, the bead flow rate, spacing, and spacing uniformity may be adjusted as needed by controlling the pressure in reservoirs 2502 and 2514.

Rectifiers 2501 can provide additional control over bead spacing and spacing uniformity. Sample (e.g., a third liquid) may be loaded into reservoir 2542 and allowed to flow to droplet formation region 2550 through two second channels 2540. At an intersection between first channel 2500 and second channels 2540, the bead stream is combined with the sample stream, and the combined beads, first liquid, and sample proceed to droplet formation region 2550, where the combined stream contacts a second liquid in droplet collection region 2560 to form droplets, preferably, droplets containing a single bead. Rectifiers 2501 and side channel 2510 thus can be used to control particle (e.g., bead) spacing to allow for the formation of droplets containing a single particle.

The inset shows an isometric view of distal intersection 2512 with first-side channel 2510 having a first side-channel depth that is smaller than the first depth and a first side-channel width that is greater than the first width. Droplet collection region 2560 is in fluid communication with first reservoir 2502, first side-channel reservoir 2514, and second reservoir 2542. In operation, beads flow with the first liquid L1 along first channel 2500, and excess first liquid L1 is removed through first side-channel 2510, and beads are sized to reduce or even substantially eliminate their ingress into first side-channel 2510.

Figure 25B:
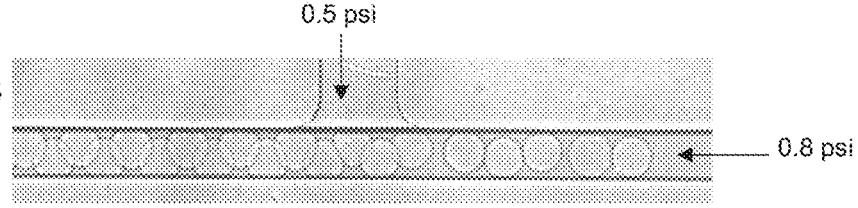
FIG. 25B is an image showing a top view of an intersection between a first channel and a first side-channel in use. In this figure, the first liquid and beads flow along a first channel at a pressure of 0.8 psi, the first liquid pressure applied in the first side-channel is 0.5 psi. Accordingly, excess first liquid is removed from the space between consecutive beads, and these beads are then tightly packed in the first channel.

FIG. 25B shows an intersection between a first channel and a first side-channel in use. In this figure, the first liquid and beads flow along a first channel at a pressure of 0.8 psi, the first liquid pressure applied in the first side-channel is 0.5 psi. Accordingly, excess first liquid is removed from the space between consecutive beads, and these beads are then tightly packed in the first channel.

Figure 25C:
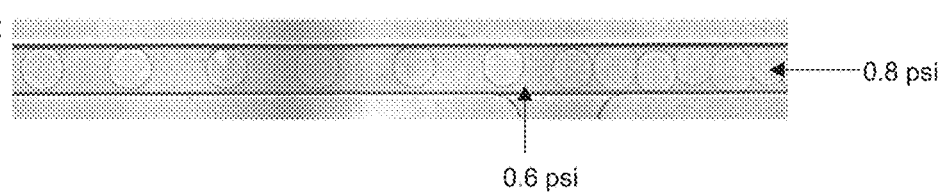
FIG. 25C is an image showing a top view of an intersection between a first channel and a first side-channel in use in a device having only one intersection between channel 2500 and side-channel 2510. In this figure, the first liquid and beads flow along a first channel. The pressure applied to reservoir 2502 is 0.8 psi, and the pressure applied to reservoir 2514 is 0.6 psi. The beads are tightly packed in the first channel upstream of the channel intersection. The first liquid added to the first channel from the first side-channel is evenly distributed between consecutive beads, thereby providing a stream of evenly spaced beads.

FIG. 25C shows an intersection between a first channel and a first side-channel in use. In this figure, the first liquid and beads flow along a first channel. The pressure applied to reservoir 2502 is 0.8 psi, and the pressure applied to reservoir 2514 is 0.6 psi. The beads are tightly packed in the first channel upstream of the channel intersection. The first liquid added to the first channel from the first side-channel is evenly distributed between consecutive beads, thereby providing a stream of evenly spaced beads.

Figure 25D:
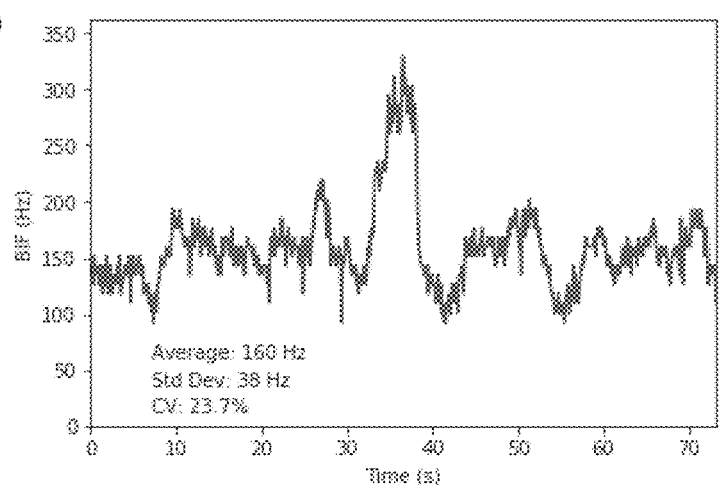
FIG. 25D is a chart showing the frequency at which beads flow through a fixed region in the chip (Bead Injection Frequency, or BIF) as a function of time, during normal chip operation. The measurement was carried out by video analysis of a fixed region of the first channel, after the intersection between the first channel and first side-channel.

FIG. 25D is a chart showing the frequency at which beads flow through a fixed region in the chip (Bead Injection Frequency, or BIF) as a function of time, during normal chip operation. The measurement was carried out by video analysis of a fixed region of the first channel, after the intersection between the first channel and first side-channel.

Example 25

Figure 26A:
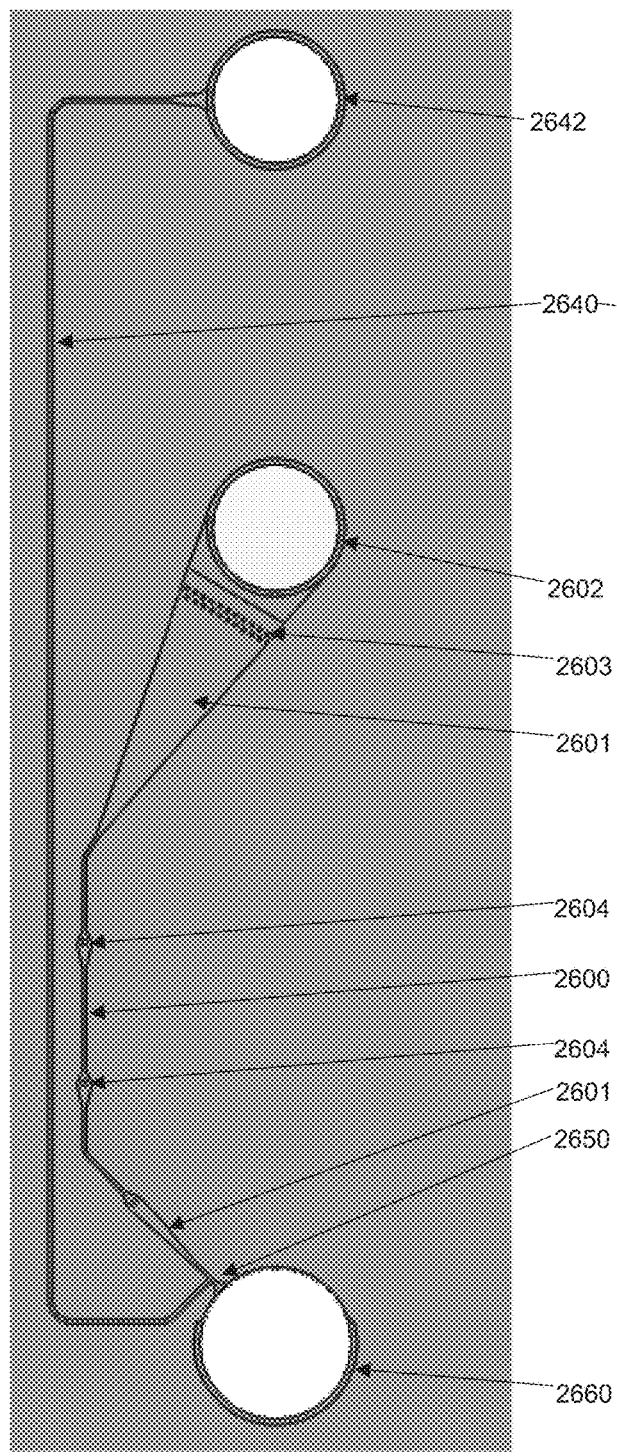
FIG. 26A is an image showing the top view of an exemplary device of the invention. The device includes first channel 2600 having two funnels 2601 and two mini-rectifiers 2604, first reservoir 2602, second channel 2640 fluidically connected to second reservoir 2642, droplet formation region 2650, and droplet collection region 2660. The proximal funnel width is substantially equal to the width of first reservoir 2602. Funnels 2601 and mini-rectifiers 2604 include pegs 2603 as hurdles. There are two rows of pegs 2603 in proximal funnel 2601 as hurdles. Droplet collection region 2660 is in fluid communication with first reservoir 2602 and second reservoir 2642. The spacing between pegs 2603 is 100 µm.

FIG. 26A illustrates an exemplary device of the invention. The device includes first channel 2600 having two funnels 2601 and two mini-rectifiers 2604, first reservoir 2602, second channel 2640 fluidically connected to second reservoir 2642, droplet formation region 2650, and droplet collection region 2660. The proximal funnel width is substantially equal to the width of first reservoir 2602. Funnels 2601 and mini-rectifiers 2604 include pegs 2603 as hurdles. There are two rows of pegs 2603 in proximal funnel 2601 as hurdles. Droplet collection region 2660 is in fluid communication with first reservoir 2602 and second reservoir 2642. The spacing between pegs 2603 is 100 µm.

In use, beads and a first liquid, preloaded into reservoir 2602, are allowed to flow from reservoir 2602 to droplet formation region 2650. The bead flow rate and spacing may be adjusted as needed by controlling the pressure in reservoir 2602. Rectifiers 2601 and mini-rectifiers 2604 can also provide control over bead spacing and spacing uniformity. Sample (e.g., a third liquid) may be loaded into reservoir 2642 and allowed to flow to droplet formation region 2650 through second channel 2640. At an intersection between first channel 2600 and second channel 2640, the bead stream is combined with the sample stream, and the combined beads, first liquid, and sample proceed to droplet formation region 2650, where the combined stream contacts a second liquid in droplet collection region 2660 to form droplets, preferably, droplets containing a single bead. Rectifiers 2601, mini-rectifiers 2604, and hurdles 2603 thus can be used to control particle (e.g., bead) spacing to allow for the formation of droplets containing a single particle.

Figure 26B:
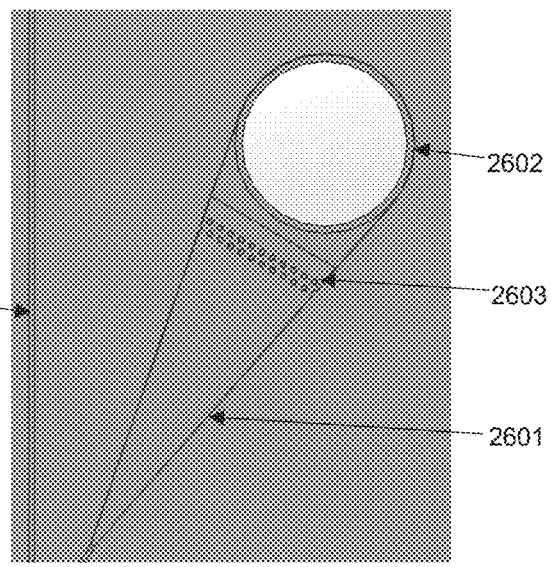
FIG. 26B is an image focused on the combination of proximal funnel 2601 and first reservoir 2602 in the device of FIG. 26A. Proximal funnel 2601 is fluidically connected to first reservoir 2602 and includes two rows of pegs 2603 as hurdles.
Figure 26C:
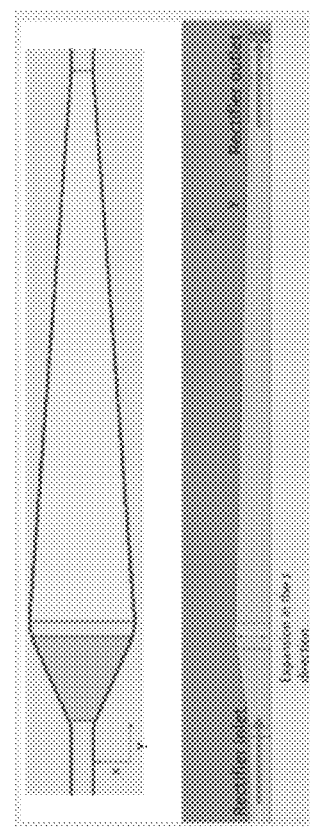
FIG. 26C is an image illustrating the depth changes in distal funnel 2601. Distal funnel 2601 has a depth and width increasing until a maximum width and depth are reached (i.e., the maximum depth is at the same location as the maximum width). In this drawing, the depth and width maxima are closer to the funnel inlet than to the funnel outlet.

FIG. 26B is an image focused on the combination of proximal funnel 2601 and first reservoir 2602 in the device of FIG. 26A. Proximal funnel 2601 is fluidically connected to first reservoir 2602 and includes two rows of pegs 2603 as hurdles.

Example 26

FIG. 27A illustrates an exemplary device of the invention. The device includes two first channels 2700, each first channel having two funnels 2701 and two mini-rectifiers 2704; first reservoir 2702; two second channels 2740 fluidically connected to the same second reservoir 2742; two droplet formation regions 2750; and one droplet collection region 2760. The proximal funnel 2701 on the left includes one barrier 2705 as a hurdle. The proximal funnel 2701 on the right includes three rows of pegs 2703 as hurdles. Droplet collection region 2760 is in fluid communication with first reservoir 2702 and second reservoir 2742. Barrier 2705 has a height of 30 µm, and pegs 2703 are spaced at 100 µm intervals.

In use, beads and a first liquid, preloaded into reservoir 2702, are allowed to flow from reservoir 2702 to droplet formation regions 2750. The bead flow rate and spacing may be adjusted as needed by controlling the pressure in reservoir 2702. Rectifiers 2701 and mini-rectifiers 2704 can also provide control over bead spacing and spacing uniformity. Sample (e.g., a third liquid) may be loaded into reservoir 2742 and allowed to flow to droplet formation regions 2750 through second channels 2740. At intersections between first channels 2700 and second channels 2740, the bead stream is combined with the sample stream, and the combined beads, first liquid, and sample proceed to droplet formation regions 2750, where the combined streams contact a second liquid in droplet collection region 2760 to form droplets, preferably, droplets containing a single bead. Rectifiers 2701, mini-rectifiers 2704, and hurdles 2703 and 2705 thus can be used to control particle (e.g., bead) spacing to allow for the formation of droplets containing a single particle.

FIG. 27B is an image focused on the combination of two proximal funnels 2701 and first reservoir 2702. Proximal funnel 2701 on the left is fluidically connected to first reservoir 2702 and includes one barrier 2705 as a hurdle. Proximal funnel 2701 on the right is fluidically connected to first reservoir 2702 includes three rows of pegs 2703 as hurdles.

Example 27

Figure 28A:
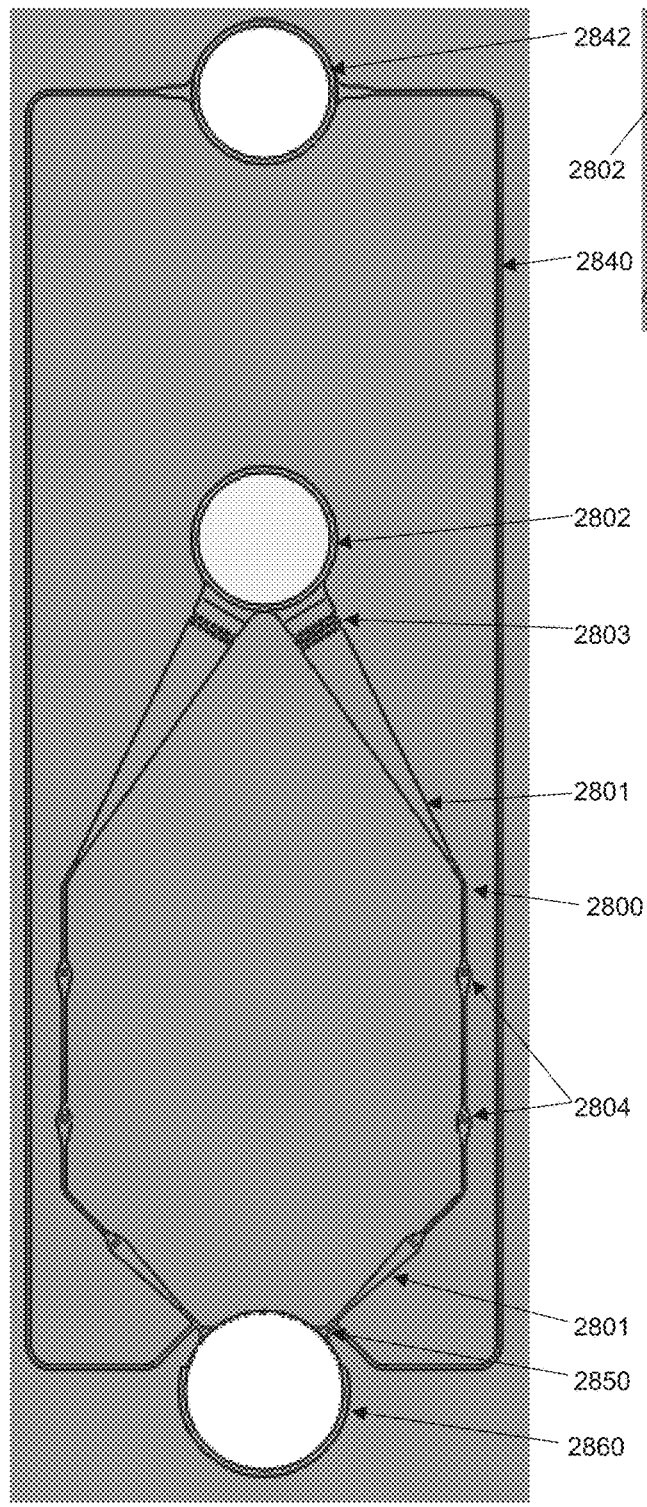
FIG. 28A is an image showing the top view of an exemplary device of the invention. The device includes two first channels 2800, each first channel having two funnels 2801 and two mini-rectifiers 2804; first reservoir 2802; two second channels 2840 fluidically connected to the same second reservoir 2842; two droplet formation regions 2850; and one droplet collection region 2860. Proximal funnel 2801 on the left includes two rows of pegs 2803 as hurdles. Proximal funnel 2801 on the right includes three rows of pegs 2803 as hurdles. Droplet collection region 2860 is in fluid communication with first reservoir 2802 and second reservoir 2842. The spacing between pegs 2803 is 65 µm.

FIG. 28A is an image showing the top view of an exemplary device of the invention. The device includes two first channels 2800, each first channel having two funnels 2801 and two mini-rectifiers 2804; first reservoir 2802; two second channels 2840 fluidically connected to the same second reservoir 2842; two droplet formation regions 2850; and one droplet collection region 2860. Proximal funnel 2801 on the left includes two rows of pegs 2803 as hurdles. Proximal funnel 2801 on the right includes three rows of pegs 2803 as hurdles. Droplet collection region 2860 is in fluid communication with first reservoir 2802 and second reservoir 2842. The spacing between pegs 2803 is 65 µm.

In use, beads and a first liquid, preloaded into reservoir 2802, are allowed to flow from reservoir 2802 to droplet formation regions 2850. The bead flow rate and spacing may be adjusted as needed by controlling the pressure in reservoir 2802. Rectifiers 2801 and mini-rectifiers 2804 can also provide control over bead spacing and spacing uniformity. Sample (e.g., a third liquid) may be loaded into reservoir 2842 and allowed to flow to droplet formation regions 2850 through second channels 2840. At intersections between first channels 2800 and second channels 2840, the bead stream is combined with the sample stream, and the combined beads, first liquid, and sample proceed to droplet formation regions 2850, where the combined streams contact a second liquid in droplet collection region 2860 to form droplets, preferably, droplets containing a single bead. Rectifiers 2801, mini-rectifiers 2804, and hurdles 2803 thus can be used to control particle (e.g., bead) spacing to allow for the formation of droplets containing a single particle.

Figure 28B:
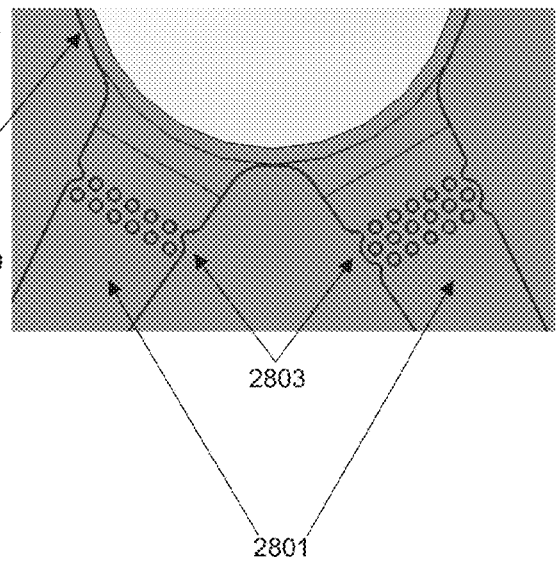
FIG. 28B is an image focused on the combination of proximal funnels 2801 and first reservoir 2802. Proximal funnel 2801 on the left is fluidically connected to first reservoir 2802 and includes two rows of pegs 2803 as hurdles. Proximal funnel 2801 on the right is fluidically connected to first reservoir 2802 and includes three rows of pegs 2803 as hurdles.

FIG. 28B is an image focused on the combination of proximal funnels 2801 and first reservoir 2802. Proximal funnel 2801 on the left is fluidically connected to first reservoir 2802 and includes two rows of pegs 2803 as hurdles. Proximal funnel 2801 on the right is fluidically connected to first reservoir 2802 and includes three rows of pegs 2803 as hurdles.

Example 28

FIG. 29A is an image showing the top view of an exemplary device of the invention. The device includes two first channels 2900, each first channel having two funnels 2901 and two mini-rectifiers 2904; first reservoir 2902; two second channels 2940 fluidically connected to the same second reservoir 2942; two droplet formation regions 2950; and one droplet collection region 2960. Proximal funnel 2901 on the left includes a barrier with two rows of pegs disposed on top of the barrier as hurdle 2906. Proximal funnel 2901 on the right includes a barrier with three rows of pegs disposed on top of the barrier as a hurdle 2906. Droplet collection region 2960 is in fluid communication with first reservoir 2902 and second reservoir 2942. Each hurdle 2906 is a 30 μm-tall barrier with pegs spaced at 100 μm.

In use, beads and a first liquid, preloaded into reservoir 2902, are allowed to flow from reservoir 2902 to droplet formation regions 2950. The bead flow rate and spacing may be adjusted as needed by controlling the pressure in reservoir 2902. Rectifiers 2901 and mini-rectifiers 2904 can also provide control over bead spacing and spacing uniformity. Sample (e.g., a third liquid) may be loaded into reservoir 2942 and allowed to flow to droplet formation regions 2950 through second channels 2940.

At intersections between first channels 2900 and second channels 2940, the bead stream is combined with the sample stream, and the combined beads, first liquid, and sample proceed to droplet formation regions 2950, where the combined streams contact a second liquid in droplet collection region 2960 to form droplets, preferably, droplets containing a single bead. Rectifiers 2901, mini-rectifiers 2904, and hurdles 2906 thus can be used to control particle (e.g., bead) spacing to allow for the formation of droplets containing a single particle.

FIG. 29B is an image focused on the combination of proximal funnels 2901 and first reservoir 2902. Proximal funnel 2901 on the left is fluidically connected to first reservoir 2902 and includes a barrier with two rows of pegs disposed on top of the barrier as hurdle 2906. Proximal funnel 2901 on the right is fluidically connected to first reservoir 2902 includes a barrier with three rows of pegs disposed on top of the barrier as hurdle 2906.

Example 29

FIG. 30A is an image showing the top view of an exemplary device of the invention. The device includes two first channels 3000, each first channel having two funnels 3001; first reservoir 3002; two second channels 3040 fluidically connected to the same second reservoir 3042; two droplet formation regions 3050; and one droplet collection region 3060. Proximal funnel 3001 on the left includes two rows of pegs 3003 as hurdles. Pegs 3003 are spaced at 100 μm. Proximal funnel 3001 on the right includes a barrier with two rows of pegs disposed on top of the barrier as a hurdle 3006. Hurdle 3006 is a 60 μm-tall barrier with pegs spaced at 65 μm. Distal funnel 3001 on the left is elongated (2 mm in length). Droplet collection region 3060 is in fluid communication with first reservoir 3002 and second reservoir 3042.

In use, beads and a first liquid, preloaded into reservoir 3002, are allowed to flow from reservoir 3002 to droplet formation regions 3050. The bead flow rate and spacing may be adjusted as needed by controlling the pressure in reservoir 3002. Rectifiers 3001 can also provide control over bead spacing and spacing uniformity. Sample (e.g., a third liquid) may be loaded into reservoir 3042 and allowed to flow to droplet formation regions 3050 through second channels 3040. At intersections between first channels 3000 and second channels 3040, the bead stream is combined with the sample stream, and the combined beads, first liquid, and sample proceed to droplet formation regions 3050, where the combined streams contact a second liquid in droplet collection region 3060 to form droplets, preferably, droplets containing a single bead. Rectifiers 3001 and hurdles 3003 and 3006 thus can be used to control particle (e.g., bead) spacing to allow for the formation of droplets containing a single particle.

FIG. 30B is an image focused on the combination of proximal funnels 3001 and first reservoir 3002. Proximal funnel 3001 on the left is fluidically connected to first reservoir 3002 and includes two rows of pegs 3003 as hurdles. Proximal funnel 3001 on the right is fluidically connected to first reservoir 3002 includes a barrier with two rows of pegs disposed on top of the barrier as hurdle 3006.

Example 30

FIG. 31A is an image showing the top view of an exemplary device of the invention. The device includes two first channels 3100, each first channel having two funnels 3101, where first channel 3100 on the left includes two mini-rectifiers 3104, and first channel 3100 on the right does not; first reservoir 3102; two second channels 3140 fluidically connected to the same second reservoir 3142; two droplet formation regions 3150; and one droplet collection region 3160. First channel 3100 on the left has dimensions of 65×60 μm, and first channel 3100 on the right has dimensions of 70×65 μm. Each proximal funnel 3101 includes a barrier with two rows of pegs 3103 as hurdles. Droplet collection region 3160 is in fluid communication with first reservoir 3102 and second reservoir 3142.

In use, beads and a first liquid, preloaded into reservoir 3102, are allowed to flow from reservoir 3102 to droplet formation regions 3150. The bead flow rate and spacing may be adjusted as needed by controlling the pressure in reservoir 3102. Rectifiers 3101 alone or in combination with mini-rectifiers 3104 can also provide control over bead spacing and spacing uniformity. Sample (e.g., a third liquid) may be loaded into reservoir 3142 and allowed to flow to droplet formation regions 3150 through second channels 3140. At intersections between first channels 3100 and second channels 3140, the bead stream is combined with the sample stream, and the combined beads, first liquid, and sample proceed to droplet formation regions 3150, where the combined streams contact a second liquid in droplet collection region 3160 to form droplets, preferably, droplets containing a single bead. Rectifiers 3101, mini-rectifiers 3104, and hurdles 3103 thus can be used to control particle (e.g., bead) spacing to allow for the formation of droplets containing a single particle.

FIG. 31B is an image focused on the combination of proximal funnels 3101 and first reservoir 3102. Each proximal funnel 3101 on the left is fluidically connected to first reservoir 3102 and includes two rows of pegs 3103 as hurdles.

Example 31

Figure 32:
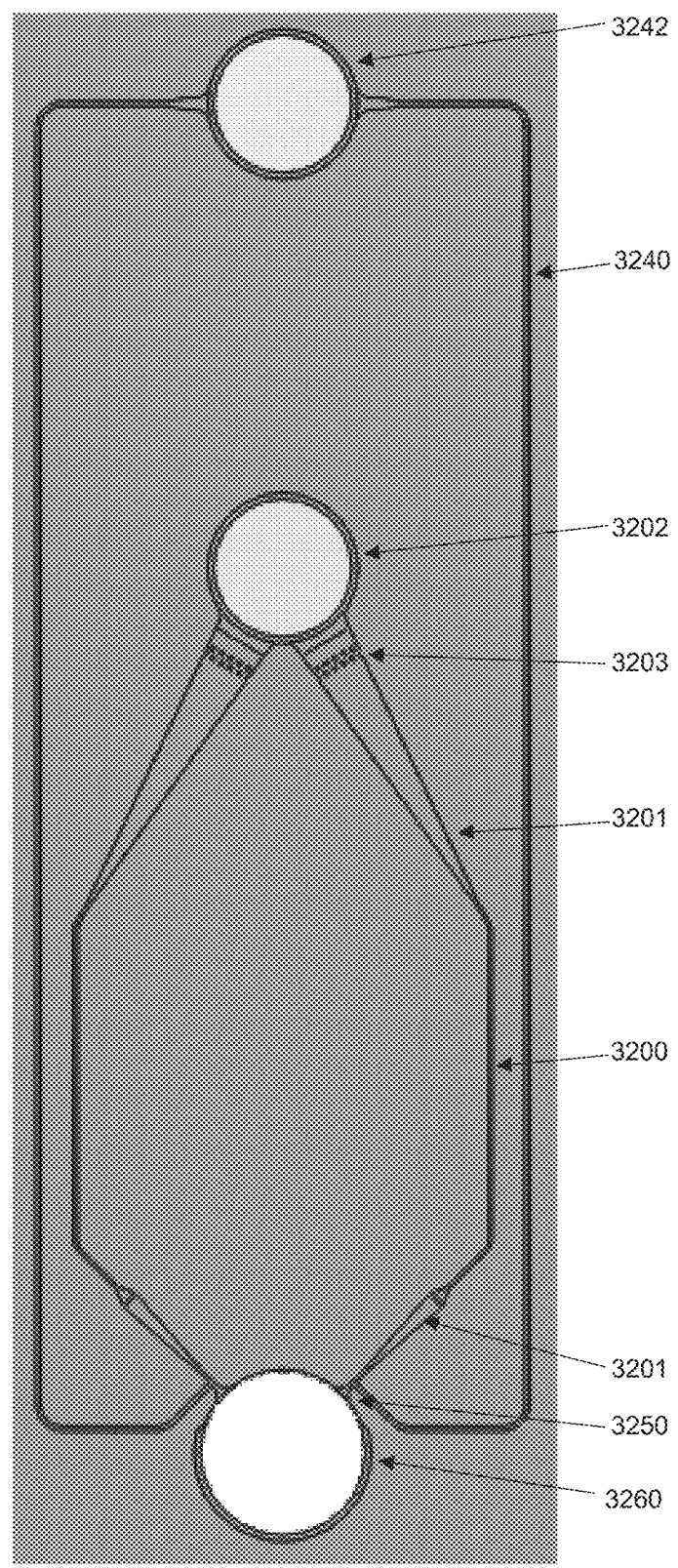
FIG. 32 illustrates an exemplary device of the invention. The device includes two first channels 3200, each first channel having two funnels 3201; first reservoir 3202; two second channels 3240 fluidically connected to the same second reservoir 3242; two droplet formation regions 3250; and one droplet collection region 3260. First channel 3200 on the left has dimensions of 65×110 µm, and first channel 3200 on the right has dimensions of 60×55 µm. Each proximal funnel 3201 includes two rows of pegs 3203 as hurdles. Droplet collection region 3260 is in fluid communication with first reservoir 3202 and second reservoir 3242.

FIG. 32 illustrates an exemplary device of the invention. The device includes two first channels 3200, each first channel having two funnels 3201; first reservoir 3202; two second channels 3240 fluidically connected to the same second reservoir 3242; two droplet formation regions 3250; and one droplet collection region 3260. First channel 3200 on the left has dimensions of 65×110 µm, and first channel 3200 on the right has dimensions of 60×55 µm. Each proximal funnel 3201 includes two rows of pegs 3203 as hurdles. Droplet collection region 3260 is in fluid communication with first reservoir 3202 and second reservoir 3242.

In use, beads and a first liquid, preloaded into reservoir 3202, are allowed to flow from reservoir 3202 to droplet formation regions 3250. The bead flow rate and spacing may be adjusted as needed by controlling the pressure in reservoir 3202. Rectifiers 3201 can also provide control over bead spacing and spacing uniformity. Sample (e.g., a third liquid) may be loaded into reservoir 3242 and allowed to flow to droplet formation regions 3250 through second channels 3240. At intersections between first channels 3200 and second channels 3240, the bead stream is combined with the sample stream, and the combined beads, first liquid, and sample proceed to droplet formation regions 3250, where the combined streams contact a second liquid in droplet collection region 3260 to form droplets, preferably, droplets containing a single bead. Rectifiers 3201 and hurdles 3203 thus can be used to control particle (e.g., bead) spacing to allow for the formation of droplets containing a single particle.

Example 32

Figure 33A:
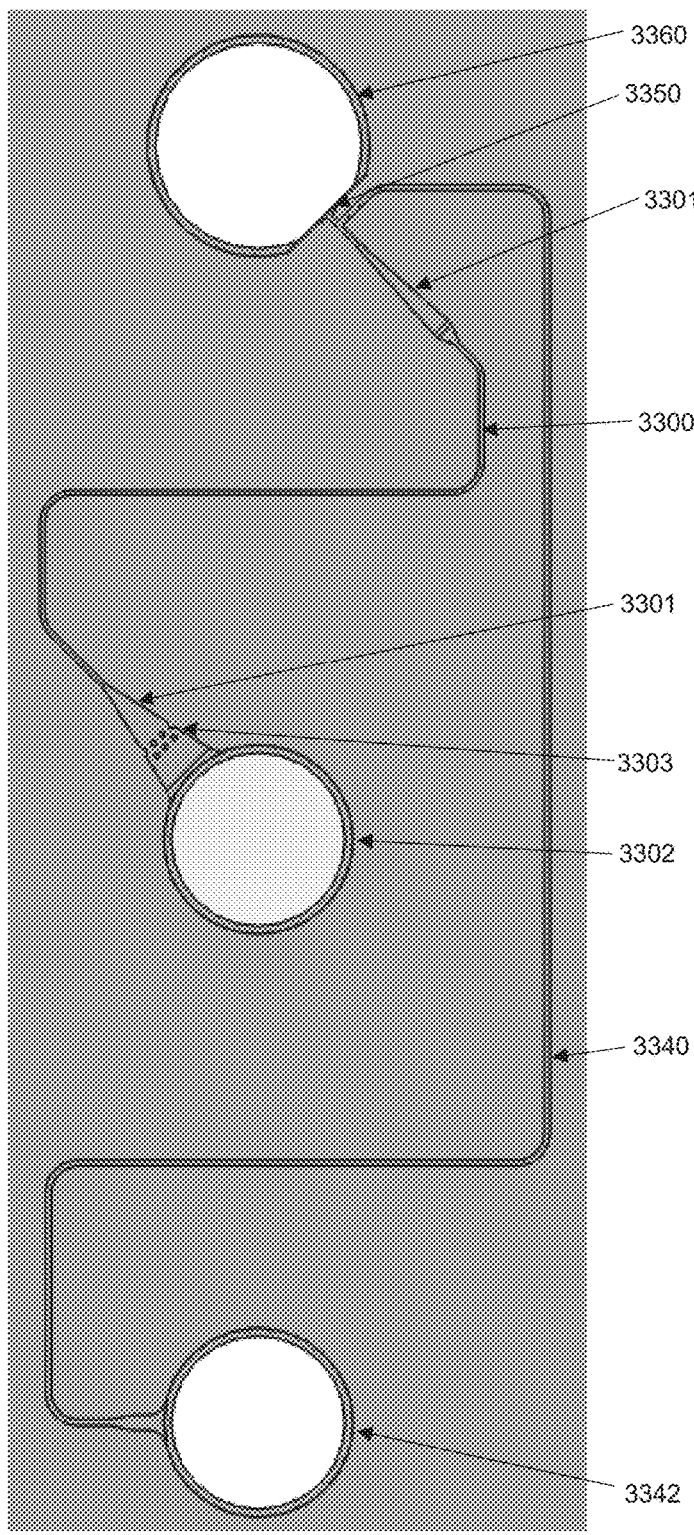
FIG. 33A is an image showing the top view of an exemplary device of the invention. The device includes first channel 3300 having two funnels 3301, first reservoir 3302, second channel 3340 fluidically connected to second reservoir 3342, droplet formation region 3350, and droplet collection region 3360. First channel 3300 on the left has dimensions of 55×50 µm, and first channel 3300 on the right has dimensions of 50×50 µm. Proximal funnel 3301 includes two rows of pegs 3303 as hurdles. Droplet collection region 3360 is in fluid communication with first reservoir 3302 and second reservoir 3342.

FIG. 33A is an image showing the top view of an exemplary device of the invention. The device includes first channel 3300 having two funnels 3301, first reservoir 3302, second channel 3340 fluidically connected to second reservoir 3342, droplet formation region 3350, and droplet collection region 3360. First channel 3300 on the left has dimensions of 55×50 µm, and first channel 3300 on the right has dimensions of 50×50 µm. Proximal funnel 3301 includes two rows of pegs 3303 as hurdles. Droplet collection region 3360 is in fluid communication with first reservoir 3302 and second reservoir 3342.

In use, beads and a first liquid, preloaded into reservoir 3302, are allowed to flow from reservoir 3302 to droplet formation region 3350. The bead flow rate and spacing may be adjusted as needed by controlling the pressure in reservoir 3302. Rectifiers 3301 can also provide control over bead spacing and spacing uniformity. Sample (e.g., a third liquid) may be loaded into reservoir 3342 and allowed to flow to droplet formation region 3350 through second channel 3340. At an intersection between first channel 3300 and second channel 3340, the bead stream is combined with the sample stream, and the combined beads, first liquid, and sample proceed to droplet formation region 3350, where the combined streams contact a second liquid in droplet collection region 3360 to form droplets, preferably, droplets containing a single bead. Rectifiers 3301 and hurdles 3303 thus can be used to control particle (e.g., bead) spacing to allow for the formation of droplets containing a single particle.

Figure 33B:
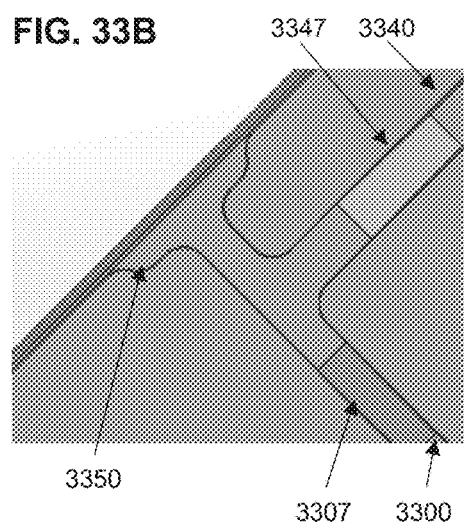
FIG. 33B, FIG. 33C, and FIG. 33D focus on droplet formation region 3350 and intersection between first channel 3300 and second channel 3340. In these figures, first channel 3300 includes channel portion 3307 where first depth is reduced in proximal-to-distal direction, second channel 3340 includes a channel portion 3347 where second depth is reduced in proximal-to-distal direction.
Figure 33C:
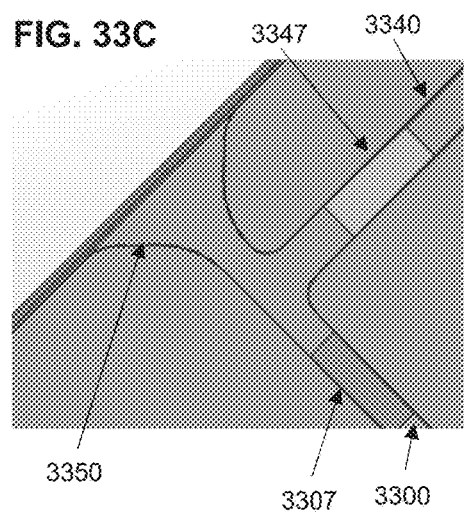
Figure 33D:
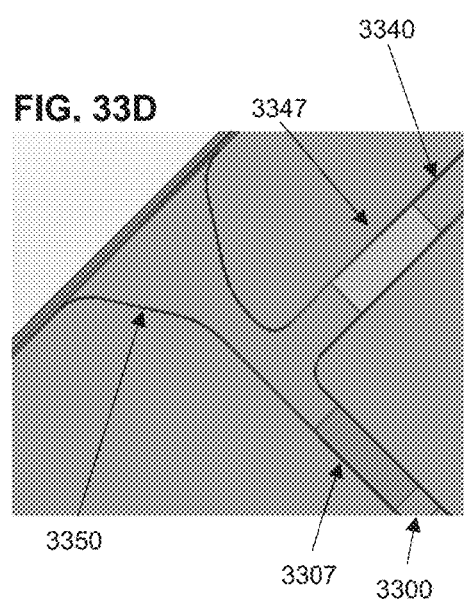

FIG. 33B, FIG. 33C, and FIG. 33D focus on droplet formation region 3350 and intersection between first channel 3300 and second channel 3340. In these figures, first channel 3300 includes channel portion 3307 where first depth is reduced in proximal-to-distal direction, second channel 3340 includes a channel portion 3347 where second depth is reduced in proximal-to-distal direction.

Example 33

Figure 35:
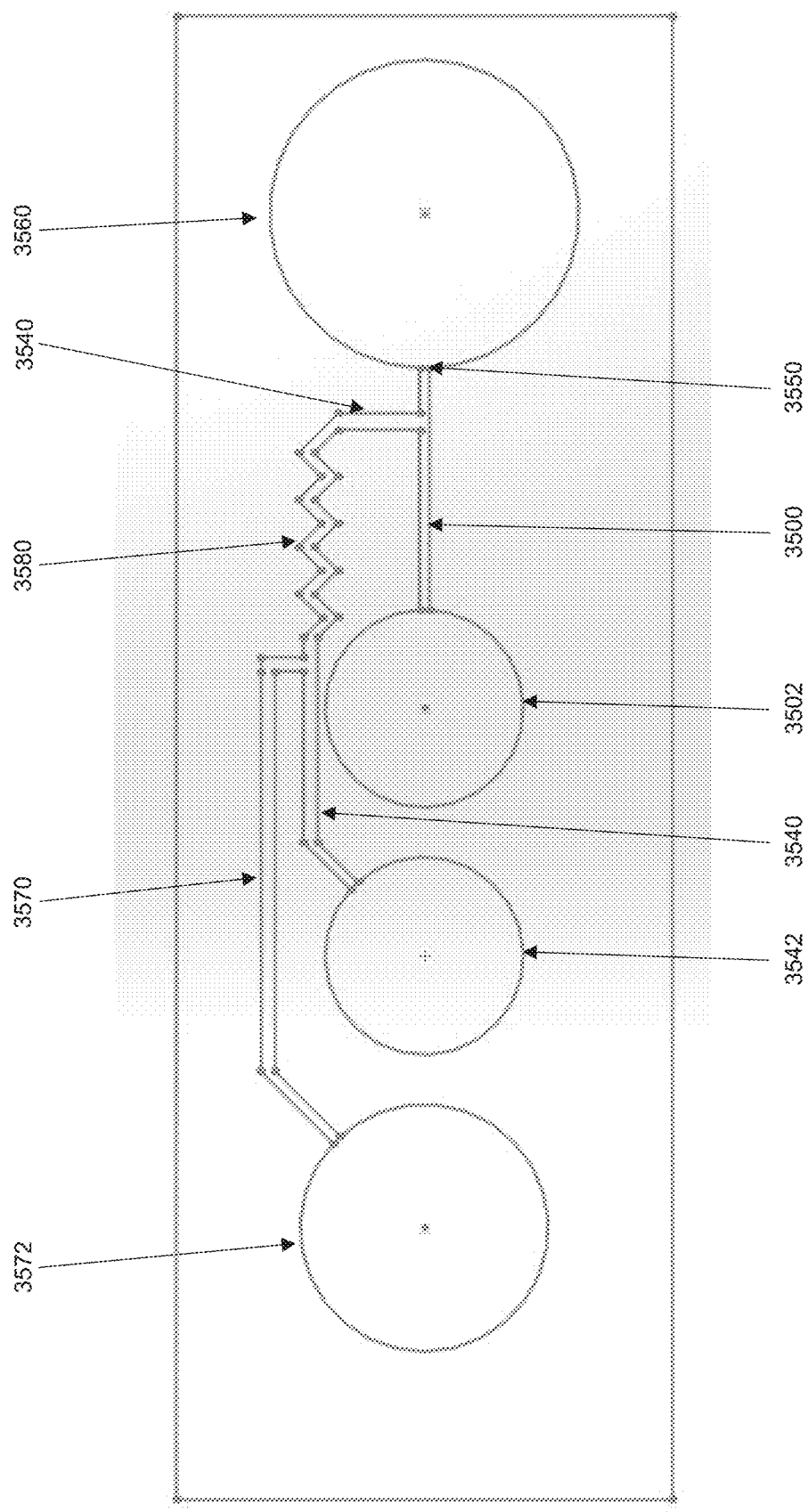
FIG. 35 is an image showing the top view of an exemplary device of the invention. The device includes first channel 3500 fluidically connected to first reservoir 3502, second channel 3540 including mixer 3580 and fluidically connected to second reservoir 3542, third channel 3570 fluidically connected to third reservoir 3572, droplet formation region 3550, and droplet collection region 3560. Third channel 3570 intersects second channel 3540, the distal end of which is fluidically connected to first channel 3500. Droplet collection region 3560 is in fluid communication with first reservoir 3502, second reservoir 3542, and third reservoir 3572.

FIG. 35 is an image showing the top view of an exemplary device of the invention. The device includes first channel 3500 fluidically connected to first reservoir 3502, second channel 3540 including mixer 3580 and fluidically connected to second reservoir 3542, third channel 3570 fluidically connected to third reservoir 3572, droplet formation region 3550, and droplet collection region 3560. Third channel 3570 intersects second channel 3540, the distal end of which is fluidically connected to first channel 3500. Droplet collection region 3560 is in fluid communication with first reservoir 3502, second reservoir 3542, and third reservoir 3572.

In use, beads and a first liquid, preloaded into reservoir 3502, are allowed to flow from reservoir 3502 to droplet formation region 3550. The bead flow rate and spacing may be adjusted as needed by controlling the pressure in reservoir 3502. Channel 3500 may be modified upstream of the intersection between first channel 3500 and second channel 3540 to include one or more funnels to control bead spacing as needed. Sample (e.g., cells in a third liquid) may be loaded into reservoir 3542 and allowed to flow to droplet formation region 3550 through second channel 3540. Lysing reagents (e.g., a fourth liquid) may be loaded into reservoir 3572 and allowed to flow to droplet formation region 3550 through third channel 3570. At an intersection between second channel 3540 and third channel 3570, the sample stream is combined with the lysing reagent stream, and the combined liquids are mixed in mixer 3580. At an intersection between first channel 3500 and second channel 3540, the bead stream is combined with the mixed sample/lysing reagent stream, and the combined beads, sample, and lysing reagent proceed to droplet formation region 3550, where the combined streams contact a second liquid in droplet collection region 3560 to form droplets, preferably, droplets containing a single bead.

Mixer 3580 thus can be used to mix a sample (e.g., cells) and lysing reagents to avoid prolonged exposure of a sample portion to a localized high concentration of lysing reagents, which, absent mixing in a mixer, can result in sample (e.g., cell) lysis prior to droplet formation.

The channel/mixer configuration described in this Example is particularly advantageous, as it provides superior control over relative proportions of beads, cells, and lysing reagent. This is because each of the beads, cells, and lysing reagent proportions can be controlled independently through controlling pressures in reservoirs 3502, 3542, and 3572.

Example 34

FIG. 36A is an image showing the top view of an exemplary device of the invention. The device includes first channel 3600 fluidically connected to first reservoir 3602, first side channel 3610 including mixer 3680, second channel 3640 fluidically connected to second reservoir 3642 and to first side-channel 3610, droplet formation region 3650, and droplet collection region 3660. Droplet collection region 3660 is in fluid communication with first reservoir 3602 and second reservoir 3642.

FIG. 36B focuses on a portion of the device of FIG. 36A in use. A mixture of first liquid L1 and beads 3630 is carried through first channel 3600 in the proximal-to-distal direction. Excess first liquid L1 is diverted from first channel 3600 at intersection 3611 into first side-channel 3610. Excess L1 is then combined with L3 at the intersection of first side-channel 3610 and second channel 3640. The combination of first liquid L1 and third liquid L3 then enters mixer 3680 and, after mixing, is combined with beads 3630/first liquid L1 at intersection 3612. As shown in FIG. 36B, beads 3630 are unevenly spaced in the proximal portion of first channel 3600 before intersection 3611. Between intersections 3611 and 3612 beads 3630 are tightly packed in first channel 3600. After intersection 3612, beads 3630 are substantially evenly spaced.

In use, beads and a first liquid containing lysing reagents, preloaded into reservoir 3602, are allowed to flow from reservoir 3602 to droplet formation region 3650. The bead flow rate and spacing may be adjusted as needed by controlling the pressure in reservoir 3602 and in first side-channel 3610. Channel 3600 may also be modified upstream of intersection 3612 to include one or more funnels to control bead spacing as needed. Sample (e.g., cells in a third liquid) may be loaded into reservoir 3642 and allowed to flow to droplet formation region 3650 through second channel 3640. At an intersection between first side-channel 3610 and second channel 3640, the sample stream is combined with the bead-free lysing reagent stream, and the combined liquids are mixed in mixer 3680. At intersection 3612, the bead stream is combined with the mixed sample/lysing reagent stream, and the combined beads, sample, and lysing reagent proceed to droplet formation region 3650, where the combined streams contact a second liquid in droplet collection region 3660 to form droplets, preferably, droplets containing a single bead.

Mixer 3680 thus can be used to mix a sample (e.g., cells) and lysing reagents to avoid prolonged exposure of a sample portion to a localized high concentration of lysing reagents, which, absent mixing in a mixer, can result in sample (e.g., cell) lysis prior to droplet formation.

The channel/mixer configuration described in this Example is particularly advantageous, as control over fewer fluid pressure parameters is required. In particular, the channel/mixer configuration described in this Example requires control over relative pressures in only two reservoirs, 3602 and 3642.

Example 35

Figure 37:
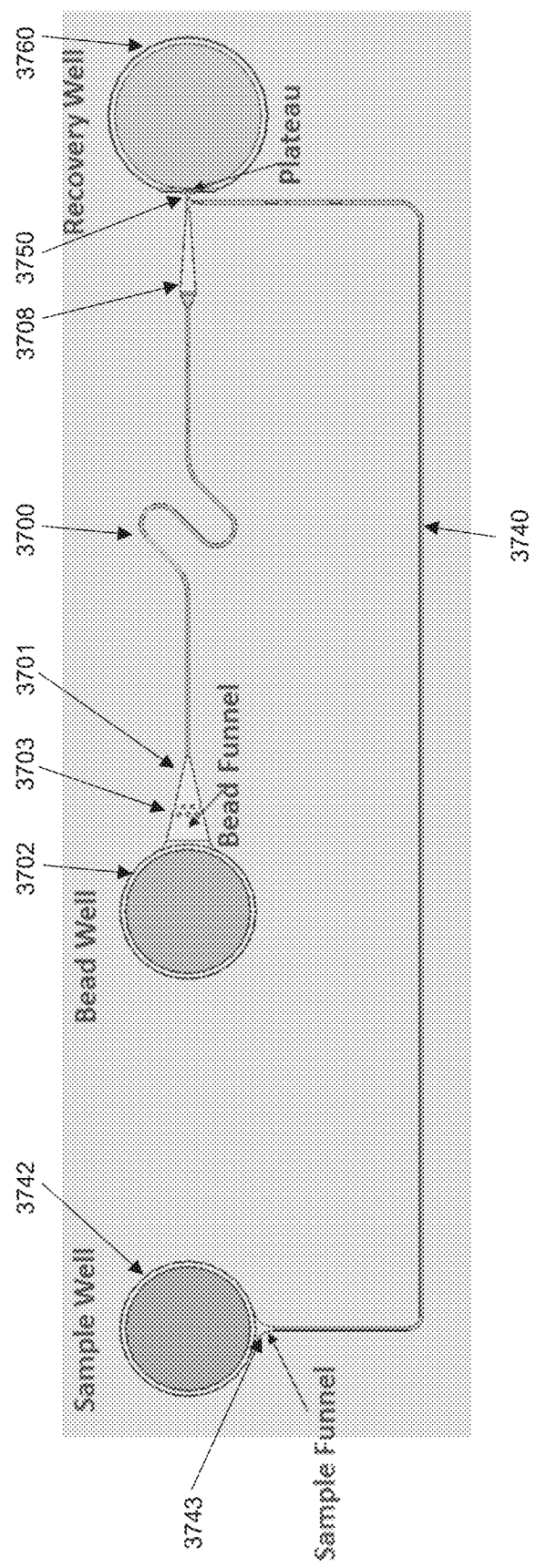
FIG. 37 is an image showing a top view of an exemplary device of the invention. The device includes first channel 3700 fluidically connected to first reservoir 3702. First channel 3700 includes funnel 3701 disposed at its proximal end. Funnel 3701 at the proximal end of first channel 3700 includes pegs 3703. The device includes droplet collection region 3760 fluidically connected to droplet formation region 3750. The device also includes second reservoir 3742 fluidically connected to second channel 3740 that includes funnel 3743 at its proximal end. Second channel 3740 intersect channel 3700 between the first distal end and funnel 3708.

FIG. 37 illustrates an exemplary device of the invention. The device includes first channel 3700 fluidically connected to first reservoir 3702. First channel 3700 includes funnel 3701 disposed at its proximal end. Funnel 3701 at the proximal end of first channel 3700 includes pegs 3703. The device includes droplet collection region 3760 fluidically connected to droplet formation region 3750. The device also includes second reservoir 3742 fluidically connected to second channel 3740 that includes funnel 3743 at its proximal end. Second channel 3740 intersects channel 3700 between the first distal end and funnel 3708.

In use, beads and a first liquid containing lysing reagents, preloaded into reservoir 3702, are allowed to flow from reservoir 3702 to droplet formation region 3750. Sample (e.g., cells in a third liquid) may be loaded into reservoir 3742 and allowed to flow to droplet formation region 3750 through second channel 3740. At an intersection between first channel 3700 and second channel 3740, the sample stream is combined with the bead/lysing reagent stream, and the combined liquids proceed to droplet formation region 3750 to form droplets, preferably, droplets containing a single bead, for collection in droplet collection region 3760.

Example 36

FIGS. 38A, 38B, 38C, 38D, 39A, 39B, 39C, and 39D show exemplary funnel configurations that may be included in any of the devices described herein (e.g., in a first channel).

Figure 38A:
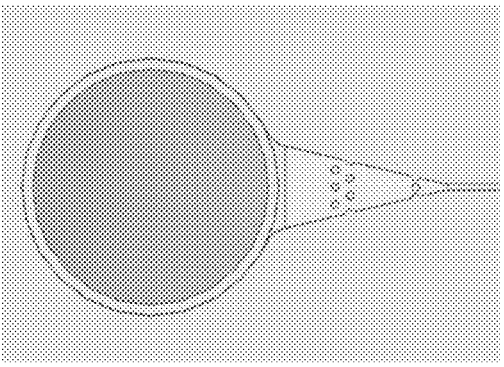
FIG. 38A is a top view of an exemplary funnel that may be included, e.g., at the proximal end of a first channel. The funnel includes two rows of pegs as hurdles closer to the funnel inlet and a single row of pegs (in this instance, a single peg) closer to the funnel outlet.
Figure 38B:
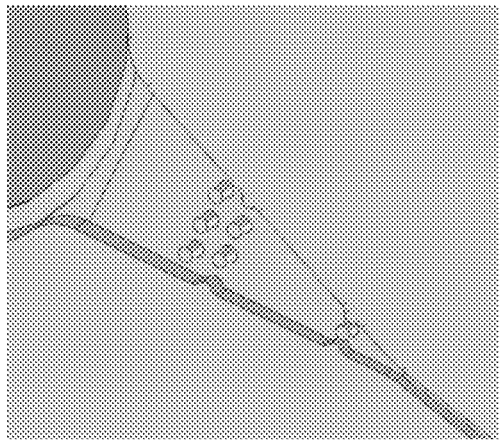
FIG. 38B is a perspective view of an exemplary funnel shown in FIG. 38A.
Figure 38C:
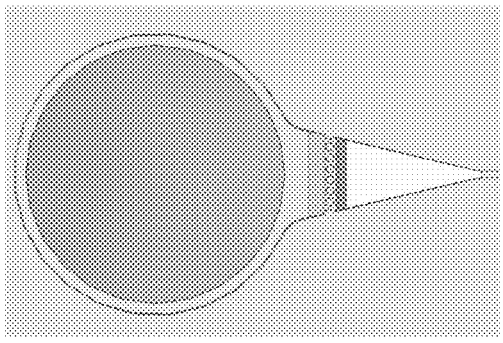
FIG. 38C is a top view of an exemplary funnel that may be included, e.g., at the proximal end of a first channel. The funnel includes a barrier with one row of pegs disposed on top of the barrier as hurdle.
Figure 38D:
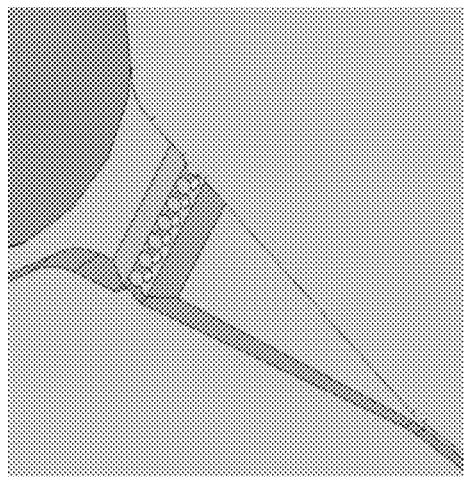
FIG. 38D is a perspective view of an exemplary funnel shown in FIG. 38C.

FIG. 38A is a top view of an exemplary funnel that may be included, e.g., at the proximal end of a first channel. The funnel includes two rows of pegs as hurdles closer to the funnel inlet and a single row of pegs (in this instance, a peg) closer to the funnel outlet. FIG. 38B is a perspective view of an exemplary funnel shown in FIG. 38A.

Figure 39A:
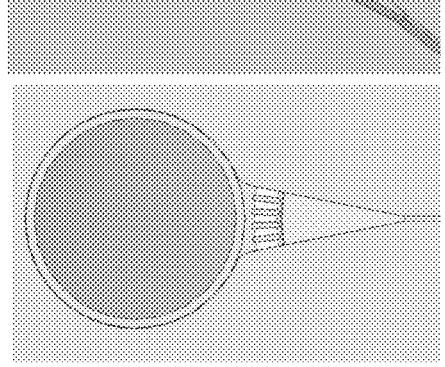
FIG. 39A is a top view of an exemplary funnel that may be included, e.g., at the proximal end of a first channel. The funnel includes a barrier with one row of pegs disposed on top of the barrier as hurdle. The pegs have a peg length that is greater than the peg width.
Figure 39B:
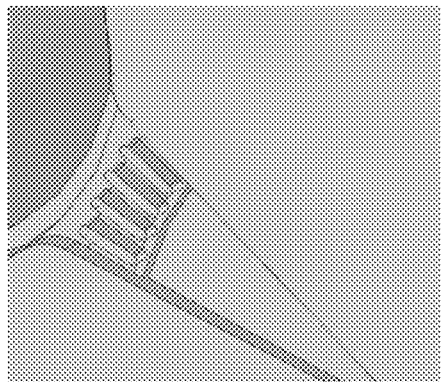
FIG. 39B is a perspective view of an exemplary funnel shown in FIG. 39A.

FIG. 39A is a top view of an exemplary funnel that may be included, e.g., at the proximal end of a first channel. The funnel includes a barrier with one row of pegs disposed on top of the barrier as hurdle. FIG. 39B is a perspective view of an exemplary funnel shown in FIG. 39A.

Figure 39C:
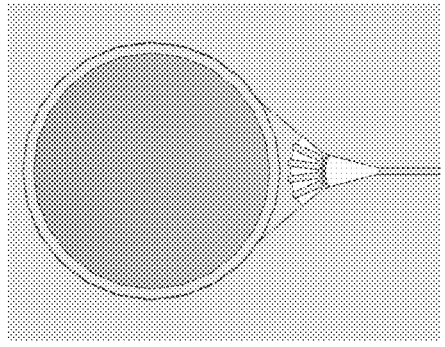
FIG. 39C is a top view of an exemplary funnel that may be included, e.g., at the proximal end of a first channel. The funnel includes a barrier with one row of pegs disposed on top of the barrier as hurdle. The pegs have a peg length that is greater than the peg width.
Figure 39D:
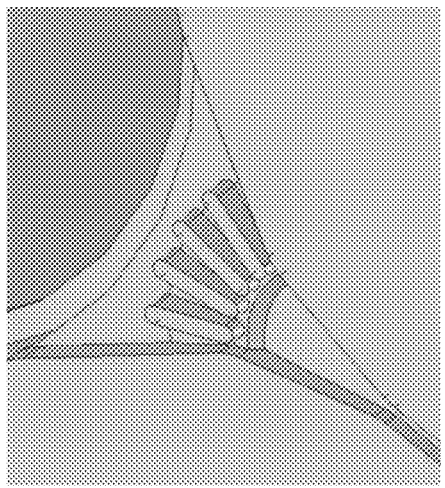
FIG. 39D is a perspective view of an exemplary funnel shown in FIG. 39C.

FIG. 39C is a top view of an exemplary funnel that may be included, e.g., at the proximal end of a first channel. The funnel includes a barrier with one row of pegs disposed on top of the barrier as hurdle. The pegs have a peg length that is greater than the peg width. FIG. 39D is a perspective view of an exemplary funnel shown in FIG. 39C.

Example 37

FIGS. 40A, 40B, 40C, 40D, 40E, and 40F show exemplary funnel configurations that may be included in any of the devices described herein (e.g., in a second channel).

Figure 40A:
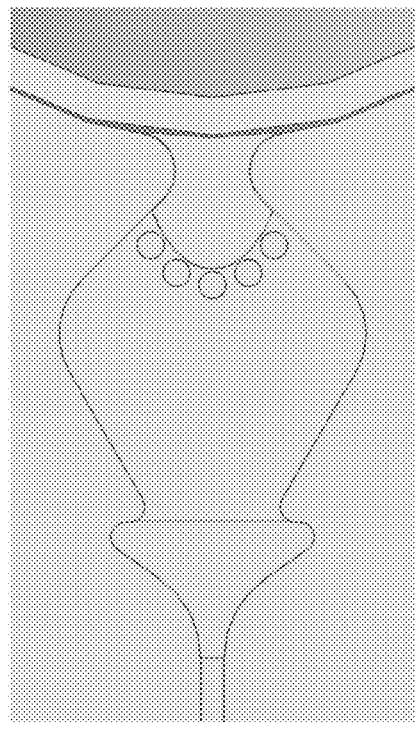
FIG. 40A is a top view of an exemplary funnel that may be included, e.g., at the proximal end of a second channel. The funnel includes a barrier with one row of pegs disposed along a curve on top of the barrier as hurdle.
Figure 40B:
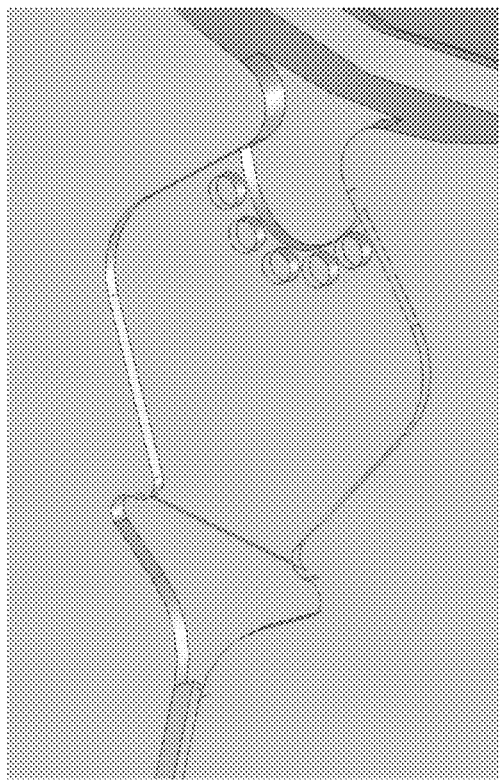
FIG. 40B is a perspective view of an exemplary funnel shown in FIG. 40A.

FIG. 40A is a top view of an exemplary funnel that may be included, e.g., at the proximal end of a second channel. The funnel includes a barrier with one row of pegs disposed along a curve on top of the barrier as hurdle. FIG. 40B is a perspective view of an exemplary funnel shown in FIG. 40B.

Figure 40C:
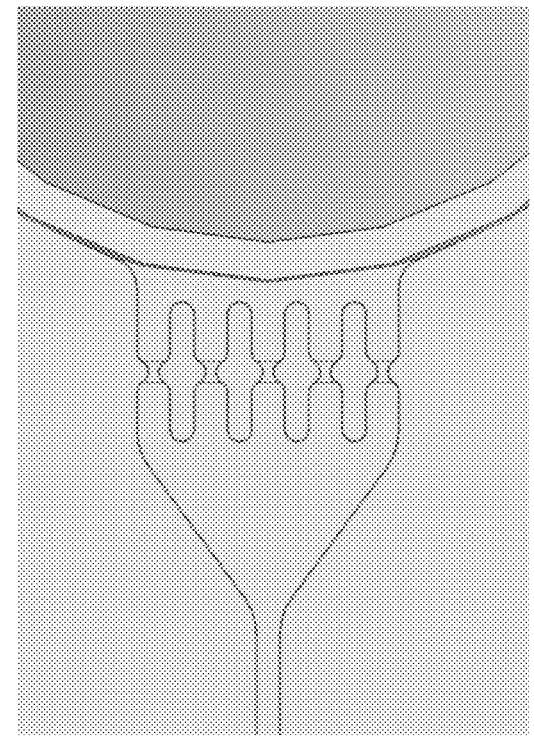
FIG. 40C is a top view of an exemplary funnel that may be included, e.g., at the proximal end of a first channel. The funnel includes a barrier with one row of pegs disposed on top of the barrier as hurdle. The pegs have a peg length that is greater than the peg width.
Figure 40D:
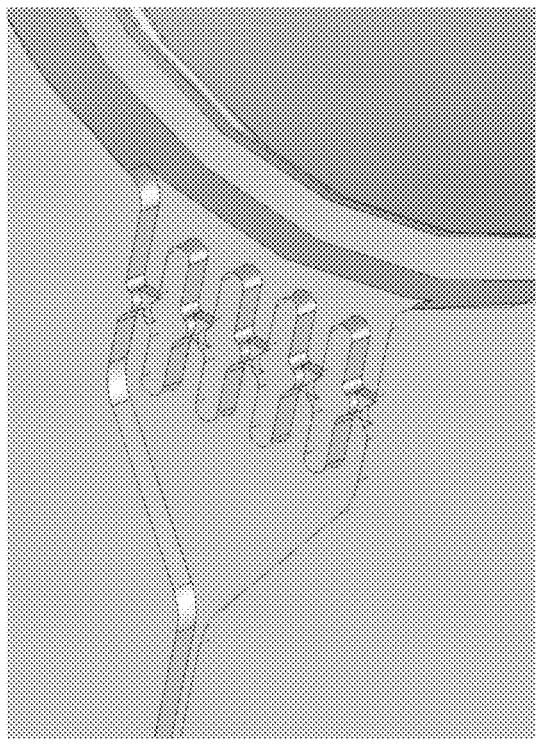
FIG. 40D is a perspective view of an exemplary funnel shown in FIG. 40C.

FIG. 40C is a top view of an exemplary funnel that may be included, e.g., at the proximal end of a first channel. The funnel includes a barrier with one row of pegs disposed on top of the barrier as hurdle. The pegs have a peg length that is greater than the peg width. FIG. 40D is a perspective view of an exemplary funnel shown in FIG. 40C.

Figure 40F:
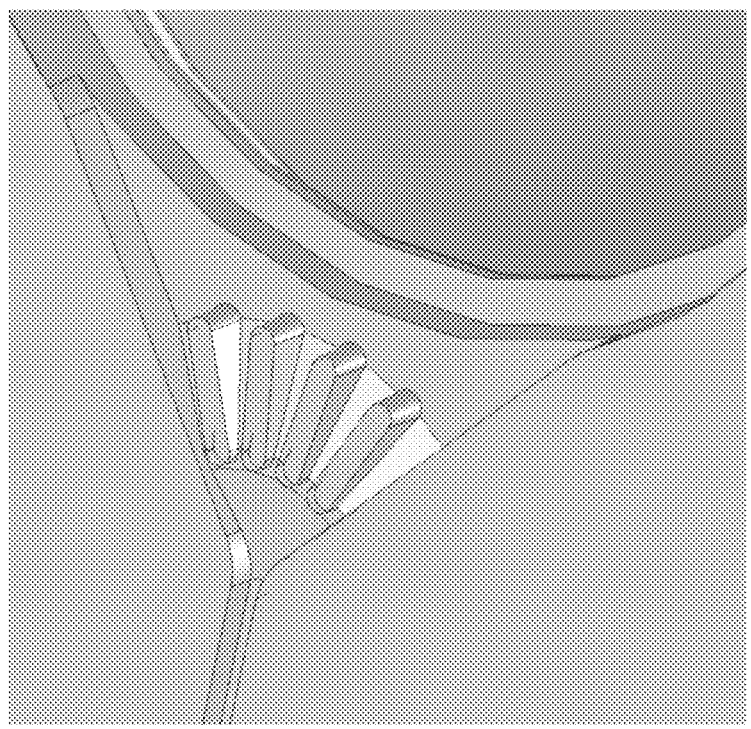
FIG. 40F is a perspective view of an exemplary funnel shown in FIG. 40E
Figure 40E:
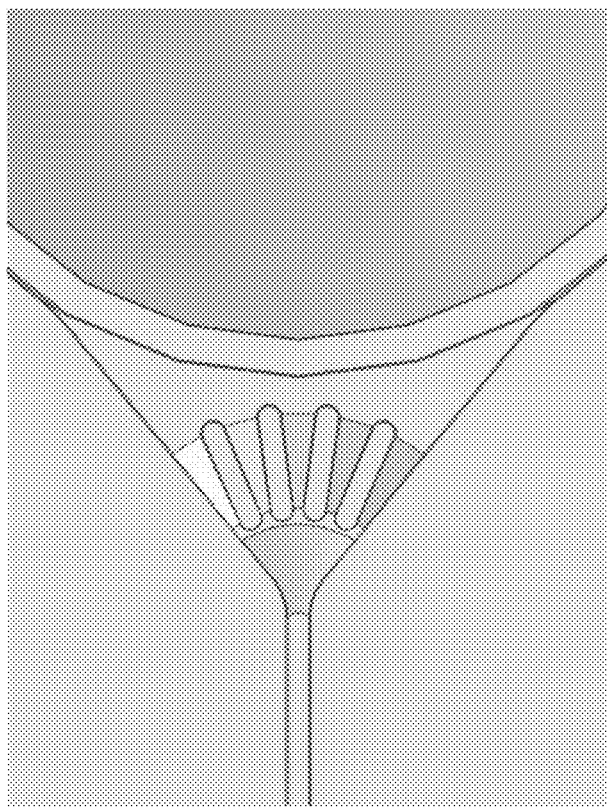
FIG. 40E is a top view of an exemplary funnel that may be included, e.g., at the proximal end of a first channel. The funnel includes a barrier with one row of pegs disposed along a curve. The pegs have a peg length that is greater than the peg width. The funnel also includes a ramp.

FIG. 40E is a top view of an exemplary funnel that may be included, e.g., at the proximal end of a first channel. The funnel includes a barrier with one row of pegs disposed along a curve. The pegs have a peg length that is greater than the peg width. The funnel also includes a ramp. FIG. 40F is a perspective view of an exemplary funnel shown in FIG. 40E.

Example 38

Figure 41A:
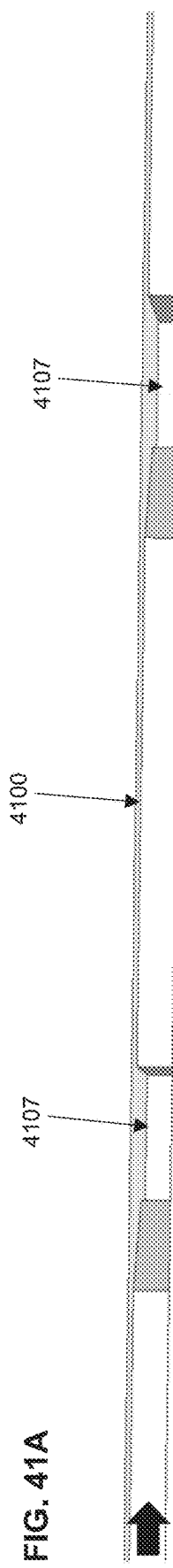
FIG. 41A is a top view of an exemplary series of traps. In this figure, channel 4100 includes two traps 4107. The solid-fill arrow indicates the liquid flow direction through the channel including a series of traps.
Figure 41C:
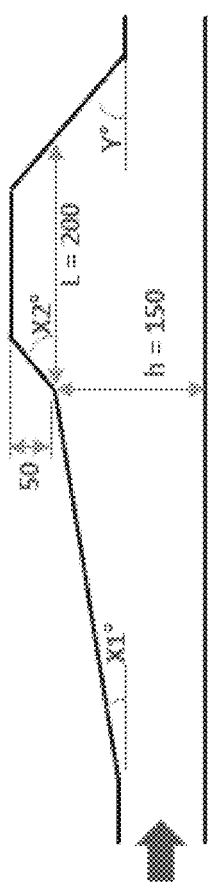
FIG. 41C is a side view cross section of a channel including a trap. The trap has a length (L) and depth (h+50). In operation, air bubbles that might be carried with a liquid can be lifted by the air buoyancy and thus removed from the liquid flow.
Figure 41B:
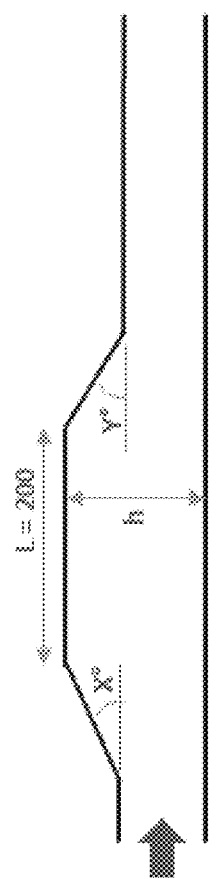
FIG. 41B is a side view cross section of a channel including a trap. The trap has a length (L) and depth (h). In operation, air bubbles that might be carried with a liquid can be lifted by the air buoyancy and thus removed from the liquid flow.

FIGS. 41A, 41B, and 41C show exemplary traps arranged in a channel. These traps can be included in any of the devices described herein (e.g., in a first channel, a second channel, a third channel, a first side-channel, or a second side-channel). FIG. 41A is a top view of an exemplary series of traps. In this figure, channel 4100 includes two traps 4107. The solid-fill arrow indicates the liquid flow direction through the channel including a series of traps. FIG. 41B is a side view cross section of a channel including a trap. The trap has a length (L) and depth (h). In operation, air bubbles that might be carried with a liquid can be lifted by the air buoyancy and thus are removed from the liquid flow. FIG. 41C is a side view cross section of a channel including a trap. The trap has a length (L) and depth (h+50). In operation, air bubbles that might be carried with a liquid can be lifted by the air buoyancy and thus are removed from the liquid flow.

Example 39

Figure 42A:
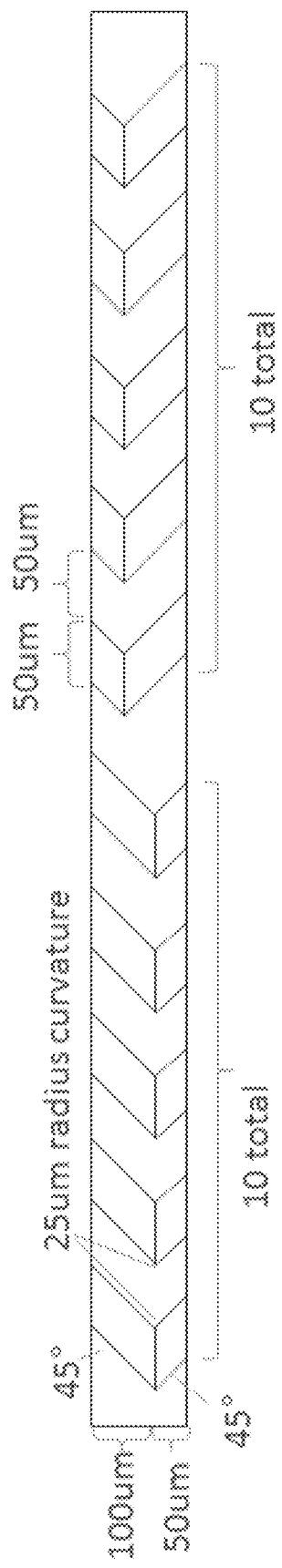
FIG. 42A is a top view of an exemplary herringbone mixer. This herringbone mixer may be used to provide a single mix cycle in a channel. The herringbone mixer includes and grooves extending transversely across the channel. In this drawing, um stands for microns.
Figure 42B:
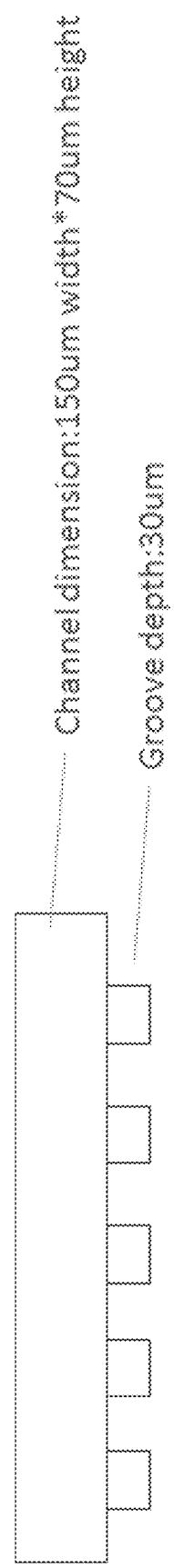
FIG. 42B is a side view cross section of an exemplary herringbone mixer portion shown in FIG. 42A. In this drawing, um stands for microns.
Figure 42C:
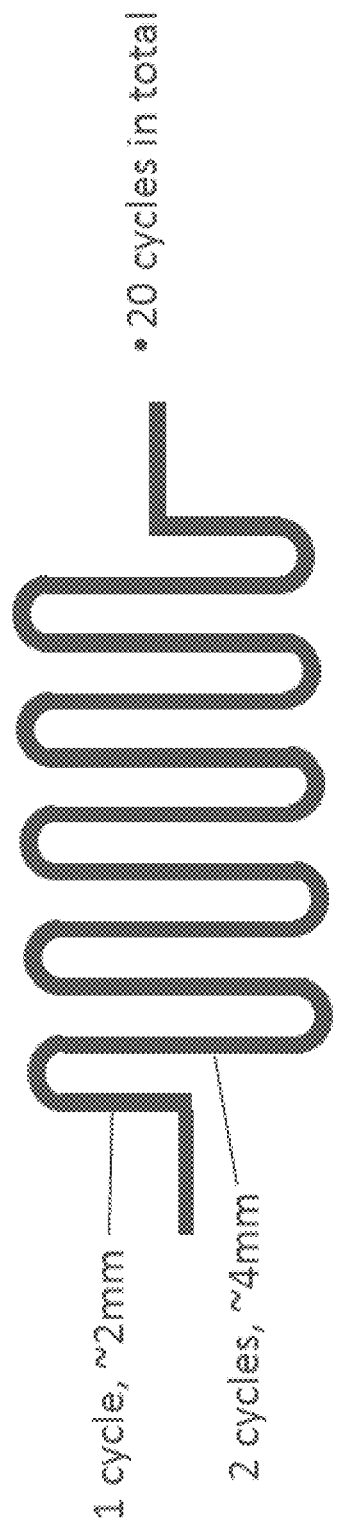
FIG. 42C is a top view of an exemplary herringbone mixer including twenty mix cycles assembled from herringbone mixers shown in FIG. 42A.

FIGS. 42A, 42B, and 42C show an exemplary herringbone mixer and its arrangement in a channel. These mixers can be included in any of the devices described herein (e.g., in a first channel or a second channel, preferably, after an intersection in which two or more liquids from different liquid sources mix). FIG. 42A is a top view of an exemplary herringbone mixer. This herringbone mixer may be used to provide a single mix cycle in a channel. The herringbone mixer includes and grooves extending transversely across the channel. In this drawing, um stands for microns. FIG. 42B is a side view cross section of an exemplary herringbone mixer portion shown in FIG. 42A. In this drawing, um stands for microns. FIG. 42C is a top view of an exemplary herringbone mixer including twenty mix cycles assembled from herringbone mixers shown in FIG. 42A.

Example 40

Figure 43A:
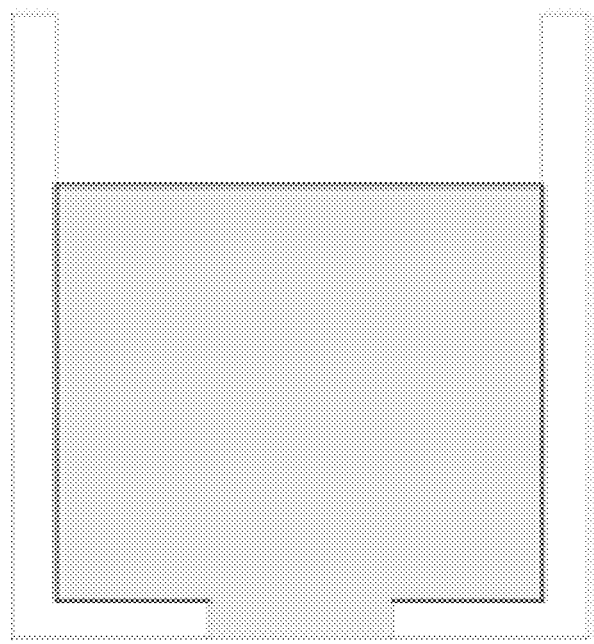
FIG. 43A is a side view cross section of a collection reservoir.
Figure 43B:
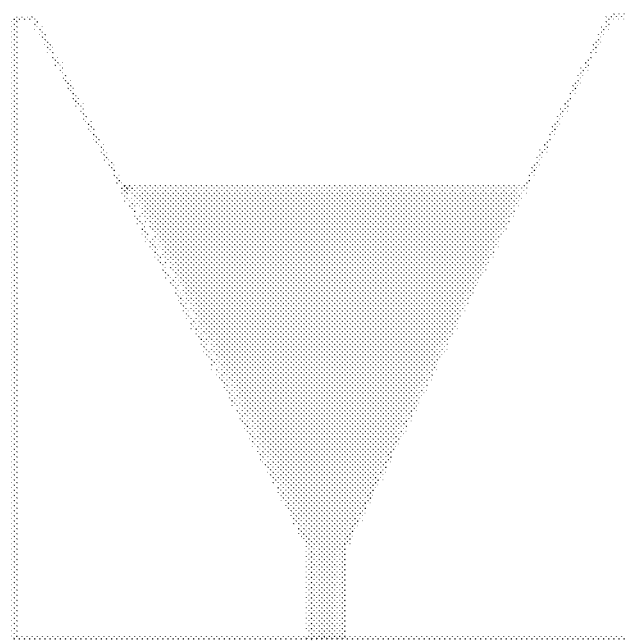
FIG. 43B is a side view cross section of a collection reservoir including a canted sidewall.
Figure 44A:
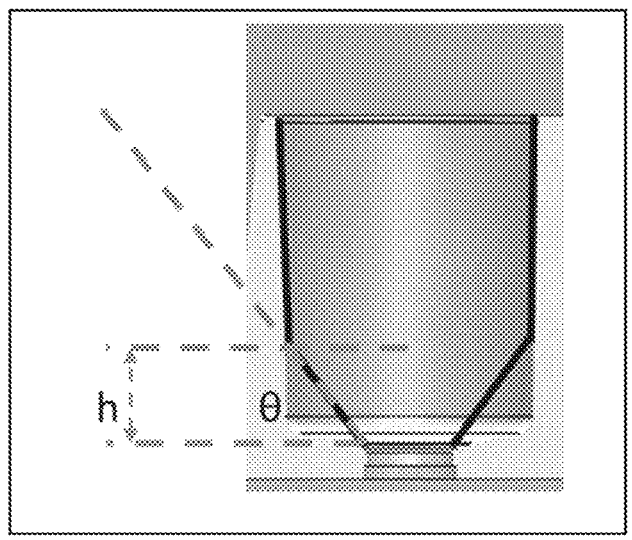
FIGS. 44A-44C are side view cross sections of exemplary collection reservoir including canted sidewalls.
Figure 44B:
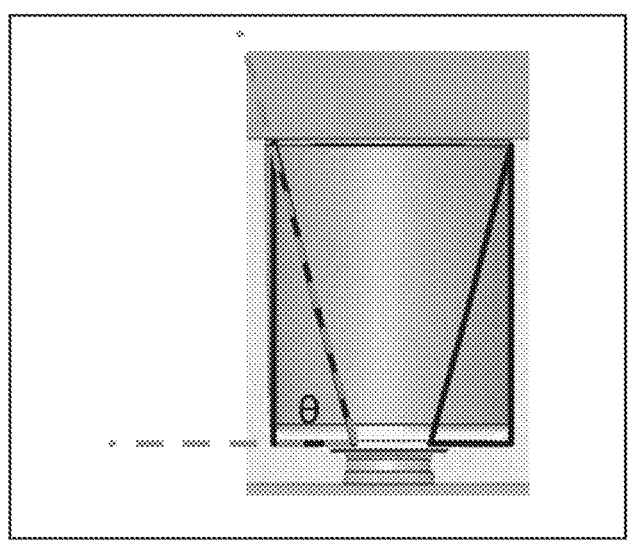
Figure 44C:
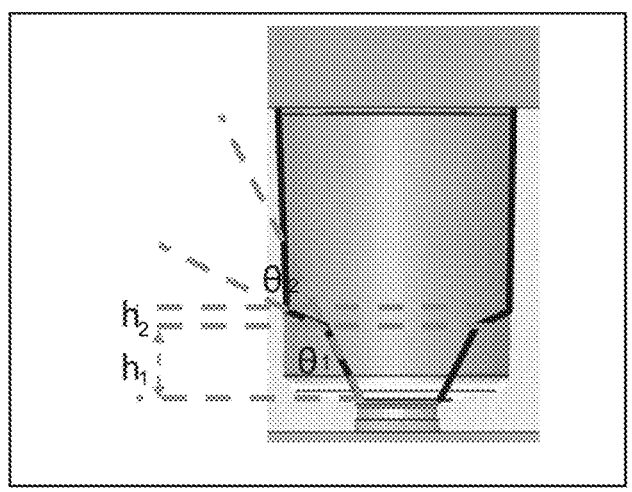

FIG. 43A shows a collection reservoir with a vertical side wall. FIGS. 43B and FIGS. 44A-44C show exemplary collection reservoirs including a canted side wall (e.g., side walls canted at angles between 89.5° and 4°, e.g., between 85° and 5°, e.g., 5°≤θ≤85°). The canted side walls may increase the collection efficiency of droplets by a collection device (e.g., a pipette tip) by up to about 20%.

Example 41

Figure 45:
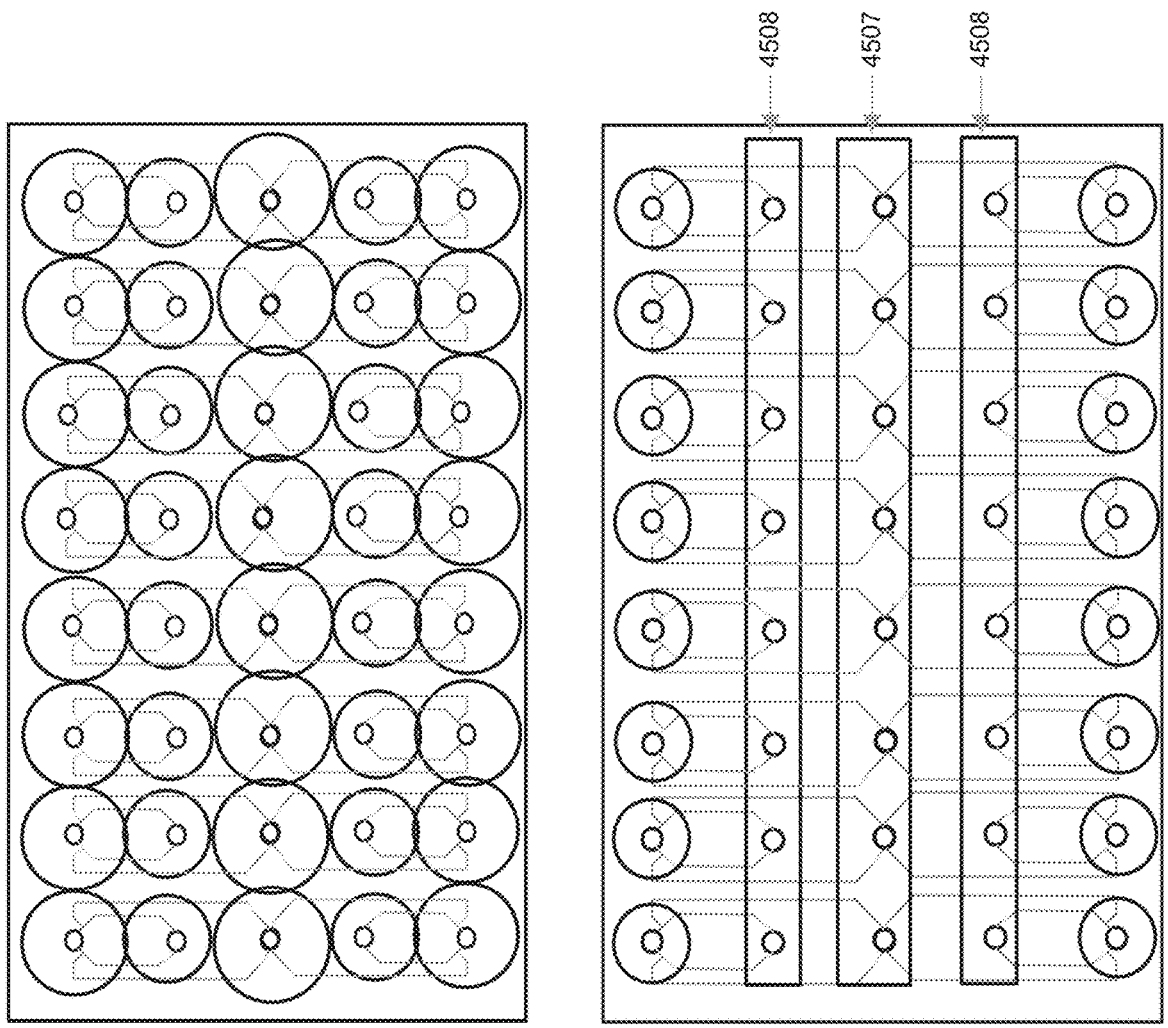
FIG. 45 is a depiction of a multiplex flow path and devices incorporating multiple multiplex flow paths.
Figure 45:
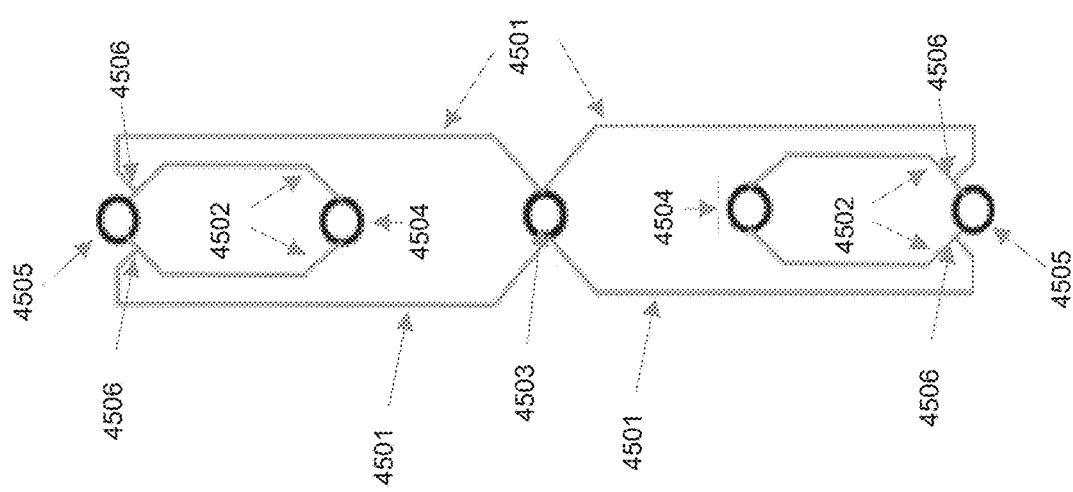

FIG. 45 shows an exemplary multiplex flow path and devices incorporating multiple of the multiplex flow paths. In the flow path, a single sample inlet 4503 is connected to four sample channels 4501. Two reagent inlets 4504 are each connected to two reagent channels 4502. Each sample channel intersects with a reagent channel 4506. A droplet formation region (not shown) is downstream of each intersection. Two sets of intersecting channels empty into each of two collection reservoirs 4505. As shown, the inlets and collection reservoirs may be in a substantially linear arrangement. Multiple multiplex flow paths may be included in a single device. The individual flow paths may be fluidically distinct or may be fluidically connected with one or more troughs. In the upper device, each inlet and collection reservoir includes its own reservoir (shown by circles). In the lower device, each collection reservoir includes its own reservoir, while the sample inlets and reagent inlets are connected by troughs, 4507 and 4508, respectively.

Example 42

Figure 46:
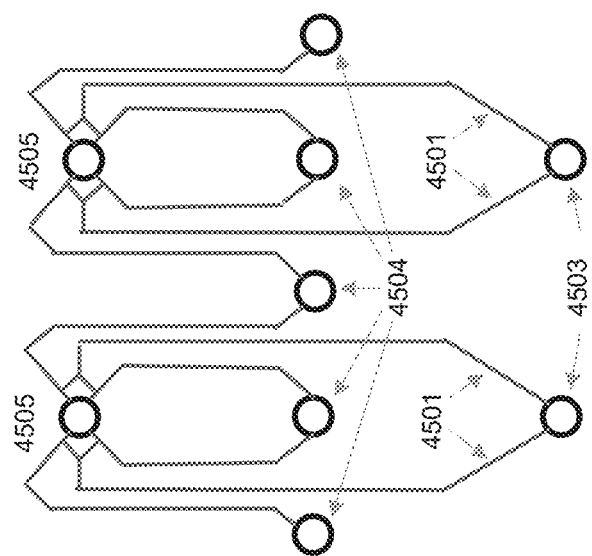
FIG. 46 is a depiction of a multiplex flow path and a device incorporating multiple multiplex flow paths.
Figure 46:
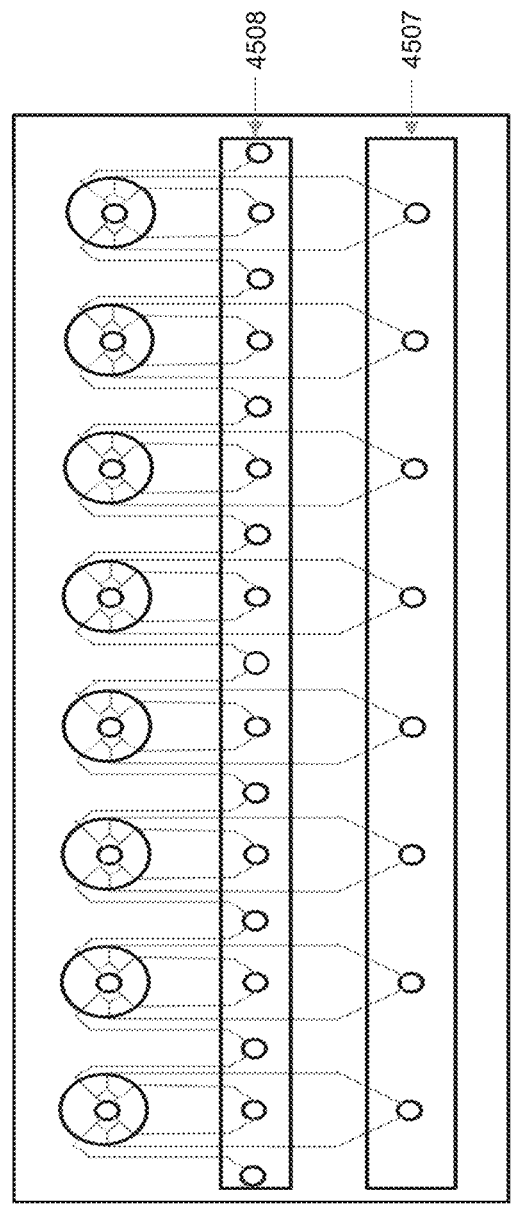

FIG. 46 shows an exemplary multiplex flow path and a device incorporating multiple of the multiplex flow paths. In the flow path, a single sample inlet 4503 is connected to two sample channels 4501 that branch. Reagent channels from three reagent inlets intersect the sample channels. A droplet formation region (not shown) is downstream of each intersection. The four intersecting channels empty into a collection reservoir 4505. Multiple multiplex flow paths may be included in a single device. Parallel flow paths share reagent inlets disposed between them. The individual flow paths may otherwise be fluidically distinct or may be fluidically connected with one or more troughs. In the device shown, each collection reservoir 4505 is a separate reservoir (circle), and the sample inlets 4503 and reagent inlets 4504 are connected via troughs 4507 and 4508, respectively.

Figure 49:
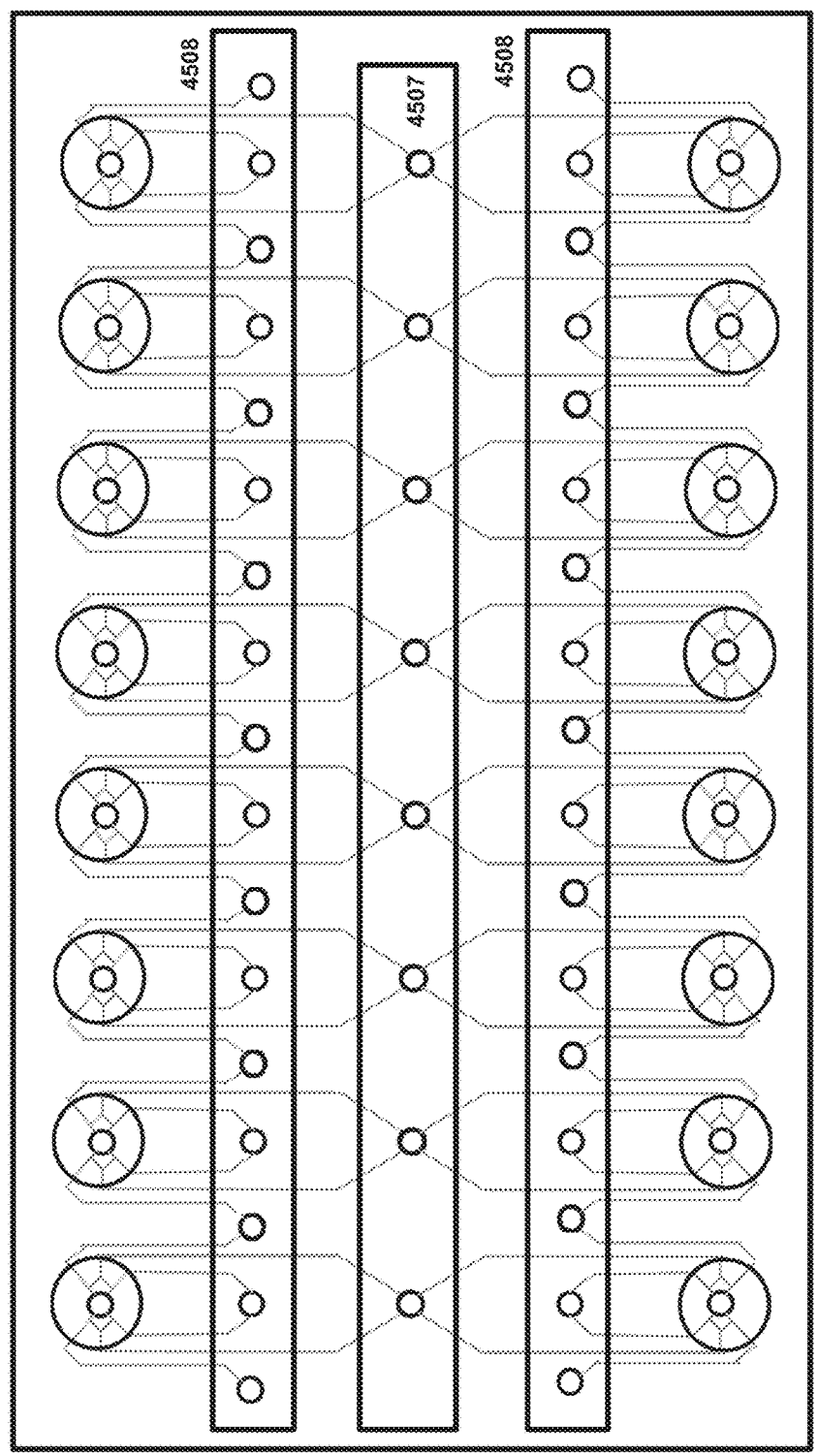
FIG. 49 is a depiction of a multiplex flow path and a device incorporating multiple multiplex flow paths.
Figure 49:
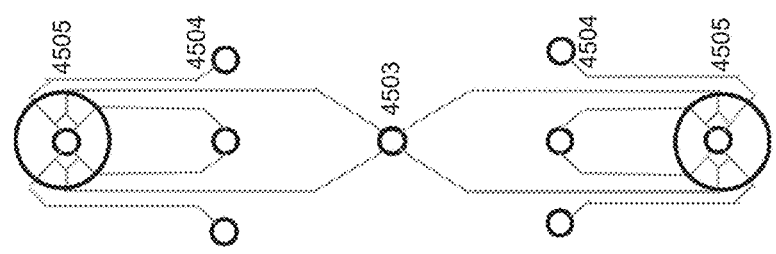

FIG. 49 shows a multiplex flow path and a device incorporating multiple of the multiplex flow paths. The flow path is substantially the same as in FIG. 46 except that it includes twice the number of channels 4501, reagent inlets 4503, droplet formation regions, and collection reservoirs 4505. As shown, the duplicate set of channels 4501, reagent inlets 4503, droplet formation regions, and collection reservoirs 4505 is arranged as a mirror image.

Example 43

Figure 47:
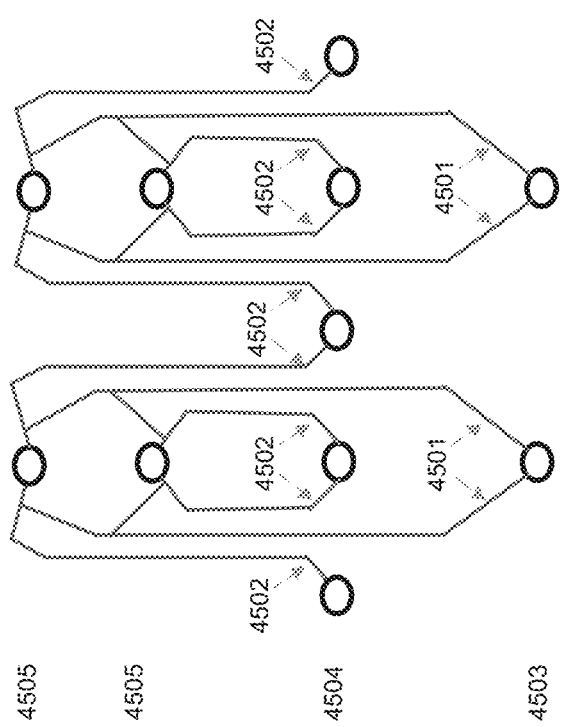
FIG. 47 is a depiction of a multiplex flow path and a device incorporating multiple multiplex flow paths.
Figure 47:
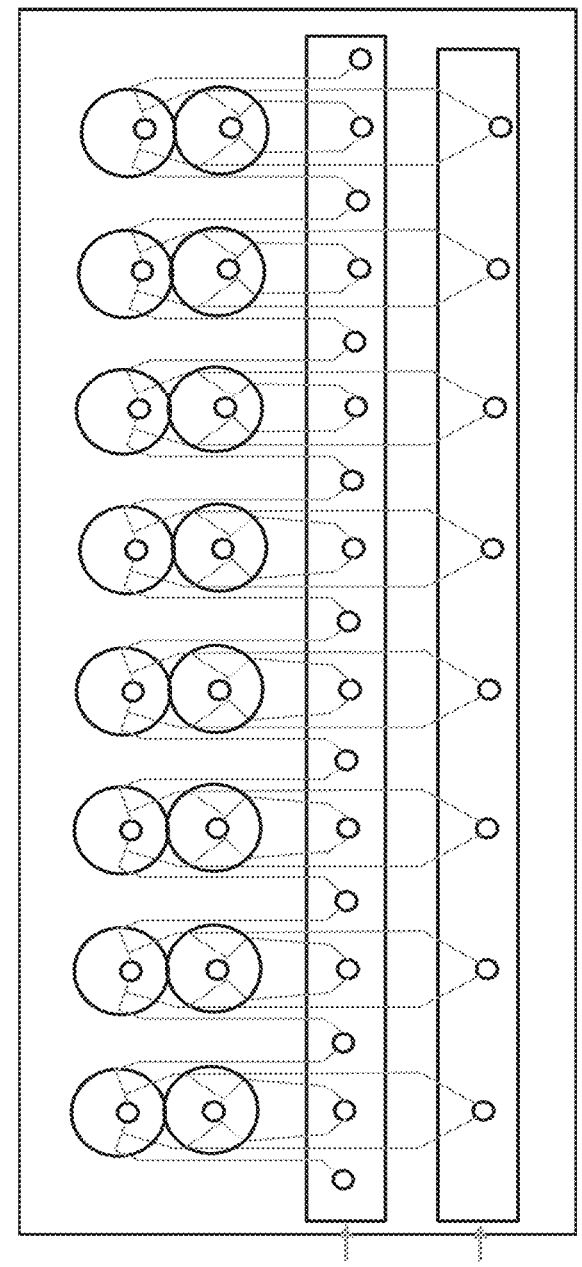

FIG. 47 shows an exemplary multiplex flow path and a device incorporating multiple of the multiplex flow paths. In the flow path, a single sample inlet 4503 is connected to two sample channels 4501 that branch. Reagent channels 4502 from three reagent inlets 4504 intersect the sample channels. A droplet formation region (not shown) is downstream of each intersection. Two intersecting channels empty into each of two collection reservoirs 4505. Multiple multiplex flow paths may be included in a single device. Parallel flow paths share reagent inlets 4505 disposed between them. The individual flow paths may otherwise be fluidically distinct or may be fluidically connected with one or more troughs. In the device shown, each collection reservoir 4505 is a separate reservoir (circle), and the sample inlets and reagent inlets are connected via troughs 4507 and 4508, respectively.

FIG. 48 shows a multiplex flow path and a device incorporating multiple of the multiplex flow paths. The flow path is substantially the same as in FIG. 47 except that it includes twice the number of channels 4501, reagent inlets 4504, droplet formation regions, and collection reservoirs 4505. As shown, the duplicate set of channels 4501, reagent inlets 4504, droplet formation regions, and collection reservoirs 4505 is arranged as a mirror image.

Example 44

Figure 50B:
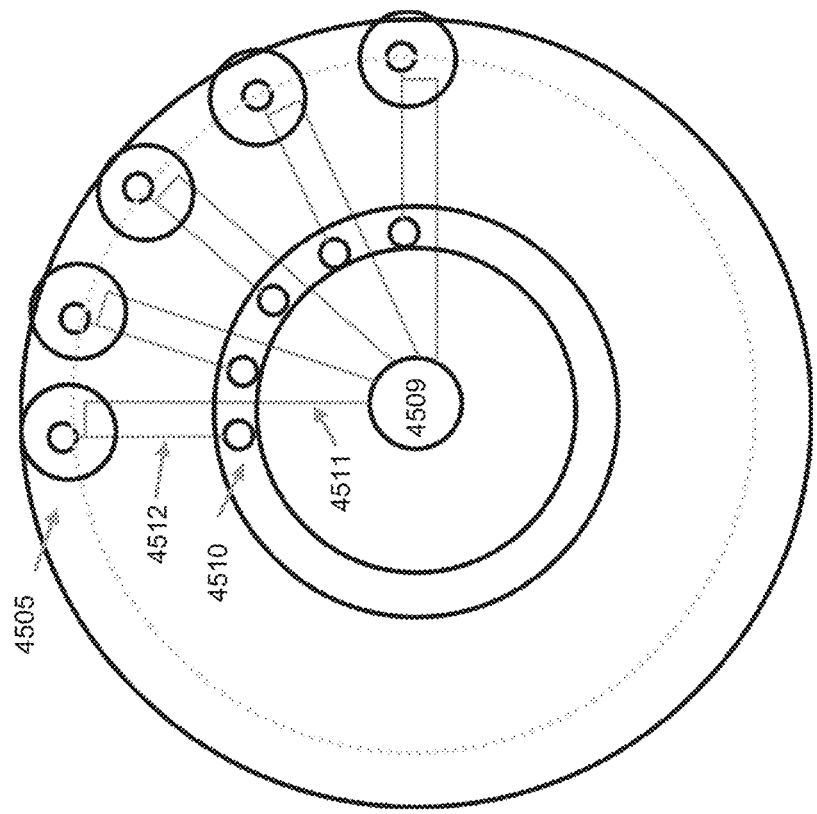
FIGS. 50A-50C are depictions of multiplex devices having a common sample or reagent inlet (A and B) or a common collection reservoir (C).
Figure 50A:
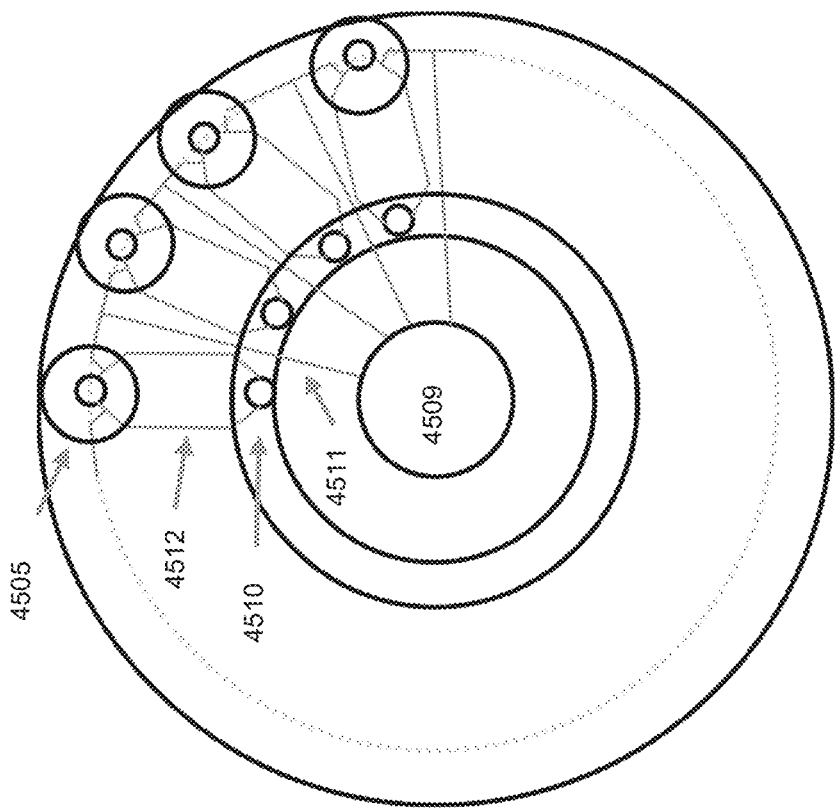
Figure 50C:
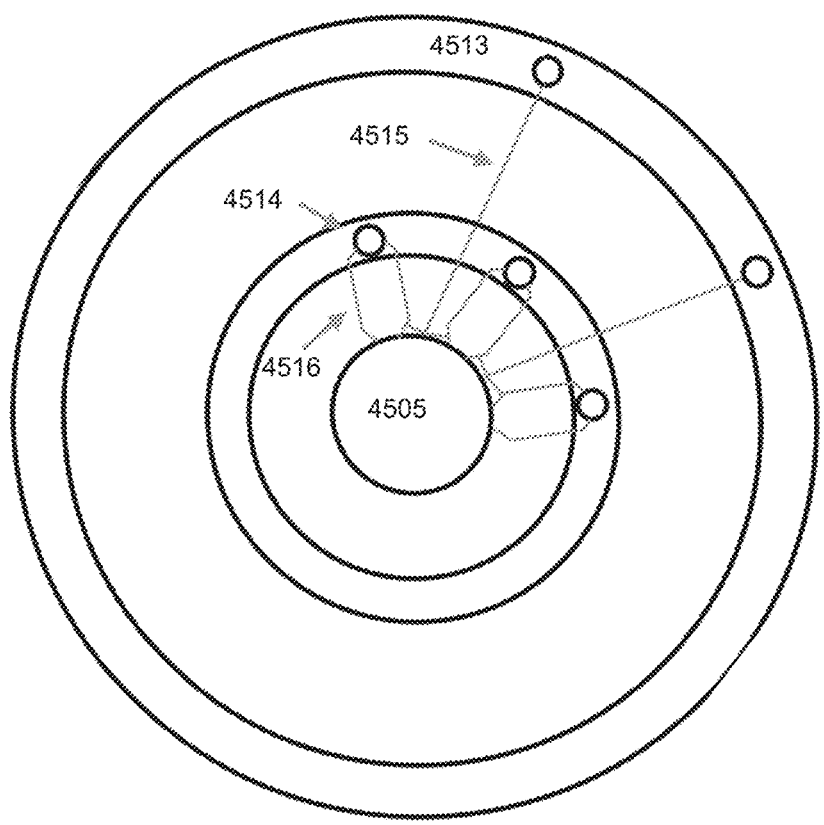

FIGS. 50A-50C show multiplex devices that share a common sample inlet, reagent inlet, or collection reservoir

4509. The flow paths are arranged radially but other geometries are possible. In 50A and 50B, the collection reservoirs 4505 are arranged as the outmost element. Either the sample inlet or the reagent inlet is a common inlet 4509 disposed centrally, with the other inlets 4510 disposed between the common inlet 4509 and the collection reservoirs 4505. In 50A, channels 4511 from the common inlet 4509 branch and intersect with channels 4512 from the other inlets 4510. Droplet formation regions are downstream of the intersections. Two sets of intersecting channels empty into each collection reservoir 4505. In 50B, single channels 4511 from the common inlet 4509 intersect with single channels 4512 from the other inlets 4510. Droplet formation regions are downstream of the intersections. One set of intersecting channels empties into each collection reservoir 4505. In 50C, the collection reservoir 4505 is centrally located and common to the sample and reagent inlets. Channels 4515 from one type of inlet 4513 branch and intersect with channels 4516 from the other 4514 inlets. Droplet formation regions are downstream of the intersections. All of the intersecting channels empty into the collection reservoir 4505.

Example 45

Figure 52:
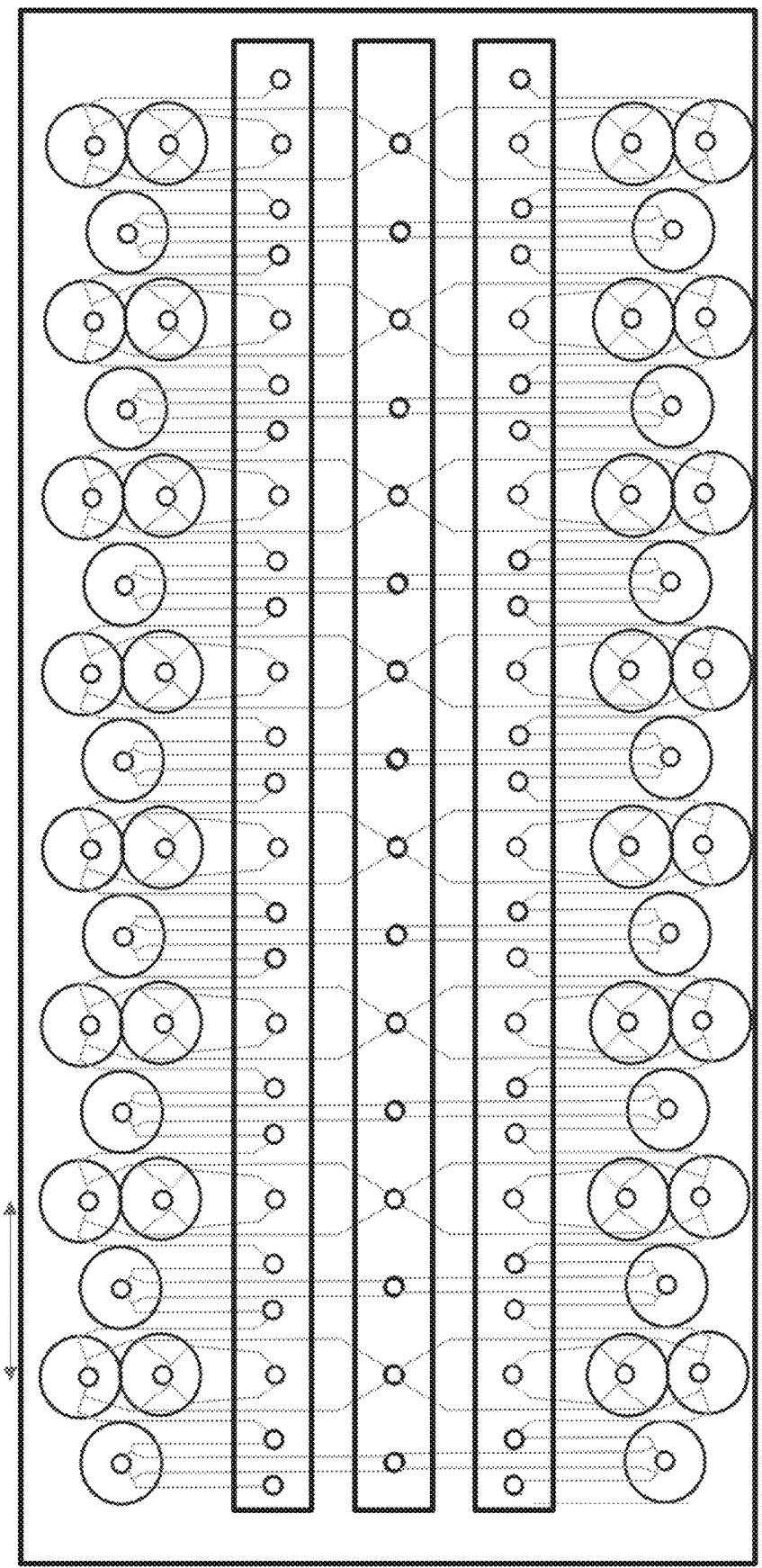
FIG. 52 is a depiction of a device incorporating two different multiplex flow paths.

FIG. 52 shows a device including multiple multiplex flow paths. The flow path shown in FIG. 48 is interspersed with a different flow path. The other flow path includes a sample inlet with four sample channels. Each sample channel intersects with a reagent channel, each of which comes from a separate reagent inlet. A droplet formation region (not shown) is downstream of each intersection, and two sets of intersection channels empty into one of two collection reservoirs. As shown, each collection reservoir is an individual reservoir (circle). The sample inlets are connected by a trough. Two rows of reagent inlets are connected by separate troughs.

Example 46

Figure 54A:
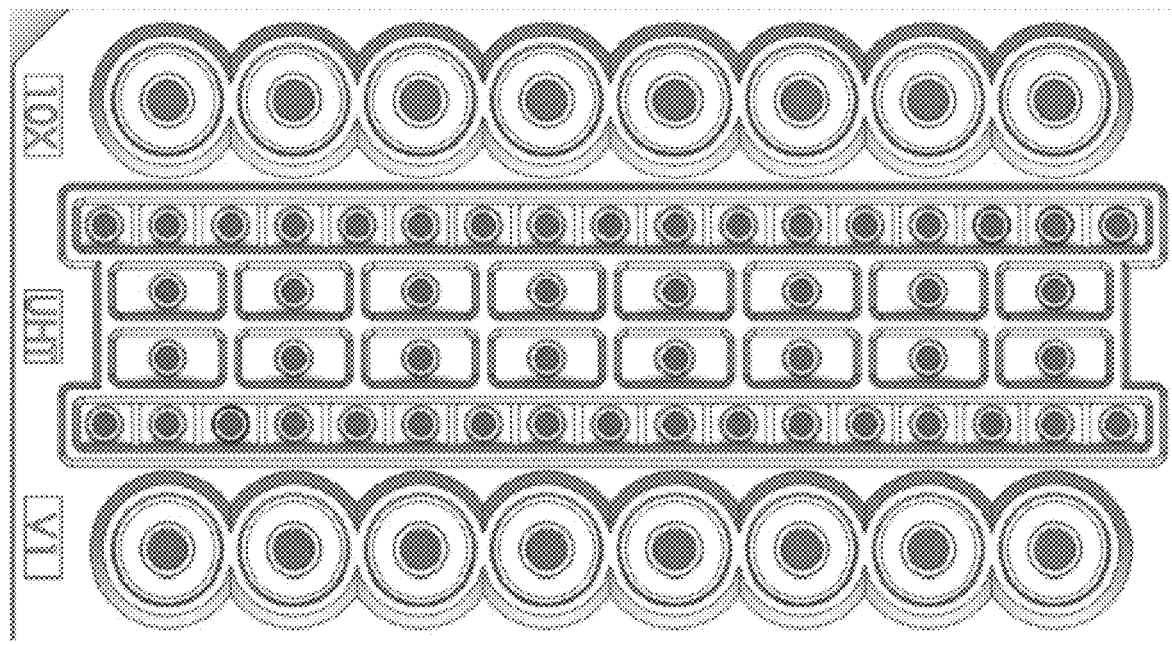
FIGS. 54A and 54B are depictions of reservoirs in a multiplex device of the invention.
Figure 54B:
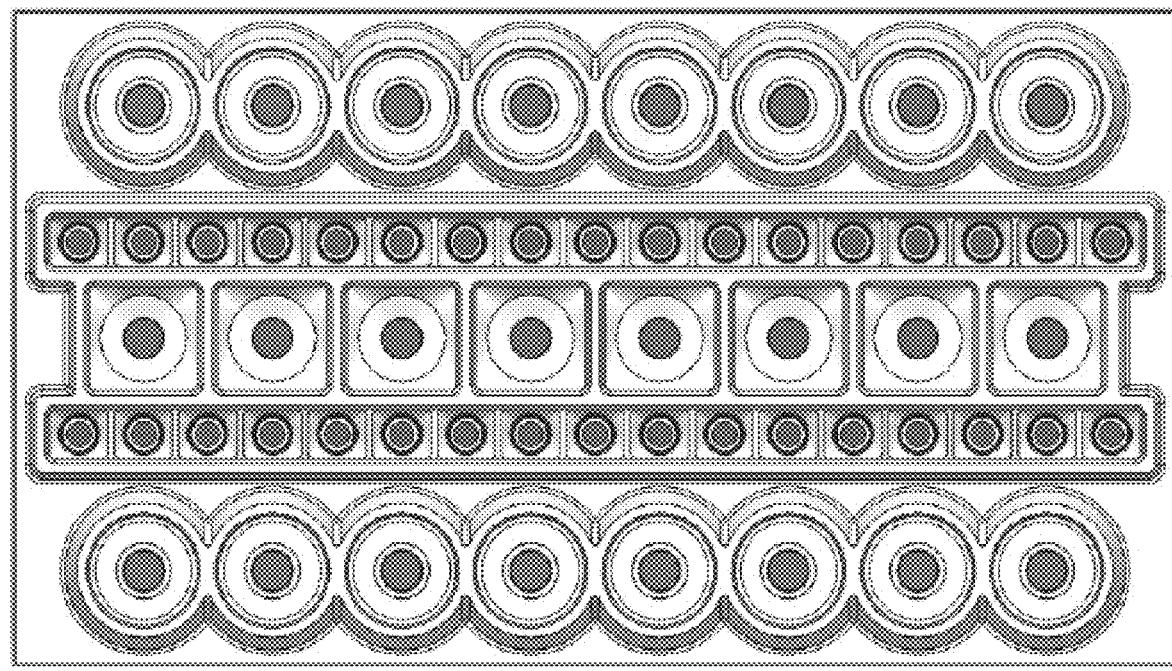

FIGS. 54A and 54B are depictions of reservoirs in a multiplex device of the invention. FIG. 54A is a depiction of a device comprising multiple collection reservoirs, multiple sample reservoirs, and multiple reagent reservoirs that are connected by way of a trough. FIG. 54B is a depiction of an alternative architecture of device comprising multiple collection reservoirs, multiple sample reservoirs, and multiple reagent reservoirs that are connected by way of a trough. FIG. 54A depicts a device with twice as many sample reservoirs as the device depicted in FIG. 54B.

Example 47

Figure 55A:
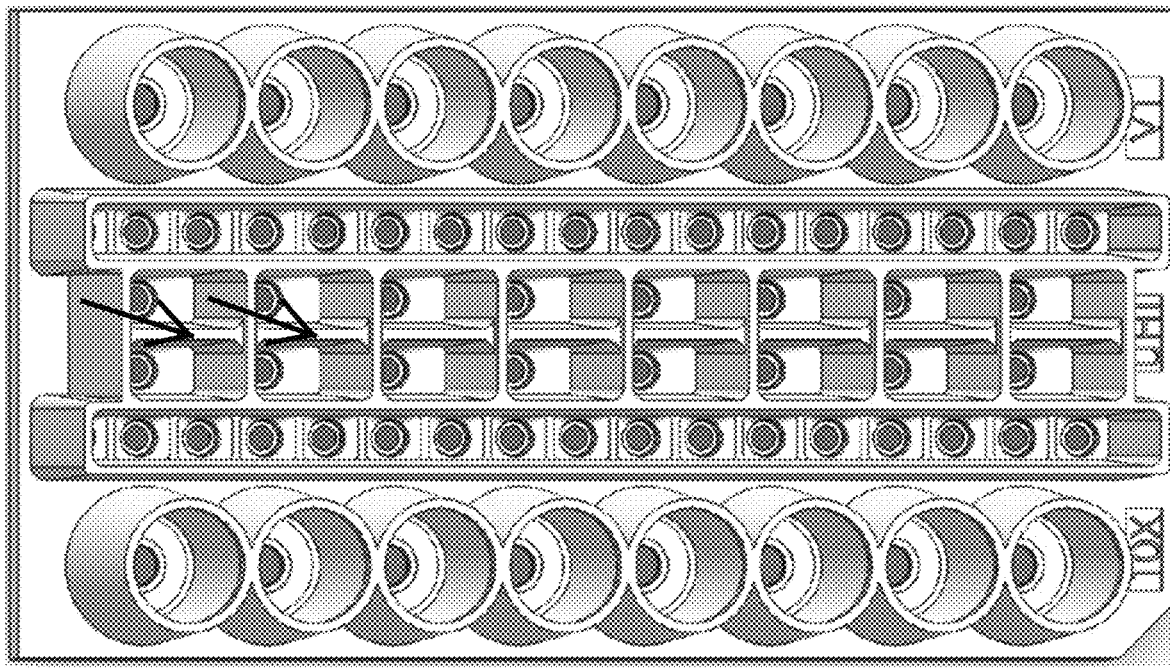
FIGS. 55A-55C are depictions of reservoirs in a multiplex device of the invention, where the sample reservoirs are surrounded by at least one common wall and have a dividing wall that has at least a portion of the dividing wall that is shorter than one common wall, as indicated by the black arrows.
Figure 55B:
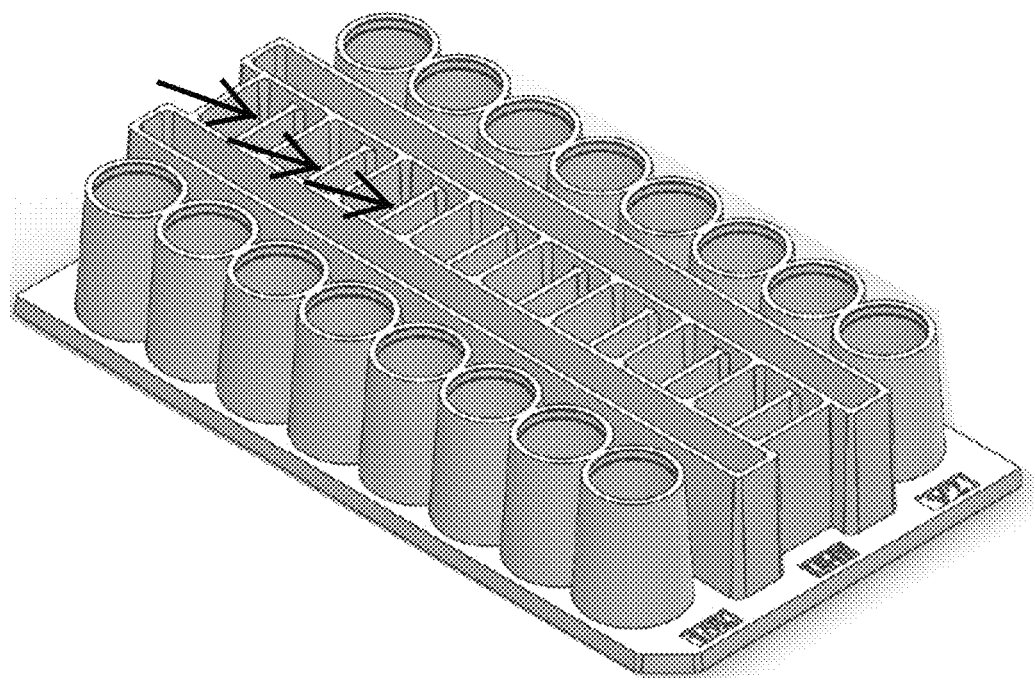
Figure 55C:
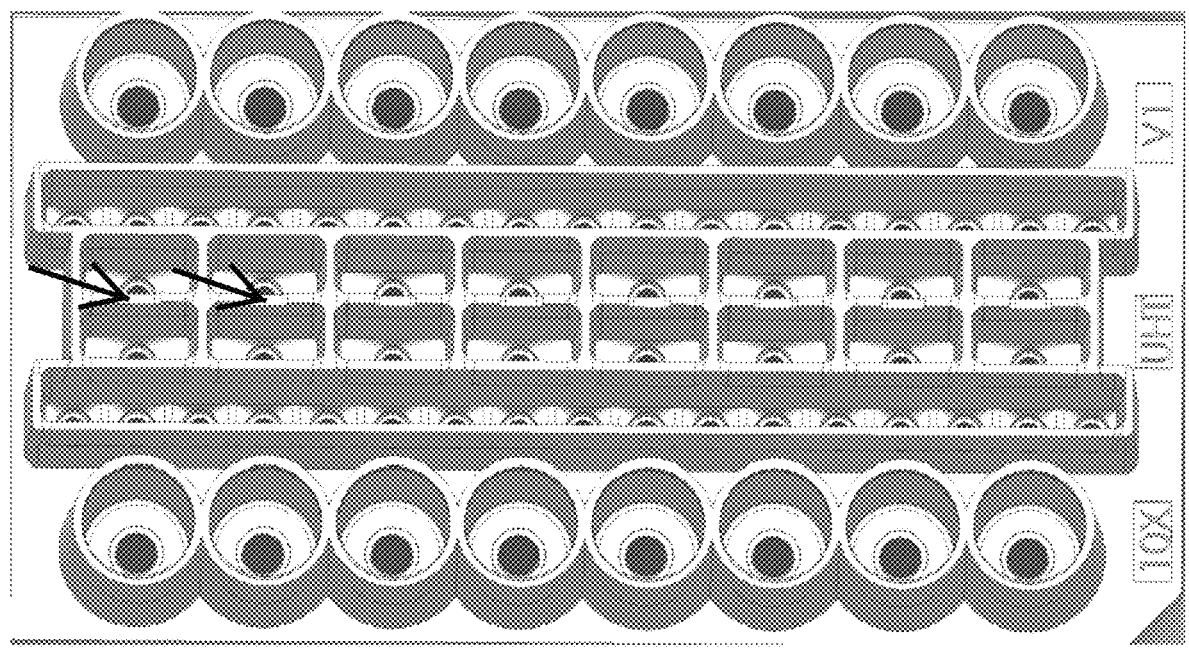

FIGS. 55A-55C are depictions of reservoirs in a multiplex device of the invention, where the sample reservoirs are surrounded by at least one common wall and have a dividing wall that has at least a portion of the dividing wall that is shorter than one common wall. FIGS. 55A and 55B are depictions of reservoirs in a multiplex device showing two different multiplex device architectures where the dividing wall is shorter than the one surrounding wall. FIG. 55C is a depiction of reservoirs in a multiplex device where a portion of the dividing wall is shorter than the one common wall. This arrangement allows a single pressure source to control fluid flow in two different inlets.

Example 48

Figure 56B:
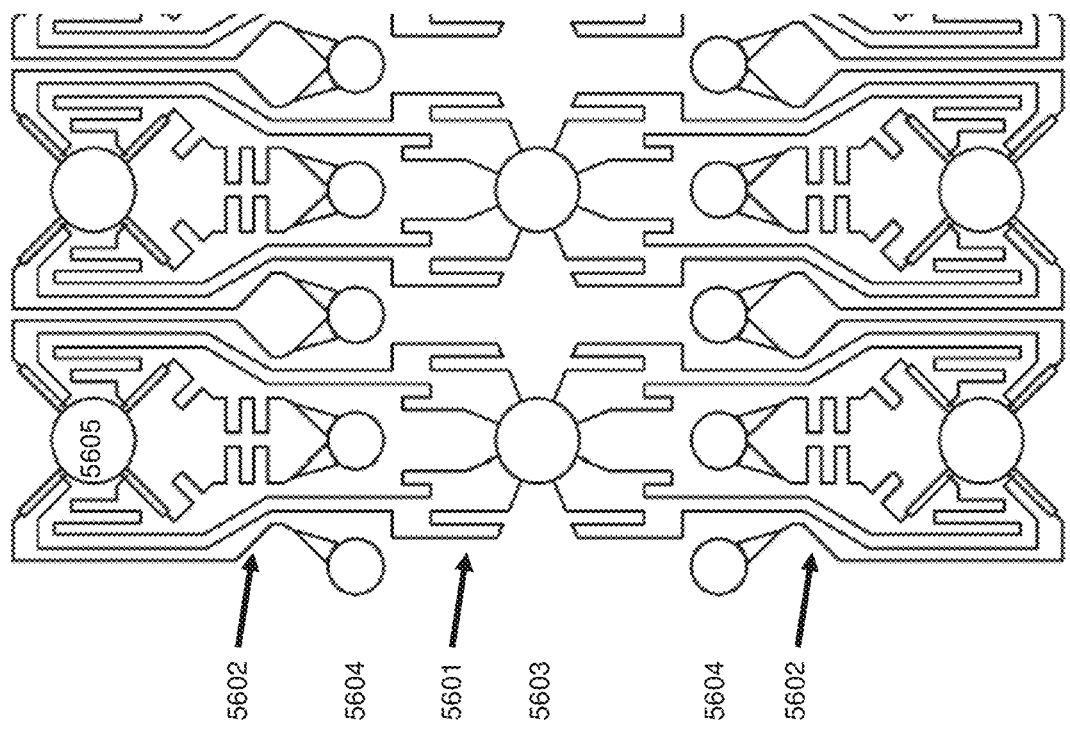
FIGS. 56A and 56B are depictions of devices incorporating multiple multiplex flow paths.
Figure 56A:
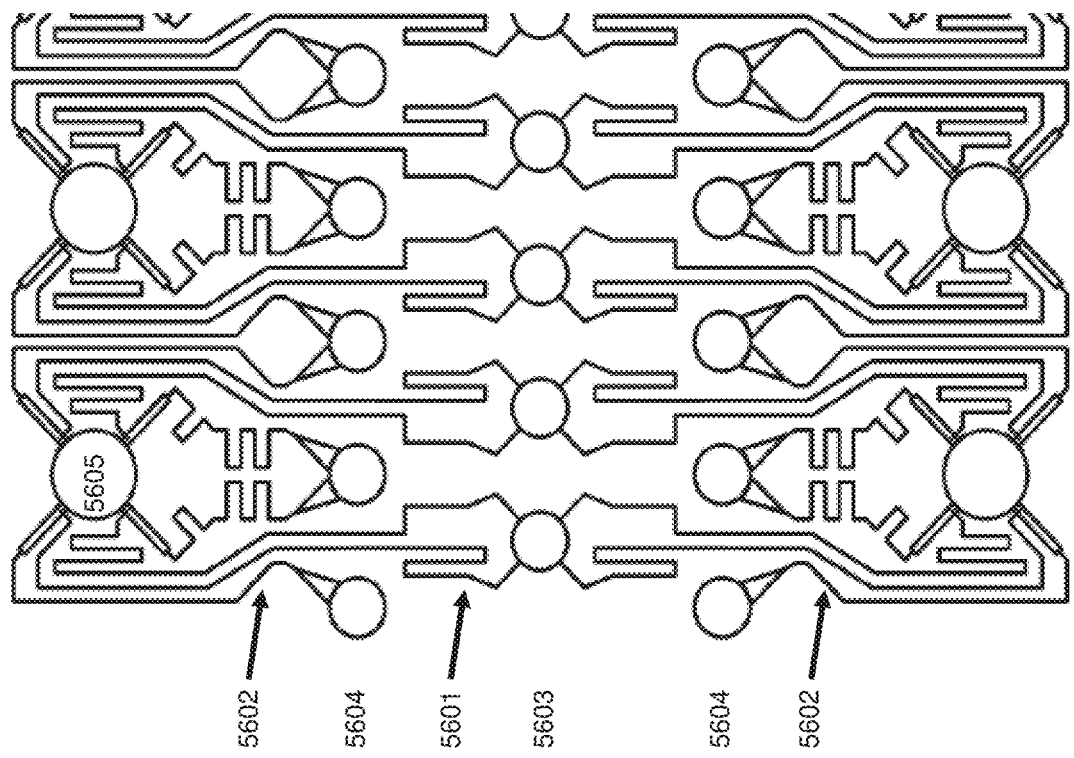

FIG. 56A shows an exemplary multiplex flow path and a device incorporating multiple of the multiplex flow paths. In the flow path, two sample inlets 5603 are each connected to four sample channels 5601. Reagent channels 5602 from six reagent inlets 5604 intersect the sample channels. A droplet formation region (not shown) is downstream of each intersection. Four intersecting channels empty into each of two collection reservoirs 5605. Multiple multiplex flow paths may be included in a single device. FIG. 56B shows another flow path having half the amount of sample inlets 5603, and each sample inlet is connected to twice as many sample channels 5601. Parallel flow paths share reagent inlets 5604 disposed between them. The individual flow paths may otherwise be fluidically distinct or may be fluidically connected with one or more troughs, as seen in FIGS. 54A and 54B.

Example 49

Figure 57A:
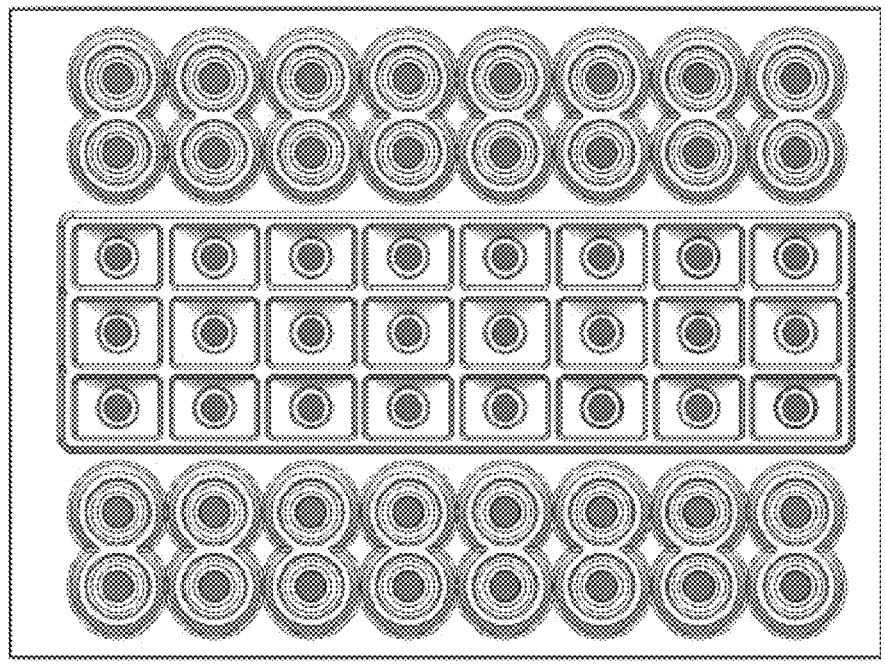
Figure 57B:
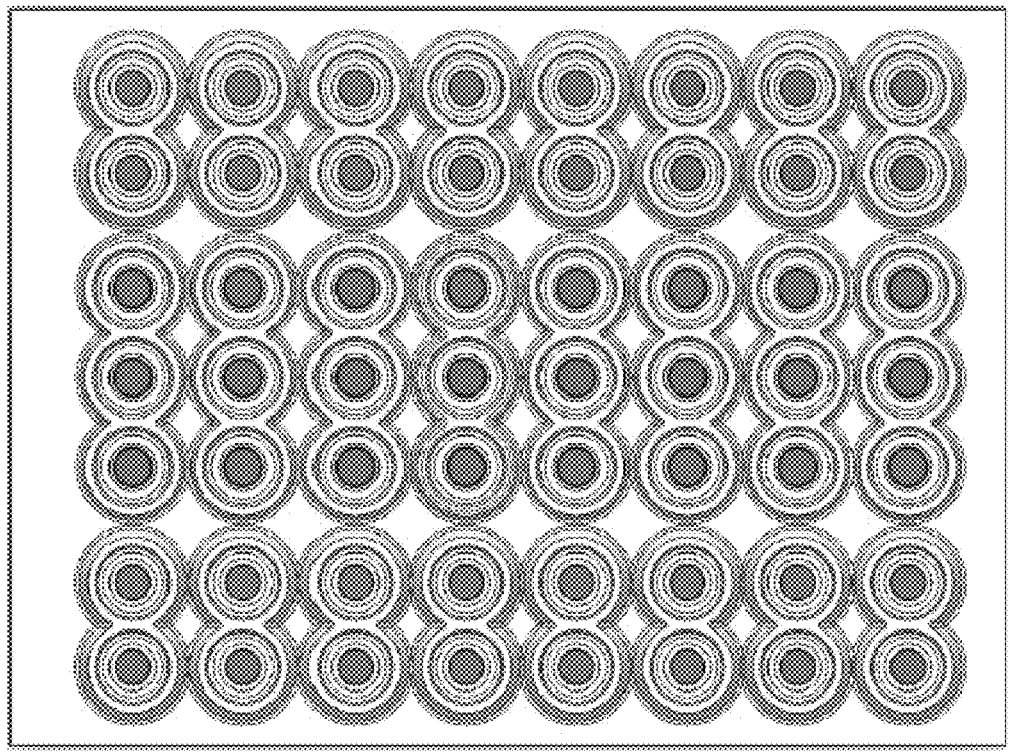
Figure 58B:
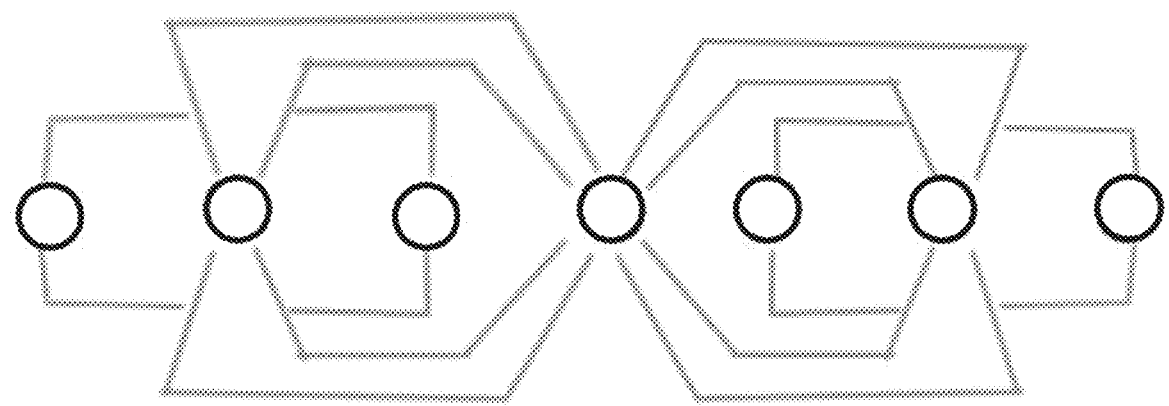
FIGS. 58A and 58B are depictions of architectures of multiplex flow paths.
Figure 58A:
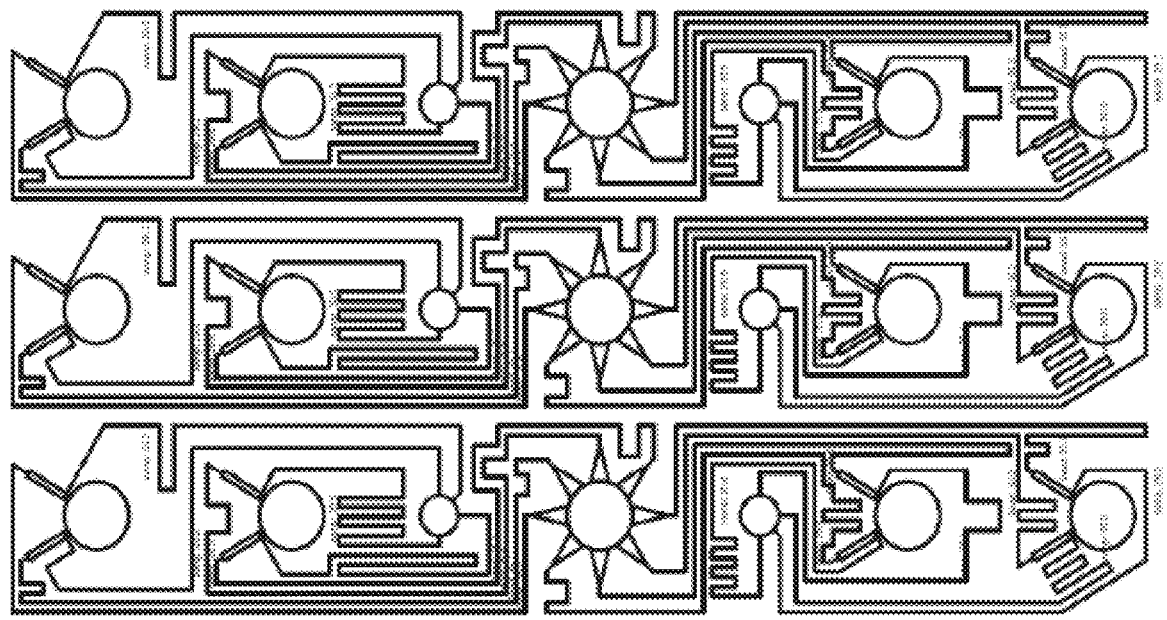

FIGS. 57A-57B shows exemplary reservoirs in a multiplex device of the invention. FIG. 57A is a depiction of a device comprising multiple collection reservoirs, multiple sample reservoirs, and multiple reagent reservoirs. FIG. 57B is a depiction of an alternative architecture of device comprising multiple collection reservoirs, multiple sample reservoirs, and multiple reagent reservoirs. The multiple reagent reservoirs or multiple sample reservoirs may be connected by a trough. Exemplary flow paths of the device are depicted in FIGS. 58A and 58B.

Example 50

Figure 59:
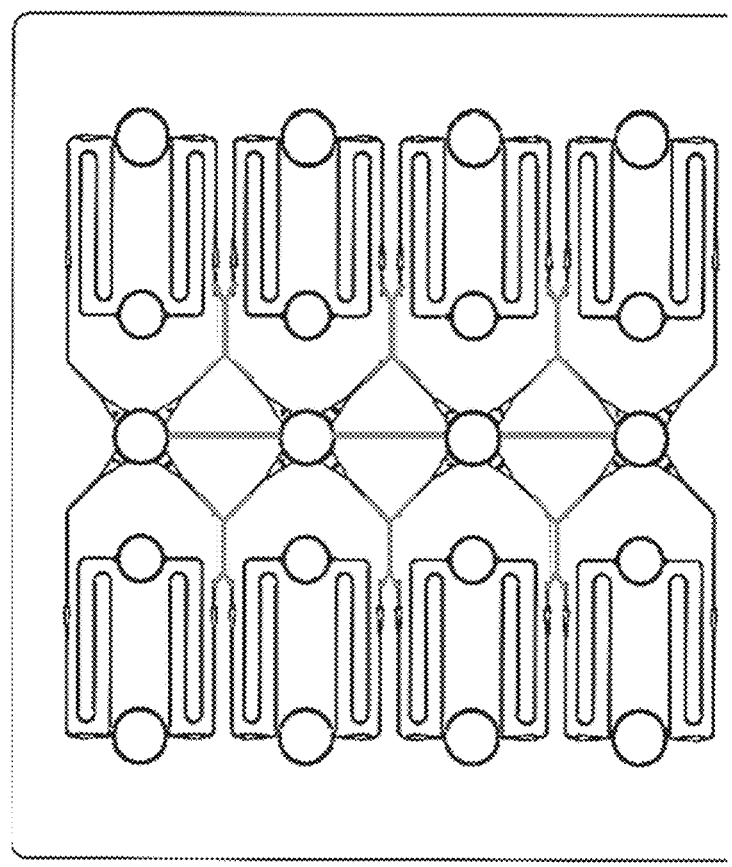
FIG. 59 is a depiction of a multiplex flow path.

FIG. 59 shows a multiplex flow path having either a shunt in fluid communication with one or more sample inlets or one reagent channel that combines with another reagent channel for a distance before splitting into two separate reagent channels. While FIG. 59 portrays both a shunt and reagent channels combining, it will be understood the one, or both, may be used in a multiplex flow path.

Example 51

Figure 60:
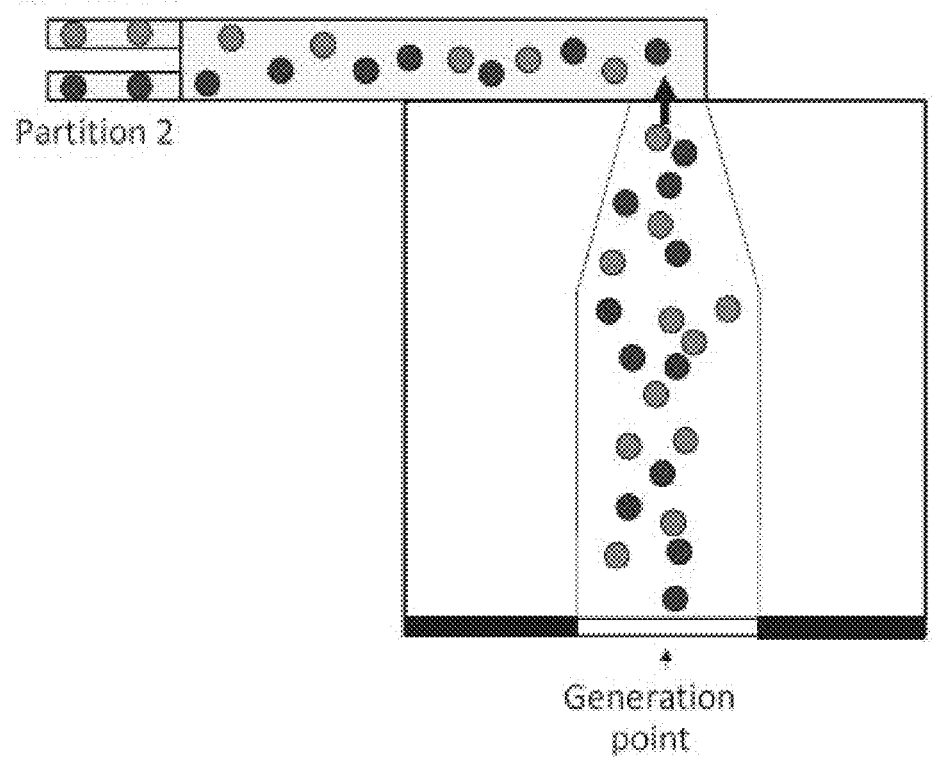
FIG. 60 is a schematic drawing showing droplets produced at a generation point and moving into a single channel.

FIG. 60 shows a general embodiment of a device according to the invention that includes reentrainment channels. The droplets are formed in the droplet formation region (generation point) and move in a large reservoir. The droplets are then funneled into a narrower channel where the droplets line up in single file for further manipulation, e.g., holding, reaction, incubation, detection, or sorting.

Example 52

Figure 61A:
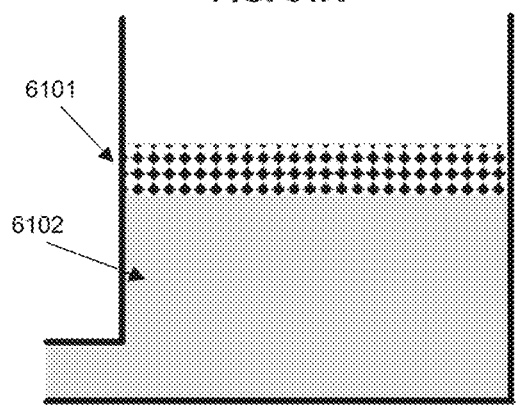
FIGS. 61A-61D are schematic drawings of an embodiment of a device of the disclosure for reentrainment of buoyant droplets or particles.
Figure 61B:
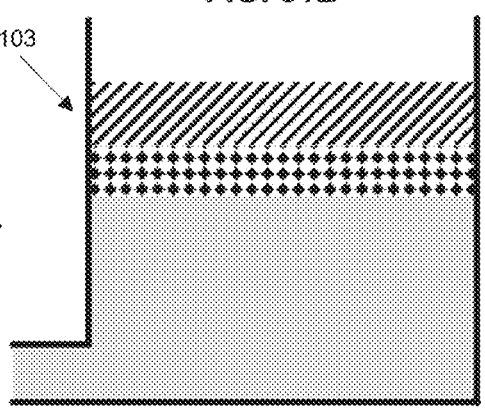
Figure 61C:
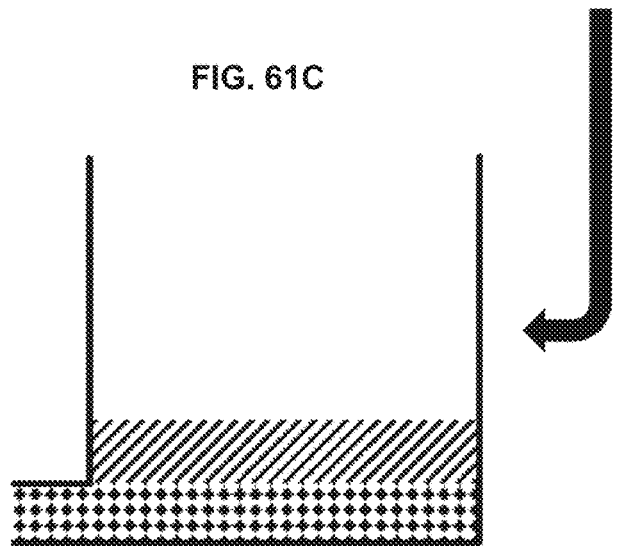
Figure 61D:
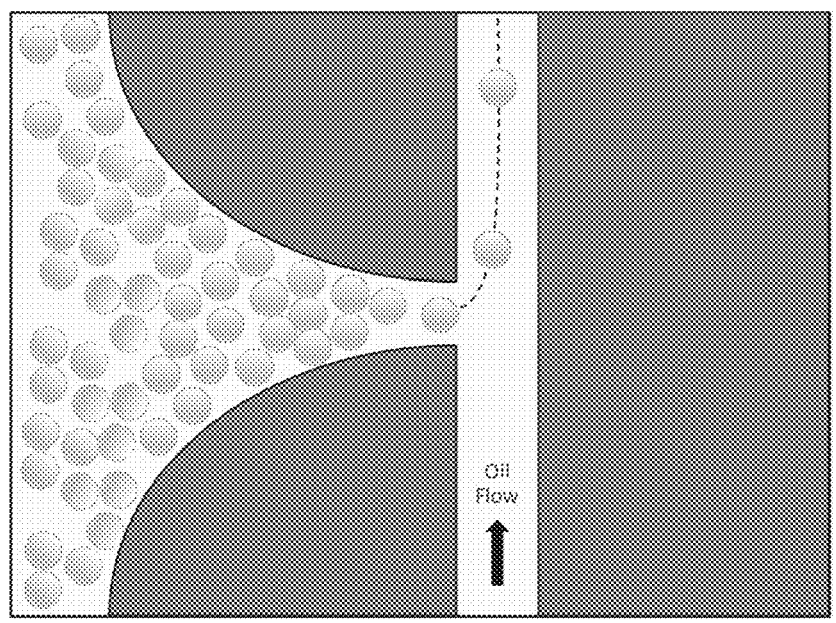

FIGS. 61A-61D are schematic drawings of an embodiment of a device of the disclosure for reentrainment of droplets or particles. FIGS. 61A-61D are schematic drawings of an embodiment of a device of the disclosure for reentrainment of droplets. FIG. 61A shows an emulsion layer (6101) at the top of a partitioning oil (6102) within a reservoir. FIG. 61B shows a spacing liquid (e.g., mineral oil) (6103) added on top of the emulsion layer. FIG. 61C shows the emulsion layer reentrainment into a reentrainment channel. The spacing liquid allows for the emulsion layer to be reentrained without introducing air into the channel. FIG. 61D is a close-up view of droplets in a reentrainment channel including an oil flow to meter droplets and dilute concentrated droplets prior to detection.

Example 53

Figure 62:
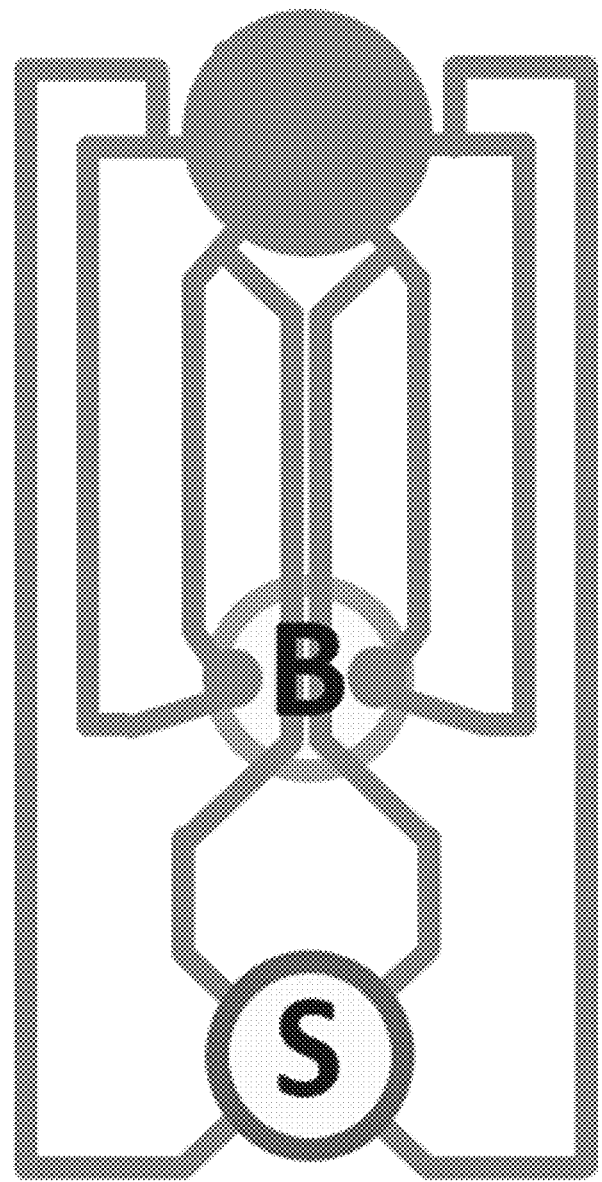
FIG. 62 is a depiction of an alternative multiplex flow path.

FIG. 62 is a is a depiction of an alternative multiplex flow path that allows at least 4-plexing within a single flow path.

For reagent input, there are two landing pads from which the channels originate, but both connect to a single reagent inlet. Liquid containing the sample flows from the sample inlet via the sample channels to the intersections where it meets liquid containing reagents flowing from the reagent inlets via reagent channels. The two liquids combine at the intersection and the combined liquids pass through the droplet formation regions to form droplets in the third liquid which are collected in the collection reservoir.

Example 54

FIG. 63A is a depiction of a plurality of multiplex flow paths in a 96-well multi well plate. The multiplex flow paths are aligned for use in a 96-well multi well plate, allowing for the use of the multiplex flow paths with common microtiter pipetting equipment. FIG. 63B is a depiction of a plurality of multiplex flow paths in a 384-well multi well plate. FIG. 63C is a close-up depiction of a flow path from FIG. 63B. Liquid containing the sample flows from the sample inlet via the sample channels to the intersections where it meets liquid containing reagents flowing from the reagent inlets via reagent channels. The two liquids combine at the intersection, and the combined liquids form droplets in the droplet formation regions.

Example 55

Figure 64:
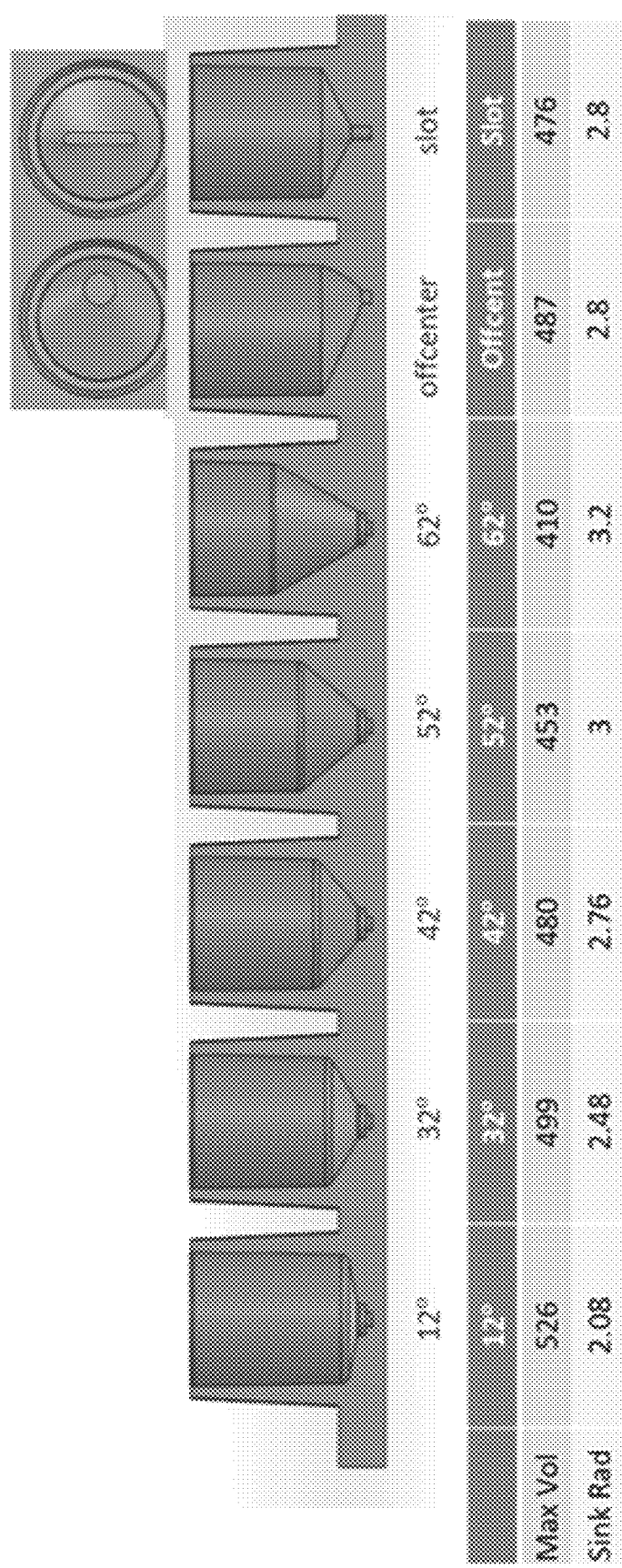
FIG. 64 is a depiction of side view cross sections of exemplary collection reservoirs including canted sidewalls, an oblique circular cone shape, and a circular cone that tapers to a slot.

FIG. 64 is a depiction of side view cross sections of exemplary reservoirs including canted sidewalls, an oblique circular cone shape, and a circular cone that tapers to a slot. The canted side walls, and/or oblique circular cone shape, and/or circular cone that tapers to a slot shapes may increase the collection efficiency of droplets by a collection device (e.g., a pipette tip).

Example 56

Figure 65:
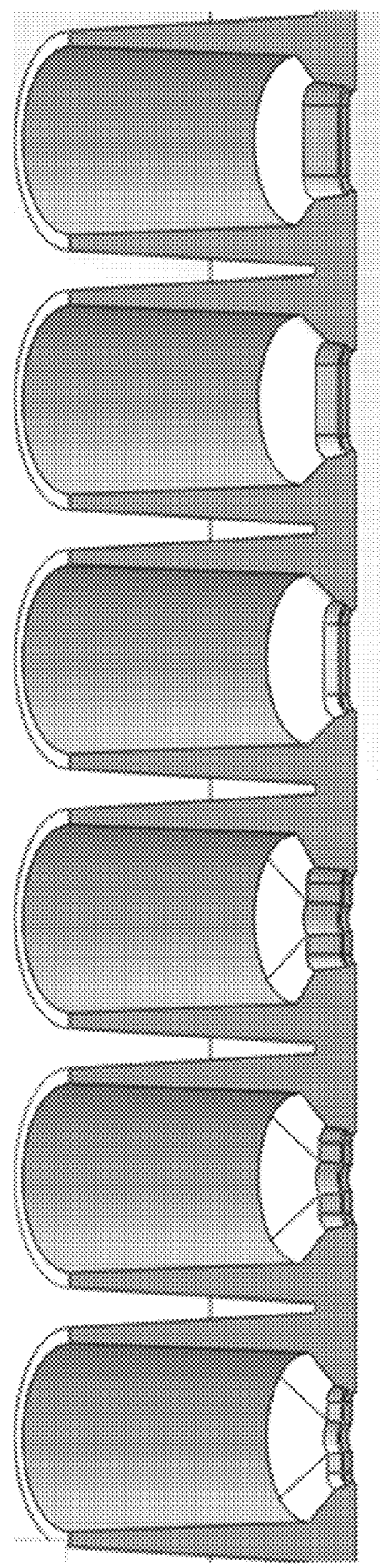
FIG. 65 is a depiction of side view cross sections of exemplary collection reservoir including canted sidewalls and slots, and slots with protrusions.

FIG. 65 is a depiction of side view cross sections of exemplary reservoir including canted sidewalls and slots, and slots with protrusions. The canted side walls, and/or slot shapes with or without protrusions may increase the collection efficiency of droplets by a collection device (e.g., a pipette tip), while also reducing droplet coalescence during extraction. These designs may shape the bottom of the reservoir to guide a pipette tip to the bottom, prevent sealing the tip against the bottom-most surface, and/or introduce a gap between the tip and the bottom-most surface that does not induce coalescence of droplets through high shear during retrieval of the emulsion. These designs may also allow high efficiency collection of droplets without tilting the device.

Example 57

Figure 66:
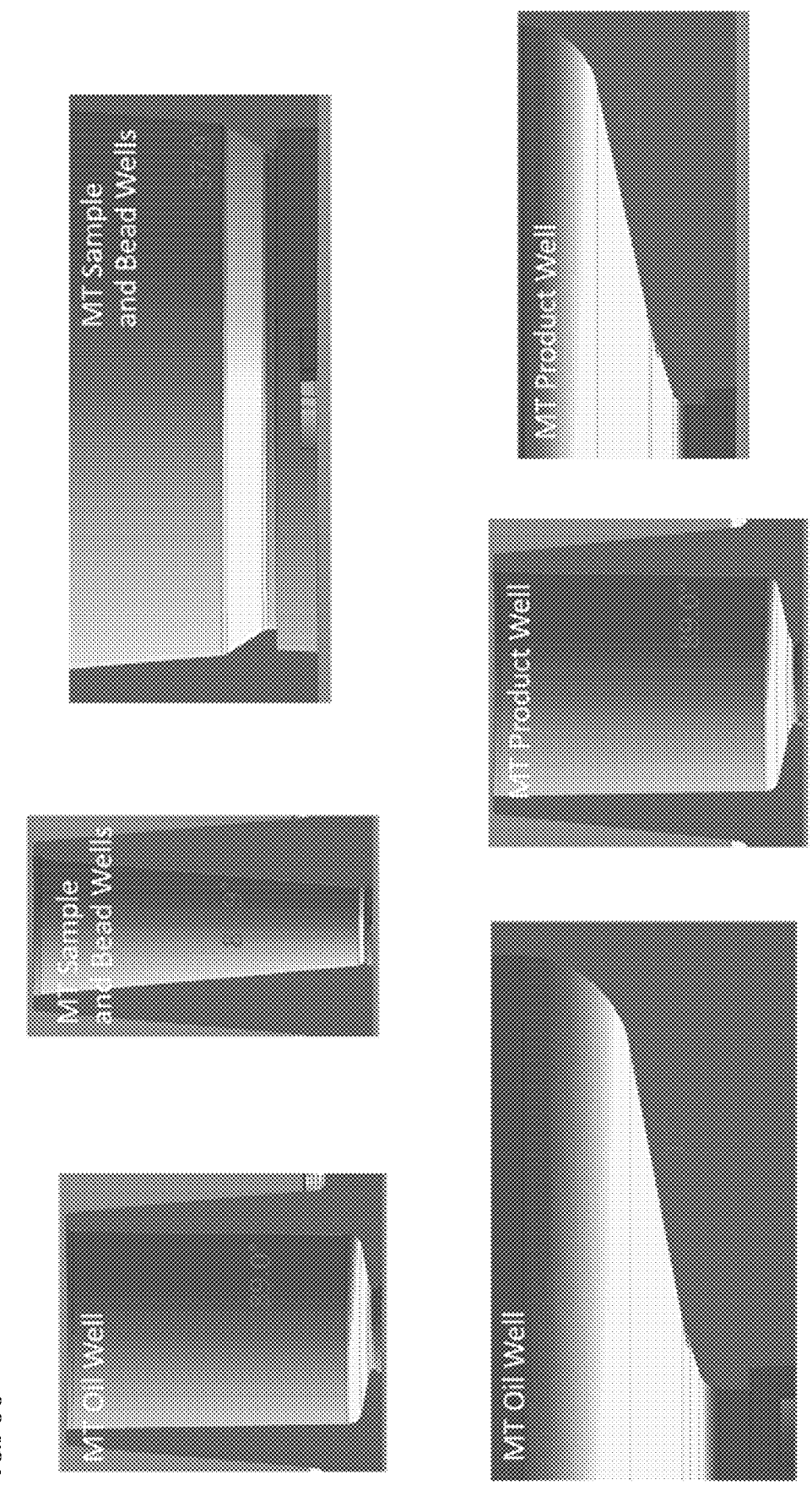
FIG. 66 is a depiction of side view cross sections of exemplary collection reservoirs or sample inlets.

FIG. 66 is a depiction of side view cross sections of exemplary reservoirs or inlets. The canted side walls may increase the collection efficiency of droplets, or introduction efficiency of samples or reagents, e.g., by up to about 20%.

Example 58

Figure 67:
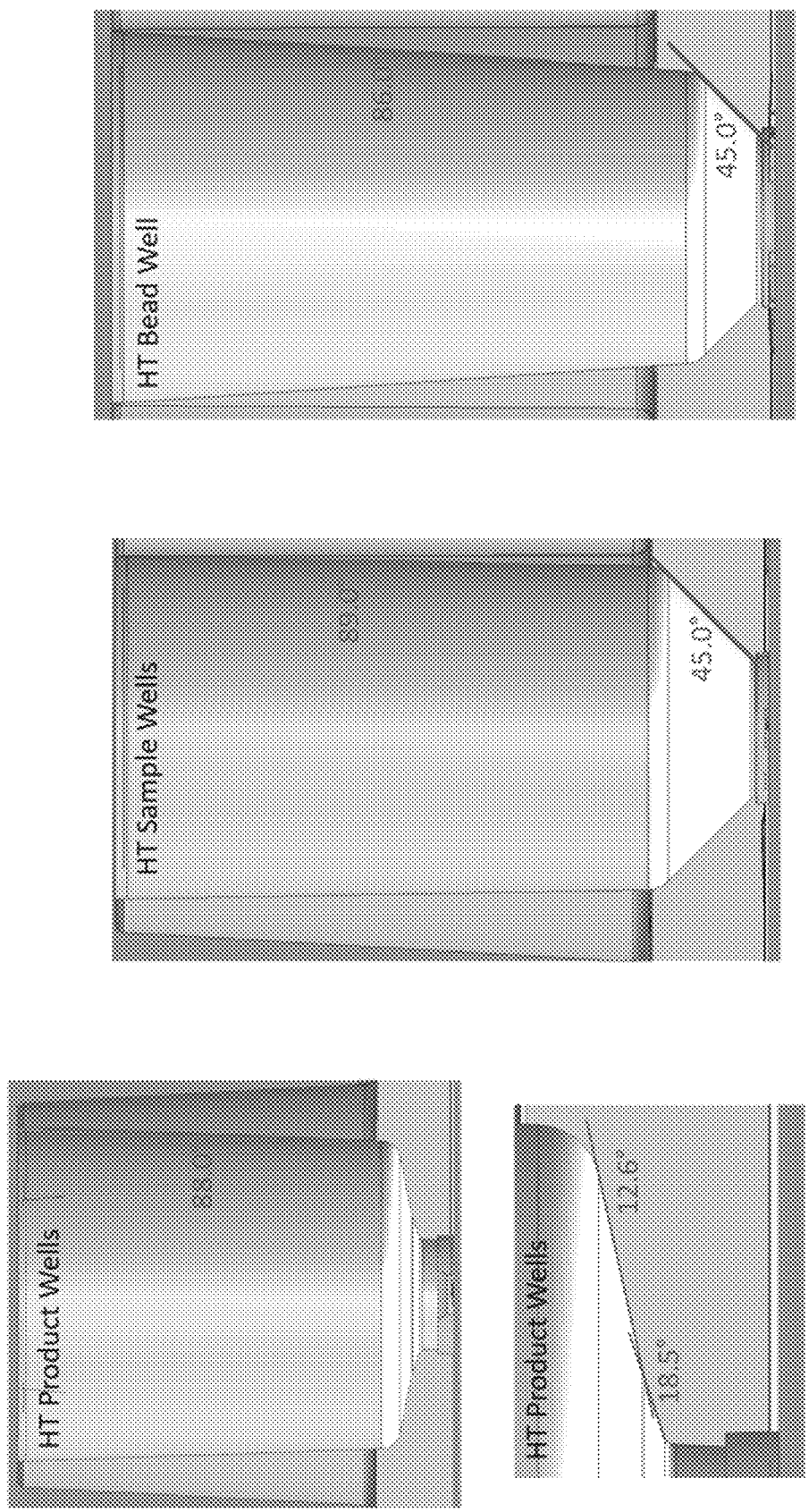
FIG. 67 is a depiction of side view cross sections of exemplary collection reservoirs or sample inlets.

FIG. 67 is a depiction of side view cross sections of exemplary reservoirs or inlets. The canted side walls may increase the collection efficiency of droplets, or introduction efficiency of samples or reagents, e.g., by up to about 20%.

Ordered Embodiments

The following sections describe various embodiments of the invention.

Embodiment A

1. A device for producing droplets, the device comprising:
    (i) one or more first channels, each first channel having independently a first depth, a first width, a first proximal end, and a first distal end, the first distal end comprising a first channel outlet;
    (ii) one or more second channels, each second channel having independently a second depth, a second width, a second proximal end, and a second distal end, wherein each second channel intersects one of the first channels between the first proximal and first distal ends;
    (iii) a droplet collection region; and
    (iv) a droplet formation region comprising a shelf region, wherein the droplet formation region is in fluid communication with the first channel outlets and the droplet collection region, and
        (a) wherein the width of the droplet formation region is at least five times greater than the combined widths of the first channel outlets, or
        (b) wherein the droplet formation region comprises a protrusion from the first channel outlet towards the droplet collection region;
    wherein the first channels, the second channels, the droplet formation region, and the droplet collection region are configured to produce droplets.
2. The device of embodiment 1, wherein the droplet formation region comprises a row of pegs disposed along the width of the shelf region.
3. The device of embodiment 2, wherein the width of each peg is smaller than the width of a single first channel outlet by 50% or less.
4. The device of embodiment 2 or 3, wherein the width of each peg is greater than the width of a single first channel outlet by 100% or less.
5. The device of any one of embodiments 2 to 4, wherein the length of each peg is at least equal to the width of the peg.
6. The device of any one of embodiments 2 to 5, wherein the length of each peg is greater than the width of the peg by 200% or less.
7. The device of any one of embodiments 2 to 6, wherein the row of pegs comprises at least 10 pegs for each first channel outlet.
8. The device of any one of embodiments 2 to 7, wherein the row of pegs comprises 30 or fewer pegs for each first channel outlet.
9. The device of any one of embodiments 2 to 8, wherein the pegs are spaced at a distance that is smaller than the width of a single first channel outlet by 50% or less.
10. The device of any one of embodiments 2 to 9, wherein the pegs are spaced at a distance that is equal to or smaller than the width of a single first channel outlet.
11. The device of any one of embodiments 1 to 10, wherein the length of the shelf region is greater than the width of one first channel outlet by at least 100%.
12. The device of any one of embodiments 1 to 11, wherein the length of the shelf region is greater than the width of a single first channel outlet by 1000% or less.

13. The device of any one of embodiments 1 to 12, wherein the depth of the shelf region increases in the direction from the funnel outlet to the droplet collection region.
14. The device of any one of embodiments 1 to 13, wherein the droplet formation region occupies at least 25% of the perimeter of the droplet collection region.
15. The device of embodiment 1, wherein the droplet formation region comprises a shelf region protruding from the first channel outlet towards the droplet collection region.
16. The device of embodiment 15, wherein the shelf region has a shelf region width that is less than twice the width of the first channel outlet.
17. The device of embodiment 15 or 16, wherein the droplet formation region comprises a step region, and the shelf region protrudes into the step region.
18. A device for producing droplets, the device comprising:
    (i) one or more first channels, each first channel having independently a first depth, a first width, a first proximal end, and a first distal end, the first distal end comprising a first channel outlet;
    (ii) one or more second channels, each second channel having independently a second depth, a second width, a second proximal end, and a second distal end, wherein each second channel intersects one of the first channels between the first proximal and first distal ends;
    (iii) a droplet collection region; and
    (iv) one or more droplet formation regions in fluid communication with the first channel outlets and the droplet collection region;
    wherein at least one of the one or more first channels bifurcates into two downstream first channels after the intersection between the first channel and the second channel, and the downstream first channels are fluidically connected to the one or more droplet formation regions; and
    wherein the first channels, the downstream first channels, the second channels, the droplet formation region, and the droplet collection region are configured to produce droplets.
19. The device of embodiment 18, wherein the two downstream first channels are curved.
20. The device of any one of embodiments 1 to 19, wherein at least one of the second channels comprises a funnel.
21. The device of any one of embodiments 1 to 20, wherein the funnel is disposed between the second proximal end and the intersection between the first channel and the second channel.
22. The device of any one of embodiments 1 to 21, wherein the first channel comprises a mixer.
23. The device of embodiment 22, wherein the mixer is disposed between the first distal end and the intersection between the first channel and the second channel.
24. The device of embodiment 22 or 23, wherein the mixer is a herringbone mixer.
25. A system for producing droplets, the system comprising:
    (a) a device comprising:
        (i) one or more first channels, each first channel having independently a first depth, a first width, a first proximal end, and a first distal end, the first distal end comprising a first channel outlet;
        (ii) one or more second channels, each second channel having independently a second depth, a second width, a second proximal end, and a second distal end, wherein each second channel intersects one of the first channels between the first proximal and first distal ends;
        (iii) a droplet collection region; and
        (iv) a droplet formation region comprising a shelf region, wherein the droplet formation region is in fluid communication with the first channel outlets and the droplet collection region, and
            wherein the width of the droplet formation region is at least five times greater than the combined widths of the first channel outlets, or
            wherein the droplet formation region comprises a protrusion from the first channel outlet towards the droplet collection region;
    (b) a first liquid disposed in the first channel;
    (c) a second liquid disposed in the droplet collection region; and
    (d) a third liquid disposed in the second channel;
    wherein the first liquid and the second liquid are immiscible;
    wherein the first liquid and the third liquid are miscible; and
    wherein the system is configured to produce droplets of the first and third liquids in the second liquid.
26. The system of embodiment 25, wherein the device is of any one of embodiments 2 to 17.
27. A system for producing droplets, the system comprising:
    (a) a device comprising:
        (i) one or more first channels, each first channel having independently a first depth, a first width, a first proximal end, and a first distal end, the first distal end comprising a first channel outlet;
        (ii) one or more second channels, each second channel having independently a second depth, a second width, a second proximal end, and a second distal end, wherein each second channel intersects one of the first channels between the first proximal and first distal ends;
        (iii) a droplet collection region; and
        (iv) one or more droplet formation regions in fluid communication with the first channel outlets and the droplet collection region;
    wherein at least one of the one or more first channels bifurcates into two downstream first channels after the intersection between the first channel and the second channel, and the downstream first channels are fluidically connected to the one or more droplet formation regions;
    (b) a first liquid disposed in the first channel;
    (c) a second liquid disposed in the droplet collection region; and
    (d) a third liquid disposed in the second channel;
    wherein the first liquid and the second liquid are immiscible;
    wherein the first liquid and the third liquid are miscible; and
    wherein the system is configured to produce droplets of the first and third liquids in the second liquid.
28. The system of embodiment 27, wherein the device is of embodiment 19.
29. The system of any one of embodiments 25 to 28, wherein the device is of any one of embodiments 20 to 24.

30. The system of any one of embodiments 25 to 29, further comprising a plurality of particles disposed in the first channel.
31. A method of producing droplets in a second liquid, the droplets comprising a first liquid and a third liquid, the method comprising:
   (a) providing the system of any one of embodiments 25 to 30; and
   (b) allowing the first liquid to flow from the first channel to the droplet formation region to produce droplets in the second liquid, the droplets comprising the first liquid and the third liquid.

Embodiment B

1. A device for producing droplets of a first liquid in a second liquid comprising:
   a) a first channel having a first proximal end, a first distal end, a first width, and a first depth;
   b) a droplet formation region having a width or depth greater than the first width or first depth and being in fluid communication with the first distal end; and
   c) a reentrainment channel having a proximal end and a distal end, wherein the proximal end is in fluid communication with the droplet formation region.
2. The device of embodiment 1, further comprising a second channel have a second proximal end, a second distal end, a second width, and a second depth, wherein either the second channel intersects the first channel between the first proximal and first distal ends or the second distal end is in fluid communication with the droplet formation region.
3. The device of embodiment 1 or 2, wherein the droplet formation region comprises a shelf region having a third width and third depth, wherein the third width is greater than the first width.
4. The device of embodiment 3, wherein the droplet formation region further comprises a step region comprising a wall having a fourth depth, wherein the step region is in fluid communication with the shelf region and the shelf region is disposed between the first distal end and the step region.
5. The device of embodiment 1 or 2, wherein the droplet formation region comprises a step region comprising a wall having a fourth depth, wherein the step region is in fluid communication with the first distal end.
6. The device of any one of embodiments 1-5, wherein the droplet formation region is contiguous with a reservoir, wherein the proximal end of the reentrainment channel is at the top or the bottom of the reservoir.
7. The device of any one of embodiments 1-6, further comprising a magnetic actuator disposed to apply a magnetic force to direct droplets to the reentrainment channel.
8. The device of any one of embodiments 1-7, further comprising a controller operably coupled to flow fluid in the reentrainment channel.
9. A system for producing droplets of a first liquid in a second liquid comprising:
   a) a device comprising
      i) a first channel having a first proximal end, a first distal end, a first width, and a first depth;
      ii) a droplet formation region having a width or depth greater than the first width or first depth and being in fluid communication with the first distal end; and
      iii) a reentrainment channel having a proximal end and a distal end, wherein the proximal end is in fluid communication with the droplet formation region; and
   b) a second liquid in the droplet formation region.
10. The system of embodiment 9, wherein the droplet formation region is contiguous with a reservoir, wherein the proximal end of the reentrainment channel is at the top or the bottom of the reservoir.
11. The system of embodiment 9, wherein the second liquid comprises a ferrofluid and the system further comprises a magnetic actuator disposed to apply a magnetic force to direct droplets to the reentrainment channel.
12. The system of embodiment 10, wherein the reservoir comprises the second liquid and a spacing liquid, wherein the density of the droplets is between that of the second and spacing liquids.
13. The system of embodiment 9, wherein the device further comprises a second channel have a second proximal end, a second distal end, a second width, and a second depth, wherein either the second channel intersects the first channel between the first proximal and first distal ends or the second distal end is in fluid communication with the droplet formation region.
14. The system of embodiment 9, wherein the droplet formation region comprises a shelf region having a third width and third depth, wherein the third width is greater than the first width.
15. The system of embodiment 14, wherein the droplet formation region further comprises a step region comprising a wall having a fourth depth, wherein the step region is in fluid communication with the shelf region and the shelf region is disposed between the first distal end and the step region.
16. The system of embodiment 9, wherein the droplet formation region comprises a step region comprising a wall having a fourth depth, wherein the step region is in fluid communication with the first distal end.
17. The system of embodiment 9, further comprising a controller operably coupled to flow fluid in the reentrainment channel.
18. A method of manipulating droplets of a first liquid in a second liquid comprising:
   a) providing a device of any of embodiments 1-8 or a system of any one of embodiment 9-17;
   b) producing droplets in the droplet formation region;
   c) directing the droplets into the reentrainment channel.
19. The method of embodiment 18, wherein the second liquid comprises a ferrofluid and the droplets are directed by application of a magnetic field to the ferrofluid.
20. The method of embodiment 18, wherein the droplet formation region is contiguous with a reservoir, wherein the proximal end of the reentrainment channel is at the top or the bottom of the reservoir.
21. The method of embodiment 20, wherein the reservoir comprises the second liquid and spacing liquid, wherein the density of the droplets is between that of the second and spacing liquids, and wherein the droplets are directed to the reentrainment channel by pressure.
22. The method of embodiment 21, further comprising flowing a liquid in the reentrainment channel.

Embodiment C

1. A device for producing droplets, the device comprising:
   a) a first channel having a first depth, a first width, a first proximal end, and a first distal end;
   b) a droplet formation region in fluid communication with the first channel; and
   c) a collection reservoir in fluid communication with the droplet formation region and configured to collect droplets formed in the droplet formation region, wherein the collection reservoir comprises a side wall canted at an angle between 89.5° and 4°,
   wherein the first channel and droplet formation region are configured to produce droplets of a first liquid in a second liquid.
2. The device of embodiment 1, wherein the side wall is canted at about a 45° angle.
3. The device of embodiment 1, wherein the side wall is canted at an angle between 89.5° and 4° for a vertical expanse for between 1 and 20 mm.
4. The device of embodiment 1, further comprising a second channel having a second depth, a second width, a second proximal end, and a second distal end, wherein the second channel intersects the first channel between the first proximal and first distal ends.
5. The device of embodiment 1, wherein the droplet formation region comprises a shelf region having a third depth, a third width, at least one inlet, and at least one outlet, wherein the third width is greater than the first width to allow the first liquid to expand in at least one dimension.
6. The device of embodiment 1, wherein the droplet formation region comprises a step region having a fourth depth greater than the first depth.
7. The device of embodiment 1, wherein the device is configured to produce droplets that are substantially stationary in the collection reservoir.
8. The device of embodiment 1, further comprising a first reservoir in fluid communication with the first proximal end.
9. The device of embodiment 4, further comprising a second reservoir in fluid communication with the second proximal end.
10. The device of embodiment 1, wherein the collection reservoir comprises a first sidewall section canted at an angle between 89.5° and 4° and a second sidewall section canted at a different angle between 89.5° and 4°.
11. A method of producing droplets comprising:
    a) providing a device comprising:
       i) a first channel having a first depth, a first width, a first proximal end, and a first distal end;
       ii) a droplet formation region in fluid communication with the first channel; and
       iii) a collection reservoir configured to collect droplets formed in the droplet formation region, wherein the collection reservoir comprises a side wall canted at an angle between 89.5° and 4°; wherein the collection reservoir comprises a second liquid; and
    wherein a first liquid is immiscible with a second liquid;
    b) allowing a first liquid to flow from the first channel to the droplet formation region to produce droplets of the first liquid in the second liquid;
    c) collecting the droplets in the collection reservoir; and
    d) removing the droplets from the collection reservoir.
12. The method of embodiment 11, wherein the side wall is canted at about a 45° angle.
13. The method of embodiment 11, wherein the side wall is canted at an angle between 89.5° and 4° for a vertical expanse for between 1 and 20 mm.
14. The method of embodiment 11, wherein the removal of droplets comprises use of a pipette.
15. The method of embodiment 11, wherein the device further comprises a second channel having a second depth, a second width, a second proximal end, and a second distal end, wherein the second channel intersects the first channel between the first proximal and first distal ends.
16. The method of embodiment 11, wherein the droplet formation region comprises a shelf region having a third depth, a third width, at least one inlet, and at least one outlet, wherein the third width is greater than the first width.
17. The method of embodiment 11, wherein the droplet formation region comprises a step region having a fourth depth that is greater than the first depth.
18. The method of embodiment 11, wherein the droplets are substantially stationary in the collection reservoir.
19. The method of embodiment 11, wherein the first liquid comprises particles.
20. The method of embodiment 11, wherein the collection reservoir comprises a first sidewall section canted at an angle between 89.5° and 4° and a second sidewall section canted at a different angle between 89.5° and 4°.
21. A system for producing droplets comprising:
    a) a device comprising:
       i) a first channel having a first depth, a first width, a first proximal end, and a first distal end;
       ii) a droplet formation region in fluid communication with the first channel; and
       iii) a collection reservoir configured to collect droplets formed in the droplet formation region, wherein the collection reservoir comprises a side wall canted at an angle between 89.5° and 4°; wherein the collection reservoir comprises the second liquid; and
    wherein a first liquid is substantially immiscible with a second liquid; and
    b) particles in the first channel and/or droplets in the collection reservoir.
22. The system of embodiment 21, wherein the side wall is canted at about a 45° angle.
23. The system of embodiment 21, wherein the side wall is canted at an angle between 89.5° and 4° for a vertical distance of between 1 and 20 mm.
24. The system of embodiment 21, wherein the device further comprises a second channel having a second depth, a second width, a second proximal end, and a second distal end, wherein the second channel intersects the first channel between the first proximal and first distal ends.
25. The system of embodiment 21, wherein the droplet formation region comprises a shelf region having a third depth, a third width, at least one inlet, and at least one outlet, wherein the third width is greater than the first width.
26. The system of embodiment 21, wherein the droplet formation region comprises a step region having a fourth depth that is greater than the first depth.
27. The system of embodiment 21, wherein the first liquid comprises particles.

28. The system of embodiment 21, wherein the device further comprises a first reservoir in fluid communication with the first proximal end.
29. The system of embodiment 24, wherein the device further comprises a second reservoir in fluid communication with the second proximal end.
30. The system of embodiment 21, wherein the collection reservoir comprises a first sidewall section canted at an angle between 89.5° and 4° and a second sidewall section canted at a different angle between 89.5° and 4°.
31. A device for producing droplets, the device comprising:
   a) a first reservoir in fluid communication with a first channel having a first depth, a first width, a first proximal end, and a first distal end, wherein the first reservoir comprises a side wall canted at an angle between 89.5° and 4°;
   b) a droplet formation region in fluid communication with the first channel; and
   c) a collection reservoir in fluid communication with the droplet formation region and configured to collect droplets formed in the droplet formation region, wherein the first channel and droplet formation region are configured to produce droplets of a first liquid in a second liquid.
32. The device of embodiment 31, wherein the side wall is canted at about a 45° angle.
33. The device of embodiment 31, wherein the side wall is canted at an angle between 89.5° and 4° for a vertical expanse for between 1 and 20 mm.
34. The device of embodiment 31, further comprising a second reservoir in fluid communication with a second channel having a second depth, a second width, a second proximal end, and a second distal end, wherein the second channel intersects the first channel between the first proximal and first distal ends, wherein the second reservoir comprises a side wall canted at an angle between 89.5° and 4°.
35. The device of embodiment 31, wherein the droplet formation region comprises a shelf region having a third depth, a third width, at least one inlet, and at least one outlet, wherein the third width is greater than the first width to allow the first liquid to expand in at least one dimension.
36. The device of embodiment 31, wherein the droplet formation region comprises a step region having a fourth depth greater than the first depth.
37. The device of embodiment 31, wherein the device is configured to produce droplets that are substantially stationary in the collection reservoir.
40. The device of embodiment 31, wherein the first reservoir comprises a first sidewall section canted at an angle between 89.5° and 4° and a second sidewall section canted at a different angle between 89.5° and 4°.
41. The device of embodiment 34, wherein the second reservoir comprises a first sidewall section canted at an angle between 89.5° and 4° and a second sidewall section canted at a different angle between 89.5° and 4°.
42. A method of for producing droplets comprising:
   a) providing the device of any one of embodiments 31-41; wherein droplet formation region comprises a second liquid; and
   b) allowing a first liquid to flow from the first channel to the droplet formation region to produce droplets of the first liquid in the second liquid.
43. A system for producing droplets, the system comprising:
   a) a device of any one of embodiments 31-41; and
   b) particles in the first channel or first reservoir and/or droplets in the collection reservoir.
44. A device for producing droplets of a first liquid in a second liquid, the device comprising:
   a) a sample inlet;
   b) first, second, and third sample channels, each of which is in fluid communication with the sample inlet;
   c) first and second reagent inlets;
   d) first, second, and third reagent channels, wherein the first and second reagent channels are in fluid communication with the first reagent inlet; the third reagent channel is in fluid communication with the second reagent inlet; the first sample channel and the first reagent channel intersect at a first intersection, the second sample channel and the second reagent channel intersect at a second intersection, and the third sample channel and the third reagent channel intersect at a third intersection;
   e) first, second, and third droplet formation regions; and
   f) first and second collection reservoirs,
   wherein the first droplet formation region is fluidically disposed between the first intersection and the first collection reservoir, the second droplet formation region is fluidically disposed between the second intersection and the first collection reservoir, and the third droplet formation region is fluidically disposed between the third intersection and the second collection reservoir.
45. The device of embodiment 44, further comprising i) a fourth sample channel in fluid communication with the sample inlet; ii) a fourth reagent channel in fluid communication with the second reagent inlet, and iii) a fourth droplet formation region, wherein the fourth sample channel and fourth reagent channel intersect at a fourth intersection, and the fourth droplet formation region is fluidically disposed between the fourth intersection and the second collection reservoir.
46. The device of embodiment 44, wherein the inlets are arranged substantially linearly.
47. The device of embodiment 44, wherein the first, second, and third sample channels are co-planar.
48. The device of embodiment 44, wherein the first, second, and third reagent channels are co-planar.
49. The device of embodiment 44, wherein the length of the first reagent channel is at least 85% of the length of the second reagent channel.
50. The device of embodiment 45, wherein the length of the third reagent channel is at least 85% of the length of the fourth reagent channel.
51. The device of embodiment 44, wherein the first and second collection reservoirs and the first and second reagent inlets are disposed radially about the sample inlet.
52. The device of embodiment 45, comprising a plurality of first and second reagent inlets, sample inlets, first and second collection reservoirs, first, second, third, and fourth sample channels, first, second, third, and fourth reagent channels, first, second, third, and fourth intersections, and first, second, third, and fourth droplet formation regions.

53. The device of embodiment 52, wherein:
  a) at least two of the plurality of sample inlets are in fluid communication with each other via a connecting channel; or
  b) a sample channel in fluid communication with one of the plurality of sample inlets and one of the plurality of collection reservoirs intersects with a sample channel in fluid communication with a separate one of the plurality of sample inlets and a separate one of the plurality of collection reservoirs.

54. The device of embodiment 44 wherein at least one of the droplet formation regions comprises a shelf that allows a liquid to expand in one dimension and a step that allows the liquid to expand in an orthogonal dimension.

55. The device of any one of embodiments 52-54, further comprising one or more troughs, wherein the one or more troughs connects the plurality of sample inlets, the plurality of first reagent inlets, and/or connects the plurality of second reagent inlets.

56. A method for producing droplets comprising:
  a) providing a device comprising:
    i) a sample inlet;
    ii) first, second, and third sample channels, each of which is in fluid communication with the sample inlet;
    iii) first and second reagent inlets;
    iv) first, second, and third reagent channels, wherein the first and second reagent channels are in fluid communication with the first reagent inlet; the third reagent channel is in fluid communication with the second reagent inlet; the first sample channel and the first reagent channel intersect at a first intersection, the second sample channel and the second reagent channel intersect at a second intersection, and the third sample channel and the third reagent channel intersect at a third intersection;
    v) first, second, and third droplet formation regions each comprising a second liquid; and
    vi) first and second collection reservoirs,
    wherein the first droplet formation region is fluidically disposed between the first intersection and the first collection reservoir, the second droplet formation region is fluidically disposed between the second intersection and the first collection reservoir, and the third droplet formation region is fluidically disposed between the third intersection and the second collection reservoir;
  b) allowing a first liquid to flow from the sample inlet via the first, second, and third sample channels to the first, second, and third intersections, and allowing a third liquid to flow from the first reagent inlet via the first and second reagent channels, and allowing the third liquid to flow from the second reagent inlet via the third reagent channel to the first, second, and third intersections, wherein the first liquid and third liquid combine at the first, second, and third intersections and produce droplets in the second liquid at the first, second, and third droplet formation regions.

57. The method of embodiment 56, wherein the device further comprises i) a fourth sample channel in fluid communication with the sample inlet; ii) a fourth reagent channel in fluid communication with the second reagent inlet, and iii) a fourth droplet formation region, wherein the fourth sample channel and fourth reagent channel intersect at a fourth intersection, and the fourth droplet formation region is fluidically disposed between the fourth intersection and the second collection reservoir, the method further comprising allowing the first liquid to flow from the sample inlet via the fourth sample channel to the fourth intersection, and allowing the third liquid to flow from the second reagent inlet via the fourth reagent channel to the fourth intersection, wherein the first liquid and the third liquid combine at the fourth intersection and produce droplets in the second liquid at the fourth droplet formation region.

58. A system for producing droplets comprising:
  a) a device comprising:
    i) a sample inlet;
    ii) first, second, and third sample channels, each of which is in fluid communication with the sample inlet;
    iii) first and second reagent inlets;
    iv) first, second, and third reagent channels, wherein the first and second reagent channels are in fluid communication with the first reagent inlet; the third reagent channel is in fluid communication with the second reagent inlet; the first sample channel and the first reagent channel intersect at a first intersection, the second sample channel and the second reagent channel intersect at a second intersection, and the third sample channel and the third reagent channel intersect at a third intersection;
    v) first, second, and third droplet formation regions; and
    vi) first and second collection reservoirs,
    wherein the first droplet formation region is fluidically disposed between the first intersection and the first collection reservoir, the second droplet formation region is fluidically disposed between the second intersection and the first collection reservoir, and the third droplet formation region is fluidically disposed between the third intersection and the second collection reservoir;
  b) particles in the sample inlet, first and/or second reagent inlet, and/or droplets in the first and/or second collection reservoir.

59. The system of embodiment 58, wherein the device further comprises i) a fourth sample channel in fluid communication with the sample inlet; ii) a fourth reagent channel in fluid communication with the second reagent inlet, and iii) a fourth droplet formation region, wherein the fourth sample channel and fourth reagent channel intersect at a fourth intersection, and the fourth droplet formation region is fluidically disposed between the fourth intersection and the second collection reservoir.

60. The system of embodiment 58, wherein the inlets are arranged substantially linearly.

61. The system of embodiment 58, wherein the first, second, and third sample channels are co-planar.

62. The system of embodiment 58, wherein the first, second, and third reagent channels are co-planar.

63. The system of embodiment 58, wherein the length of the first reagent channel is at least 85% of the length of the second reagent channel.

64. The system of embodiment 59, wherein the length of the third reagent channel is at least 85% of the length of the fourth reagent channel.

65. The system of embodiment 59, wherein the device comprises a plurality of reagent inlets, sample inlets, first and second collection reservoirs, first, second, third, and fourth sample channels, first, second, third, and fourth reagent channels, first, second, third, and fourth intersections, and first, second, third, and fourth droplet formation regions.

66. The system of embodiment 65, wherein:
   i) at least two of the plurality of reagent inlets are in fluid communication with each other via a connecting channel; or
   ii) a sample channel in fluid communication with one of the plurality of sample inlets and one of the plurality of collection reservoirs intersects with a sample channel in fluid communication with a separate one of the plurality of sample inlets and a separate one of the plurality of collection reservoirs.

67. The system of embodiment 58, wherein at least one of the droplet formation regions comprises a shelf that allows a liquid to expand in one dimension and a step that allows the liquid to expand in an orthogonal dimension.

68. The system of any one of embodiments 65-67, further comprising one or more troughs, wherein the one or more troughs connects the plurality of sample inlets, the plurality of first reagent inlets, and/or the plurality of second reagent inlets.

69. A device for producing droplets, the device comprising:
   a) first and second sample inlets;
   b) first, second, and third sample channels, wherein the first and second sample channels are in fluid communication with the first sample inlet, and the third sample channel is in fluid communication with the second sample inlet;
   c) first, second, and third reagent inlets;
   d) first, second, and third reagent channels, wherein the first reagent channel is in fluid communication with the first reagent inlet; the second reagent channel is in fluid communication with the second reagent inlet; and the third reagent channel is in fluid communication with the third reagent inlet, the first sample channel and the first reagent channel intersect at a first intersection, the second sample channel and the second reagent channel intersect at a second intersection, and the third sample channel and the third reagent channel intersect at a third intersection;
   e) first, second, and third droplet formation regions; and
   f) one or more collection reservoirs,
   wherein the first droplet formation region is fluidically disposed between the first intersection and the one or more collection reservoirs, the second droplet formation region is fluidically disposed between the second intersection and the one or more collection reservoirs, and the third droplet formation region is fluidically disposed between the third intersection and the one or more collection reservoirs.

70. The device of embodiment 69, further comprising i) a fourth sample channel in fluid communication with the second sample inlet; ii) a fourth reagent inlet; iii) a fourth reagent channel in fluid communication with the fourth reagent inlet; and iv) a fourth droplet formation region, wherein the fourth sample channel and the fourth reagent channel intersect at a fourth intersection, and the fourth droplet formation region is fluidically disposed between the fourth intersection and the one or more collection reservoirs.

71. The device of embodiment 69 or 70, further comprising i) a fifth reagent channel in fluid communication with the first reagent inlet and ii) a fifth droplet formation region, wherein the second sample channel splits into first and second branches, wherein the first branch leads to the second intersection and the second branch intersects with the fifth reagent channel to form a fifth intersection, wherein the fifth droplet formation region is fluidically disposed between the fifth intersection and the one or more collection reservoirs.

72. The device of embodiment 69 or 70, further comprising i) a fifth reagent channel in fluid communication with the first reagent inlet; ii) a fifth sample channel; and iii) a fifth droplet formation region, wherein the fifth sample channel is in fluid communication with the first sample inlet and intersects with the fifth reagent channel to form a fifth intersection, wherein the fifth droplet formation region is fluidically disposed between the fifth intersection and the one or more collection reservoirs.

73. The device of embodiment 69-70, wherein the one or more collection reservoirs comprises first and second reservoirs, wherein the first droplet formation region is fluidically disposed between the first intersection and the first reservoir and the second droplet formation region is fluidically disposed between the second intersection and the second reservoir.

74. The device of embodiment 69-70, wherein the one or more collection reservoirs comprises a first reservoir, wherein the first droplet formation region is fluidically disposed between the first intersection and the first reservoir and the second droplet formation region is fluidically disposed between the second intersection and the first reservoir.

75. The device of embodiment 71-74, further comprising i) a sixth reagent channel in fluid communication with the second reagent inlet and ii) a sixth droplet formation region, wherein the third sample channel splits into first and second branches, wherein the first branch leads to the third intersection and the second branch intersects with the sixth reagent channel to form a sixth intersection, wherein the sixth droplet formation region is fluidically disposed between the sixth intersection and the one or more collection reservoirs.

76. The device of embodiment 71-74, further comprising i) a sixth reagent channel in fluid communication with the second reagent inlet; ii) a sixth sample channel; and iii) a sixth droplet formation region, wherein the sixth sample channel is in fluid communication with the second sample inlet and intersects with the sixth reagent channel to form a sixth intersection, wherein the sixth droplet formation region is fluidically disposed between the sixth intersection and the one or more collection reservoirs.

77. The device of any one of embodiments 70-76, further comprising i) a seventh reagent channel in fluid communication with the third reagent inlet and ii) a seventh droplet formation region, wherein the fourth sample channel splits into first and second branches, wherein the first branch leads to the fourth intersection and the second branch intersects with the seventh reagent channel to form a seventh intersection, wherein the seventh droplet formation region is fluidically disposed between the seventh intersection and the one or more collection reservoirs.

78. The device of any one of embodiments 70-76, further comprising i) a seventh reagent channel in fluid communication with the third reagent inlet, ii) a seventh sample channel, and iii) a seventh droplet formation region, wherein the seventh sample channel is in fluid communication with the second sample inlet and intersects with the seventh reagent channel to form a seventh intersection, wherein the seventh droplet formation region is fluidically disposed between the seventh intersection and the one or more collection reservoirs.

79. The device of embodiment 70-78, further comprising i) a fifth reagent inlet, ii) an eighth reagent channel in fluid communication with the fifth reagent inlet, and iii) an eighth droplet formation region, wherein the first sample channel splits into first and second branches, wherein the first branch leads to the first intersection and the second branch intersects with the eighth reagent channel to form an eighth intersection, wherein the eighth droplet formation region is fluidically disposed between the eighth intersection and the one or more collection reservoirs.

80. The device of embodiment 70-78, further comprising i) a fifth reagent inlet, ii) and eighth reagent channel in fluid communication with the fifth reagent inlet, iii) an eighth sample channel, and iv) an eighth droplet formation region, wherein the eighth sample channel is in fluid communication with the first sample inlet and intersects with the eighth reagent channel to form an eighth intersection, wherein the eighth droplet formation region is fluidically disposed between the eighth intersection and the one or more collection reservoirs.

81. The device of embodiment 69-80, wherein the one or more collection reservoirs comprises a first and a second collection reservoir and wherein the first and second collection reservoirs are disposed radially about the first sample inlet, and wherein the device further comprises i) a sixth reagent inlet, ii) a ninth reagent channel in fluid communication with the sixth reagent inlet; iii) a ninth sample channel; and iv) a ninth droplet formation region, wherein the ninth sample channel is in fluid communication with the first sample inlet and intersects with the ninth reagent channel to form a ninth intersection, wherein the first droplet formation region is fluidically disposed between the first intersection and the first collection reservoir, and wherein the ninth droplet formation region is fluidically disposed between the ninth intersection and the second collection reservoir.

82. The device of embodiment 81, further comprising i) a seventh reagent inlet; ii) a tenth reagent channel in fluid communication with the seventh reagent inlet; iii) a tenth sample channel; and iv) a tenth droplet formation region, wherein the tenth sample channel is in fluid communication with the first sample inlet and intersects with the tenth reagent channel to form a tenth intersection, wherein the tenth droplet formation region is fluidically disposed between the tenth intersection and the one or more collection reservoirs.

83. The device of embodiment 70, wherein the one or more collection reservoirs comprises a third and a fourth collection reservoir and wherein the third and fourth collection reservoirs are disposed radially about the second sample inlet, and wherein the device further comprises i) an eighth reagent inlet; ii) an eleventh reagent channel in fluid communication with the eighth reagent inlet; iii) an eleventh sample channel; and iv) an eleventh droplet formation region, wherein the eleventh sample channel is in fluid communication with the second sample inlet and intersects with the eleventh reagent channel to form an eleventh intersection, wherein the third droplet formation region is fluidically disposed between the third intersection and the third collection reservoir, and wherein the eleventh droplet formation region is fluidically disposed between the eleventh intersection and the fourth collection reservoir.

84. The device of embodiment 83, wherein the device further comprises i) a ninth reagent inlet; ii) a twelfth reagent channel in fluid communication with the ninth reagent inlet; iii) a twelfth sample channel; and iv) a twelfth droplet formation region, wherein the twelfth sample channel is in fluid communication with the second sample inlet and intersects with the twelfth reagent channel to form a twelfth intersection, wherein the third droplet formation region is fluidically disposed between the third intersection and the third collection reservoir, and wherein the twelfth droplet formation region is fluidically disposed between the twelfth intersection and the fourth collection reservoirs.

85. The device of embodiment 82, further comprising i) a thirteenth reagent channel in fluid communication with the sixth reagent inlet, and ii) a thirteenth droplet formation region, wherein the tenth sample channel splits into first and second branches, wherein the first branch leads to the tenth intersection and the second branch intersects with the thirteenth reagent channel to form a thirteenth intersection, wherein the thirteenth droplet formation region is fluidically disposed between the thirteenth intersection and the one or more collection reservoirs.

86. The device of embodiment 71, further comprising i) a thirteenth reagent channel in fluid communication with the sixth reagent inlet; ii) a thirteenth sample channel; and iii) a thirteenth droplet formation region, wherein the thirteenth sample channel is in fluid communication with the first sample inlet and intersects with the thirteenth reagent channel to form a thirteenth intersection, wherein the thirteenth droplet formation region is fluidically disposed between the thirteenth intersection and the one or more collection reservoirs.

87. The device of embodiment 82, further comprising i) a fourteenth reagent channel in fluid communication with the seventh reagent inlet, and ii) a fourteenth droplet formation region, wherein the eleventh sample channel splits into first and second branches, wherein the first branch leads to the eleventh intersection and the second branch intersects with the fourteenth reagent channel to form a fourteenth intersection, wherein the fourteenth droplet formation region is fluidically disposed between the fourteenth intersection and the one or more collection reservoirs.

88. The device of embodiment 82, further comprising i) a fourteenth reagent channel in fluid communication with the seventh reagent inlet; ii) a fourteenth sample channel; and iii) a fourteenth droplet formation region, wherein the fourteenth sample channel is in fluid communication with the second sample inlet and intersects with the fourteenth reagent channel to form a fourteenth intersection, wherein the fourteenth droplet formation region is fluidically disposed between the fourteenth intersection and the one or more collection reservoirs.

89. The device of embodiment 83, further comprising i) a fifteenth reagent channel in fluid communication with the eighth reagent inlet, and ii) a fifteenth droplet formation region, wherein the twelfth sample channel splits into first and second branches, wherein the first branch leads to the twelfth intersection and the second branch intersects with the fifteenth reagent channel to form a fifteenth intersection, wherein the fifteenth droplet formation region is fluidically disposed between the fifteenth intersection and the one or more collection reservoirs.

90. The device of embodiment 83, further comprising i) a fifteenth reagent channel in fluid communication with the eighth reagent inlet; ii) a fifteenth sample channel; and iii) a fifteenth droplet formation region, wherein the fifteenth sample channel is in fluid communication with the second sample inlet and intersects with the fifteenth reagent channel to form a fifteenth intersection, wherein the fifteenth droplet formation region is fluidically disposed between the fifteenth intersection and the one or more collection reservoirs.

91. The device of any one of embodiments 82, 85 or 86, further comprising i) a sixteenth reagent channel in fluid communication with the tenth reagent inlet, and ii) a sixteenth droplet formation region, wherein the ninth sample channel splits into first and second branches, wherein the first branch leads to the ninth intersection and the second branch intersects with the sixteenth reagent channel to form a sixteenth intersection, wherein the sixteenth droplet formation region is fluidically disposed between the sixteenth intersection and the one or more collection reservoirs.

92. The device of any one of embodiments 81, 82, 85, or 86, further comprising i) a tenth reagent inlet, ii) a sixteenth reagent channel in fluid communication with the tenth reagent inlet; iii) a sixteenth sample channel; and iv) a sixteenth droplet formation region, wherein the sixteenth sample channel is in fluid communication with the first sample inlet and intersects with the sixteenth reagent channel to form a sixteenth intersection, wherein the sixteenth droplet formation region is fluidically disposed between the sixteenth intersection and the one or more collection reservoirs.

93. The device of any one of embodiments 69-92, wherein at least one of the droplet formation regions comprises a shelf that allows a liquid to expand in one dimension and a step that allows the liquid to expand in an orthogonal dimension.

94. The device of embodiment 69, further comprising a first trough connecting the first and second sample inlets.

95. The device of embodiment 69, further comprising a second trough connecting at least two of the first, second, and third reagent inlets.

96. The device of embodiment 69, wherein the second trough connects the first, second, and third reagent inlets.

97. The device of any one of embodiments 69-96, wherein the first and second sample inlets or reagent inlets are surrounded by at least one common wall and are separated by a dividing wall, wherein at least a portion of the dividing wall is shorter than the at least one common wall.

98. A method for producing droplets comprising:
 a) providing the device of any one of embodiments 69-96, wherein the first, second, and third droplet formation regions comprise the second liquid; and
 b) allowing the first liquid to flow from the first sample inlet via the first and second sample channels to the first and second intersections, and allowing a third liquid to flow from the first and second reagent inlets via the first and second reagent channels to the first and second intersections, wherein the first liquid and the third liquid combine at the first and second intersections and produce droplets in the second liquid at the first and second droplet formation regions, and allowing the first liquid to flow from the second sample inlet via the third sample channel to the third intersection, and allowing the third liquid to flow from the third reagent inlet via the third reagent channel to the third intersection, wherein the first liquid and the third liquid combine at the third intersection and produce droplets in the second liquid at the third droplet formation regions.

99. A method for producing droplets comprising:
 a) providing the device of embodiment 92, wherein the first through sixteenth droplet formation regions comprise the second liquid; and
 b) allowing the first liquid to flow from the first through fourth sample inlets via the first through sixteenth sample channels to the first through sixteenth intersections, and allowing a third liquid to flow from the first through tenth reagent inlets via the first through sixteenth reagent channels wherein the first liquid and the third liquid combine at the first through sixteenth intersections and produce droplets in the second liquid at the first through sixteenth droplet formation regions.

100. A system for producing droplets, the system comprising:
 a) a device of any one of embodiments 69-97; and
 b) particles in the sample inlets and/or the first and second reagent inlets, and/or droplets in the one or more collection reservoirs.

101. A device for producing droplets, the device comprising:
 a) one or more sample inlets;
 b) one or more sample channels in fluid communication with the one or more sample inlets;
 c) one or more reagent inlets;
 d) one or more reagent channels in fluid communication with the one or more reagent inlets and wherein the one or more reagent channels intersect with the one or more sample channels to form one or more intersections;
 e) one or more droplet formation regions;
 f) one or more collection reservoirs; and
 g) one or more troughs,
 wherein the one or more droplet formation regions are fluidically disposed between the one or more intersections and the one or more collection reservoirs, provided that the one or more sample inlets comprise at least two sample inlets or the one or more reagent inlets comprises at least two reagents inlets, wherein one of the one or more troughs connects the at least two sample inlets or the at least two reagent inlets to deliver liquid thereto.

102. The device of embodiment 101, wherein the one or more sample inlets comprise the at least two sample inlets, 103. The device of embodiment 101 or 102, wherein the one or more reagent inlets comprise the at least two reagent inlets.

104. The device of embodiment 101, wherein the one or more troughs comprises a single trough that connects the at least two sample inlets or the at least two reagent inlets.

105. The device of embodiment 103, wherein the one or more troughs comprise first and second troughs, wherein the first trough connects the at least two sample inlets and the second trough connects the at least two reagent inlets.

106. The device of embodiment 101, wherein at least one of the droplet formation regions comprises a shelf that allows a liquid to expand in one dimension and a step that allows the liquid to expand in an orthogonal dimension.

107. A method for producing droplets, comprising:
  a) providing the device of any one of embodiments 101-106, wherein the one or more droplet formation regions comprise the second liquid; and
  b) allowing the first liquid to flow from the one or more sample inlets via the one or more sample channels to the one or more intersections, and allowing a third liquid to flow from the one or more reagent inlets via the one or more reagent channels to the one or more intersections, wherein the first and third liquids combine at the one or more intersections and produce droplets in the second liquid at the one or more droplet formation regions.

108. A system for producing droplets, comprising:
  a) a device of any one of embodiments 101-106; and
  b) particles in one of the one or more reagent inlets or one of the one or more sample inlets, and/or droplets in one of the one or more collection reservoirs.

109. A device for producing droplets, the device comprising a plurality of flow paths, each flow path comprising:
  a) one or more sample inlets;
  b) one or more sample channels in fluid communication with the one or more sample inlets;
  c) one or more reagent inlets;
  d) one or more reagent channels in fluid communication with the one or more reagent inlets, and wherein the one or more reagent channels intersect with the one or more sample channels to form one or more intersections;
  e) one or more droplet formation regions; and
  f) one or more collection reservoirs;
  wherein the one or more droplet formation regions are fluidically disposed between the one or more intersections and the one or more collection reservoirs, provided that the one or more sample inlets comprise at least two sample inlets or the one or more reagent inlets comprise at least two reagents inlets, wherein the maximum cross sectional dimension of the sample channels is 250 µm, or the maximum cross-sectional dimension of the reagent channels is 250 µm, and wherein the number of droplet formation regions is at least 4 per collection reservoir, wherein the pitch between adjacent flow paths is less than 20 mm, wherein the one or more sample channels and reagent channels are co-planar.

110. The device of embodiment 109, wherein the number of droplet formation regions is at least 8 per collection reservoir.

111. The device of embodiment 109, wherein the one or more droplet formation regions comprise a shelf that allows a liquid to expand in one dimension and a step that allows the liquid to expand in an orthogonal dimension.

112. The device of embodiment 111, further comprising one or more troughs, wherein the one or more sample inlets comprise at least two sample inlets, wherein one or more reagent inlets comprise at least two reagent inlets, and of the one or more troughs connects at least two sample inlets or at least two reagent inlets.

113. A method of producing droplets, comprising:
  a) providing a device of any one of embodiments 109-112, wherein the droplet formation regions comprise a second liquid; and
  b) allowing a first liquid to flow from the one or more sample inlets via the one or more sample channels to the one or more intersections, and allowing a third liquid to flow from the one or more reagent inlets via the one or more reagent channels to the one or more intersections, wherein the first liquid and the third liquid combine at the one or more intersections and produce droplets in the second liquid at the one or more droplet formation regions.

114. A system for producing droplets, comprising:
  a) a device of any one of embodiments 109-113; and
  b) particles in the one or more sample or reagent inlets and/or droplets in the one or more collection reservoirs.

115. A device for producing droplets, the device comprising:
  a) a common inlet;
  b) two or more secondary inlets;
  c) two or more tertiary inlets;
  d) two or more sets of channels, wherein each set intersects to form an intersection and renders one of the secondary inlets and one of the tertiary inlets in fluid communication with the common inlet; and
  e) two or more droplet formation regions, wherein each droplet formation region is fluidically disposed between the common inlet and one of the intersections or fluidically between one of the secondary or tertiary inlets and one of the intersections.

116. The device of embodiment 115, wherein at least one of the droplet formation regions comprises a shelf that allows a liquid to expand in one dimension and a step that allows the liquid to expand in an orthogonal dimension.

117. The device of embodiment 115, wherein the common inlet is a collection reservoir and each droplet formation region is fluidically disposed between the common inlet and one of the intersections.

118. The device of embodiment 115, wherein the secondary or tertiary inlets are collection reservoirs and each droplet formation region is fluidically disposed between one of the secondary or tertiary inlets and one of the intersections.

119. The device of embodiment 115, wherein the common inlet is a sample inlet, wherein the two or more secondary inlets comprise first and second reagent inlets, wherein the two or more tertiary inlets are collection reservoirs, wherein a first of the two or more sets of channels comprises a first sample channel in fluid communication with the sample inlet and a first reagent channel in fluid communication with a first reagent inlet, wherein the first sample channel and first reagent channel intersect to form a first intersection, wherein a first of the two or more droplet formation regions is fluidically disposed between the first intersection and a first of the collection reservoirs, wherein a second of the two or more sets of channels comprises a second sample channel in fluid communication with the sample inlet and a second reagent channel in fluid communication with a second reagent inlet, wherein the second sample channel and second reagent channel intersect at a second intersection, wherein a second of the two or more droplet formation regions is fluidically disposed between the second intersection and a second of the collection reservoirs.

120. The device of embodiment 119, wherein the first sample channel, first reagent inlet, first reagent channel, first intersection, first droplet formation region, and first collection reservoir define a flow path, and wherein the device further comprises a plurality of flow paths disposed radially around and in fluid communication with the sample inlet.

121. The device of embodiment 119, further comprising a third reagent channel in fluid communication with the second reagent inlet and a fourth reagent channel in fluid communication with the first reagent inlet, wherein the first sample channel splits to form two branches, wherein a first branch leads to the first intersection and a second branch intersects with the third reagent channel to form a third intersection, wherein a third droplet formation region is fluidically disposed between the third intersection and the second collection reservoir.

122. The device of embodiment 121, wherein the sample inlet, first sample channel, first and second branches, first and second reagent inlets, first, second, third, and fourth reagent channels, first, second, and third intersections, first, second, and third droplet formation regions, and first and second collection reservoirs define a flow path, and wherein the device further comprises a plurality of flow paths disposed radially around and in fluid communication with the sample inlet.

123. The device of embodiment 122, wherein the second sample channel of each of the plurality of flow paths splits to form first and second branches, wherein for a given flow path, the first branch leads to the second intersection of the given flow path and the second branch intersects with the fourth reagent channel of an adjacent flow path to form a fourth intersection, wherein a fourth droplet formation region is fluidically disposed between the fourth intersection and the first collection reservoir of the adjacent flow path.

124. The device of embodiment 115, wherein the common inlet is a collection reservoir, wherein the two or more secondary inlets comprise first and second reagent inlets, wherein the two or more tertiary inlets are sample inlets, wherein a first of the two or more sets of channels comprises a first sample channel in fluid communication with a first sample inlet and a first reagent channel in fluid communication with a first reagent inlet, wherein the first sample channel and first reagent channel intersect to form a first intersection, wherein a first of the two or more droplet formation regions is fluidically disposed between the first intersection and the collection reservoir, wherein a second of the two or more sets of channels comprises a second sample channel in fluid communication with a second sample inlet and a second reagent channel in fluid communication with a second reagent inlet, wherein the second sample channel and second reagent channel intersect at a second intersection, wherein a second of the two or more droplet formation regions is fluidically disposed between the second intersection and the collection reservoir.

125. The device of embodiment 124, wherein the first sample channel, first reagent inlet, first reagent channel, first intersection, first droplet formation, and first sample inlet define a flow path, and wherein the device further comprises a plurality of flow paths disposed radially around and in fluid communication with the collection reservoir.

126. The device of embodiment 124, further comprising a third reagent channel in fluid communication with the second reagent inlet and a fourth reagent channel in fluid communication with the first reagent inlet, wherein the first sample channel splits to form two branches, wherein the first branch leads to the first intersection and the second branch intersects with the third reagent channel to form a third intersection, wherein a third droplet formation region is fluidically disposed between the third intersection and the collection reservoir.

127. The device of embodiment 126, wherein the first and second sample inlets, first sample channel, first and second branches, first and second reagent inlets, first, second, third, and fourth reagent channels, first, second, and third intersections, first, second, and third droplet formation regions, and collection reservoir define a flow path, and wherein the device further comprises a plurality of flow paths disposed radially around and in fluid communication with the collection reservoir.

128. The device of embodiment 127, wherein the second sample channel of each of the plurality of flow paths splits to form first and second branches, wherein for a given flow path, the first branch leads to the second intersection of the given flow path and the second branch intersects with the fourth reagent channel of an adjacent flow path to form a fourth intersection, wherein a fourth droplet formation region is fluidically disposed between the fourth intersection and the first collection reservoir of the adjacent flow path.

129. The device any one of embodiments 115-128, wherein at least one of the droplet formation regions comprises a shelf that allows a liquid to expand in one dimension and a step that allows the liquid to expand in an orthogonal dimension 130. A method for producing droplets comprising:
 a) providing a device of any one of embodiments 115-123, wherein the droplet formation regions comprise a second liquid, wherein each set comprises a sample channel and a reagent channel; and
 b) allowing a first liquid to flow from the common inlet via the sample channels to the intersections, and allowing a third liquid to flow from the one or more secondary inlets via the one or more reagent channels to the one or more intersections, wherein the first and third liquids combine at the one or more intersections and produce droplets in the second liquid at the one or more droplet formation regions.

131. A system for producing droplets, the system comprising:
 a) a device of any one of embodiments 115-123; and
 b) particles in the common inlet, the secondary inlets, or the tertiary inlets and/or droplets in the common inlet, secondary inlets, or tertiary inlets.

132. A method for producing droplets comprising:
 a) providing a device of any one of embodiments 124-128, wherein the droplet formation regions comprise a second liquid, and wherein each set comprises a sample and reagent channel; and
 b) allowing a first liquid to flow from the tertiary inlets via the sample channels to the one or more intersections, and allowing a third liquid to flow from the one or more secondary inlets via the one or more reagent channels to the intersections, wherein the first and third liquids combine at the one or more intersections and produce droplets in the second liquid at the one or more droplet formation regions 133. A system for producing droplets, the system comprising:
   a) a device of any one of embodiments 124-128; and
   b) particles in the common inlet, the secondary inlets, or the tertiary inlets and/or droplets in the common inlet, secondary inlets, or tertiary inlets.

134. A device for producing droplets, the device comprising:
   a) a first sample inlet;
   b) a reagent inlet;
   c) first and second collection reservoirs;
   d) first, second, third, and fourth sample channels in fluid communication with the first sample inlet, wherein the first and second sample channels are in fluid communication with the first collection reservoir; and the third and fourth sample channels are in fluid communication with the second collection reservoir;
   e) first, second, third, and fourth reagent channels in fluid communication with the reagent inlet, wherein the first and second reagent channels are in fluid communication with the first collection reservoir; the third and fourth reagent channels are in fluid communication with the second collection reservoir; and the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and
   f) first, second, third, and fourth droplet formation regions,
   wherein the first droplet formation region is fluidically disposed between the first intersection and the first collection reservoir, the second droplet formation region is fluidically disposed between the second intersection and the first collection reservoir, the third droplet formation region is fluidically disposed between the third intersection and the second collection reservoir, and the fourth droplet formation region is fluidically disposed between the fourth intersection and the second collection reservoir.

135. The device of embodiment 134, wherein the first sample inlet, the reagent inlet, and the first and second collection reservoirs are arranged substantially linearly.

136. The device of embodiment 134, wherein the first, second, third, and fourth sample channels are co-planar.

137. The device of embodiment 134, wherein the first, second, third, and fourth reagent channels are co-planar.

138. The device of embodiment 134, wherein at least one of the droplet formation regions comprises a shelf that allows a liquid to expand in one dimension and a step that allows the liquid to expand in an orthogonal dimension.

139. The device of embodiment 134, further comprising:
   g) a second sample inlet;
   h) third and fourth collection reservoirs;
   i) fifth, sixth, seventh, and eighth sample channels in fluid communication with the second sample inlet, wherein the fifth and sixth sample channels are in fluid communication with the third collection reservoir; and the seventh and eighth sample channels are in fluid communication with the fourth collection reservoir;
   j) fifth, sixth, seventh, and eighth reagent channels in fluid communication with the reagent inlet, wherein the fifth and sixth reagent channels are in fluid communication with the third collection reservoir; the seventh and eighth reagent channels are in fluid communication with the fourth collection reservoir; and the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and
   k) fifth, sixth, seventh, and eighth droplet formation regions,
   wherein the fifth droplet formation region is fluidically disposed between the fifth intersection and the third collection reservoir, the sixth droplet formation region is fluidically disposed between the sixth intersection and the third collection reservoir, the seventh droplet formation region is fluidically disposed between the seventh intersection and the fourth collection reservoir, and the eighth droplet formation region is disposed between the eighth intersection and the fourth collection reservoir.

140. The device of embodiment 139, wherein the first and second sample inlets, the reagent inlet, first through fourth collection reservoirs, first through eighth sample channels, first through eighth reagent channels, first through eighth intersections, and first through eighth droplet formation regions define a flow path and wherein the device further comprises a plurality of flow paths.

141. The device of embodiment 139, wherein the second sample inlet, the reagent inlet, and the third and fourth collection reservoirs are arranged substantially linearly.

142. The device of embodiment 139, wherein the fifth, sixth, seventh, and eighth sample channels are co-planar.

143. The device of embodiment 139, wherein the fifth, sixth, seventh, and eighth reagent channels are co-planar.

144. The device of embodiment 139, wherein at least one of the droplet formation regions comprises a shelf that allows a liquid to expand in one dimension and a step that allows the liquid to expand in an orthogonal dimension.

145. The device of embodiment 144, further comprising one or more troughs that connect the plurality of reagent inlets, the plurality of first sample inlets, and/or the plurality of second sample inlets.

146. A method for producing droplets comprising:
   a) providing a device comprising:
      i) a first sample inlet;
      ii) a reagent inlet;
      iii) first and second collection reservoirs;
      iv) first, second, third, and fourth sample channels in fluid communication with the first sample inlet, wherein the first and second sample channels are in fluid communication with the first collection reservoir; and the third and fourth sample channels are in fluid communication with the second collection reservoir;

v) first, second, third, and fourth reagent channels in fluid communication with the reagent inlet, wherein the first and second reagent channels are in fluid communication with the first collection reservoir; the third and fourth reagent channels are in fluid communication with the second collection reservoir; and the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and vi) first, second, third, and fourth droplet formation regions each comprising a second liquid, wherein the first droplet formation region is fluidically disposed between the first intersection and the first collection reservoir, the second droplet formation region is fluidically disposed between the second intersection and the first collection reservoir, the third droplet formation region is fluidically disposed between the third intersection and the second collection reservoir, and the fourth droplet formation region is fluidically disposed between the fourth intersection and the second collection reservoir; and b) allowing a first liquid to flow from the first sample inlet via the first, second, third, and fourth sample channels to the first, second, third, and fourth intersections, and allowing a third liquid to flow from the reagent inlet via the first, second, third, and fourth reagent channels to the first, second, third, and fourth intersections, wherein the first liquid and the third liquid combine at the first, second, third, and fourth intersections and produce droplets in the second liquid at the first, second, third, and fourth droplet formation regions.

147. The method of embodiment 146, wherein at least one of the droplet formation regions comprises a shelf that allows a liquid to expand in one dimension and a step that allows the liquid to expand in an orthogonal dimension.

148. The method of embodiment 146, further comprising:
a) the device further comprising:
vii) a second sample inlet;
viii) third and fourth collection reservoirs;
ix) fifth, sixth, seventh, and eighth sample channels in fluid communication with the second sample inlet, wherein the fifth and sixth sample channels are in fluid communication with the third collection reservoir; and the seventh and eighth sample channels are in fluid communication with the fourth collection reservoir;
x) fifth, sixth, seventh, and eighth reagent channels in fluid communication with the reagent inlet, wherein the fifth and sixth reagent channels are in fluid communication with the third collection reservoir; the seventh and eighth reagent channels are in fluid communication with the fourth collection reservoir; and the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and xi) fifth, sixth, seventh, and eighth droplet formation regions each comprising the second liquid, wherein the fifth droplet formation region is fluidically disposed between the fifth intersection and the third collection reservoir, the sixth droplet formation region is fluidically disposed between the sixth intersection and the third collection reservoir, the seventh droplet formation region is fluidically disposed between the seventh intersection and the fourth collection reservoir, and the eighth droplet formation region is disposed between the eighth intersection and the fourth collection reservoir; and b) allowing a first liquid to flow from the second sample inlet via the fifth, sixth, seventh, and eighth sample channels to the fifth, sixth, seventh, and eighth intersections, and allowing a third liquid to flow from the fifth, sixth, seventh, and eighth reagent channels to the fifth, sixth, seventh, and eighth intersections, wherein the first liquid and the third liquid combine at the fifth, sixth, seventh, and eighth intersections and produce droplets in the second liquid at the fifth, sixth, seventh, and eighth droplet formation regions.

149. A system for producing droplets comprising:
a) a device comprising:
i) a first sample inlet;
ii) a reagent inlet;
iii) first and second collection reservoirs;
iv) first, second, third, and fourth sample channels in fluid communication with the first sample inlet, wherein the first and second sample channels are in fluid communication with the first collection reservoir; and the third and fourth sample channels are in fluid communication with the second collection reservoir;
v) first, second, third, and fourth reagent channels in fluid communication with the reagent inlet, wherein the first and second reagent channels are in fluid communication with the first collection reservoir; the third and fourth reagent channels are in fluid communication with the second collection reservoir; and the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and
vi) first, second, third, and fourth droplet formation regions,
wherein the first droplet formation region is fluidically disposed between the first intersection and the first collection reservoir, the second droplet formation region is fluidically disposed between the second intersection and the first collection reservoir, the third droplet formation region is fluidically disposed between the third intersection and the second collection reservoir, and the fourth droplet formation region is fluidically disposed between the fourth intersection and the second collection reservoir b) particles in the sample inlet and/or reagent inlet, and/or droplets in the first and/or second collection reservoir.

150. The system of embodiment 149, wherein the first sample inlet, the reagent inlet, and the first and second collection reservoirs are arranged substantially linearly.

151. The system of embodiment 149, wherein the first, second, third, and fourth sample channels are co-planar.

152. The system of embodiment 149, wherein the first, second, third, and fourth reagent channels are co-planar.

153. The system of embodiment 149, wherein at least one of the droplet formation regions comprises a shelf that allows a liquid to expand in one dimension and a step that allows the liquid to expand in an orthogonal dimension.

154. The system of embodiment 149, wherein the device further comprises:
  vii) a second sample inlet;
  viii) third and fourth collection reservoirs;
  ix) fifth, sixth, seventh, and eighth sample channels in fluid communication with the second sample inlet, wherein the fifth and sixth sample channels are in fluid communication with the third collection reservoir; and the seventh and eighth sample channels are in fluid communication with the fourth collection reservoir;
  x) fifth, sixth, seventh, and eighth reagent channels in fluid communication with the reagent inlet, wherein the fifth and sixth reagent channels are in fluid communication with the third collection reservoir; the seventh and eighth reagent channels are in fluid communication with the fourth collection reservoir; and the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and
  xi) fifth, sixth, seventh, and eighth droplet formation regions,
  wherein the fifth droplet formation region is fluidically disposed between the fifth intersection and the third collection reservoir, the sixth droplet formation region is fluidically disposed between the sixth intersection and the third collection reservoir, the seventh droplet formation region is fluidically disposed between the seventh intersection and the fourth collection reservoir, and the eighth droplet formation region is disposed between the eighth intersection and the fourth collection reservoir.

155. The system of embodiment 154, wherein the first and second sample inlets, the reagent inlet, first through fourth collection reservoirs, first through eighth sample channels, first through eighth reagent channels, first through eighth intersections, and first through eighth droplet formation regions of the device define a flow path, and wherein the device further comprises a plurality of flow paths.

156. The system of embodiment 154, wherein the second sample inlet, the reagent inlet, and the third and fourth collection reservoirs are arranged substantially linearly.

157. The system of embodiment 154, wherein the fifth, sixth, seventh, and eighth sample channels are co-planar.

158. The system of embodiment 154, wherein the fifth, sixth, seventh, and eighth reagent channels are co-planar.

159. The system of embodiment 154, wherein at least one of the droplet formation regions comprises a shelf that allows a liquid to expand in one dimension and a step that allows the liquid to expand in an orthogonal dimension.

160. The system of embodiment 155, further comprising one or more troughs, wherein the one or more troughs connect the plurality of reagent inlets, the plurality of first sample inlets, and/or the plurality of second sample inlets.

161. A device for producing droplets, the device comprising:
  a) a reagent inlet;
  b) first and second sample inlets;
  c) a collection reservoir;
  d) first, second, third, and fourth reagent channels in fluid communication with the reagent inlet;
  e) first, second, third, and fourth sample channels, wherein the first and second sample channels are in fluid communication with the first sample inlet and the third and fourth sample channels are in fluid communication with the second sample inlet; wherein the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and
  f) first, second, third, and fourth droplet formation regions,
  wherein the first droplet formation region is fluidically disposed between the first intersection and the collection reservoir, the second droplet formation region is fluidically disposed between the second intersection and the collection reservoir, the third droplet formation region is fluidically disposed between the third intersection and the third collection reservoir, and the fourth droplet formation region is fluidically disposed between the fourth intersection and the collection reservoir.

162. The device of embodiment 161, wherein the reagent inlet, the first and second sample inlets, and the collection reservoir are arranged substantially linearly.

163. The device of embodiment 161, wherein the first, second, third, and fourth reagent channels are co-planar.

164. The device of embodiment 161, wherein the first, second, third, and fourth sample channels are co-planar.

165. The device of embodiment 161, wherein at least one of the droplet formation regions comprises a shelf that allows a liquid to expand in one dimension and a step that allows the liquid to expand in an orthogonal dimension.

166. The device of embodiment 161, further comprising:
  g) third and fourth sample inlets;
  h) a second collection reservoir;
  i) fifth, sixth, seventh, and eighth reagent channels in fluid communication with the reagent inlet;
  j) fifth, sixth, seventh, and eighth sample channels, wherein the fifth and sixth sample channels are in fluid communication with the third sample inlet and the seventh and eighth sample channels are in fluid communication with the fourth sample inlet; wherein the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and k) fifth, sixth, seventh, and eighth droplet formation regions, wherein the fifth droplet formation region is fluidically disposed between the fifth intersection and the second collection reservoir, the sixth droplet formation region is fluidically disposed between the sixth intersection and the second collection reservoir, the seventh droplet formation region is fluidically disposed between the seventh intersection and the second collection reservoir, and the eighth droplet formation region is fluidically disposed between the eighth intersection and the second collection reservoir.

167. The device of embodiment 166, wherein the first through fourth sample inlets, the reagent channel, the first through eighth reagent channels, the first through eighth sample channels, the first through eighth droplet formation regions, and the first and second reagent inlets define a flow path and wherein the device further comprises a plurality of flow paths.

168. The device of embodiment 167, wherein the reagent inlet, the third and fourth sample inlets, and the second collection reservoir are arranged substantially linearly.

169. The device of embodiment 167, wherein the fifth, sixth, seventh, and eighth reagent channels are coplanar.

170. The device of embodiment 167, wherein the fifth, sixth, seventh, and eighth sample channels are coplanar.

171. The device of embodiment 167, wherein at least one of the droplet formation regions comprises a shelf that allows a liquid to expand in one dimension and a step that allows the liquid to expand in an orthogonal dimension.

172. The device of embodiment 167, further comprising one or more troughs, wherein the one or more troughs connect the plurality of reagent inlets, and/or the plurality of sample inlets.

173. A method for producing droplets comprising:
a) providing a device comprising:
i) a reagent inlet;
ii) first and second sample inlets;
iii) a collection reservoir;
iv) first, second, third, and fourth reagent channels in fluid communication with the reagent inlet;
v) first, second, third, and fourth sample channels, wherein the first and second sample channels are in fluid communication with the first sample inlet and the third and fourth sample channels are in fluid communication with the second sample inlet; wherein the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and vi) first, second, third, and fourth droplet formation regions each comprising a second liquid, wherein the first droplet formation region is fluidically disposed between the first intersection and the collection reservoir, the second droplet formation region is fluidically disposed between the second intersection and the collection reservoir, the third droplet formation region is fluidically disposed between the third intersection and the third collection reservoir, and the fourth droplet formation region is fluidically disposed between the fourth intersection and the collection reservoir;

b) allowing a first liquid to flow from the first and second sample inlets via the first, second, third, and fourth sample channels to the first, second, third, or fourth intersections, and allowing a third liquid to flow from the reagent inlet via the first, second, third, and fourth reagent channels to the first, second, third, and fourth intersections, wherein the first liquid and the third liquid combine at the first, second, third, and fourth intersections and produce droplets in the second liquid at the first, second, third, and fourth droplet formation regions.

174. The method of embodiment 173, wherein the method further comprises:
a) the device further comprising:
vii) third and fourth sample inlets;
viii) a second collection reservoir;
ix) fifth, sixth, seventh, and eighth reagent channels in fluid communication with the reagent inlet;
x) fifth, sixth, seventh, and eighth sample channels, wherein the fifth and sixth sample channels are in fluid communication with the third sample inlet and the seventh and eighth sample channels are in fluid communication with the fourth sample inlet; wherein the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and xi) fifth, sixth, seventh, and eighth droplet formation regions each comprising a second liquid, wherein the fifth droplet formation region is fluidically disposed between the fifth intersection and the second collection reservoir, the sixth droplet formation region is fluidically disposed between the sixth intersection and the second collection reservoir, the seventh droplet formation region is fluidically disposed between the seventh intersection and the second collection reservoir, and the eighth droplet formation region is fluidically disposed between the eighth intersection and the second collection reservoir; and b) allowing the first liquid to flow from the third sample inlet via the fifth and sixth sample channels to the fifth and sixth intersections, allowing the first liquid to flow from the fourth sample inlet via the seventh and eighth sample channels to the seventh and eighth intersections, allowing the third liquid to flow from the reagent inlet via the fifth, sixth, seventh, and eighth reagent channels to the fifth, sixth, seventh, and eighth intersections, wherein the first and third liquids combine at the fifth, sixth, seventh, and eighth intersections and produce droplets in the second liquid at the fifth, sixth, seventh, and eighth droplet formation regions.

175. A system for producing droplets comprising:
   a) a device comprising:
      i) a reagent inlet;
      ii) first and second sample inlets;
      iii) a collection reservoir;
      iv) first, second, third, and fourth reagent channels in fluid communication with the reagent inlet;
      v) first, second, third, and fourth sample channels, wherein the first and second sample channels are in fluid communication with the first sample inlet and the third and fourth sample channels are in fluid communication with the second sample inlet; wherein the first reagent channel and the first sample channel intersect at a first intersection, the second reagent channel and the second sample channel intersect at a second intersection, the third reagent channel and the third sample channel intersect at a third intersection, and the fourth reagent channel and the fourth sample channel intersect at a fourth intersection; and
      vi) first, second, third, and fourth droplet formation regions,
      wherein the first droplet formation region is fluidically disposed between the first intersection and the collection reservoir, the second droplet formation region is fluidically disposed between the second intersection and the collection reservoir, the third droplet formation region is fluidically disposed between the third intersection and the third collection reservoir, and the fourth droplet formation region is fluidically disposed between the fourth intersection and the collection reservoir; and
   b) particles in the reagent inlet and/or sample inlet, and/or droplets in the collection reservoir.

176. The system of embodiment 175, further comprising:
   vii) third and fourth sample inlets;
   viii) a second collection reservoir;
   ix) fifth, sixth, seventh, and eighth reagent channels in fluid communication with the reagent inlet;
   x) fifth, sixth, seventh, and eighth sample channels, wherein the fifth and sixth sample channels are in fluid communication with the third sample inlet and the seventh and eighth sample channels are in fluid communication with the fourth sample inlet; wherein the fifth reagent channel and the fifth sample channel intersect at a fifth intersection, the sixth reagent channel and the sixth sample channel intersect at a sixth intersection, the seventh reagent channel and the seventh sample channel intersect at a seventh intersection, and the eighth reagent channel and the eighth sample channel intersect at an eighth intersection; and
   xi) fifth, sixth, seventh, and eighth droplet formation regions,
   wherein the fifth droplet formation region is fluidically disposed between the fifth intersection and the second collection reservoir, the sixth droplet formation region is fluidically disposed between the sixth intersection and the second collection reservoir, the seventh droplet formation region is fluidically disposed between the seventh intersection and the second collection reservoir, and the eighth droplet formation region is fluidically disposed between the eighth intersection and the second collection reservoir.

177. The system of embodiment 176, wherein the first through fourth sample inlets, the reagent inlet, the first through eighth reagent channels, first through eighth sample channels, first through eighth droplet formation regions, and first and second collection reservoirs of the device define a flow path and wherein the device further comprises a plurality of flow paths.

178. The system of embodiment 176, wherein the reagent inlet, the third and fourth sample inlets, and the second collection reservoir are arranged substantially linearly.

179. The system of embodiment 176, wherein the fifth, sixth, seventh, and eighth reagent channels are coplanar.

180. The system of embodiment 176, wherein the fifth, sixth, seventh, and eighth sample channels are coplanar.

181. The system of embodiment 176, wherein at least one of the droplet formation regions comprises a shelf that allows a liquid to expand in one dimension and a step that allows the liquid to expand in an orthogonal dimension.

182. The system of embodiment 177, further comprising one or more troughs, wherein the one or more troughs comprise a first trough connecting the plurality of reagent inlets.

183. A device for producing droplets, the device comprising:
   (i) one or more first channels, each first channel having independently a first depth, a first width, a first proximal end, and a first distal end, the first distal end comprising a first channel outlet;
   (ii) one or more second channels, each second channel having independently a second depth, a second width, a second proximal end, and a second distal end, wherein each second channel intersects one of the first channels between the first proximal and first distal ends;
   (iii) a droplet collection region; and
   (iv) one or more droplet formation regions in fluid communication with the first channel outlets and the droplet collection region;
   wherein at least one of the one or more first channels bifurcates into two downstream first channels after the intersection between the first channel and the second channel, and the downstream first channels are fluidically connected to the one or more droplet formation regions; and
   wherein the first channels, the downstream first channels, the second channels, the droplet formation region, and the droplet collection region are configured to produce droplets.

184. The device of embodiment 183, wherein the two downstream first channels are curved.

185. The device of embodiment 183 or 184, wherein at least one of the second channels comprises a funnel.

186. The device of any one of embodiments 183-185, wherein the funnel is disposed between the second proximal end and the intersection between the first channel and the second channel.

187. The device of any one of embodiments 183-186, wherein the first channel comprises a mixer.

188. The device of embodiment 187, wherein the mixer is disposed between the first distal end and the intersection between the first channel and the second channel.

189. The device of embodiment 187 or 188, wherein the mixer is a herringbone mixer.

190. A system for producing droplets, the system comprising:
(a) a device comprising:
(i) one or more first channels, each first channel having independently a first depth, a first width, a first proximal end, and a first distal end, the first distal end comprising a first channel outlet;
(ii) one or more second channels, each second channel having independently a second depth, a second width, a second proximal end, and a second distal end, wherein each second channel intersects one of the first channels between the first proximal and first distal ends;
(iii) a droplet collection region; and
(iv) a droplet formation region comprising a shelf region, wherein the droplet formation region is in fluid communication with the first channel outlets and the droplet collection region, and
wherein the width of the droplet formation region is at least five times greater than the combined widths of the first channel outlets, or
wherein the droplet formation region comprises a protrusion from the first channel outlet towards the droplet collection region;
(b) a first liquid disposed in the first channel;
(c) a second liquid disposed in the droplet collection region; and
(d) a third liquid disposed in the second channel;
wherein the first liquid and the second liquid are immiscible;
wherein the first liquid and the third liquid are miscible; and
wherein the system is configured to produce droplets of the first and third liquids in the second liquid.

191. The system of embodiment 190, wherein the device is of any one of embodiments 183-189.

192. A system for producing droplets, the system comprising:
(a) a device comprising:
(i) one or more first channels, each first channel having independently a first depth, a first width, a first proximal end, and a first distal end, the first distal end comprising a first channel outlet;
(ii) one or more second channels, each second channel having independently a second depth, a second width, a second proximal end, and a second distal end, wherein each second channel intersects one of the first channels between the first proximal and first distal ends;
(iii) a droplet collection region; and
(iv) one or more droplet formation regions in fluid communication with the first channel outlets and the droplet collection region;
wherein at least one of the one or more first channels bifurcates into two downstream first channels after the intersection between the first channel and the second channel, and the downstream first channels are fluidically connected to the one or more droplet formation regions;
(b) a first liquid disposed in the first channel;
(c) a second liquid disposed in the droplet collection region; and
(d) a third liquid disposed in the second channel;
wherein the first liquid and the second liquid are immiscible;
wherein the first liquid and the third liquid are miscible; and
wherein the system is configured to produce droplets of the first and third liquids in the second liquid.

193. The system of embodiment 192, wherein the device is of embodiment 184.

194. The system of any one of embodiments 190 to 193, wherein the device is of any one of embodiments 185 to 190.

195. The system of any one of embodiments 190 to 193, further comprising a plurality of particles disposed in the first channel.

196. A method of producing droplets in a second liquid, the droplets comprising a first liquid and a third liquid, the method comprising:
(a) providing the system of any one of embodiments 190-195; and
(b) allowing the first liquid to flow from the first channel to the droplet formation region and produce droplets in the second liquid, the droplets comprising the first liquid and the third liquid.

197. A device for producing droplets, the device comprising:
a) one or more sample inlets;
b) one or more sample channels in fluid communication with the one or more sample inlets;
c) one or more reagent inlets;
d) one or more reagent channels in fluid communication with the one or more reagent inlets wherein the one or more reagent channels intersect with the one or more sample channels to form one or more intersections;
e) one or more droplet formation regions;
f) one or more collection reservoirs
wherein the one or more droplet formation regions are fluidically disposed between the one or more intersections and the one or more collection reservoirs;
wherein the one or more sample inlets, one or more reagent inlets, one or more collection reservoirs, one or more sample channels, one or more reagent channels, one or more intersections, and one or more droplet formation regions define a flow path; and
wherein the one or more sample inlets, one or more reagent inlets, and one or more collection reservoirs are sized and spaced to be in a linear sequence according to a row or column of a multi-well plate.

198. The device of embodiment 197, wherein the one or more sample inlets comprise a first sample inlet, wherein the one or more reagent inlets comprise a first reagent inlet, wherein the one or more collection reservoirs comprise a first collection reservoir, wherein the one or more sample channels comprise a first sample channel in fluid communication with the first sample inlet, wherein the one or more reagent channels comprise a first reagent channel in fluid communication with the first reagent inlet, wherein the one or more intersections comprise a first intersection, wherein the one or more droplet formation regions comprise a first droplet formation region, wherein the first reagent channel intersects the first sample channel at the first intersection, and wherein the first droplet formation region is fluidically disposed between the first intersection and the first collection reservoir.

199. The device of embodiment 198, further comprising a second sample channel in fluid communication with the first sample inlet, a second reagent channel in fluid communication with the first reagent inlet, a second intersection, and a second droplet formation region; wherein the second reagent channel intersects the second sample channel at the second intersection; wherein the second droplet formation region is fluidically disposed between the second intersection and the first collection reservoir.

200. The device of any one of embodiments 197-199, further comprising a second reagent inlet, a second collection reservoir, a third sample channel in fluid communication with the first sample inlet, a third reagent channel in fluid communication with the second reagent inlet, a third intersection, and a third droplet formation region; wherein the third sample channel intersects the third reagent channel at the third intersection; wherein the third droplet formation region is fluidically disposed between the third intersection and the second collection reservoir; and wherein the first and second collection reservoirs and the first and second reagent inlets are disposed ±90 or 180° radially about the sample inlet.

201. The device of embodiment 200, further comprising a fourth sample channel in fluid communication with the first sample inlet, and a fourth reagent channel in fluid communication with the second reagent inlet, a fourth intersection, and a fourth droplet formation region; wherein the fourth sample channel intersects the fourth reagent channel at the fourth intersection; and wherein the fourth droplet formation region is fluidically disposed between the fourth intersection and the second collection reservoir.

202. The device of any one of embodiments 197-201, wherein at least one of the one or more droplet formation regions comprises a shelf that allows a liquid to expand in one dimension and a step that allows the liquid to expand in an orthogonal dimension.

203. The device of any one of embodiments 198-202, further comprising a plurality of flow paths, wherein each flow path is disposed in alignment with a row or column of the multi-well plate.

204. The device of any one of embodiments 198-203, wherein the multi well plate is a 96 well plate, a 384 well plate, or a 1536 well plate.

205. A method for producing droplets comprising:
  a) providing the device of any one of embodiments 197-204, wherein the one or more droplet formation regions comprise a second liquid; and
  b) allowing the first liquid to flow from the one or more sample inlets via the one or more sample channels to the one or more intersections, and allowing a third liquid to flow from the one or more reagent inlets via the one or more reagent channels to the one or more intersections, wherein the first liquid and the third liquid combine at the one or more intersections and produce droplets in the second liquid at the one or more droplet formation regions.

206. A system for producing droplets, the system comprising:
  a) a device of any one of embodiments 197-204; and
  b) particles in the one or more sample inlets and/or the one or more reagent inlets, and/or droplets in the one or more collection reservoirs.

207. A device for producing droplets, the device comprising:
  a) a sample inlet;
  b) first, second, third, and fourth sample channels, each of which is in fluid communication with the sample inlet;
  c) first and second reagent inlets;
  d) first, second, third, and fourth reagent channels, wherein the first and second reagent channels are in fluid communication with the first reagent inlet; wherein the third and fourth reagent channels are in fluid communication with the second reagent inlet; wherein the first sample channel and the first reagent channel intersect at a first intersection, the second sample channel and the second reagent channel intersect at a second intersection, the third sample channel and the third reagent channel intersect at a third intersection, and the fourth sample channel and the fourth reagent channel intersect at a fourth intersection;
  e) first, second, third, and fourth droplet formation regions; and
  f) a collection reservoir,
  wherein the first droplet formation region is fluidically disposed between the first intersection and the collection reservoir, the second droplet formation region is fluidically disposed between the second intersection and the collection reservoir, the third droplet formation region is fluidically disposed between the third intersection and the collection reservoir, and the fourth droplet formation region is fluidically disposed between the fourth intersection and the collection reservoir.

208. The device of embodiment 207, further comprising:
  g) a third reagent inlet;
  h) fifth and sixth sample channels, each of which is in fluid communication with the sample inlet;
  i) fifth and sixth reagent channels, each of which is in fluid communication with the third reagent inlet, wherein the fifth sample channel and the fifth reagent channel intersect at a fifth intersection, and the sixth sample channel and sixth reagent channel intersect at a sixth intersection; and
  j) fifth and sixth droplet formation regions,
  wherein the fifth droplet formation region is fluidically disposed between the fifth intersection and the collection reservoir, and the sixth droplet formation region is fluidically disposed between the sixth intersection and the collection reservoir.

209. The device of embodiment 208, further comprising:
  k) a fourth reagent inlet;
  j) seventh, and eighth sample channels, each of which is in fluid communication with the sample inlet;
  k) seventh, and eighth reagent channels, each of which is in fluid communication with the reagent inlet, wherein the fifth sample channel and the fifth reagent channel intersect at a fifth intersection, the sixth sample channel and sixth reagent channel intersect at a sixth intersection, the seventh sample channel and the seventh reagent channel intersect at a seventh intersection, and the eighth sample channel and the eighth reagent channel intersect at an eighth intersection
  l) fifth, sixth, seventh, and eighth droplet formation regions,
  wherein the seventh droplet formation region is fluidically disposed between the seventh intersection and the collection reservoir, and the eighth droplet formation region is fluidically disposed between the eighth intersection and the collection reservoir.

210. The device of any one of embodiments 207-209, further comprising at least one trough connecting at least two of the reagent inlets.

211. The device of embodiment 207, wherein the sample inlet, first through fourth sample channels, first and second reagent inlets, first through fourth reagent channels, first through fourth intersections, and first through fourth droplet formation regions define a flow path and wherein the device comprises a plurality of flow paths disposed radially about the sample inlet.

212. The device of embodiment 209, wherein the sample inlet, first through eighth sample channels, first through fourth reagent inlets, first through eighth reagent channels, first through eighth intersection, and first through eighth droplet formation regions define a flow path and wherein the device comprises a plurality of flow paths disposed radially about the sample inlet.

213. The device of embodiment 207, wherein the first, second, third, and fourth sample channels are co-planar.

214. The device of embodiment 207, wherein the first, second, third, and fourth reagent channels are co-planar.

215. The device of embodiment 207, wherein the length of each of the first through fourth reagent channels is at least 85% of the length of each other of the reagent channel.

216. A method for producing droplets comprising:
  a) providing the device of any one of embodiments 207-215, wherein first through fourth droplet formation regions comprise a second liquid; and
  b) allowing a first liquid to flow from the sample inlet via the first through fourth sample channels to the first through fourth intersections, and allowing a third liquid to flow from the first and second reagent inlets via the first through fourth reagent channels to the first through fourth intersections, wherein the first liquid and the third liquid combine at the first through fourth intersections and produce droplets in the second liquid at the first through fourth droplet formation regions.

217. A system for producing droplets, the system comprising:
  a) a device of any one of embodiments 207-215; and
  b) particles in the sample inlet and/or the first and/or second reagent inlets, and/or droplets in the collection reservoir.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A device for producing droplets of a first liquid in a second liquid, the device comprising:
  a) a sample inlet;
  b) first, second, and third sample channels, each of which is in fluid communication with the sample inlet;
  c) first and second reagent inlets;
  d) first, second, and third reagent channels, wherein the first and second reagent channels are in fluid communication with the first reagent inlet; the third reagent channel is in fluid communication with the second reagent inlet; the first sample channel and the first reagent channel intersect at a first intersection, the second sample channel and the second reagent channel intersect at a second intersection, and the third sample channel and the third reagent channel intersect at a third intersection;
  e) first, second, and third droplet formation regions; and
  f) first and second collection reservoirs,
wherein the first droplet formation region is fluidically disposed between the first intersection and the first collection reservoir, the second droplet formation region is fluidically disposed between the second intersection and the first collection reservoir, and the third droplet formation region is fluidically disposed between the third intersection and the second collection reservoir.

2. The device of claim 1, further comprising i) a fourth sample channel in fluid communication with the sample inlet; ii) a fourth reagent channel in fluid communication with the second reagent inlet, and iii) a fourth droplet formation region, wherein the fourth sample channel and fourth reagent channel intersect at a fourth intersection, and the fourth droplet formation region is fluidically disposed between the fourth intersection and the second collection reservoir.

3. The device of claim 1, wherein the inlets are arranged substantially linearly.

4. The device of claim 1, wherein the first, second, and third sample channels are co-planar.

5. The device of claim 1, wherein the first, second, and third reagent channels are co-planar.

6. The device of claim 1, wherein the length of the first reagent channel is at least 85% of the length of the second reagent channel.

7. The device of claim 2, wherein the length of the third reagent channel is at least 85% of the length of the fourth reagent channel.

8. The device of claim 1, wherein the first and second collection reservoirs and the first and second reagent inlets are disposed radially about the sample inlet.

9. The device of claim 2, comprising a plurality of first and second reagent inlets; sample inlets; first and second collection reservoirs; first, second, third, and fourth sample channels; first, second, third, and fourth reagent channels; first, second, third, and fourth intersections; and first, second, third, and fourth droplet formation regions.

10. The device of claim 9, wherein:
  a) at least two of the plurality of sample inlets are in fluid communication with each other via a connecting channel; or
  b) a sample channel in fluid communication with one of the plurality of sample inlets and one of the plurality of collection reservoirs intersects with a sample channel in fluid communication with a separate one of the plurality of sample inlets and a separate one of the plurality of collection reservoirs.

11. The device of claim 1, wherein at least one of the droplet formation regions comprises a shelf that allows a liquid to expand in one dimension and a step that allows the liquid to expand in an orthogonal dimension.

12. The device of claim 9, further comprising one or more troughs, wherein the one or more troughs connects the plurality of sample inlets, the plurality of first reagent inlets, and/or connects the plurality of second reagent inlets.

13. A device for producing droplets, the device comprising:
   a) a sample inlet;
   b) first, second, third, and fourth sample channels, each of which is in fluid communication with the sample inlet;
   c) first and second reagent inlets;
   d) first, second, third, and fourth reagent channels, wherein the first and second reagent channels are in fluid communication with the first reagent inlet; wherein the third and fourth reagent channels are in fluid communication with the second reagent inlet; wherein the first sample channel and the first reagent channel intersect at a first intersection, the second sample channel and the second reagent channel intersect at a second intersection, the third sample channel and the third reagent channel intersect at a third intersection, and the fourth sample channel and the fourth reagent channel intersect at a fourth intersection;
   e) first, second, third, and fourth droplet formation regions; and
   f) a collection reservoir,
wherein the first droplet formation region is fluidically disposed between the first intersection and the collection reservoir, the second droplet formation region is fluidically disposed between the second intersection and the collection reservoir, the third droplet formation region is fluidically disposed between the third intersection and the collection reservoir, and the fourth droplet formation region is fluidically disposed between the fourth intersection and the collection reservoir.

14. The device of claim 13, further comprising:
   g) a third reagent inlet;
   h) fifth and sixth sample channels, each of which is in fluid communication with the sample inlet;
   i) fifth and sixth reagent channels, each of which is in fluid communication with the third reagent inlet, wherein the fifth sample channel and the fifth reagent channel intersect at a fifth intersection, and the sixth sample channel and sixth reagent channel intersect at a sixth intersection; and
   j) fifth and sixth droplet formation regions,
wherein the fifth droplet formation region is fluidically disposed between the fifth intersection and the collection reservoir, and the sixth droplet formation region is fluidically disposed between the sixth intersection and the collection reservoir.

15. The device of claim 14, further comprising:
   k) a fourth reagent inlet;
   l) seventh, and eighth sample channels, each of which is in fluid communication with the sample inlet;
   m) seventh, and eighth reagent channels, each of which is in fluid communication with the reagent inlet, wherein the fifth sample channel and the fifth reagent channel intersect at a fifth intersection, the sixth sample channel and sixth reagent channel intersect at a sixth intersection, the seventh sample channel and the seventh reagent channel intersect at a seventh intersection, and the eighth sample channel and the eighth reagent channel intersect at an eighth intersection
   n) fifth, sixth, seventh, and eighth droplet formation regions,
wherein the seventh droplet formation region is fluidically disposed between the seventh intersection and the collection reservoir, and the eighth droplet formation region is fluidically disposed between the eighth intersection and the collection reservoir.

16. The device of claim 13, further comprising at least one trough connecting at least two of the reagent inlets.

17. The device of claim 13, wherein the sample inlet, first through fourth sample channels, first and second reagent inlets, first through fourth reagent channels, first through fourth intersections, and first through fourth droplet formation regions define a flow path and wherein the device comprises a plurality of flow paths disposed radially about the sample inlet.

18. The device of claim 15, wherein the sample inlet, first through eighth sample channels, first through fourth reagent inlets, first through eighth reagent channels, first through eighth intersection, and first through eighth droplet formation regions define a flow path and wherein the device comprises a plurality of flow paths disposed radially about the sample inlet.

19. The device of claim 13, wherein the first, second, third, and fourth sample channels are co-planar, and/or wherein the first, second, third, and fourth reagent channels are co-planar.

20. The device of claim 13, wherein the length of each of the first through fourth reagent channels is at least 85% of the length of each other of the reagent channel.

* * * * *